US012753419B2

(12) United States Patent
Wilson et al.

(10) Patent No.: US 12,753,419 B2
(45) Date of Patent: Oct. 6, 2026

(54) COMPOSITIONS USEFUL FOR TREATMENT OF CHARCOT-MARIE-TOOTH DISEASE

(71) Applicant: The Trustees of the University of Pennsylvania, Philadelphia, PA (US)

(72) Inventors: James M. Wilson, Philadelphia, PA (US); Christian Hinderer, Baltimore, MD (US); Eileen Workman, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 351 days.

(21) Appl. No.: 18/694,823

(22) PCT Filed: Sep. 23, 2022

(86) PCT No.: PCT/US2022/076939

§ 371 (c)(1),
(2) Date: Mar. 22, 2024

(87) PCT Pub. No.: WO2023/049846

PCT Pub. Date: Mar. 30, 2023

(65) Prior Publication Data

US 2024/0401078 A1 Dec. 5, 2024

Related U.S. Application Data

(60) Provisional application No. 63/341,583, filed on May 13, 2022, provisional application No. 63/297,962, filed on Jan. 10, 2022, provisional application No. 63/248,132, filed on Sep. 24, 2021.

(51) Int. Cl.

*C12N 15/86* (2006.01)
*A61P 25/02* (2006.01)
*C12N 9/14* (2006.01)

(52) U.S. Cl.

CPC .............. *C12N 15/86* (2013.01); *A61P 25/02* (2018.01); *C12N 9/14* (2013.01); *C12N 2750/14143* (2013.01); *C12N 2830/42* (2013.01); *C12N 2830/50* (2013.01)

(58) Field of Classification Search

CPC C12N 15/86; C12N 9/14; C12N 2750/14143; C12N 2830/42; C12N 2830/50; C12N 2830/15; A61P 25/02; A01K 2227/105; C07K 14/705

See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,660,514 | B1 | 12/2003 | Zolotukhin et al. |
| 6,759,237 | B1 | 7/2004 | Wilson et al. |
| 6,951,753 | B2 | 10/2005 | Shenk et al. |
| 7,094,604 | B2 | 8/2006 | Snyder et al. |
| 7,105,345 | B2 | 9/2006 | Wilson et al. |
| 7,172,893 | B2 | 2/2007 | Rabinowitz et al. |
| 7,186,552 | B2 | 3/2007 | Wilson et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,588,772 | B2 | 9/2009 | Kay et al. |
| 7,790,449 | B2 | 9/2010 | Gao et al. |

(Continued)

FOREIGN PATENT DOCUMENTS

| | | |
|---|---|---|
| EP | 1310571 | 2/2006 |
| WO | WO-2003/042397 | 5/2003 |

(Continued)

OTHER PUBLICATIONS

Baloh et al., Altered axonal mitochondrial transport in the pathogenesis of Charcot-Marie-Tooth disease from mitofusin 2 mutations, Journal of Neuroscience, vol. 27(2):422-30, Jan. 2007.

Barbullushi et al., Disease Modeling and Therapeutic Strategies in CMT2A: State of the Art, Molecular Neurobiology, Humana Press, vol. 56(9):6460-6471, Mar. 2019.

Bassam et al., Charcot-Marie-Tooth Disease Variants—Classification, Clinical, and Genetic Features and Rational Diagnostic Evaluation, Journal of Clinical Neuromuscular Disease, vol. 15(3):117-128, Mar. 2014.

(Continued)

*Primary Examiner* — Jeremy C Flinders
*Assistant Examiner* — Masudur Rahman
(74) *Attorney, Agent, or Firm* — Howson & Howson LLP; Cathy A Kodroff

(57) ABSTRACT

Provided herein are rAAV and other vectors and compositions useful for treating a patient having CMT2 comprising: (a) a recombinant nucleic acid sequence encoding an engineered human mitofusin 2 coding sequence operably linked to regulatory sequences which direct expression thereof in a human target cell. Also provided are rAAV and other vectors and compositions useful for treating a patient having CMT2 comprising: (b) a nucleic acid sequence encoding at least one miRNA specific for an endogenous human mitofusin 2 sequence in a human CMT2A subject, wherein the miRNA coding sequence is operably linked to regulatory sequences which direct expression thereof in the subject. Further provided are compositions containing both the engineered hMfn2 coding sequence and the at least one miRNA coding sequence, wherein the engineered human mitofusin 2 coding sequence has a sequence which differs from endogenous human mitofusin 2 in the CMT2A patient in the target site of the encoded miRNA.

22 Claims, 29 Drawing Sheets

Specification includes a Sequence Listing.

(56) References Cited

U.S. PATENT DOCUMENTS

| | | | |
|---|---|---|---|
| 7,906,111 | B2 | 3/2011 | Wilson et al. |
| 8,637,255 | B2 | 1/2014 | Wilson et al. |
| 8,853,377 | B2 | 10/2014 | Guild et al. |
| 8,992,891 | B2 | 3/2015 | Cohen et al. |
| 9,238,025 | B2 | 1/2016 | Bosch et al. |
| 9,567,607 | B2 | 2/2017 | Wilson et al. |
| 9,670,152 | B2 | 6/2017 | Payne et al. |
| 10,077,452 | B2 | 9/2018 | Flotte et al. |
| 10,597,656 | B2 | 3/2020 | Flotte et al. |
| 2007/0036760 | A1 | 2/2007 | Wilson et al. |
| 2009/0197338 | A1 | 8/2009 | Vandenberghe et al. |
| 2011/0296555 | A1 | 12/2011 | Ivashuta et al. |
| 2013/0037977 | A1 | 2/2013 | Burke et al. |
| 2013/0045186 | A1 | 2/2013 | Gao et al. |
| 2014/0010861 | A1 | 1/2014 | Bancel et al. |
| 2018/0080926 | A1 | 3/2018 | Mochly-Rosen et al. |
| 2018/0339065 | A1 | 11/2018 | Wilson et al. |
| 2018/0353616 | A1 | 12/2018 | Guild et al. |
| 2020/0053991 | A1 | 2/2020 | Scheideler et al. |

FOREIGN PATENT DOCUMENTS

| | | |
|---|---|---|
| WO | WO-2005/033321 | 4/2005 |
| WO | WO-2006/110689 | 10/2006 |
| WO | WO-2010/053572 | 5/2010 |
| WO | WO-2011/126808 | 10/2011 |
| WO | WO-2012/170930 | 12/2012 |
| WO | WO-2013/049493 | 4/2013 |
| WO | WO-2013/182683 | 12/2013 |
| WO | WO-2014/089486 | 6/2014 |
| WO | WO-2015/074085 | 5/2015 |
| WO | WO-2017/100674 | 6/2017 |
| WO | WO-2017/100676 | 6/2017 |
| WO | WO-2017/100704 | 6/2017 |
| WO | WO-2017/136500 | 8/2017 |
| WO | WO-2017/160360 | 9/2017 |
| WO | WO-2018/160582 | 9/2018 |
| WO | WO-2018/168961 | 9/2019 |
| WO | WO-2019/169004 | 9/2019 |
| WO | WO-2020/047268 | 3/2020 |
| WO | WO-2020/132455 | 6/2020 |
| WO | WO 2020/223231 | 11/2020 |
| WO | WO 2020/223232 | 11/2020 |
| WO | WO 2020/223236 | 11/2020 |
| WO | WO-2020/247815 | 12/2020 |
| WO | WO-2021/080991 | 4/2021 |
| WO | WO-2022/015715 | 1/2022 |
| WO | WO-2022/082109 | 4/2022 |

OTHER PUBLICATIONS

BLOCK-iT Pol II miR RNAi Expression Vector Kits, Gateway—adapted expression vector for the expression of microRNA (miRNA) in mammalian cells under control of Pol II promotoers, Invitrogen, Version F, Dec. 2010.

Buning et al., Recent developments in adeno-associated virus vector technology, Journal of Gene Medicine, vol. 10(7):717-733, May 2008.

Carter, in “Handbook of Parvoviruses”, ed., P. Tijsser, CRC Press, pp. 155 168, Jan. 1990.

Cartoni et al., Role of mitofusin 2 mutations in the physiopathology of Charcot-Marie-Tooth disease type 2A, Experimental Neurology, vol. 218(2):268-273, May 2009.

Chen et al., Emerging functions of mammalian mitochondrial fusion and fission, Human Molecular Genetics, vol. 14 Spec No. 2:R283-9, Oct. 2005.

Chen et al., Real-time quantification of micr-RNAs by stem-loop RT-PCR, Nucleic Acid Research, vol. 33(20):e179, Nov. 2005.

Chung et al., Early onset severe and late-onset mild Charcot-Marie-Tooth disease with mitofusin 2 (MFN2) mutations, Brain, vol. 129(Pt 8):2103-2118, Aug. 2006.

Detmer S., & Chan, D., Complementation between mouse Mfn1 and Mfn2 protects mitochondrial fusion defects caused by CMT2A disease mutations, Journal of Cell Biology, vol. 176(4):405-414, Feb. 2007.

Feely et al., MFN2 mutations cause severe phenotypes in most patients with CMT2A, Neurology, vol. 76(20):1690-1696, May 2011.

Filadi et al., Mitofusin 2: from functions to disease, Cell Death and Disease, vol. 9(3):330, Feb. 2018.

Fisher et al., Transduction with recombinant adeno-associated virus for gene therapy is limited by leading-strand synthesis., Journal of Virology, vol. 70(1):520 532, Jan. 1996.

Flotte, T., & Mueller, C., Gene Therapy for alpha-1 antitrypsin deficiency, Human Molecular Genetics, vol. 20(1):R89-R92, Apr. 2011.

Fridman et al., CMT Subtypes and Disease Burden in Patients Enrolled in the INC Natural History Study: a cross-sectional analysis, Journal of Neurology, Neurosurgery, and Psychiatry, vol. 86(8):873-8, Aug. 2015.

Gao et al., Adeno-associated viruses undergo substantial evolution in primates during natural infections, PNAS U.S.A., vol. 100(10):6081-6086, May 2003.

Grieger, J., & Samulski, R., Adeno-associated virus as a gene therapy vector: Vector development, production and clinical applications, Advances in Biochemical EngInerring/Biotechnology, vol. 99:119-45, 2005.

Grimm et al., Titration of AAV-2 particles via a novel capsid ELISA: packaging of genomes can limit production of recombinant AAV-2, Gene Therapy, vol. 6(7):1322-1330, Jul. 1999.

Kingsman et al., “Potential Oncogene Activity of the Woodchuck Hepatitis Post-Transcriptional Regulatory Element (WPRE),” Gene Ther., vol. 12(1):3-4, Jan. 2005.

Klein et al., Inherited neuropathies: Clinical overview and update, Muscle Nerve, vol. 48(4):604-22, Oct. 2013.

Kowalski et al., Delivering the Messenger: Advances in Technologies for Therapeutic mRNA Delivery, Molecular Therapy, vol. 27(4):710-728, Apr. 2019.

Lawson et al., Clinical and electrophysiologic features of CMT2A with mutations in the mitofusin 2 gene, Neurology, vol. 65(2):197-204, Jul. 2005.

Lock et al., Absolute determination of single-stranded and self-complementary adeno-associated viral vector genome titers by droplet digital PCR, Human Gene Therapy Methods, vol. 25(2):115-25, Apr. 2014.

Lopes, J., #AANAM—Combined Gene Therapy/RNA Strategy May Correct Cellular Changes in CMT2A, Study Suggests, BioNews, Inc., p. 1-2, (Published online ) [retrieved on May 2023], [PDF] Retrieved from the internet <https://charcot-marie-toothnews.com/news/a.

Misko et al., Mitofusin2 mutations disrupt axonal mitochondrial positioning and promote axon degeneration, Journal of Neuroscience, vol. 32(12):4145-55, Mar. 2012.

Morelli et al., Gene therapies for axonal neuropathies: Available strategies, success to date, and what to target next, Brain Research, vol. 1732:146683, Jan. 2020.

Mueller et al., Development of Simultaneous Gene Augumentaiton and Reduction of Mutant Gene Expression with a Single Recombinant AAV for Alpha One Antitrypsin Disease, Abstract, Molecular Therapy, vol. 17(1):S391, May 2009.

Nicholson et al., Severe early-onset axonal neuropathy with homozygous and compound heterozygous MFN2 mutations, Neurology, vol. 70(19):1678-1681, May 2008.

Oh et al., “Hereditary Motor and Sensory Neuropathy Type VI with Bilateral Middle Cerebellar Peduncle Involvement,” Exp Neurobiol., vol. 23(3):266-269, Sep. 2014.

OMIM.org, “MITOFUSIN 2; MFN2, Allelic Variants,” accessed Aug. 15, 2024 from omim.org/allelicVariants/608507, pp. 1-2.

OMIM.org, “Charcot-Marie-Tooth Disease, Axonal, Autosomal Dominant, Type 2A2A; CMT2A2A,” Mar. 2005, accessed Jul. 12, 2020 and Aug. 15, 2024 from OMIM.ORG/entry/609260, pp. 1-6.

Pardo et al., “Technical Guide for Nervous System Sampling of the Cynomolgus Monkey for General Toxicity Studies,” Toxicologic Pathology, vol. 40: 624-636, Jun. 2012.

(56) References Cited

OTHER PUBLICATIONS

Pipis et al., "Natural history of Charcot-Marie-Tooth disease type 2A: a large international multicentre study," Brain, vol. 143: 3589-3602, Dec. 2020.
Qiu et al., A construct with fluorescent indicators for conditional expression of miRNA, BMC Biotechnology, vol. 8:77, Oct. 2008.
Rizzo et al., RNAi/gene therapy combined approach as therapeutic strategy for Charcot-Marie-Tooth 2A, Neurology, vol. 92(15 Supplement):S58.005, Apr. 2019.
Rocha et al., Human biallelic MFN2 mutations induce mitochondrial dysfunction, upper body adipose hyperplasia, and suppression of leptin expression, Elife, vol. 6:e23813, Apr. 2017.
Sambrook et al., "Molecular Cloning. A Laboratory Manual", 2d ed., Cold Spring Harbor Laboratory, New York , pp. 16.5-16.6, (Jan. 1989, Jan. 2012).
Scherer et al. in Peripheral neuropathies in Rosenberg's Molecular and Genetic Basis of Neurological and Psychiatric Disease (5th ed.), Elsevier, Philadelphia, pp. 1051-1074, Jan. 2015.
Sommer et al., Quantification of adeno-associated virus particles and empty capsids by optical density measurement, Molecular Therapy, vol. 7(1):122-128, Jan. 2003.
Su et al., In vitro and in vivo mRNA delivery using lipid-enveloped pH-responsive polymer nanoparticles, Molecular Pharmaceutics, vol. 8(3):774-787, Jun. 2011.
Thompson et al., A comprehensive comparison of multiple sequence alignments, Nucleic Acids Research, vol. 27(13):2682-2690, May 1999.
Verhoeven et al., MFN2 mutation distribution and genotype/phenotype correlation in Charcot-Marie-Tooth type 2, Brain, vol. 129(Pt 8):2093-2102, Aug. 2006.
White et al., Voice of the Patient Report for Charcot-Marie-Tooth Disease and Inherited Neuropathies—Externally-led Patient-Focused Drug Development Meeting, Hereditary Neuropathy Foundation, Sep. 2018.
Wobus et al., Monoclonal antibodies against the adeno-associated virus type 2 (AAV-2) capsid: epitope mapping and identification of capsid domains involved in AAV-2-cell interaction and neutralization of AAV-2 infection, Journal of Virology, vol. 74(19).
Xie et al., MicroRNA-regulated, Systemically Delivered rAAV9: A Step Closer to CNS-restricted Transgene Expression, Molecular Therapy, vol. 19(3):526-535, Mar. 2011.
Zanta-Boussif et al., Validation of a mutated PRE sequence allowing high and sustained transgene expression while abrogating WHV-X protein synthesis: application to the gene therapy of WASGene Therapy, vol. 16:605-619, Mar. 2009.
Zhang et al., Adenovirus-adeno-associated virus hybrid for large-scale recombinant adeno-associated virus production, Human Gene Therapy, vol. 20(9):922-929, Sep. 2009.
Zhou et al., Restoring mitofusin balance prevents axonal degeneration in a Charcot-Marie-Tooth 2A model, The Journal of Clinical Investigation, vol. 129(4):1756-1771, Mar. 2019.
Zuchner et al., Mutations in the mitochondrial GTPase mitofusin 2 cause Charcot-Marie-Tooth neuropathy type 2A, Nature Genetics, vol. 36(5):449-451, May 2004.
U.S. Appl. No. 62/924,112, filed Oct. 21, 2019.
U.S. Appl. No. 63/023,593, filed May 12, 2020.
U.S. Appl. No. 63/025,753, filed May 15, 2020.
U.S. Appl. No. 63/038,488, filed Jun. 12, 2020.
U.S. Appl. No. 63/051,336, filed Jul. 13, 2020.
U.S. Appl. No. 63/065,616, filed Aug. 14, 2020.
U.S. Appl. No. 63/093,275, filed Oct. 18, 2020.
U.S. Appl. No. 63/109,734, filed Nov. 4, 2020.
U.S. Appl. No. 63/119,863, filed Dec. 1, 2020.
U.S. Appl. No. 63/173,045, filed Apr. 9, 2021.
U.S. Appl. No. 63/248,132, filed Sep. 24, 2021.
U.S. Appl. No. 63/297,962, filed Jan. 10, 2022.
U.S. Appl. No. 63/341,583, filed May 13, 2022.
U.S. Appl. No. 63/371,592, filed Aug. 16, 2022.
U.S. Appl. No. 63/371,597, filed Aug. 16, 2022.
International Search Report and Written Opinion issued on International Patent Application No. PCT/US22/76939, dated Dec. 28, 2022.
International Search Report and Written Opinion issued on International Patent Application No. PCT/US2021/041406, dated Nov. 9, 2021.

- 1: WT, G1 PBS
- 2: MFN2[R94Q], G2 PBS
- 3: MFN2[R94Q], G3 Cb7.hMfn2
- 4: MFN2[R94Q], G4 Cb7.hMfn2.miR1518
- 5: MFN2[R94Q], G5 Cb7.hMn2.miR538
- 6: MFN2[R94Q], G6 CAG.hMfn2.miR1518
- 7: MFN2[R94Q], G7 CAG.hMfn2.miR538

- 1: WT, G1 PBS
- 2: MFN2$^{R94Q}$, G2 PBS
- 3: MFN2$^{R94Q}$, G3 Cb7.hMfn2
- 4: MFN2$^{R94Q}$, G4 Cb7.hMfn2.miR1518
- 5: MFN2$^{R94Q}$, G5 Cb7.hMn2.miR538
- 6: MFN2$^{R94Q}$, G6 CAG.hMfn2.miR1518
- 7: MFN2$^{R94Q}$, G7 CAG.hMfn2.miR538

- Group 1: WT + PBS
- Group 2: MFN2$^{R94Q}$ + PBS
- Group 3: MFN2$^{R94Q}$ + Cb7.hMfn2
- Group 4: MFN2$^{R94Q}$ + Cb7.hMfn2.miR1518
- Group 5: MFN2$^{R94Q}$ + Cb7.hMfn2.miR538
- Group 6: MFN2$^{R94Q}$ + CAG.hMfn2.miR1518
- Group 7: MFN2$^{R94Q}$ + CAG.hMfn2.miR538

SEQUENCE LISTING

```
Sequence total quantity: 107
SEQ ID NO: 1            moltype = DNA  length = 4585
FEATURE                 Location/Qualifiers
misc_feature            1..4585
                        note = Vector Genome Syn.PI.hMfn2opt.link.hMfn2
                         miR1693.WPRE.bGH
repeat_region           1..141
                        note = 5'ITR
regulatory              223..682
                        note = promoter - hSynapsin
                        regulatory_class = promoter
misc_feature            694..826
                        note = Intron - Promega Chimeric Intron
misc_feature            857..862
                        note = Kozak
misc_feature            3134..3139
                        note = Dbl stop codon
misc_feature            3140..3229
                        note = linker
misc_feature            3230..3252
                        note = 5' flank
misc_feature            3253..3316
                        note = hMfn2 miR1693
misc_feature            3317..3360
                        note = 3' flank
misc_feature            3463..4045
                        note = WRPE
misc_feature            4410..4455
                        note = Additional AAV squences
repeat_region           4456..4585
                        note = 3'ITR
source                  1..4585
                        mol_type = other DNA
                        organism = synthetic construct
CDS                     863..3136
                        note = human Mfn2 engineered
                        protein_id = 2
                        translation = MSLLFSRCNSIVTVKKNKRHMAEVNASPLKHFVTAKKKINGIFEQL
                         GAYIQESATFLEDTYRNAELDPVTTEEQVLDVKGYLSKVRGISEVLARRHMKVAFFGRT
                         SNGKSTVINAMLWDKVLPSGIGHTTNCFLRVEGTDGHEAFLLTEGSEEKRSAKTVNQLA
                         HALHQDKQLHAGSLVSVMWPNSKCPLLKDDLVLMDSPGIDVTTELDSWIDKFCLDADVF
                         VLVANSESTLMQTEKHFFHKVSERLSRPNIFILNNRWDASASEPEYMEEVRRQHMERCT
                         SFLVDELGVVDRSQAGDRIFFVSAKEVLNARIQKAQGMPEGGGALAEGFQVRMFEFQNF
                         ERRFEECISQSAVKTKFEQHTVRAKQIAEAVRLIMDSLHMAAREQQVYCEEMREERQDR
                         LKFIDKQLELLAQDYKLRIKQITEEVERQVSTAMAEEIRRLSVLVDDYQMDFHPSPVVL
                         KVYKNELHRHIEEGLGRNMSDRCSTAITNSLQTMQQDMIDGLKPLLPVSVRSQIDMLVP
                         RQCFSLNYDLNCDKLCADFQEDIEFHFSLGWTMLVNRFLGPKNSRRALMGYNDQVQRPI
                         PLTPANPSMPPLPQGSLTQEEFMVSMVTGLASLTSRTSMGILVVGGVVWKAVGWRLIAL
                         SFGLYGLLYVYERLTWTTKAKERAFKRQFVEHASEKLQLVISYTGSNCSHQVQQELSGT
                         FAHLCQQVDVTRENLEQEIAAMNKKIEVLDSLQSKAKLLRNKAGWLDSELNMFTHQYLQ
                         PSR
SEQUENCE: 1
ccttaattag gctgcgcgct cgctcgctca ctgaggccgg gcgaccaaag gtcgcccgac  60
gcccgggctt tgcccgggcg gcctcagtga gcgagcgagc gcgcagagag ggagtggcca  120
actccatcac taggggttcc ttgtagttaa tgattaaccc gccatgctac ttatctacgt  180
agccatgctc taggaagatc ggaattcgcc cttaagctag actcgagctg cagagggccc  240
```

-continued

```
tgcgtatgag tgcaagtggg ttttaggacc aggatgaggc ggggtggggg tgcctacctg  300
acgaccgacc ccgacccact ggacaagcac ccaaccccca ttccccaaat tgcgcatccc  360
ctatcagaga gggggagggg aaacaggatg cggcgaggcg cgtgcgcact gccagcttca  420
gcaccgcgga cagtgccttc gcccccgcct ggcggcgcgc gccaccgccg cctcagcact  480
gaaggcgcgc tgacgtcact cgccggtccc ccgcaaactc cccttcccgg ccaccttggt  540
cgcgtccgcg ccgccgccgg cccagccgga ccgcaccacg cgaggcgcga gatagggggg  600
cacgggcgcg accatctgcg ctgcggcgcc ggcgactcag cgctgcctca gtctgcggtg  660
ggcagcggag gagtcgtgtc gtgcctgaga gcggtaagta tcaaggttac aagacaggtt  720
taaggagacc aatagaaact gggcttgtcg agacagagaa gactcttgcg tttctgatag  780
gcacctattg gtcttactga catccacttt gcctttctct ccacagtacg tagaattcac  840
gcgtgctagc accggtgcca ccatgagcct gctgttcagc cggtgcaaca gcatcgtgac  900
cgtgaagaaa aacaagcggc acatggccga agtgaacgcc tctccactga agcacttcgt  960
gaccgccaag aagaagatca acggcatctt cgagcagctg ggcgcctaca tccaagagag  1020
cgccaccttc ctggaagata cctacagaaa cgccgagctg gaccccgtga ccacagagga  1080
acaggtgctg gatgtgaagg gctacctgag caaagtgcgg ggcatctctg aagtgctggc  1140
cagacggcat atgaaggtgg cctttttcgg ccggaccagc aacggcaaga gcaccgtgat  1200
caatgccatg ctgtgggaca aagtgctgcc ctctggaatc ggccacacca ccaactgctt  1260
tctgagagtg gaaggcaccg acggccacga ggcatttctg ctgacagagg gctccgagga  1320
aaagcggagc gccaagacag tgaaccagct ggcccatgct ctgcaccagg ataagcagct  1380
gcatgccgga agcctggtgt ccgtgatgtg gcccaatagc aagtgccctc tgctgaagga  1440
cgacctggtg ctgatggata gccccgggat cgatgtgacc accgaactgg acagctggat  1500
cgacaagttc tgcctggacg ccgacgtgtt cgtgctggtg gccaatagcg agagcaccct  1560
gatgcagacc gagaagcact ttttccacaa ggtgtccgag cggctgagca gacccaatat  1620
ctttatcctg aacaacagat gggacgccag cgccagcgag cccgagtata tggaagaagt  1680
gcggcggcag catatggaac ggtgcacatc ctttctggtg gacgagctgg gcgtcgtgga  1740
tagatctcag gccggcgaca gaatcttctt tgtgtccgcc aaagaggtgc tgaacgcccg  1800
gattcagaaa gcccagggaa tgcctgaagg cggaggtgca ctggccgagg gatttcaagt  1860
gcggatgttc gagttccaga acttcgagcg gagattcgag gagtgcatca gccagagcgc  1920
cgtcaagacc aagttcgagc agcataccgt gcgggccaag cagattgccg aagccgtcag  1980
actgatcatg gacagcctgc atatggccgc cagagagcag caggtctact gcgaggaaat  2040
gcgggaagag agacaggacc ggctgaagtt catcgacaag cagctggaac tgctggccca  2100
ggactacaag ctgcggatca agcagatcac cgaagaggtg gaaagacagg tgtccaccgc  2160
tatggccgag gaaatcagac ggctgagcgt gctggtcgac gactaccaga tggactttca  2220
cccctctcca gtggtgctga aagtctacaa aaacgagctg caccggcaca tcgaggaagg  2280
cctgggcaga aacatgagcg acagatgcag caccgccatc accaatagcc tgcagaccat  2340
gcagcaggac atgatcgacg gcctgaaacc tctgctgcct gtgtccgtca gatcccagat  2400
cgatatgctg gtgccccggc agtgctttag cctgaactac gacctgaact gcgacaagct  2460
gtgcgccgat ttccaagagg acatcgagtt tcacttcagc ctcggctgga caatgctggt  2520
caacagattt ctgggcccca agaacagcag acgggccctg atgggctaca acgatcaggt  2580
gcagaggccc attcctctga cacccgccaa tcctagcatg cctccactgc ctcagggcag  2640
cctgacacaa gaggaattca tggtgtctat ggtcaccggc ctggccagcc tgaccagcag  2700
aacatctatg ggcatcctgg tcgtcggcgg cgttgtgtgg aaagctgttg gctggcggct  2760
gatcgccctg agctttggcc tgtatggcct gctgtacgtg tacgagagac tgacctggac  2820
caccaaggcc aaagagcggg ccttcaagcg gcagtttgtg gaacacgcct ccgagaaact  2880
gcagctggtg atcagctaca ccggcagcaa ttgcagccac caggtgcagc aagagctgtc  2940
cggaacattc gcccacctgt gtcagcaggt cgacgtgacc agagagaacc tggaacaaga  3000
gatcgccgcc atgaataaga aaatcgaggt gctcgactcc ctgcagagca aggccaagct  3060
gctgagaaac aaggccggct ggctggacag cgagctgaat atgttcaccc accagtacct  3120
gcagcctagc cgctaataat gtacaagtaa agcgcccgca ggcttgcacc cgtacctttg  3180
ggagcgcgcg ccctcgtcgt gtcgtgacgt cacccgttct gttggatccc tggaggcttg  3240
ctgaaggctg tatgctgttc ttataaacct tgaggactgt tttggccact gactgacagt  3300
cctcagttta taagaacagg acacaaggcc tgttactagc actcacatgg aacaaatggc  3360
ccagatctag ggtggggcca cctgccggta ggtgtgcggt aggcttttct ccgtcgcagg  3420
acgcagggtt cgggcctagc ttaagcttct cgagatcgat aatcaacctc tggattacaa  3480
aatttgtgaa agattgactg gtattcttaa ctatgttgct ccttttacgc tatgtggata  3540
cgctgcttta atgcctttgt atcatgctat tgcttcccgt atggctttca ttttctcctc  3600
cttgtataaa tcctggttgc tgtctcttta tgaggagttg tggcccgttg tcaggcaacg  3660
tggcgtggtg tgcactgtgt ttgctgacgc aacccccact ggttggggca ttgccaccac  3720
ctgtcagctc ctttccggga ctttcgcttt ccccctccct attgccacgg cggaactcat  3780
cgccgcctgc cttgcccgct gctggacagg ggctcggctg ttgggcactg acaattccgt  3840
ggtgttgtcg gggaaatcat cgtcctttcc ttggctgctc gcctgtgttg ccacctggat  3900
tctgcgcggg acgcccttct gctacgtccc ttcggccctc aatccagcgg accttccttc  3960
ccgcggcctg ctgccggctc tgcggcctct tccgcgtctt cgccttcgcc ctcagacgag  4020
tcggatctcc ctttgggccg cctccccgcc tgctgatcgc cctgagcctg gccctggtga  4080
ccaacagcca ggtgcaattg ctagagtcga ctctagagcg gccgcctaag gctcgactag  4140
agctcgctga tcagcctcga ctgtgccttc tagttgccag ccatctgttg tttgcccctc  4200
ccccgtgcct tccttgaccc tggaaggtgc cactcccact gtcctttcct aataaaatga  4260
ggaaattgca tcgcattgtc tgagtaggtg tcattctatt ctggggggtg gggtggggca  4320
ggacagcaag ggggaggatt gggaagacaa tagcaggcat gctggggact cgagttaagg  4380
gcgaattccc gataaggatc ttcctagagc atggctacgt agataagtag catggcgggt  4440
taatcattaa ctacaaggaa cccctagtga tggagttggc cactccctct ctgcgcgctc  4500
gctcgctcac tgaggccggg cgaccaaagg tcgcccgacg cccgggcttt gcccgggcgg  4560
cctcagtgag cgagcgagcg cgcag                                        4585

SEQ ID NO: 2           moltype = AA  length = 757
FEATURE                Location/Qualifiers
REGION                 1..757
                       note = Synthetic Construct
source                 1..757
```

-continued

```
                       mol_type = protein
                       organism = synthetic construct
SEQUENCE: 2
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 3           moltype = DNA  length = 4560
FEATURE                Location/Qualifiers
misc_feature           1..4560
                       note = Vector Genome Syn.PI.rMnf2opt.link.rMfn2 miR1518
                        WPRE.BGH
repeat_region          1..141
                       note = 5'ITR
regulatory             223..682
                       note = promoter - hSynapsin
                       regulatory_class = promoter
misc_feature           694..826
                       note = Intron - Promega Chimeric Intron
misc_feature           3134..3139
                       note = Dbl stop codon
misc_feature           3140..3229
                       note = linker
misc_feature           3230..3252
                       note = 5' flank
misc_feature           3253..3316
                       note = rMfn2 miR1518
misc_feature           3317..3360
                       note = 3'flank
regulatory             3457..4044
                       note = enhancer - WRPE
                       regulatory_class = enhancer
misc_feature           4385..4430
                       note = Additional AAV sequences
repeat_region          4431..4560
                       note = 3'ITR
source                 1..4560
                       mol_type = other DNA
                       organism = synthetic construct
CDS                    863..3133
                       note = rMfn2 engineered
                       protein_id = 4
                       translation = MSLLFSRCNSIVTVKKDKRHMAEVNASPLKHFVTAKKKINGIFEQL
                        GAYIQESAGFLEDTHRNTELDPVTTEEQVLDVKGYLSKVRGISEVLARRHMKVAFFGRT
                        SNGKSTVINAMLWDKVLPSGIGHTTNCFLRVGGTDGHEAFLLTEGSEEKKSVKTVNQLA
                        HALHQDEQLHAGSLVSVMWPNSKCPLLKDDLVLMDSPGIDVTTELDSWIDKFCLDADVF
                        VLVANSESTLMQTEKQFFHKVSERLSRPNIFILNNRWDASASEPEYMEEVRRQHMERCT
                        SFLVDELGVVDRAQAGDRIFFVSAKEVLSARVQKAQGMPEGGGALAEGFQVRMFEFQNF
                        ERRFEECISQSAVKTKFEQHTVRAKQIAEAVRLIMDSLHIAAQEQRVYCLEMREERQDR
                        LRFIDKQLELLAQDYKLRIKQMTEEVERQVSTAMAEEIRRLSVLVDEYQMDFHPSPVVL
                        KVYKNELHRHIEEGLGRNMSDRCSTAIASSLQTMQQDMIDGLKPLLPVSVRNQIDMLVP
                        RQCFSLSYDLNCDKLCADFQEDIEFHFSLGWTMLVNRFLGPKNSRRALLGYNDQVQRPL
                        PLTPANPSMPPLPQGSLTQEELMVSMVTGLASLTSRTSMGILVVGGVVWKAVGWRLIAL
                        SFGLYGLLYVYERLTWTTRAKERAFKRQFVEYASEKLQLIISYTGSNCSHQVQQELSGT
                        FAHLCQQVDITRDNLEQEIAAMNKKVEALDSLQSKAKLLRNKAGWLDSELNMFIHQYLQ
                        PSR
SEQUENCE: 3
ccttaattag gctgcgcgct cgctcgctca ctgaggccgg gcgaccaaag gtcgcccgac  60
gcccgggctt tgcccgggcg gcctcagtga gcgagcgagc gcgcagagag ggagtggcca  120
actccatcac taggggttcc ttgtagttaa tgattaaccc gccatgctac ttatctacgt  180
agccatgctc taggaagatc ggaattcgcc cttaagctag actcgagctg cagagggccc  240
tgcgtatgag tgcaagtggg ttttaggacc aggatgaggc ggggtggggg tgcctacctg  300
acgaccgacc ccgacccact ggacaagcac ccaacccccca ttccccaaat tgcgcatccc  360
ctatcagaga gggggagggg aaacaggatg cggcgaggcg cgtgcgcact gccagcttca  420
gcaccgcgga cagtgccttc gcccccgcct ggcggcgcgc gccaccgccg cctcagcact  480
gaaggcgcgc tgacgtcact cgccggtccc ccgcaaactc cccttcccgg ccaccttggt  540
cgcgtccgcg ccgccgccgg cccagccgga ccgcaccacg cgaggcgcga gatagggggg  600
cacgggcgcg accatctgcg ctgcggcgcc ggcgactcag cgctgcctca gtctgcggtg  660
ggcagcggag gagtcgtgtc gtgcctgaga gcggtaagta tcaaggttac aagacaggtt  720
```

```
taaggagacc aatagaaact gggcttgtcg agacagagaa gactcttgcg tttctgatag  780
gcacctattg gtcttactga catccacttt gcctttctct ccacagtacg tagaattcac  840
gcgtgctagc accggtgcca ccatgtctct gctgttcagc cggtgcaaca gcatcgtgac  900
cgtgaagaaa gacaagaggc acatggccga agtgaacgcc tctccactga agcacttcgt  960
gaccgccaag aagaagatca acggcatctt cgagcagctg ggcgcctaca tccaagagtc  1020
tgccggcttc ctggaagata cccacagaaa caccgagctg gaccccgtga ccacagagga  1080
acaggtgctg gacgtgaagg gctacctgtc taaagtgcgg ggcatcagcg aggtgctggc  1140
tagaaggcat atgaaggtgg cctttttcgg caggaccagc aacggcaaga gcaccgtgat  1200
caacgccatg ctgtgggaca aagtgctgcc ttctggcatc ggccacacca ccaactgctt  1260
tctgagagtc ggcggcacag acggccacga ggcttttttg ctgaccgagg gctccgaaga  1320
gaagaaatcc gtgaaaaccg tgaaccagct ggcccacgct ctgcaccagg atgaacaact  1380
gcacgccgga agcctggtgt ccgtgatgtg gcctaacagc aagtgccctc tgctgaagga  1440
cgacctggtg ctgatggact ctcctggaat cgacgtgacc actgagctgg acagctggat  1500
cgacaagttc tgcctggacg ccgacgtgtt cgtgctggtg gctaactctg agagcaccct  1560
gatgcagacc gagaagcagt tcttccacaa ggtgtccgag aggctgagca ggcccaatat  1620
ctttatcctg aacaacagat gggacgccag cgccagcgag cccgagtata tggaagaagt  1680
gcggaggcag catatggaaa ggtgtaccag cttcctggtg gacgagctgg gagtcgtgga  1740
tagagcacag gccggcgaca gaatcttctt cgtgtctgcc aaagaggtgc tgagcgccag  1800
ggtgcagaaa gcccagggaa tgcctgaagg cggcggagct ttggccgagg gatttcaagt  1860
gcggatgttc gagttccaga acttcgagcg gagattcgag gaatgcatca gccagagcgc  1920
cgtcaagaca aagttcgagc agcacacagt gcgggccaag cagatcgctg aggctgtgcg  1980
gctgatcatg gacagcctgc atatcgccgc tcaagagcag agggtgtact gcctggaaat  2040
gcgggaagag aggcaggaca ggctgagatt catcgacaag cagctggaac tgctggccca  2100
ggactacaag ctgaggatca agcagatgac cgaagaggtg gaaagacagg tgtccaccgc  2160
catggccgag gaaatccgta gactgtctgt gctggtcgac gagtaccaga tggactttca  2220
cccctctcca gtggtgctga aggtctacaa aaacgagctg cacaggcaca tcgaggaagg  2280
cctgggcaga aacatgagcg acaggtgctc taccgctatc gccagcagcc tgcagacaat  2340
gcagcaggac atgatcgacg gcctgaagcc tctgctgcct gtgtctgtgc ggaaccagat  2400
cgatatgctg gtgcccaggc agtgcttctc cctgtcctac gacctgaact gcgacaagct  2460
gtgtgccgac ttccaagagg acatcgagtt tcacttcagc ctcggctgga caatgctggt  2520
caacagattc ctgggaccta agaactccag acgggccctg ctgggataca acgatcaggt  2580
gcaaaggccc ctgcctctga caccagctaa cccttctatg cctcctctgc ctcaaggctc  2640
tctgacccaa gaggaactga tggtgtccat ggtcacaggc ctggcttccc tgaccagcag  2700
aacctctatg ggcatcctgg tcgtcggcgg agttgtgtgg aaagctgttg gctggcgcct  2760
gatcgccctg agctttggac tgtacggact gctgtacgtg tacgagagac tgacctggac  2820
caccagggcc aaagagaggg ccttcaagag gcagttcgtg gaatacgcct ccgagaaact  2880
gcagctgatt atctcctaca ccggcagcaa ctgcagccac caggtgcagc aagagctgtc  2940
tggaacattc gcccacctgt gccagcaggt cgacatcacc agagacaacc tggaacaaga  3000
gatcgccgct atgaataaga aggtggaagc cctggactcc ctgcagagca aggctaagct  3060
gctgagaaac aaggccggct ggctggactc cgagctgaat atgtttatcc accagtacct  3120
gcagcctagc cgctgatgat gtacaagtaa agcggccgca agcttgcacc cgtacctttg  3180
ggagcgcgcg ccctcgtcgt gtcgtgacgt cacccgttct gttggatccc tggaggcttg  3240
ctgaaggctg tatgctgttc ttataaacct tgaggacagt tttggccact gactgactgt  3300
cctcagttta taagaacagg acacaaggcc tgttactagc actcacatgg aacaaatggc  3360
ccagatctag ggtggggcca cctgccggta ggtgtgcggt aggcttttct ccgtcgcagg  3420
acgcagggtt cgggcctagc ttctcgagat cgataatcaa cctctggatt acaaaatttg  3480
tgaaagattg actggtattc ttaactatgt tgctcctttt acgctatgtg gatacgctgc  3540
tttaatgcct ttgtatcatg ctattgcttc ccgtatggct ttcattttct cctccttgta  3600
taaatcctgg ttgctgtctc tttatgagga gttgtggccc gttgtcaggc aacgtggcgt  3660
ggtgtgcact gtgtttgctg acgcaacccc cactggttgg ggcattgcca ccacctgtca  3720
gctcctttcc gggactttcg ctttccccct ccctattgcc acggcggaac tcatcgccgc  3780
ctgccttgcc cgctgctgga caggggctcg gctgttgggc actgacaatt ccgtggtgtt  3840
gtcggggaaa tcatcgtcct ttccttggct gctcgcctgt gttgccacct ggattctgcg  3900
cgggacgccc ttctgctacg tcccttcggc cctcaatcca gcggaccttc cttcccgcgg  3960
cctgctgccg gctctgcggc ctcttccgcg tcttcgcctt cgccctcaga cgagtcggat  4020
ctccctttgg gccgcctccc cgcctgctga tcgccctgag cctggccctg gtgaccaaca  4080
gccaggtgca attgaagctt tctagagtcg actagagctc gctgatcagc ctcgactgtg  4140
ccttctagtt gccagccatc tgttgtttgc ccctcccccg tgccttcctt gaccctggaa  4200
ggtgccactc ccactgtcct ttcctaataa aatgaggaaa ttgcatcgca ttgtctgagt  4260
aggtgtcatt ctattctggg gggtggggtg gggcaggaca gcaaggggga ggattgggaa  4320
gacaatagca ggcatgctgg ggactcgagt taagggcgaa ttcccgataa ggatcttcct  4380
agagcatggc tacgtagata agtagcatgg cgggttaatc attaactaca aggaacccct  4440
agtgatggag ttggccactc cctctctgcg cgctcgctcg ctcactgagg ccgggcgacc  4500
aaaggtcgcc cgacgcccgg gctttgcccg ggcggcctca gtgagcgagc gagcgcgcag  4560

SEQ ID NO: 4           moltype = AA  length = 757
FEATURE                Location/Qualifiers
REGION                 1..757
                       note = Synthetic Construct
source                 1..757
                       mol_type = protein
                       organism = synthetic construct
SEQUENCE: 4
MSLLFSRCNS IVTVKKDKRH MAEVNASPLK HFVTAKKKIN GIFEQLGAYI QESAGFLEDT  60
HRNTELDPVT TEEQVLDVKG YLSKVRGISE VLARRHMKVA FFGRTSNGKS TVINAMLWDK  120
VLPSGIGHTT NCFLRVGGTD GHEAFLLTEG SEEKKSVKTV NQLAHALHQD EQLHAGSLVS  180
VMWPNSKCPL LKDDLVLMDS PGIDVTTELD SWIDKFCLDA DVFVLVANSE STLMQTEKQF  240
FHKVSERLSR PNIFILNNRW DASASEPEYM EEVRRQHMER CTSFLVDELG VVDRAQAGDR  300
IFFVSAKEVL SARVQKAQGM PEGGGALAEG FQVRMFEFQN FERRFEECIS QSAVKTKFEQ  360
```

```
HTVRAKQIAE AVRLIMDSLH IAAQEQRVYC LEMREERQDR LRFIDKQLEL LAQDYKLRIK  420
QMTEEVERQV STAMAEEIRR LSVLVDEYQM DFHPSPVVLK VYKNELHRHI EEGLGRNMSD  480
RCSTAIASSL QTMQQDMIDG LKPLLPVSVR NQIDMLVPRQ CFSLSYDLNC DKLCADFQED  540
IEFHFSLGWT MLVNRFLGPK NSRRALLGYN DQVQRPLPLT PANPSMPPLP QGSLTQEELM  600
VSMVTGLASL TSRTSMGILV VGGVVWKAVG WRLIALSFGL YGLLYVYERL TWTTRAKERA  660
FKRQFVEYAS EKLQLIISYT GSNCSHQVQQ ELSGTFAHLC QQVDITRDNL EQEIAAMNKK  720
VEALDSLQSK AKLLRNKAGW LDSELNMFIH QYLQPSR                          757

SEQ ID NO: 5            moltype = DNA  length = 141
FEATURE                 Location/Qualifiers
misc_feature            1..141
                        note = 5' ITR
source                  1..141
                        mol_type = other DNA
                        organism = synthetic construct
SEQUENCE: 5
ccttaattag gctgcgcgct cgctcgctca ctgaggccgg gcgaccaaag gtcgcccgac  60
gcccgggctt tgcccgggcg gcctcagtga gcgagcgagc gcgcagagag ggagtggcca  120
actccatcac taggggttcc t                                           141

SEQ ID NO: 6            moltype = DNA  length = 460
FEATURE                 Location/Qualifiers
misc_feature            1..460
                        note = hSynapsin promoter
source                  1..460
                        mol_type = other DNA
                        organism = synthetic construct
SEQUENCE: 6
tcgagctgca gagggccctg cgtatgagtg caagtgggtt ttaggaccag gatgaggcgg  60
ggtgggggtg cctacctgac gaccgacccc gacccactgg acaagcaccc aacccccatt  120
ccccaaattg cgcatcccct atcagagagg gggaggggaa acaggatgcg gcgaggcgcg  180
tgcgcactgc cagcttcagc accgcggaca gtgccttcgc ccccgcctgg cggcgcgcgc  240
caccgccgcc tcagcactga aggcgcgctg acgtcactcg ccggtccccc gcaaactccc  300
cttcccggcc accttggtcg cgtccgcgcc gccgccggcc cagccggacc gcaccacgcg  360
aggcgcgaga tagggggca cgggcgcgac catctgcgct gcggcgccgg cgactcagcg  420
ctgcctcagt ctgcggtggg cagcggagga gtcgtgtcgt                       460

SEQ ID NO: 7            moltype = DNA  length = 133
FEATURE                 Location/Qualifiers
misc_feature            1..133
                        note = Promega Chimeric Intron
source                  1..133
                        mol_type = other DNA
                        organism = synthetic construct
SEQUENCE: 7
gtaagtatca aggttacaag acaggtttaa ggagaccaat agaaactggg cttgtcgaga  60
cagagaagac tcttgcgttt ctgataggca cctattggtc ttactgacat ccactttgcc  120
tttctctcca cag                                                    133

SEQ ID NO: 8            moltype = DNA  length = 583
FEATURE                 Location/Qualifiers
misc_feature            1..583
                        note = woodchuck hepatitis virus post-transcriptional
                         regulatory element (WPRE)
source                  1..583
                        mol_type = other DNA
                        organism = synthetic construct
SEQUENCE: 8
tcaacctctg gattacaaaa tttgtgaaag attgactggt attcttaact atgttgctcc  60
ttttacgcta tgtggatacg ctgctttaat gcctttgtat catgctattg cttcccgtat  120
ggctttcatt ttctcctcct tgtataaatc ctggttgctg tctctttatg aggagttgtg  180
gcccgttgtc aggcaacgtg gcgtggtgtg cactgtgttt gctgacgcaa cccccactgg  240
ttggggcatt gccaccacct gtcagctcct ttccgggact ttcgctttcc ccctccctat  300
tgccacggcg gaactcatcg ccgcctgcct tgcccgctgc tggacagggg ctcggctgtt  360
gggcactgac aattccgtgg tgttgtcggg gaaatcatcg tcctttcctt ggctgctcgc  420
ctgtgttgcc acctggattc tgcgcgggac gtccttctgc tacgtccctt cggccctcaa  480
tccagcggac cttccttccc gcggcctgct gccggctctg cggcctcttc cgcgtcttcg  540
ccttcgccct cagacgagtc ggatctccct ttgggccgcc tcc                   583

SEQ ID NO: 9            moltype = DNA  length = 46
FEATURE                 Location/Qualifiers
misc_feature            1..46
                        note = additonal AAV sequences
source                  1..46
                        mol_type = other DNA
                        organism = synthetic construct
SEQUENCE: 9
catggctacg tagataagta gcatggcggg ttaatcatta actaca                46
```

```
SEQ ID NO: 10           moltype = DNA  length = 130
FEATURE                 Location/Qualifiers
misc_feature            1..130
                        note = 3' ITR
source                  1..130
                        mol_type = other DNA
                        organism = synthetic construct
SEQUENCE: 10
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130

SEQ ID NO: 11           moltype = DNA  length = 2274
FEATURE                 Location/Qualifiers
misc_feature            1..2274
                        note = human Mfn2 engineered nucleic acid seuquence
                         encoding mitofusin 2protein
source                  1..2274
                        mol_type = other DNA
                        organism = synthetic construct
SEQUENCE: 11
atgagcctgc tgttcagccg gtgcaacagc atcgtgaccg tgaagaaaaa caagcggcac  60
atggccgaag tgaacgcctc tccactgaag cacttcgtga ccgccaagaa gaagatcaac  120
ggcatcttcg agcagctggg cgcctacatc caagagagcg ccaccttcct ggaagatacc  180
tacagaaacg ccgagctgga ccccgtgacc acagaggaac aggtgctgga tgtgaagggc  240
tacctgagca aagtgcgggg catctctgaa gtgctggcca gacggcatat gaaggtggcc  300
tttttcggcc ggaccagcaa cggcaagagc accgtgatca atgccatgct gtgggacaaa  360
gtgctgccct ctggaatcgg ccacaccacc aactgctttc tgagagtgga aggcaccgac  420
ggccacgagg catttctgct gacagagggc tccgaggaaa agcggagcgc caagacagtg  480
aaccagctgg cccatgctct gcaccaggat aagcagctgc atgccggaag cctggtgtcc  540
gtgatgtggc ccaatagcaa gtgccctctg ctgaaggacg acctggtgct gatggatagc  600
cccgggatcg atgtgaccac cgaactggac agctggatcg acaagttctg cctggacgcc  660
gacgtgttcg tgctggtggc caatagcgag agcaccctga tgcagaccga gaagcacttt  720
ttccacaagg tgtccgagcg gctgagcaga cccaatatct ttatcctgaa caacagatgg  780
gacgccagcg ccagcgagcc cgagtatatg gaagaagtgc ggcggcagca tatggaacgg  840
tgcacatcct ttctggtgga cgagctgggc gtcgtggata gatctcaggc cggcgacaga  900
atcttctttg tgtccgccaa agaggtgctg aacgcccgga ttcagaaagc ccagggaatg  960
cctgaaggcg gaggtgcact ggccgaggga tttcaagtgc ggatgttcga gttccagaac  1020
ttcgagcgga gattcgagga gtgcatcagc cagagcgccg tcaagaccaa gttcgagcag  1080
cataccgtgc gggccaagca gattgccgaa gccgtcagac tgatcatgga cagcctgcat  1140
atggccgcca gagagcagca ggtctactgc gaggaaatgc gggaagagag acaggaccgg  1200
ctgaagttca tcgacaagca gctggaactg ctggcccagg actacaagct gcggatcaag  1260
cagatcaccg aagaggtgga aagacaggtg tccaccgcta tggccgagga aatcagacgg  1320
ctgagcgtgc tggtcgacga ctaccagatg gactttcacc cctctccagt ggtgctgaaa  1380
gtctacaaaa acgagctgca ccggcacatc gaggaaggcc tgggcagaaa catgagcgac  1440
agatgcagca ccgccatcac caatagcctg cagaccatgc agcaggacat gatcgacggc  1500
ctgaaacctc tgctgcctgt gtccgtcaga tcccagatcg atatgctggt gccccggcag  1560
tgctttagcc tgaactacga cctgaactgc gacaagctgt gcgccgattt ccaagaggac  1620
atcgagtttc acttcagcct cggctggaca atgctggtca acagatttct gggccccaag  1680
aacagcagac gggccctgat gggctacaac gatcaggtgc agaggcccat tcctctgaca  1740
cccgccaatc ctagcatgcc tccactgcct cagggcagcc tgacacaaga ggaattcatg  1800
gtgtctatgg tcaccggcct ggccagcctg accagcagaa catctatggg catcctggtc  1860
gtcggcggcg ttgtgtggaa agctgttggc tggcggctga tcgccctgag ctttggcctg  1920
tatggcctgc tgtacgtgta cgagagactg acctggacca ccaaggccaa agagcgggcc  1980
ttcaagcggc agtttgtgga acacgcctcc gagaaactgc agctggtgat cagctacacc  2040
ggcagcaatt gcagccacca ggtgcagcaa gagctgtccg gaacattcgc ccacctgtgt  2100
cagcaggtcg acgtgaccag agagaacctg gaacaagaga tcgccgccat gaataagaaa  2160
atcgaggtgc tcgactccct gcagagcaag gccaagctgc tgagaaacaa ggccggctgg  2220
ctggacagcg agctgaatat gttcacccac cagtacctgc agcctagccg ctaa        2274

SEQ ID NO: 12           moltype = DNA  length = 2271
FEATURE                 Location/Qualifiers
misc_feature            1..2271
                        note = rMfn2 engineered nucleic acid sequence encoding
                         mitofusin 2protein
source                  1..2271
                        mol_type = other DNA
                        organism = synthetic construct
SEQUENCE: 12
atgtctctgc tgttcagccg gtgcaacagc atcgtgaccg tgaagaaaga caagaggcac  60
atggccgaag tgaacgcctc tccactgaag cacttcgtga ccgccaagaa gaagatcaac  120
ggcatcttcg agcagctggg cgcctacatc caagagtctg ccggcttcct ggaagatacc  180
cacagaaaca ccgagctgga ccccgtgacc acagaggaac aggtgctgga cgtgaagggc  240
tacctgtcta aagtgcgggg catcagcgag gtgctggcta gaaggcatat gaaggtggcc  300
tttttcggca ggaccagcaa cggcaagagc accgtgatca acgccatgct gtgggacaaa  360
gtgctgcctt ctggcatcgg ccacaccacc aactgctttc tgagagtcgg cggcacagac  420
ggccacgagg ctttttgct gaccgagggc tccgaagaga agaaatccgt gaaaaccgtg  480
aaccagctgg cccacgctct gcaccaggat gaacaactgc acgccggaag cctggtgtcc  540
gtgatgtggc ctaacagcaa gtgccctctg ctgaaggacg acctggtgct gatggactct  600
```

-continued

```
cctggaatcg acgtgaccac tgagctggac agctggatcg acaagttctg cctggacgcc  660
gacgtgttcg tgctggtggc taactctgag agcaccctga tgcagaccga gaagcagttc  720
ttccacaagg tgtccgagag gctgagcagg cccaatatct ttatcctgaa caacagatgg  780
gacgccagcg ccagcgagcc cgagtatatg gaagaagtgc ggaggcagca tatggaaagg  840
tgtaccagct tcctggtgga cgagctggga gtcgtggata gagcacaggc cggcgacaga  900
atcttcttcg tgtctgccaa agaggtgctg agcgccaggg tgcagaaagc ccagggaatg  960
cctgaaggcg gcggagcttt ggccgaggga tttcaagtgc ggatgttcga gttccagaac  1020
ttcgagcgga gattcgagga atgcatcagc cagagcgccg tcaagacaaa gttcgagcag  1080
cacacagtgc gggccaagca gatcgctgag gctgtgcggc tgatcatgga cagcctgcat  1140
atcgccgctc aagagcagag ggtgtactgc ctggaaatgc gggaagagag gcaggacagg  1200
ctgagattca tcgacaagca gctggaactg ctggcccagg actacaagct gaggatcaag  1260
cagatgaccg aagaggtgga aagacaggtg tccaccgcca tggccgagga aatccgtaga  1320
ctgtctgtgc tggtcgacga gtaccagatg gactttcacc cctctccagt ggtgctgaag  1380
gtctacaaaa acgagctgca caggcacatc gaggaaggcc tgggcagaaa catgagcgac  1440
aggtgctcta ccgctatcgc cagcagcctg cagacaatgc agcaggacat gatcgacggc  1500
ctgaagcctc tgctgcctgt gtctgtgcgg aaccagatcg atatgctggt gcccaggcag  1560
tgcttctccc tgtcctacga cctgaactgc gacaagctgt gtgccgactt ccaagaggac  1620
atcgagtttc acttcagcct cggctggaca atgctggtca acagattcct gggacctaag  1680
aactccagac gggccctgct gggatacaac gatcaggtgc aaaggcccct gcctctgaca  1740
ccagctaacc cttctatgcc tcctctgcct caaggctctc tgacccaaga ggaactgatg  1800
gtgtccatgg tcacaggcct ggcttccctg accagcagaa cctctatggg catcctggtc  1860
gtcggcggag ttgtgtggaa agctgttggc tggcgcctga tcgccctgag ctttggactg  1920
tacggactgc tgtacgtgta cgagagactg acctggacca ccagggccaa agagagggcc  1980
ttcaagaggc agttcgtgga atacgcctcc gagaaactgc agctgattat ctcctacacc  2040
ggcagcaact gcagccacca ggtgcagcaa gagctgtctg gaacattcgc ccacctgtgc  2100
cagcaggtcg acatcaccag agacaacctg gaacaagaga tcgccgctat gaataagaag  2160
gtggaagccc tggactccct gcagagcaag gctaagctgc tgagaaacaa ggccggctgg  2220
ctggactccg agctgaatat gtttatccac cagtacctgc agcctagccg c           2271

SEQ ID NO: 13          moltype = DNA  length = 23
FEATURE                Location/Qualifiers
misc_feature           1..23
                       note = 5'flank
source                 1..23
                       mol_type = other DNA
                       organism = synthetic construct
SEQUENCE: 13
ctggaggctt gctgaaggct gta                                          23

SEQ ID NO: 14          moltype = DNA  length = 44
FEATURE                Location/Qualifiers
misc_feature           1..44
                       note = 3'flank
source                 1..44
                       mol_type = other DNA
                       organism = synthetic construct
SEQUENCE: 14
caggacacaa ggcctgttac tagcactcac atggaacaaa tggc                   44

SEQ ID NO: 15          moltype = DNA  length = 64
FEATURE                Location/Qualifiers
misc_feature           1..64
                       note = hMfn2 miR1693
source                 1..64
                       mol_type = other DNA
                       organism = synthetic construct
SEQUENCE: 15
tgctgttctt ataaaccttg aggactgttt tggccactga ctgacagtcc tcagtttata  60
agaa                                                               64

SEQ ID NO: 16          moltype = DNA  length = 64
FEATURE                Location/Qualifiers
misc_feature           1..64
                       note = rMfn2 miR1518
source                 1..64
                       mol_type = other DNA
                       organism = synthetic construct
SEQUENCE: 16
tgctgttctt ataaaccttg aggacagttt tggccactga ctgactgtcc tcagtttata  60
agaa                                                               64

SEQ ID NO: 17          moltype = DNA  length = 90
FEATURE                Location/Qualifiers
misc_feature           1..90
                       note = linker
source                 1..90
                       mol_type = other DNA
                       organism = synthetic construct
SEQUENCE: 17
```

```
tgtacaagta aagcgcccgc aggcttgcac ccgtaccttt gggagcgcgc gccctcgtcg  60
tgtcgtgacg tcacccgttc tgttggatcc                                   90

SEQ ID NO: 18          moltype = DNA  length = 2274
FEATURE                Location/Qualifiers
misc_feature           1..2274
                       note = hMfn2 endogenous nucleic acid sequence
source                 1..2274
                       mol_type = other DNA
                       organism = synthetic construct
CDS                    1..2274
                       protein_id = 19
                       translation = MSLLFSRCNSIVTVKKNKRHMAEVNASPLKHFVTAKKKINGIFEQL
                        GAYIQESATFLEDTYRNAELDPVTTEEQVLDVKGYLSKVRGISEVLARRHMKVAFFGRT
                        SNGKSTVINAMLWDKVLPSGIGHTTNCFLRVEGTDGHEAFLLTEGSEEKRSAKTVNQLA
                        HALHQDKQLHAGSLVSVMWPNSKCPLLKDDLVLMDSPGIDVTTELDSWIDKFCLDADVF
                        VLVANSESTLMQTEKHFFHKVSERLSRPNIFILNNRWDASASEPEYMEEVRRQHMERCT
                        SFLVDELGVVDRSQAGDRIFFVSAKEVLNARIQKAQGMPEGGGALAEGFQVRMFEFQNF
                        ERRFEECISQSAVKTKFEQHTVRAKQIAEAVRLIMDSLHMAAREQQVYCEEMREERQDR
                        LKFIDKQLELLAQDYKLRIKQITEEVERQVSTAMAEEIRRLSVLVDDYQMDFHPSPVVL
                        KVYKNELHRHIEEGLGRNMSDRCSTAITNSLQTMQQDMIDGLKPLLPVSVRSQIDMLVP
                        RQCFSLNYDLNCDKLCADFQEDIEFHFSLGWTMLVNRFLGPKNSRRALMGYNDQVQRPI
                        PLTPANPSMPPLPQGSLTQEEFMVSMVTGLASLTSRTSMGILVVGGVVWKAVGWRLIAL
                        SFGLYGLLYVYERLTWTTKAKERAFKRQFVEHASEKLQLVISYTGSNCSHQVQQELSGT
                        FAHLCQQVDVTRENLEQEIAAMNKKIEVLDSLQSKAKLLRNKAGWLDSELNMFTHQYLQ
                        PSR
SEQUENCE: 18
atgtccctgc tcttctctcg atgcaactct atcgtcacag tcaagaaaaa taagagacac  60
atggctgagg tgaatgcatc cccacttaag cactttgtca ctgccaagaa gaagatcaat  120
ggcatttttg agcagctggg ggcctacatc caggagagcg ccaccttcct tgaagacacg  180
tacaggaatg cagaactgga ccccgttacc acagaagaac aggttctgga cgtcaaaggt  240
tacctatcca aagtgagagg catcagtgag gtgctggctc ggaggcacat gaaagtggct  300
ttttttggcc ggacgagcaa tgggaagagc accgtgatca atgccatgct ctgggacaaa  360
gttctgccct ctgggattgg ccacaccacc aattgcttcc tgcgggtaga gggcacagat  420
ggccatgagg cctttctcct taccgagggc tcagaggaaa agaggagtgc caagactgtg  480
aaccagctgg cccatgccct ccaccaggac aagcagctcc atgccggcag cctagtgagt  540
gtgatgtggc ccaactctaa gtgcccactt ctgaaggatg acctcgtttt gatggacagc  600
cctggtattg atgtcaccac agagctggac agctggattg acaagttttg tctggatgct  660
gatgtgtttg tgctggtggc caactcagag tccaccctga tgcagacgga aaagcacttc  720
ttccacaagg tgagtgagcg tctctcccgg ccaaacatct tcatcctgaa caaccgctgg  780
gatgcatctg cctcagagcc cgagtacatg gaggaggtgc ggcggcagca catggagcgt  840
tgtaccagct tcctggtgga tgagctgggc gtggtggatc gatcccaggc cggggaccgc  900
atcttctttg tgtctgctaa ggaggtgctc aacgccagga ttcagaaagc ccagggcatg  960
cctgaaggag gggcgctctc cgcagaaggc tttcaagtga ggatgtttga gtttcagaat  1020
tttgagagga gatttgagga gtgcatctcc cagtctgcag tgaagaccaa gtttgagcag  1080
cacacggtcc gggccaagca gattgcagag gcggttcgac tcatcatgga ctccctgcac  1140
atggcggctc gggagcagca ggtttactgc gaggaaatgc gtgaagagcg gcaagaccga  1200
ctgaaattta ttgacaaaca gctggagctc ttggctcaag actataagct gcgaattaag  1260
cagattacgg aggaagtgga gaggcaggtg tcgactgcaa tggccgagga gatcaggcgc  1320
ctctctgtac tggtggacga ttaccagatg gacttccacc cttctccagt agtcctcaag  1380
gtttataaga atgagctgca ccgccacata gaggaaggac tgggtcgaaa catgtctgac  1440
cgctgctcca cggccatcac caactccctg cagaccatgc agcaggacat gatagatggc  1500
ttgaaacccc tccttcctgt gtctgtgcgg agtcagatag acatgctggt cccacgccag  1560
tgcttctccc tcaactatga cctaaactgt gacaagctgt gtgctgactt ccaggaagac  1620
attgagttcc atttctctct cggatggacc atgctggtga ataggttcct gggccccaag  1680
aacagccgtc gggccttgat gggctacaat gaccaggtcc agcgtcccat ccctctgacg  1740
ccagccaacc ccagcatgcc ccccactgcca cagggctcgc tcacccagga ggagttcatg  1800
gtttccatgg ttaccggcct ggcctccttg acatccagga cctccatggg cattcttgtt  1860
gttggaggag tggtgtggaa ggcagtgggc tggcggctca ttgccctctc ctttgggctc  1920
tatggcctcc tctacgtcta tgagcgtctg acctggacca ccaaggccaa ggagagggcc  1980
ttcaagcgcc agtttgtgga gcatgccagc gagaagctgc agcttgtcat cagctacact  2040
ggctccaact gcagccacca agtccagcag gaactgtctg ggacctttgc tcatctgtgt  2100
cagcaagttg acgtcacccg ggagaacctg gagcaggaaa ttgccgccat gaacaagaaa  2160
attgaggttc ttgactcact tcagagcaaa gcaaagctgc tcaggaataa agccggttgg  2220
ttggacagtg agctcaacat gttcacacac cagtacctgc agcccagcag atag        2274

SEQ ID NO: 19          moltype = AA  length = 757
FEATURE                Location/Qualifiers
REGION                 1..757
                       note = Synthetic Construct
source                 1..757
                       mol_type = protein
                       note = translation of SEQ ID NO: 18
                       organism = synthetic construct
SEQUENCE: 19
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
```

-continued

```
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                           757

SEQ ID NO: 20          moltype = DNA  length = 2274
FEATURE                Location/Qualifiers
misc_feature           1..2274
                       note = rMfn2 endogenous nucleic acid sequence
source                 1..2274
                       mol_type = other DNA
                       organism = synthetic construct
CDS                    1..2274
                       protein_id = 21
                       translation = MSLLFSRCNSIVTVKKDKRHMAEVNASPLKHFVTAKKKINGIFEQL
                        GAYIQESAGFLEDTHRNTELDPVTTEEQVLDVKGYLSKVRGISEVLARRHMKVAFFGRT
                        SNGKSTVINAMLWDKVLPSGIGHTTNCFLRVGGTDGHEAFLLTEGSEEKKSVKTVNQLA
                        HALHQDEQLHAGSLVSVMWPNSKCPLLKDDLVLMDSPGIDVTTELDSWIDKFCLDADVF
                        VLVANSESTLMQTEKQFFHKVSERLSRPNIFILNNRWDASASEPEYMEEVRRQHMERCT
                        SFLVDELGVVDRAQAGDRIFFVSAKEVLSARVQKAQGMPEGGGALAEGFQVRMFEFQNF
                        ERRFEECISQSAVKTKFEQHTVRAKQIAEAVRLIMDSLHIAAQEQRVYCLEMREERQDR
                        LRFIDKQLELLAQDYKLRIKQMTEEVERQVSTAMAEEIRRLSVLVDEYQMDFHPSPVVL
                        KVYKNELHRHIEEGLGRNMSDRCSTAIASSLQTMQQDMIDGLKPLLPVSVRNQIDMLVP
                        RQCFSLSYDLNCDKLCADFQEDIEFHFSLGWTMLVNRFLGPKNSRRALLGYNDQVQRPL
                        PLTPANPSMPPLPQGSLTQEELMVSMVTGLASLTSRTSMGILVVGGVVWKAVGWRLIAL
                        SFGLYGLLYVYERLTWTTRAKERAFKRQFVEYASEKLQLIISYTGSNCSHQVQQELSGT
                        FAHLCQQVDITRDNLEQEIAAMNKKVEALDSLQSKAKLLRNKAGWLDSELNMFIHQYLQ
                        PSR
SEQUENCE: 20
atgtccctgc tcttttctcg atgcaactcc atcgtcaccg tcaagaagga taagcgacac  60
atggctgagg tgaatgcttc ccctctcaag cactttgtca ctgccaagaa aaagatcaat  120
ggcatctttg agcagctggg ggcctacatc caagagagtg ccggcttcct tgaagacacc  180
cacaggaata cagaactgga cccagttact acagaagagc aggtcctgga tgtcaaaggg  240
tacctgtcca aggtcagggg aatcagcgag gtgctggcca ggcggcacat gaaggtggct  300
ttttttggcc ggacgagcaa tgggaagagc accgtgatca atgccatgct ttgggacaaa  360
gttctgccat ctgggattgg ccacaccacc aattgcttcc tgcgggttgg gggcacggat  420
ggccacgagg ccttcctcct cacggagggc tcagaagaga agaagagtgt caagaccgtg  480
aaccagctag cccatgccct ccatcaggat gagcagctgc atgcaggcag cctggtgagt  540
gtgatgtggc ccaactccaa gtgtccactt ctgaaggatg acctcgtgct gatggacagc  600
cctgggatcg atgtcaccac ggagctggac agctggattg ataagttttg cctggatgct  660
gatgtgtttg tactggtggc caactcagag tccacgctga tgcagacgga gaagcagttc  720
ttccacaaag tgagtgagcg tctctcccgg cccaacatct tcatcctgaa caaccgctgg  780
gatgcgtctg cctcggagcc tgagtacatg gaggaggtgc ggcggcagca catggaacgc  840
tgcaccagct ttctggtgga tgagctaggc gtggtggatc gagctcaggc cggggaccgg  900
atcttctttg tgtctgccaa ggaggtgctc agtgccaggg tccagaaagc ccagggcatg  960
ccagaaggag gtggcgctct tgcagaaggt tttcaagtga ggatgtttga gtttcagaat  1020
ttcgagaggc gatttgagga gtgcatttcc cagtctgcag taaagaccaa atttgagcag  1080
cacacagtcc gggccaagca gattgcagag gccgtccgtc tcatcatgga ttccctgcac  1140
attgcggctc aggagcagcg ggtttattgt cttgaaatgc gggaagagcg gcaagaccgg  1200
ctgagattca ttgacaagca gctggagctc ctggctcaag actataagct acggattaag  1260
cagatgacag aggaagtgga aaggcaggtg tccacagcca tggctgaaga gatcaggcgc  1320
ctctctgtgc tggttgacga gtaccagatg gactttcacc catccccagt tgtcctcaag  1380
gtttataaga atgaactgca ccgccatata gaggaaggcc tgggacgaaa catgtctgac  1440
cgctgctcca cagccattgc cagttcactg cagactatgc agcaagacat gatagacggc  1500
ttgaagcccc ttcttcctgt gtctgtgcgg aatcagatag acatgctggt ccctcgacag  1560
tgtttctccc tcagctatga cctgaactgt gacaagctgt gcgctgactt tcaggaggac  1620
atcgaattcc atttctccct tggatggact atgctagtga ataggttcct gggccctaag  1680
aatagccggc gggccttgct gggctacaat gatcaggttc agcgtcctct ccctctgaca  1740
cctgccaacc ccagcatgcc acccttgcca cagggctccc tcacccagga ggagctcatg  1800
gtctccatgg ttactggcct ggcctctctg acttccagga cctctatggg cattctcgtg  1860
gtcggaggag tggtgtggaa ggcagtgggc tggagactca tcgccctctc ctttggactg  1920
tatggcctcc tgtacgtgta tgagcggctg acctggacca ccagagccaa ggagagggcc  1980
ttcaagcgcc agtttgtgga gtatgccagt gagaagctgc agctcattat cagttatacc  2040
ggctctaact gcagccacca agttcagcaa gaattgtctg ggacatttgc tcatctgtgc  2100
cagcaagttg acatcacccg ggataatctg gagcaggaaa ttgctgccat gaacaagaaa  2160
gttgaggctc tggattcact tcagagcaaa gccaaattgc tcaggaataa agctggctgg  2220
ttggacagcg aactcaacat gttcatacac cagtacctgc agcccagcag atag        2274

SEQ ID NO: 21          moltype = AA  length = 757
FEATURE                Location/Qualifiers
REGION                 1..757
                       note = Synthetic Construct
source                 1..757
                       mol_type = protein
```

```
                       note = translation of SEQ ID NO: 20
                       organism = synthetic construct
SEQUENCE: 21
MSLLFSRCNS IVTVKKDKRH MAEVNASPLK HFVTAKKKIN GIFEQLGAYI QESAGFLEDT  60
HRNTELDPVT TEEQVLDVKG YLSKVRGISE VLARRHMKVA FFGRTSNGKS TVINAMLWDK  120
VLPSGIGHTT NCFLRVGGTD GHEAFLLTEG SEEKKSVKTV NQLAHALHQD EQLHAGSLVS  180
VMWPNSKCPL LKDDLVLMDS PGIDVTTELD SWIDKFCLDA DVFVLVANSE STLMQTEKQF  240
FHKVSERLSR PNIFILNNRW DASASEPEYM EEVRRQHMER CTSFLVDELG VVDRAQAGDR  300
IFFVSAKEVL SARVQKAQGM PEGGGALAEG FQVRMFEFQN FERRFEECIS QSAVKTKFEQ  360
HTVRAKQIAE AVRLIMDSLH IAAQEQRVYC LEMREERQDR LRFIDKQLEL LAQDYKLRIK  420
QMTEEVERQV STAMAEEIRR LSVLVDEYQM DFHPSPVVLK VYKNELHRHI EEGLGRNMSD  480
RCSTAIASSL QTMQQDMIDG LKPLLPVSVR NQIDMLVPRQ CFSLSYDLNC DKLCADFQED  540
IEFHFSLGWT MLVNRFLGPK NSRRALLGYN DQVQRPLPLT PANPSMPPLP QGSLTQEELM  600
VSMVTGLASL TSRTSMGILV VGGVVWKAVG WRLIALSFGL YGLLYVYERL TWTTRAKERA  660
FKRQFVEYAS EKLQLIISYT GSNCSHQVQQ ELSGTFAHLC QQVDITRDNL EQEIAAMNKK  720
VEALDSLQSK AKLLRNKAGW LDSELNMFIH QYLQPSR                          757

SEQ ID NO: 22          moltype = DNA  length = 215
FEATURE                Location/Qualifiers
misc_feature           1..215
                       note = bGH polyA
source                 1..215
                       mol_type = other DNA
                       organism = synthetic construct
SEQUENCE: 22
gcctcgactg tgccttctag ttgccagcca tctgttgttt gcccctcccc cgtgccttcc  60
ttgaccctgg aaggtgccac tcccactgtc ctttcctaat aaaatgagga aattgcatcg  120
cattgtctga gtaggtgtca ttctattctg gggggtgggg tggggcagga cagcaagggg  180
gaggattggg aagacaatag caggcatgct gggga                            215

SEQ ID NO: 23          moltype = DNA  length = 232
FEATURE                Location/Qualifiers
misc_feature           1..232
                       note = SV40 polyA
source                 1..232
                       mol_type = other DNA
                       organism = synthetic construct
SEQUENCE: 23
cgagcagaca tgataagata cattgatgag tttggacaaa ccacaactag aatgcagtga  60
aaaaaatgct ttatttgtga aatttgtgat gctattgctt tatttgtaac cattataagc  120
tgcaataaac aagttaacaa caacaattgc attcatttta tgtttcaggt tcagggggag  180
atgtgggagg ttttttaaag caagtaaaac ctctacaaat gtggtaaaat cg          232

SEQ ID NO: 24          moltype = DNA  length = 2315
FEATURE                Location/Qualifiers
misc_feature           1..2315
                       note = hMfn2 engineered nucleic acid sequnece V1
source                 1..2315
                       mol_type = other DNA
                       organism = synthetic construct
CDS                    1..2274
                       protein_id = 25
                       translation = ASTGATMSLLFSRCNSIVTVKKNKRHMAEVNASPLKHFVTAKKKIN
                        GIFEQLGAYIQESATFLEDTYRNAELDPVTTEEQVLDVKGYLSKVRGISEVLARRHMKV
                        AFFGRTSNGKSTVINAMLWDKVLPSGIGHTTNCFLRVEGTDGHEAFLLTEGSEEKRSAK
                        TVNQLAHALHQDKQLHAGSLVSVMWPNSKCPLLKDDLVLMDSPGIDVTTELDSWIDKFC
                        LDADVFVLVANSESTLMQTEKHFFHKVSERLSRPNNFILNNRWDASASEPEYMEEVRRQ
                        HMERCTSFLVDELGVVDRSQAGDRIFFVSAKEVLNARIQKAQGMPEGGGALAEGFQVRM
                        FEFQNFERRFEECISQSAVKTKFEQHTVRAKQIAEAVRLIMDSLHMAAREQQVYCEEMR
                        EERQDRLKFIDKQLELLAQDYKLRIKQITEEVERQVSTAMAEEIRRLSVLVDDYQMDFH
                        PSPVVLKVYKNELHRHIEEGLGRNMSDRCSTAITNSLQTMQQDMIDGLKPLLPVSVRSQ
                        IDMLVPRQCFSLNYDLNCDKLCADFQEDIEFHFSLGWTMLVNRFLGPKNSRRALMGYND
                        QVQRPIPLTPANPSMPPLPQGSLTQEEFMVSMVTGLASLTSRTSMGILVVGGVVWKAVG
                        WRLIALSFGLYGLLYVYERLTWTTKAKERAFKRQFVEHASEKLQLVISYTGSNCSHQVQ
                        QELSGTFAHLCQQVDVTRENLEQEIAAMNKKIEVLDSLQSKAKLLRNKAGWLDSELNMF
                        THQY
SEQUENCE: 24
gctagcaccg gtgccaccat gagcctgctg ttcagccggt gcaacagcat cgtgaccgtg  60
aagaaaaaca agcggcacat ggccgaagtg aacgcctctc cactgaagca cttcgtgacc  120
gccaagaaga agatcaacgg catcttcgag cagctgggcg cctacatcca agagagcgcc  180
accttcctgg aagataccta cagaaacgcc gagctggacc ccgtgaccac agaggaacag  240
gtgctggatg tgaagggcta cctgagcaaa gtgcggggca tctctgaagt gctggccaga  300
cggcatatga aggtggcctt tttcggccgg accagcaacg gcaagagcac cgtgatcaat  360
gccatgctgt gggacaaagt gctgccctct ggaatcggcc acaccaccaa ctgctttctg  420
agagtggaag gcaccgacgg ccacgaggca tttctgctga cagagggctc cgaggaaaag  480
cggagcgcca agacagtgaa ccagctggcc catgctctgc accaggataa gcagctgcat  540
gccggaagcc tggtgtccgt gatgtggccc aatagcaagt gccctctgct gaaggacgac  600
ctggtgctga tggatagccc cgggatcgat gtgaccaccg aactggacag ctggatcgac  660
aagttctgcc tggacgccga cgtgttcgtg ctggtggcca atagcgagag caccctgatg  720
```

```
cagaccgaga agcacttttt ccacaaggtg tccgagcggc tgagcagacc caacaatttt  780
atcctgaaca acagatggga cgccagcgcc agcgagcccg agtatatgga agaagtgcgg  840
cggcagcata tggaacggtg cacatccttt ctggtggacg agctgggcgt cgtggataga  900
tctcaggccg gcgacagaat cttctttgtg tccgccaaag aggtgctgaa cgcccggatt  960
cagaaagccc agggaatgcc tgaaggcgga ggtgcactgg ccgagggatt tcaagtgcgg  1020
atgttcgagt tccagaactt cgagcggaga ttcgaggaat gcatcagcca gagcgccgtc  1080
aagaccaagt ttgagcagca taccgtgcgg gccaagcaga ttgccgaagc cgtcagactg  1140
atcatggaca gcctgcatat ggccgccaga gagcagcagg tctactgcga ggaaatgcgg  1200
gaagagagac aggaccggct gaagttcatc gacaagcagc tggaactgct ggcccaggac  1260
tacaagctgc ggatcaagca gatcaccgaa gaggtggaaa gacaggtgtc caccgctatg  1320
gccgaggaaa tcagacggct gagcgtgctg gtcgacgact accagatgga ctttcacccc  1380
tctccagtgg tgctgaaggt ctacaagaac gagctgcacc ggcacatcga ggaaggcctg  1440
ggcagaaaca tgagcgacag atgcagcacc gccatcacca atagcctgca gaccatgcag  1500
caggacatga tcgacggcct gaaacctctg ctgcctgtgt ccgtcagatc ccagatcgat  1560
atgctggtgc cccggcagtg ctttagcctg aactacgacc tgaactgcga caagctgtgc  1620
gccgatttcc aagaggacat cgagtttcac ttcagcctcg gctggacaat gctggtcaac  1680
agatttctgg gccccaagaa cagcagacgg gccctgatgg gctacaacga tcaggtgcag  1740
aggcccattc ctctgacacc cgccaatcct agcatgcctc cactgcctca gggcagcctg  1800
acacaagagg aattcatggt gtctatggtc accggcctgg ccagcctgac cagcagaaca  1860
tctatgggca tcctggtcgt cggcggcgtt gtgtggaaag ctgttggctg gcggctgatc  1920
gccctgagct ttggcctgta tggcctgctg tacgtgtacg agagactgac ctggaccacc  1980
aaggccaaag agcgggcctt caagcggcag tttgtggaac acgcctccga gaaactgcag  2040
ctggtgatca gctacaccgg cagcaattgc agccaccagg tgcagcaaga gctgtccgga  2100
acattcgccc acctgtgtca gcaggtcgac gtgaccagag agaacctgga acaagagatc  2160
gccgccatga acaagaaaat cgaggtgctc gactccctgc agagcaaggc caagctgctg  2220
agaaacaagg ccggctggct ggacagcgag ctgaatatgt tcacccacca gtacctgcag  2280
cctagccgct aataatgtac agcggccgca agctt                             2315
```

```
SEQ ID NO: 25          moltype = AA  length = 758
FEATURE                Location/Qualifiers
REGION                 1..758
                       note = Synthetic Construct
source                 1..758
                       mol_type = protein
                       note = translation of SEQ ID NO: 24
                       organism = synthetic construct
SEQUENCE: 25
ASTGATMSLL FSRCNSIVTV KKNKRHMAEV NASPLKHFVT AKKKINGIFE QLGAYIQESA  60
TFLEDTYRNA ELDPVTTEEQ VLDVKGYLSK VRGISEVLAR RHMKVAFFGR TSNGKSTVIN  120
AMLWDKVLPS GIGHTTNCFL RVEGTDGHEA FLLTEGSEEK RSAKTVNQLA HALHQDKQLH  180
AGSLVSVMWP NSKCPLLKDD LVLMDSPGID VTTELDSWID KFCLDADVFV LVANSESTLM  240
QTEKHFFHKV SERLSRPNNF ILNNRWDASA SEPEYMEEVR RQHMERCTSF LVDELGVVDR  300
SQAGDRIFFV SAKEVLNARI QKAQGMPEGG GALAEGFQVR MFEFQNFERR FEECISQSAV  360
KTKFEQHTVR AKQIAEAVRL IMDSLHMAAR EQQVYCEEMR EERQDRLKFI DKQLELLAQD  420
YKLRIKQITE EVERQVSTAM AEEIRRLSVL VDDYQMDFHP SPVVLKVYKN ELHRHIEEGL  480
GRNMSDRCST AITNSLQTMQ QDMIDGLKPL LPVSVRSQID MLVPRQCFSL NYDLNCDKLC  540
ADFQEDIEFH FSLGWTMLVN RFLGPKNSRR ALMGYNDQVQ RPIPLTPANP SMPPLPQGSL  600
TQEEFMVSMV TGLASLTSRT SMGILVVGGV VWKAVGWRLI ALSFGLYGLL YVYERLTWTT  660
KAKERAFKRQ FVEHASEKLQ LVISYTGSNC SHQVQQELSG TFAHLCQQVD VTRENLEQEI  720
AAMNKKIEVL DSLQSKAKLL RNKAGWLDSE LNMFTHQY                          758

SEQ ID NO: 26          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 26
aaaccttgag gactactgga g                                            21

SEQ ID NO: 27          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 27
ttgacgtcca gaacctgttc t                                            21

SEQ ID NO: 28          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 28
```

```
agaagtgggc acttagagtt g                                              21

SEQ ID NO: 29          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 29
ttcagaagtg ggcacttaga g                                              21

SEQ ID NO: 30          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 30
ttgtcaatcc agctgtccag c                                              21

SEQ ID NO: 31          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 31
caaacttggt cttcactgca g                                              21

SEQ ID NO: 32          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 32
aaaccttgag gactactgga g                                              21

SEQ ID NO: 33          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 33
taaccatgga aaccatgaac t                                              21

SEQ ID NO: 34          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 34
acaacaagaa tgcccatgga g                                              21

SEQ ID NO: 35          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 35
aaaggtccca gacagttcct g                                              21

SEQ ID NO: 36          moltype = DNA  length = 21
FEATURE                Location/Qualifiers
misc_feature           1..21
                       note = antisense sequence
source                 1..21
                       mol_type = other DNA
                       organism = synthetic construct
```

```
SEQUENCE: 36
tgttcatggc ggcaatttcc t                                             21

SEQ ID NO: 37          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 37
tgaggttggc tattgattga c                                             21

SEQ ID NO: 38          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 38
ttctcacaca gtcaacacct t                                             21

SEQ ID NO: 39          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 39
tttcctcgca gtaaacctgc t                                             21

SEQ ID NO: 40          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 40
agaaatggaa ctcaatgtct t                                             21

SEQ ID NO: 41          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 41
tgaacaggac atcacctgtg a                                             21

SEQ ID NO: 42          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 42
aatacaagca ggtatgtgaa c                                             21

SEQ ID NO: 43          moltype = DNA  length = 21
FEATURE                Location/Qualifiers
misc_feature           1..21
                       note = antisense sequence
source                 1..21
                       mol_type = other DNA
                       organism = synthetic construct
SEQUENCE: 43
taaacctgct gctcccgagc c                                             21

SEQ ID NO: 44          moltype = DNA  length = 21
FEATURE                Location/Qualifiers
misc_feature           1..21
                       note = antisense sequence
source                 1..21
                       mol_type = other DNA
```

```
                        organism = synthetic construct
SEQUENCE: 44
tagaggaggc catagagccc a                                              21

SEQ ID NO: 45           moltype = DNA  length = 21
FEATURE                 Location/Qualifiers
misc_feature            1..21
                        note = antisense sequence
source                  1..21
                        mol_type = other DNA
                        organism = synthetic construct
SEQUENCE: 45
tctacccgca ggaagcaatt g                                              21

SEQ ID NO: 46           moltype = DNA  length = 21
FEATURE                 Location/Qualifiers
misc_feature            1..21
                        note = antisense sequence
source                  1..21
                        mol_type = other DNA
                        organism = synthetic construct
SEQUENCE: 46
ctccttagca gacacaaaga a                                              21

SEQ ID NO: 47           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 47
agaacaggtt ctggacgtca a                                              21

SEQ ID NO: 48           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 48
caactctaag tgcccacttc t                                              21

SEQ ID NO: 49           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 49
ctctaagtgc ccacttctga a                                              21

SEQ ID NO: 50           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 50
gctggacagc tggattgaca a                                              21

SEQ ID NO: 51           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 51
ctgcagtgaa gaccaagttt g                                              21

SEQ ID NO: 52           moltype = DNA  length = 21
FEATURE                 Location/Qualifiers
misc_feature            1..21
                        note = Target hMfn2 Sequence
source                  1..21
```

```
                         mol_type = other DNA
                         organism = synthetic construct
SEQUENCE: 52
ctccagtagt cctcaaggtt t                                             21

SEQ ID NO: 53            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 53
agttcatggt ttccatggtt a                                             21

SEQ ID NO: 54            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 54
ctccatgggc attcttgttg t                                             21

SEQ ID NO: 55            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 55
caggaactgt ctgggacctt t                                             21

SEQ ID NO: 56            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 56
aggaaattgc cgccatgaac a                                             21

SEQ ID NO: 57            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 57
agtcctcaag gtttataaga a                                             21

SEQ ID NO: 58            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 58
gtcaatcaat agccaacctc a                                             21

SEQ ID NO: 59            moltype = DNA  length = 21
FEATURE                  Location/Qualifiers
misc_feature             1..21
                         note = Target hMfn2 Sequence
source                   1..21
                         mol_type = other DNA
                         organism = synthetic construct
SEQUENCE: 59
aaggtgttga ctgtgtgaga a                                             21

SEQ ID NO: 60            moltype = DNA  length = 21
FEATURE                  Location/Qualifiers
misc_feature             1..21
                         note = Target hMfn2 Sequence
```

```
source                  1..21
                        mol_type = other DNA
                        organism = synthetic construct
SEQUENCE: 60
agcaggttta ctgcgaggaa a                                              21

SEQ ID NO: 61           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 61
aagacattga gttccatttc t                                              21

SEQ ID NO: 62           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 62
tcacaggtga tgtcctgttc a                                              21

SEQ ID NO: 63           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 63
gttcacatac ctgcttgtat t                                              21

SEQ ID NO: 64           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 64
ggctcgggag cagcaggttt a                                              21

SEQ ID NO: 65           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 65
tgggctctat ggcctcctct a                                              21

SEQ ID NO: 66           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 66
caattgcttc ctgcgggtag a                                              21

SEQ ID NO: 67           moltype = DNA  length = 21
FEATURE                 Location/Qualifiers
misc_feature            1..21
                        note = Target hMfn2 Sequence
source                  1..21
                        mol_type = other DNA
                        organism = synthetic construct
SEQUENCE: 67
ttctttgtgt ctgctaagga g                                              21

SEQ ID NO: 68           moltype = DNA  length = 21
FEATURE                 Location/Qualifiers
misc_feature            1..21
```

```
                        note = miR1693(21-mer)
source                  1..21
                        mol_type = other DNA
                        organism = synthetic construct
SEQUENCE: 68
ttcttataaa ccttgaggac t                                              21

SEQ ID NO: 69           moltype = DNA  length = 4771
FEATURE                 Location/Qualifiers
misc_feature            1..4771
                        note = Vector genome CAG.CI.hMfn2.GA.link.miR538.WPRE.SV40
repeat_region           1..188
                        note = 5'ITR
misc_feature            192..1032
                        note = CAG(CBA)
regulatory              194..436
                        note = enhancer - CMV enhancer
                        regulatory_class = enhancer
regulatory              439..720
                        note = promoter - CB promoter
                        regulatory_class = promoter
misc_feature            720..1127
                        note = Intron - Hybrid Intron in CAG
misc_feature            720..950
                        note = Intron - b-actin intron
misc_feature            1158..1163
                        note = Kozak
misc_feature            1379..1399
                        note = miR538 mut
misc_feature            2534..2554
                        note = miR1518 mutated
misc_feature            3438..3519
                        note = linker p4271
misc_feature            3520..3547
                        note = miR538 AS
misc_feature            3569..3587
                        note = loop
misc_feature            3588..3606
                        note = miR538 sense
misc_feature            3607..3651
                        note = 3' flank
misc_feature            3678..4266
                        note = WRPE
misc_feature            4355..4474
                        note = SV40 PA temrinator
repeat_region           4584..4771
                        note = 3'ITR
source                  1..4771
                        mol_type = other DNA
                        organism = synthetic construct
CDS                     1164..3437
                        note = human Mfn2 engineered
                        protein_id = 70
                        translation = MSLLFSRCNSIVTVKKNKRHMAEVNASPLKHFVTAKKKINGIFEQL
                         GAYIQESATFLEDTYRNAELDPVTTEEQVLDVKGYLSKVRGISEVLARRHMKVAFFGRT
                         SNGKSTVINAMLWDKVLPSGIGHTTNCFLRVEGTDGHEAFLLTEGSEEKRSAKTVNQLA
                         HALHQDKQLHAGSLVSVMWPNSKCPLLKDDLVLMDSPGIDVTTELDSWIDKFCLDADVF
                         VLVANSESTLMQTEKHFFHKVSERLSRPNIFILNNRWDASASEPEYMEEVRRQHMERCT
                         SFLVDELGVVDRSQAGDRIFFVSAKEVLNARIQKAQGMPEGGGALAEGFQVRMFEFQNF
                         ERRFEECISQSAVKTKFEQHTVRAKQIAEAVRLIMDSLHMAAREQQVYCEEMREERQDR
                         LKFIDKQLELLAQDYKLRIKQITEEVERQVSTAMAEEIRRLSVLVDDYQMDFHPSPVVL
                         KVYKNELHRHIEEGLGRNMSDRCSTAITNSLQTMQQDMIDGLKPLLPVSVRSQIDMLVP
                         RQCFSLNYDLNCDKLCADFQEDIEFHFSLGWTMLVNRFLGPKNSRRALMGYNDQVQRPI
                         PLTPANPSMPPLPQGSLTQEEFMVSMVTGLASLTSRTSMGILVVGGVVWKAVGWRLIAL
                         SFGLYGLLYVYERLTWTTKAKERAFKRQFVEHASEKLQLVISYTGSNCSHQVQQELSGT
                         FAHLCQQVDVTRENLEQEIAAMNKKIEVLDSLQSKAKLLRNKAGWLDSELNMFTHQYLQ
                         PSR
SEQUENCE: 69
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacgt agccatgctc  180
taggaagagt accattgacg tcaataatga cgtatgttcc catagtaacg ccaataggga  240
ctttccattg acgtcaatgg gtggagtatt tacggtaaac tgcccacttg gcagtacatc  300
aagtgtatca tatgccaagt acgcccccta ttgacgtcaa tgacggtaaa tggcccgcct  360
ggcattatgc ccagtacatg accttatggg actttcctac ttggcagtac atctacgtat  420
tagtcatcgc tattaccatg gtcgaggtga gccccacgtt ctgcttcact ctccccatct  480
cccccccctc ccacccccca attttgtatt tatttatttt ttaattattt tgtgcagcga  540
tgggggcggg gggggggggg gggcgcgcgc caggcggggc ggggcggggc gaggggcggg  600
gcggggcgag gcggagaggt gcggcggcag ccaatcagag cggcgcgctc cgaaagtttc  660
```

```
cttttatggc gaggcggcgg cggcggcggc cctataaaaa gcgaagcgcg cggcgggcgg  720
gagtcgctgc gcgctgcctt cgccccgtgc cccgctccgc cgccgcctcg cgccgcccgc  780
cccggctctg actgaccgcg ttactcccac aggtgagcgg gcgggacggc ccttctcctc  840
cgggctgtaa ttagcgcttg gtttaatgac ggcttgtttc ttttctgtgg ctgcgtgaaa  900
gccttgaggg gctccgggag ggccctttgt gcggggggag cggctcgggg ctgtccgcgg  960
ggggacggct gccttcgggg gggacggggc agggcggggt tcggcttctg gcgtgtgacc  1020
ggcggctcta gagcctctgc taaccatgtt catgccttct tctttttcct acagctcctg  1080
ggcaacgtgc tggttattgt gctgtctcat cattttggca aagaattgga tcccgtacga  1140
cgcgtgctag caccggtgcc accatgagcc tgctgttcag ccggtgcaac agcatcgtga  1200
ccgtgaagaa aaacaagcgg cacatggccg aagtgaacgc ctctccactg aagcacttcg  1260
tgaccgccaa gaagaagatc aacggcatct tcgagcagct gggcgcctac atccaagaga  1320
gcgccacctt cctggaagat acctacagaa acgccgagct ggaccccgtg accacagagg  1380
aacaggtgct ggatgtgaag ggctacctga gcaaagtgcg gggcatctct gaagtgctgg  1440
ccagacggca tatgaaggtg gcctttttcg gccggaccag caacggcaag agcaccgtga  1500
tcaatgccat gctgtgggac aaagtgctgc cctctggaat cggccacacc accaactgct  1560
ttctgagagt ggaaggcacc gacggccacg aggcatttct gctgacagag ggctccgagg  1620
aaaagcggag cgccaagaca gtgaaccagc tggcccatgc tctgcaccag gataagcagc  1680
tgcatgccgg aagcctggtg tccgtgatgt ggcccaatag caagtgccct ctgctgaagg  1740
acgacctggt gctgatggat agccccggga tcgatgtgac caccgaactg gacagctgga  1800
tcgacaagtt ctgcctggac gccgacgtgt tcgtgctggt ggccaatagc gagagcaccc  1860
tgatgcagac cgagaagcac tttttccaca aggtgtccga gcggctgagc agacccaata  1920
tctttatcct gaacaacaga tgggacgcca gcgccagcga gcccgagtat atggaagaag  1980
tgcggcggca gcatatggaa cggtgcacat cctttctggt ggacgagctg ggcgtcgtgg  2040
atagatctca ggccggcgac agaatcttct ttgtgtccgc caaagaggtg ctgaacgccc  2100
ggattcagaa agcccaggga atgcctgaag gcggaggtgc actggccgag ggatttcaag  2160
tgcggatgtt cgagttccag aacttcgagc ggagattcga ggagtgcatc agccagagcg  2220
ccgtcaagac caagttcgag cagcataccg tgcgggccaa gcagattgcc gaagccgtca  2280
gactgatcat ggacagcctg catatggccg ccagagagca gcaggtctac tgcgaggaaa  2340
tgcgggaaga gagacaggac cggctgaagt tcatcgacaa gcagctggaa ctgctggccc  2400
aggactacaa gctgcggatc aagcagatca ccgaagaggt ggaaagacag gtgtccaccg  2460
ctatggccga ggaaatcaga cggctgagcg tgctggtcga cgactaccag atggactttc  2520
acccctctcc agtggtgctg aaagtctaca aaaacgagct gcaccggcac atcgaggaag  2580
gcctgggcag aaacatgagc gacagatgca gcaccgccat caccaatagc ctgcagacca  2640
tgcagcagga catgatcgac ggcctgaaac ctctgctgcc tgtgtccgtc agatcccaga  2700
tcgatatgct ggtgccccgg cagtgcttta gcctgaacta cgacctgaac tgcgacaagc  2760
tgtgcgccga tttccaagag gacatcgagt ttcacttcag cctcggctgg acaatgctgg  2820
tcaacagatt tctgggcccc aagaacagca gacgggccct gatgggctac aacgatcagg  2880
tgcagaggcc cattcctctg acacccgcca atcctagcat gcctccactg cctcagggca  2940
gcctgacaca agaggaattc atggtgtcta tggtcaccgg cctggccagc ctgaccagca  3000
gaacatctat gggcatcctg gtcgtcggcg gcgttgtgtg gaaagctgtt ggctggcggc  3060
tgatcgccct gagctttggc ctgtatggcc tgctgtacgt gtacgagaga ctgacctgga  3120
ccaccaaggc caaagagcgg gccttcaagc ggcagtttgt ggaacacgcc tccgagaaac  3180
tgcagctggt gatcagctac accggcagca attgcagcca ccaggtgcag caagagctgt  3240
ccggaacatt cgcccacctg tgtcagcagg tcgacgtgac cagagagaac ctggaacaag  3300
agatcgccgc catgaataag aaaatcgagg tgctcgactc cctgcagagc aaggccaagc  3360
tgctgagaaa caaggccggc tggctggaca gcgagctgaa tatgttcacc caccagtacc  3420
tgcagcctag ccgctaataa agcggccgca agcttgcacc cgtaccttgg ggagcgcgcg  3480
ccctcgtcgt gtcgtgacgt cacccgttct gttggatccc tggaggcttg ctgaaggctg  3540
tatgctgttg acgtccagaa cctgttctgt tttggccact gactgacaga acaggctgga  3600
cgtcaacagg acacaaggcc tgttactagc actcacatgg aacaaatggc ccagatctta  3660
agcttctcga gatcgataat caacctctgg attacaaaat ttgtgaaaga ttgactggta  3720
ttcttaacta tgttgctcct tttacgctat gtggatacgc tgctttaatg cctttgtatc  3780
atgctattgc ttcccgtatg gctttcattt tctcctcctt gtataaatcc tggttgctgt  3840
ctctttatga ggagttgtgg cccgttgtca ggcaacgtgg cgtggtgtgc actgtgtttg  3900
ctgacgcaac ccccactggt tggggcattg ccaccacctg tcagctcctt tccgggactt  3960
tcgctttccc cctccctatt gccacggcgg aactcatcgc cgcctgcctt gcccgctgct  4020
ggacaggggc tcggctgttg ggcactgaca attccgtggt gttgtcgggg aaatcatcgt  4080
cctttccttg gctgctcgcc tgtgttgcca cctggattct gcgcgggacg tccttctgct  4140
acgtcccttc ggccctcaat ccagcggacc ttccttcccg cggcctgctg ccggctctgc  4200
ggcctcttcc gcgtcttcgc cttcgccctc agacgagtcg gatctccctt tgggccgcct  4260
ccccgcctgc tgatcgccct gagcctggcc ctggtgacca acagccaggt gcaattgcta  4320
gagtcgactc tagagcggcc gcttcgagca gacatgataa gatacattga tgagtttgga  4380
caaaccacaa ctagaatgca gtgaaaaaaa tgctttattt gtgaaatttg tgatgctatt  4440
gctttatttg taaccattat aagctgcaat aaacaagtta acaacaacaa ttgcattcat  4500
tttatgtttc aggttcaggg ggagatgtgg gaggtttttt aaagcaagta aaacctctac  4560
aaatgtggta aaatcgataa ggatcttcct agagcatggc tacgtagata agtagcatgg  4620
cgggttaatc attaactaca aggaacccct agtgatggag ttggccactc cctctctgcg  4680
cgctcgctcg ctcactgagg ccgggcgacc aaaggtcgcc cgacgcccgg gctttgcccg  4740
ggcggcctca gtgagcgagc gagcgcgcag c                                 4771
```

```
SEQ ID NO: 70           moltype = AA  length = 757
FEATURE                 Location/Qualifiers
REGION                  1..757
                        note = Synthetic Construct
source                  1..757
                        mol_type = protein
                        organism = synthetic construct
SEQUENCE: 70
MSLLFSRCNS IVTVKKNKRH MAEVNASPLK HFVTAKKKIN GIFEQLGAYI QESATFLEDT  60
```

```
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 71           moltype = DNA  length = 4771
FEATURE                 Location/Qualifiers
misc_feature            1..4771
                        note = Vector genome CAG.CI.hMfn2.GA.link.miR1518.WPRE.SV40
repeat_region           1..188
                        note = ITR
misc_feature            192..1032
                        note = CAG (CBA)
regulatory              194..436
                        note = enhancer - CMV enhancer
                        regulatory_class = enhancer
regulatory              439..720
                        note = promoter - CB Promoter
                        regulatory_class = promoter
misc_feature            720..1127
                        note = Intron - Hybrid intron in CAG
misc_feature            720..950
                        note = Intron - b-actin intron
misc_feature            1158..1163
                        note = Kozak
misc_feature            1379..1399
                        note = miR538 mut
misc_feature            2534..2554
                        note = miR 1518 mutated
misc_feature            3438..3519
                        note = linker p4271
misc_feature            3520..3547
                        note = 5' flank
misc_feature            3569..3587
                        note = loop
misc_feature            3588..3606
                        note = rat miR 1518 sense
misc_feature            3607..3651
                        note = 3' flank
misc_feature            3678..4266
                        note = WRPE
misc_feature            4355..4474
                        note = SV40 PA terminator
repeat_region           4584..4771
                        note = ITR
misc_feature            3548..3568
                        note = rat miR1518 AS
source                  1..4771
                        mol_type = other DNA
                        organism = synthetic construct
CDS                     1164..3437
                        note = human Mfn2 optimized
                        protein_id = 72
                        translation = MSLLFSRCNSIVTVKKNKRHMAEVNASPLKHFVTAKKKINGIFEQL
                         GAYIQESATFLEDTYRNAELDPVTTEEQVLDVKGYLSKVRGISEVLARRHMKVAFFGRT
                         SNGKSTVINAMLWDKVLPSGIGHTTNCFLRVEGTDGHEAFLLTEGSEEKRSAKTVNQLA
                         HALHQDKQLHAGSLVSVMWPNSKCPLLKDDLVLMDSPGIDVTTELDSWIDKFCLDADVF
                         VLVANSESTLMQTEKHFFHKVSERLSRPNIFILNNRWDASASEPEYMEEVRRQHMERCT
                         SFLVDELGVVDRSQAGDRIFFVSAKEVLNARIQKAQGMPEGGGALAEGFQVRMFEFQNF
                         ERRFEECISQSAVKTKFEQHTVRAKQIAEAVRLIMDSLHMAAREQQVYCEEMREERQDR
                         LKFIDKQLELLAQDYKLRIKQITEEVERQVSTAMAEEIRRLSVLVDDYQMDFHPSPVVL
                         KVYKNELHRHIEEGLGRNMSDRCSTAITNSLQTMQQDMIDGLKPLLPVSVRSQIDMLVP
                         RQCFSLNYDLNCDKLCADFQEDIEFHFSLGWTMLVNRFLGPKNSRRALMGYNDQVQRPI
                         PLTPANPSMPPLPQGSLTQEEFMVSMVTGLASLTSRTSMGILVVGGVVWKAVGWRLIAL
                         SFGLYGLLYVYERLTWTTKAKERAFKRQFVEHASEKLQLVISYTGSNCSHQVQQELSGT
                         FAHLCQQVDVTRENLEQEIAAMNKKIEVLDSLQSKAKLLRNKAGWLDSELNMFTHQYLQ
                         PSR
SEQUENCE: 71
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacgt agccatgctc  180
```

-continued

```
taggaagagt accattgacg tcaataatga cgtatgttcc catagtaacg ccaataggga  240
ctttccattg acgtcaatgg gtggagtatt tacggtaaac tgcccacttg gcagtacatc  300
aagtgtatca tatgccaagt acgcccccta ttgacgtcaa tgacggtaaa tggcccgcct  360
ggcattatgc ccagtacatg accttatggg actttcctac ttggcagtac atctacgtat  420
tagtcatcgc tattaccatg gtcgaggtga gccccacgtt ctgcttcact ctccccatct  480
ccccccccctc cccaccccca attttgtatt tatttatttt ttaattattt tgtgcagcga  540
tgggggcggg gggggggggg ggcgcgcgc caggcggggc ggggcggggc gaggggcggg  600
gcggggcgag gcggagaggt gcggcggcag ccaatcagag cggcgcgctc cgaaagtttc  660
cttttatggc gaggcggcgg cggcggcggc cctataaaaa gcgaagcgcg cggcgggcgg  720
gagtcgctgc gcgctgcctt cgccccgtgc cccgctccgc cgccgcctcg cgccgcccgc  780
cccggctctg actgaccgcg ttactcccac aggtgagcgg gcgggacggc ccttctcctc  840
cgggctgtaa ttagcgcttg gtttaatgac ggcttgtttc ttttctgtgg ctgcgtgaaa  900
gccttgaggg gctccgggag ggccctttgt gcggggggag cggctcgggg ctgtccgcgg  960
ggggacggct gccttcgggg gggacggggc agggcggggt tcggcttctg gcgtgtgacc  1020
ggcggctcta gagcctctgc taaccatgtt catgccttct tctttttcct acagctcctg  1080
ggcaacgtgc tggttattgt gctgtctcat cattttggca aagaattgga tcccgtacga  1140
cgcgtgctag caccggtgcc accatgagcc tgctgttcag ccggtgcaac agcatcgtga  1200
ccgtgaagaa aaacaagcgg cacatggccg aagtgaacgc ctctccactg aagcacttcg  1260
tgaccgccaa gaagaagatc aacggcatct tcgagcagct gggcgcctac atccaagaga  1320
gcgccacctt cctggaagat acctacagaa acgccgagct ggaccccgtg accacagagg  1380
aacaggtgct ggatgtgaag ggctacctga gcaaagtgcg gggcatctct gaagtgctgg  1440
ccagacggca tatgaaggtg gcctttttcg gccggaccag caacggcaag agcaccgtga  1500
tcaatgccat gctgtgggac aaagtgctgc cctctggaat cggccacacc accaactgct  1560
ttctgagagt ggaaggcacc gacggccacg aggcatttct gctgacagag ggctccgagg  1620
aaaagcggag cgccaagaca gtgaaccagc tggcccatgc tctgcaccag gataagcagc  1680
tgcatgccgg aagcctggtg tccgtgatgt ggcccaatag caagtgccct ctgctgaagg  1740
acgacctggt gctgatggat agccccggga tcgatgtgac caccgaactg gacagctgga  1800
tcgacaagtt ctgcctggac gccgacgtgt tcgtgctggt ggccaatagc gagagcaccc  1860
tgatgcagac cgagaagcac tttttccaca aggtgtccga gcggctgagc agacccaata  1920
tctttatcct gaacaacaga tgggacgcca gcgccagcga gcccgagtat atggaagaag  1980
tgcggcggca gcatatggaa cggtgcacat cctttctggt ggacgagctg ggcgtcgtgg  2040
atagatctca ggccggcgac agaatcttct ttgtgtccgc caaagaggtg ctgaacgccc  2100
ggattcagaa agcccaggga atgcctgaag gcggaggtgc actggccgag ggatttcaag  2160
tgcggatgtt cgagttccag aacttcgagc ggagattcga ggagtgcatc agccagagcg  2220
ccgtcaagac caagttcgag cagcataccg tgcgggccaa gcagattgcc gaagccgtca  2280
gactgatcat ggacagcctg catatggccg ccagagagca gcaggtctac tgcgaggaaa  2340
tgcgggaaga gagacaggac cggctgaagt tcatcgacaa gcagctggaa ctgctggccc  2400
aggactacaa gctgcggatc aagcagatca ccgaagaggt ggaaagacag gtgtccaccg  2460
ctatggccga ggaaatcaga cggctgagcg tgctggtcga cgactaccag atggactttc  2520
acccctctcc agtggtgctg aaagtctaca aaaacgagct gcaccggcac atcgaggaag  2580
gcctgggcag aaacatgagc gacagatgca gcaccgccat caccaatagc ctgcagacca  2640
tgcagcagga catgatcgac ggcctgaaac ctctgctgcc tgtgtccgtc agatcccaga  2700
tcgatatgct ggtgccccgg cagtgcttta gcctgaacta cgacctgaac tgcgacaagc  2760
tgtgcgccga tttccaagag gacatcgagt ttcacttcag cctcggctgg acaatgctgg  2820
tcaacagatt tctgggcccc aagaacagca gacgggccct gatgggctac aacgatcagg  2880
tgcagaggcc cattcctctg acacccgcca atcctagcat gcctccactg cctcagggca  2940
gcctgacaca agaggaattc atggtgtcta tggtcaccgg cctggccagc ctgaccagca  3000
gaacatctat gggcatcctg gtcgtcggcg gcgttgtgtg gaaagctgtt ggctggcggc  3060
tgatcgccct gagctttggc ctgtatggcc tgctgtacgt gtacgagaga ctgacctgga  3120
ccaccaaggc caaagagcgg gccttcaagc ggcagtttgt ggaacacgcc tccgagaaac  3180
tgcagctggt gatcagctac accggcagca attgcagcca ccaggtgcag caagagctgt  3240
ccggaacatt cgcccacctg tgtcagcagg tcgacgtgac cagagagaac ctggaacaag  3300
agatcgccgc catgaataag aaaatcgagg tgctcgactc cctgcagagc aaggccaagc  3360
tgctgagaaa caaggccggc tggctggaca gcgagctgaa tatgttcacc caccagtacc  3420
tgcagcctag ccgctaataa agcggccgca agcttgcacc cgtacctttg ggagcgcgcg  3480
ccctcgtcgt gtcgtgacgt cacccgttct gttggatccc tggaggcttg ctgaaggctg  3540
tatgctgttc ttataaacct tgaggacagt tttggccact gactgactgt cctcagttta  3600
taagaacagg acacaaggcc tgttactagc actcacatgg aacaaatggc ccagatctta  3660
agcttctcga gatcgataat caacctctgg attacaaaat ttgtgaaaga ttgactggta  3720
ttcttaacta tgttgctcct tttacgctat gtggatacgc tgctttaatg cctttgtatc  3780
atgctattgc ttcccgtatg gctttcattt tctcctcctt gtataaatcc tggttgctgt  3840
ctctttatga ggagttgtgg cccgttgtca ggcaacgtgg cgtggtgtgc actgtgtttg  3900
ctgacgcaac ccccactggt tggggcattg ccaccacctg tcagctcctt tccgggactt  3960
tcgctttccc cctccctatt gccacggcgg aactcatcgc cgcctgcctt gcccgctgct  4020
ggacaggggc tcggctgttg ggcactgaca attccgtggt gttgtcgggg aaatcatcgt  4080
cctttccttg gctgctcgcc tgtgttgcca cctggattct gcgcgggacg tccttctgct  4140
acgtcccttc ggccctcaat ccagcggacc ttccttcccg cggcctgctg ccggctctgc  4200
ggcctcttcc gcgtcttcgc cttcgccctc agacgagtcg gatctccctt tgggccgcct  4260
ccccgcctgc tgatcgccct gagcctggcc ctggtgacca acagccaggt gcaattgcta  4320
gagtcgactc tagagcggcc gcttcgagca gacatgataa gatacattga tgagtttgga  4380
caaaccacaa ctagaatgca gtgaaaaaaa tgctttattt gtgaaatttg tgatgctatt  4440
gctttatttg taaccattat aagctgcaat aaacaagtta acaacaacaa ttgcattcat  4500
tttatgtttc aggttcaggg ggagatgtgg gaggtttttt aaagcaagta aaacctctac  4560
aaatgtggta aaatcgataa ggatcttcct agagcatggc tacgtagata agtagcatgg  4620
cgggttaatc attaactaca aggaacccct agtgatggag ttggccactc cctctctgcg  4680
cgctcgctcg ctcactgagg ccgggcgacc aaaggtcgcc cgacgcccgg gctttgcccg  4740
ggcggcctca gtgagcgagc gagcgcgcag c                                 4771
```

SEQ ID NO: 72 moltype = AA length = 757

```
FEATURE                 Location/Qualifiers
REGION                  1..757
                        note = Synthetic Construct
source                  1..757
                        mol_type = protein
                        organism = synthetic construct
SEQUENCE: 72
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 73           moltype = DNA  length = 4559
FEATURE                 Location/Qualifiers
misc_feature            1..4559
                        note = Vector genome CAG.CI.hMfn2.GA.WPRE.SV40
repeat_region           1..188
                        note = ITR
misc_feature            192..1032
                        note = CAG (CBA)
regulatory              194..1032
                        note = enhancer - CMV enhancer
                        regulatory_class = enhancer
regulatory              439..720
                        note = promoter - CB promoter
                        regulatory_class = promoter
misc_feature            720..1127
                        note = Intron - Hybrid intron in CAG
misc_feature            720..950
                        note = Intron - b-actin intron
misc_feature            1158..1163
                        note = Kozak
misc_feature            1379..1399
                        note = miR538 mut
misc_feature            2534..2554
                        note = miR1518 mutated
misc_feature            3466..4054
                        note = WRPE
misc_feature            4143..4262
                        note = SV 40 PA temrinator
repeat_region           4372..4559
                        note = ITR
source                  1..4559
                        mol_type = other DNA
                        organism = synthetic construct
CDS                     1164..3437
                        note = huamn Mfn2 engineered
                        protein_id = 74
                        translation = MSLLFSRCNSIVTVKKNKRHMAEVNASPLKHFVTAKKKINGIFEQL
                         GAYIQESATFLEDTYRNAELDPVTTEEQVLDVKGYLSKVRGISEVLARRHMKVAFFGRT
                         SNGKSTVINAMLWDKVLPSGIGHTTNCFLRVEGTDGHEAFLLTEGSEEKRSAKTVNQLA
                         HALHQDKQLHAGSLVSVMWPNSKCPLLKDDLVLMDSPGIDVTTELDSWIDKFCLDADVF
                         VLVANSESTLMQTEKHFFHKVSERLSRPNIFILNNRWDASASEPEYMEEVRRQHMERCT
                         SFLVDELGVVDRSQAGDRIFFVSAKEVLNARIQKAQGMPEGGGALAEGFQVRMFEFQNF
                         ERRFEECISQSAVKTKFEQHTVRAKQIAEAVRLIMDSLHMAAREQQVYCEEMREERQDR
                         LKFIDKQLELLAQDYKLRIKQITEEVERQVSTAMAEEIRRLSVLVDDYQMDFHPSPVVL
                         KVYKNELHRHIEEGLGRNMSDRCSTAITNSLQTMQQDMIDGLKPLLPVSVRSQIDMLVP
                         RQCFSLNYDLNCDKLCADFQEDIEFHFSLGWTMLVNRFLGPKNSRRALMGYNDQVQRPI
                         PLTPANPSMPPLPQGSLTQEEFMVSMVTGLASLTSRTSMGILVVGGVVWKAVGWRLIAL
                         SFGLYGLLYVYERLTWTTKAKERAFKRQFVEHASEKLQLVISYTGSNCSHQVQQELSGT
                         FAHLCQQVDVTRENLEQEIAAMNKKIEVLDSLQSKAKLLRNKAGWLDSELNMFTHQYLQ
                         PSR
SEQUENCE: 73
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacgt agccatgctc  180
taggaagagt accattgacg tcaataatga cgtatgttcc catagtaacg ccaataggga  240
ctttccattg acgtcaatgg gtggagtatt tacggtaaac tgcccacttg gcagtacatc  300
aagtgtatca tatgccaagt acgcccccta ttgacgtcaa tgacggtaaa tggcccgcct  360
ggcattatgc ccagtacatg accttatggg actttcctac ttggcagtac atctacgtat  420
```

tagtcatcgc tattaccatg gtcgaggtga gccccacgtt ctgcttcact ctccccatct 480
cccccccctc cccaccccca attttgtatt tatttatttt ttaattattt tgtgcagcga 540
tgggggcggg gggggggggg gggcgcgcgc caggcggggc ggggcggggc gaggggcggg 600
gcggggcgag gcggagaggt gcggcggcag ccaatcagag cggcgcgctc cgaaagtttc 660
cttttatggc gaggcggcgg cggcggcggc cctataaaaa gcgaagcgcg cggcgggcgg 720
gagtcgctgc gcgctgcctt cgccccgtgc cccgctccgc cgccgcctcg cgccgcccgc 780
cccggctctg actgaccgcg ttactcccac aggtgagcgg gcgggacggc ccttctcctc 840
cgggctgtaa ttagcgcttg gtttaatgac ggcttgtttc ttttctgtgg ctgcgtgaaa 900
gccttgaggg gctccgggag ggccctttgt gcggggggag cggctcgggg ctgtccgcgg 960
ggggacggct gccttcgggg gggacggggc agggcggggt tcggcttctg gcgtgtgacc 1020
ggcggctcta gagcctctgc taaccatgtt catgccttct tctttttcct acagctcctg 1080
ggcaacgtgc tggttattgt gctgtctcat cattttggca aagaattgga tcccgtacga 1140
cgcgtgctag caccggtgcc accatgagcc tgctgttcag ccggtgcaac agcatcgtga 1200
ccgtgaagaa aaacaagcgg cacatggccg aagtgaacgc ctctccactg aagcacttcg 1260
tgaccgccaa gaagaagatc aacggcatct tcgagcagct gggcgcctac atccaagaga 1320
gcgccacctt cctggaagat acctacagaa acgccgagct ggaccccgtg accacagagg 1380
aacaggtgct ggatgtgaag ggctacctga gcaaagtgcg gggcatctct gaagtgctgg 1440
ccagacggca tatgaaggtg gcctttttcg gccggaccag caacggcaag agcaccgtga 1500
tcaatgccat gctgtgggac aaagtgctgc cctctggaat cggccacacc accaactgct 1560
ttctgagagt ggaaggcacc gacggccacg aggcatttct gctgacagag ggctccgagg 1620
aaaagcggag cgccaagaca gtgaaccagc tggcccatgc tctgcaccag gataagcagc 1680
tgcatgccgg aagcctggtg tccgtgatgt ggcccaatag caagtgccct ctgctgaagg 1740
acgacctggt gctgatggat agccccggga tcgatgtgac caccgaactg gacagctgga 1800
tcgacaagtt ctgcctggac gccgacgtgt tcgtgctggt ggccaatagc gagagcaccc 1860
tgatgcagac cgagaagcac tttttccaca aggtgtccga gcggctgagc agacccaata 1920
tctttatcct gaacaacaga tgggacgcca gcgccagcga gcccgagtat atggaagaag 1980
tgcggcggca gcatatggaa cggtgcacat cctttctggt ggacgagctg ggcgtcgtgg 2040
atagatctca ggccggcgac agaatcttct ttgtgtccgc caaagaggtg ctgaacgccc 2100
ggattcagaa agcccaggga atgcctgaag gcggaggtgc actggccgag ggatttcaag 2160
tgcggatgtt cgagttccag aacttcgagc ggagattcga ggagtgcatc agccagagcg 2220
ccgtcaagac caagttcgag cagcataccg tgcgggccaa gcagattgcc gaagccgtca 2280
gactgatcat ggacagcctg catatggccg ccagagagca gcaggtctac tgcgaggaaa 2340
tgcgggaaga gagacaggac cggctgaagt tcatcgacaa gcagctggaa ctgctggccc 2400
aggactacaa gctgcggatc aagcagatca ccgaagaggt ggaaagacag gtgtccaccg 2460
ctatggccga ggaaatcaga cggctgagcg tgctggtcga cgactaccag atggactttc 2520
acccctctcc agtggtgctg aaagtctaca aaaacgagct gcaccggcac atcgaggaag 2580
gcctgggcag aaacatgagc gacagatgca gcaccgccat caccaatagc ctgcagacca 2640
tgcagcagga catgatcgac ggcctgaaac ctctgctgcc tgtgtccgtc agatcccaga 2700
tcgatatgct ggtgccccgg cagtgcttta gcctgaacta cgacctgaac tgcgacaagc 2760
tgtgcgccga tttccaagag gacatcgagt ttcacttcag cctcggctgg acaatgctgg 2820
tcaacagatt tctgggcccc aagaacagca gacgggccct gatgggctac aacgatcagg 2880
tgcagaggcc cattcctctg acacccgcca atcctagcat gcctccactg cctcagggca 2940
gcctgacaca agaggaattc atggtgtcta tggtcaccgg cctggccagc ctgaccagca 3000
gaacatctat gggcatcctg gtcgtcggcg gcgttgtgtg gaaagctgtt ggctggcggc 3060
tgatcgccct gagctttggc ctgtatggcc tgctgtacgt gtacgagaga ctgacctgga 3120
ccaccaaggc caaagagcgg gccttcaagc ggcagtttgt ggaacacgcc tccgagaaac 3180
tgcagctggt gatcagctac accggcagca attgcagcca ccaggtgcag caagagctgt 3240
ccggaacatt cgcccacctg tgtcagcagg tcgacgtgac cagagagaac ctggaacaag 3300
agatcgccgc catgaataag aaaatcgagg tgctcgactc cctgcagagc aaggccaagc 3360
tgctgagaaa caaggccggc tggctggaca gcgagctgaa tatgttcacc caccagtacc 3420
tgcagcctag ccgctaataa tgtacttaag cttctcgaga tcgataatca acctctggat 3480
tacaaaattt gtgaaagatt gactggtatt cttaactatg ttgctccttt tacgctatgt 3540
ggatacgctg ctttaatgcc tttgtatcat gctattgctt cccgtatggc tttcattttc 3600
tcctccttgt ataaatcctg gttgctgtct ctttatgagg agttgtggcc cgttgtcagg 3660
caacgtggcg tggtgtgcac tgtgtttgct gacgcaaccc ccactggttg gggcattgcc 3720
accacctgtc agctcctttc cgggactttc gctttccccc tccctattgc cacggcggaa 3780
ctcatcgccg cctgccttgc ccgctgctgg acaggggctc ggctgttggg cactgacaat 3840
tccgtggtgt tgtcggggaa atcatcgtcc tttccttggc tgctcgcctg tgttgccacc 3900
tggattctgc gcgggacgcc cttctgctac gtcccttcgg ccctcaatcc agcggacctt 3960
ccttcccgcg gcctgctgcc ggctctgcgg cctcttccgc gtcttcgcct tcgccctcag 4020
acgagtcgga tctccctttg ggccgcctcc ccgcctgctg atcgccctga gcctggccct 4080
ggtgaccaac agccaggtgc aattgctaga gtcgactcta gagcggccgc ttcgagcaga 4140
catgataaga tacattgatg agtttggaca aaccacaact agaatgcagt gaaaaaaatg 4200
ctttatttgt gaaatttgtg atgctattgc tttatttgta accattataa gctgcaataa 4260
acaagttaac aacaacaatt gcattcattt tatgtttcag gttcaggggg agatgtggga 4320
ggttttttaa agcaagtaaa acctctacaa atgtggtaaa atcgataagg atcttcctag 4380
agcatggcta cgtagataag tagcatggcg ggttaatcat taactacaag gaacccctag 4440
tgatggagtt ggccactccc tctctgcgcg ctcgctcgct cactgaggcc gggcgaccaa 4500
aggtcgcccg acgcccgggc tttgcccggg cggcctcagt gagcgagcga gcgcgcagc 4559

SEQ ID NO: 74 moltype = AA length = 757
FEATURE Location/Qualifiers
REGION 1..757
note = Synthetic Construct
source 1..757
mol_type = protein
organism = synthetic construct
SEQUENCE: 74
MSLLFSRCNS IVTVKKNKRH MAEVNASPLK HFVTAKKKIN GIFEQLGAYI QESATFLEDT 60

-continued

```
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 75           moltype = DNA  length = 4821
FEATURE                 Location/Qualifiers
misc_feature            1..4821
                        note = Vector genome CB7.CI.hMfn2.GA.link.miR538.rBG
repeat_region           1..130
                        note = ITR
regulatory              259..562
                        note = enhancer - CMV IE enhancer
                        regulatory_class = enhancer
regulatory              561..842
                        note = promoter - CB promoter
                        regulatory_class = promoter
misc_feature            935..1907
                        note = Intron - chicken beta-actin intron
misc_feature            1953..1958
                        note = Kozak
misc_feature            2174..2194
                        note = miR538 mut
misc_feature            3329..3349
                        note = miR1518
misc_feature            4233..4314
                        note = linker p5271
misc_feature            4315..4342
                        note = 5' flank
misc_feature            4343..4363
                        note = miR538 AS
misc_feature            4364..4382
                        note = loop
misc_feature            4383..4401
                        note = miR538 Sense
misc_feature            4402..4446
                        note = 3' flank
regulatory              4500..4626
                        note = polyA_signal - rabbit beta globin (RBG) poly A
                        regulatory_class = polyA_signal_sequence
repeat_region           4692..4821
                        note = ITR
source                  1..4821
                        mol_type = other DNA
                        organism = synthetic construct
CDS                     1959..4232
                        note = human Mfn2 engineered
                        protein_id = 76
                        translation = MSLLFSRCNSIVTVKKNKRHMAEVNASPLKHFVTAKKKINGIFEQL
                         GAYIQESATFLEDTYRNAELDPVTTEEQVLDVKGYLSKVRGISEVLARRHMKVAFFGRT
                         SNGKSTVINAMLWDKVLPSGIGHTTNCFLRVEGTDGHEAFLLTEGSEEKRSAKTVNQLA
                         HALHQDKQLHAGSLVSVMWPNSKCPLLKDDLVLMDSPGIDVTTELDSWIDKFCLDADVF
                         VLVANSESTLMQTEKHFFHKVSERLSRPNIFILNNRWDASASEPEYMEEVRRQHMERCT
                         SFLVDELGVVDRSQAGDRIFFVSAKEVLNARIQKAQGMPEGGGALAEGFQVRMFEFQNF
                         ERRFEECISQSAVKTKFEQHTVRAKQIAEAVRLIMDSLHMAAREQQVYCEEMREERQDR
                         LKFIDKQLELLAQDYKLRIKQITEEVERQVSTAMAEEIRRLSVLVDDYQMDFHPSPVVL
                         KVYKNELHRHIEEGLGRNMSDRCSTAITNSLQTMQQDMIDGLKPLLPVSVRSQIDMLVP
                         RQCFSLNYDLNCDKLCADFQEDIEFHFSLGWTMLVNRFLGPKNSRRALMGYNDQVQRPI
                         PLTPANPSMPPLPQGSLTQEEFMVSMVTGLASLTSRTSMGILVVGGVVWKAVGWRLIAL
                         SFGLYGLLYVYERLTWTTKAKERAFKRQFVEHASEKLQLVISYTGSNCSHQVQQELSGT
                         FAHLCQQVDVTRENLEQEIAAMNKKIEVLDSLQSKAKLLRNKAGWLDSELNMFTHQYLQ
                         PSR
regulatory              259..842
                        note = CB7 promoter
                        regulatory_class = promoter
SEQUENCE: 75
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat gattaacccg ccatgctact tatctacgta gccatgctct  180
aggaagatct gatatcacta gttattaata gtaatcaatt acggggtcat tagttcatag  240
cccatatatg gagttccgcg ttacataact tacggtaaat ggcccgcctg gctgaccgcc  300
```

-continued

```
caacgacccc cgcccattga cgtcaataat gacgtatgtt cccatagtaa cgccaatagg  360
gactttccat tgacgtcaat gggtggagta tttacggtaa actgcccact tggcagtaca  420
tcaagtgtat catatgccaa gtacgccccc tattgacgtc aatgacggta aatggcccgc  480
ctggcattat gcccagtaca tgaccttatg ggactttcct acttggcagt acatctacgt  540
attagtcatc gctattacca tggtcgaggt gagccccacg ttctgcttca ctctccccat  600
ctcccccccc tccccacccc caattttgta tttatttatt ttttaattat tttgtgcagc  660
gatgggggcg gggggggggg gggggcgcgc gccaggcggg gcggggcggg gcgaggggcg  720
gggcggggcg aggcggagag gtgcggcggc agccaatcag agcggcgcgc tccgaaagtt  780
tccttttatg gcgaggcggc ggcggcggcg gccctataaa aagcgaagcg cgcggcgggc  840
gggagtcgct gcgcgctgcc ttcgccccgt gccccgctcc gccgccgcct cgcgccgccc  900
gccccggctc tgactgaccg cgttactccc acaggtgagc gggcgggacg gcccttctcc  960
tccgggctgt aattagcgct tggtttaatg acggcttgtt tctttctgt ggctgcgtga  1020
aagccttgag gggctccggg agggcccttt gtgcgggggg agcggctcgg ggggtgcgtg  1080
cgtgtgtgtg tgcgtgggga gcgccgcgtg cggctccgcg ctgcccggcg gctgtgagcg  1140
ctgcgggcgc ggcgcggggc tttgtgcgct ccgcagtgtg cgcgagggga gcgcggccgg  1200
gggcggtgcc ccgcggtgcg gggggggctg cgaggggaac aaaggctgcg tgcggggtgt  1260
gtgcgtgggg gggtgagcag ggggtgtggg cgcgtcggtc gggctgcaac cccccctgca  1320
cccccctccc cgagttgctg agcacggccc ggcttcgggt gcggggctcc gtacggggcg  1380
tggcgcgggg ctcgccgtgc cgggcggggg gtggcggcag gtgggggtgc cgggcggggc  1440
ggggccgcct cgggccgggg agggctcggg ggaggggcgc ggcggccccc ggagcgccgg  1500
cggctgtcga ggcgcggcga gccgcagcca ttgcctttta tggtaatcgt gcgagagggc  1560
gcagggactt cctttgtccc aaatctgtgc ggagccgaaa tctgggaggc gccgccgcac  1620
cccctctagc gggcgcgggg cgaagcggtg cggcgccggc aggaaggaaa tgggcgggga  1680
gggccttcgt gcgtcgccgc gccgccgtcc ccttctccct ctccagcctc ggggctgtcc  1740
gcggggggac ggctgccttc ggggggggacg gggcagggcg ggttcggct tctggcgtgt  1800
gaccggcggc tctagagcct ctgctaacca tgttcatgcc ttcttctttt tcctacagct  1860
cctgggcaac gtgctggtta ttgtgctgtc tcatcatttt ggcaaagaat tcacgcgtgc  1920
taggatcccg tacgacgcgt gctagcaccg gtgccaccat gagcctgctg ttcagccggt  1980
gcaacagcat cgtgaccgtg aagaaaaaca agcggcacat ggccgaagtg aacgcctctc  2040
cactgaagca cttcgtgacc gccaagaaga agatcaacgg catcttcgag cagctgggcg  2100
cctacatcca agagagcgcc accttcctgg aagataccta cagaaacgcc gagctggacc  2160
ccgtgaccac agaggaacag gtgctggatg tgaagggcta cctgagcaaa gtgcggggca  2220
tctctgaagt gctggccaga cggcatatga aggtggcctt tttcggccgg accagcaacg  2280
gcaagagcac cgtgatcaat gccatgctgt gggacaaagt gctgccctct ggaatcggcc  2340
acaccaccaa ctgctttctg agagtggaag gcaccgacgg ccacgaggca tttctgctga  2400
cagagggctc cgaggaaaag cggagcgcca agacagtgaa ccagctggcc catgctctgc  2460
accaggataa gcagctgcat gccggaagcc tggtgtccgt gatgtggccc aatagcaagt  2520
gccctctgct gaaggacgac ctggtgctga tggatagccc cgggatcgat gtgaccaccg  2580
aactggacag ctggatcgac aagttctgcc tggacgccga cgtgttcgtg ctggtggcca  2640
atagcgagag caccctgatg cagaccgaga agcacttttt ccacaaggtg tccgagcggc  2700
tgagcagacc caatatcttt atcctgaaca acagatggga cgccagcgcc agcgagcccg  2760
agtatatgga agaagtgcgg cggcagcata tggaacggtg cacatccttt ctggtggacg  2820
agctgggcgt cgtggataga tctcaggccg gcgacagaat cttctttgtg tccgccaaag  2880
aggtgctgaa cgcccggatt cagaaagccc agggaatgcc tgaaggcgga ggtgcactgg  2940
ccgagggatt tcaagtgcgg atgttcgagt tccagaactt cgagcggaga ttcgaggagt  3000
gcatcagcca gagcgccgtc aagaccaagt tcgagcagca taccgtgcgg gccaagcaga  3060
ttgccgaagc cgtcagactg atcatggaca gcctgcatat ggccgccaga gagcagcagg  3120
tctactgcga ggaaatgcgg gaagagagac aggaccggct gaagttcatc gacaagcagc  3180
tggaactgct ggcccaggac tacaagctgc ggatcaagca gatcaccgaa gaggtggaaa  3240
gacaggtgtc caccgctatg gccgaggaaa tcagacggct gagcgtgctg gtcgacgact  3300
accagatgga ctttcacccc tctccagtgg tgctgaaagt ctacaaaaac gagctgcacc  3360
ggcacatcga ggaaggcctg ggcagaaaca tgagcgacag atgcagcacc gccatcacca  3420
atagcctgca gaccatgcag caggacatga tcgacggcct gaaacctctg ctgcctgtgt  3480
ccgtcagatc ccagatcgat atgctggtgc cccggcagtg ctttagcctg aactacgacc  3540
tgaactgcga caagctgtgc gccgatttcc aagaggacat cgagtttcac ttcagcctcg  3600
gctggacaat gctggtcaac agatttctgg gccccaagaa cagcagacgg gccctgatgg  3660
gctacaacga tcaggtgcag aggcccattc ctctgacacc cgccaatcct agcatgcctc  3720
cactgcctca gggcagcctg acacaagagg aattcatggt gtctatggtc accggcctgg  3780
ccagcctgac cagcagaaca tctatgggca tcctggtcgt cggcggcgtt gtgtggaaag  3840
ctgttggctg gcggctgatc gccctgagct ttggcctgta tggcctgctg tacgtgtacg  3900
agagactgac ctggaccacc aaggccaaag agcgggcctt caagcggcag tttgtggaac  3960
acgcctccga gaaactgcag ctggtgatca gctacaccgg cagcaattgc agccaccagg  4020
tgcagcaaga gctgtccgga acattcgccc acctgtgtca gcaggtcgac gtgaccagag  4080
agaacctgga acaagagatc gccgccatga ataagaaaat cgaggtgctc gactccctgc  4140
agagcaaggc caagctgctg agaaacaagg ccggctggct ggacagcgag ctgaatatgt  4200
tcacccacca gtacctgcag cctagccgct aataaagcgg ccgcaagctt gcacccgtac  4260
ctttgggagc gcgcgccctc gtcgtgtcgt gacgtcaccc gttctgttgg atccctggag  4320
gcttgctgaa ggctgtatgc tgttgacgtc cagaacctgt tctgttttgg ccactgactg  4380
acagaacagg ctggacgtca acaggacaca aggcctgtta ctagcactca catggaacaa  4440
atggcccaga tcagctttct agagtcgacc cgggcggcgg cggccgccta aggctcgagg  4500
atctttttcc ctctgccaaa aattatgggg acatcatgaa gccccttgag catctgactt  4560
ctggctaata aaggaaattt attttcattg caatagtgtg ttggaatttt ttgtgtctct  4620
cactcggata aggatcttcc tagagcatgg ctacgtagat aagtagcatg gcgggttaat  4680
cattaactac aaggaacccc tagtgatgga gttggccact ccctctctgc gcgctcgctc  4740
gctcactgag gccgggcgac caaaggtcgc ccgacgcccg ggctttgccc gggcggcctc  4800
agtgagcgag cgagcgcgca g                                            4821

SEQ ID NO: 76           moltype = AA  length = 757
FEATURE                 Location/Qualifiers
```

```
REGION              1..757
                    note = Synthetic Construct
source              1..757
                    mol_type = protein
                    organism = synthetic construct
SEQUENCE: 76
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 77       moltype = DNA  length = 4905
FEATURE             Location/Qualifiers
misc_feature        1..4905
                    note = Vector genome CB7.CI.hMfn2.GA.link.miR1518.rBG
repeat_region       1..130
                    note = ITR
regulatory          259..562
                    note = enhancer - CMV IE enhancer
                    regulatory_class = enhancer
regulatory          561..842
                    note = promoter - CB promoter
                    regulatory_class = promoter
misc_feature        935..1907
                    note = Intron - chicken beta-actin intron
misc_feature        1953..1958
                    note = Kozak
misc_feature        2174..2194
                    note = miR538 mut
misc_feature        3329..3349
                    note = miR 1518 mutated
misc_feature        4233..4314
                    note = linker p4271
misc_feature        4315..4342
                    note = 5' flank
misc_feature        4343..4363
                    note = rat miR1518 AS
misc_feature        4364..4382
                    note = loop
misc_feature        4383..4401
                    note = rat miR 1518 sense
misc_feature        4402..4446
                    note = 3'Flank
regulatory          4584..4710
                    note = polyA_signal - rabbit beta globin (RBG) polyA
                    regulatory_class = polyA_signal_sequence
repeat_region       4776..4905
                    note = ITR
source              1..4905
                    mol_type = other DNA
                    organism = synthetic construct
CDS                 1959..4232
                    note = human Mfn2 engineered
                    protein_id = 78
                    translation = MSLLFSRCNSIVTVKKNKRHMAEVNASPLKHFVTAKKKINGIFEQL
                     GAYIQESATFLEDTYRNAELDPVTTEEQVLDVKGYLSKVRGISEVLARRHMKVAFFGRT
                     SNGKSTVINAMLWDKVLPSGIGHTTNCFLRVEGTDGHEAFLLTEGSEEKRSAKTVNQLA
                     HALHQDKQLHAGSLVSVMWPNSKCPLLKDDLVLMDSPGIDVTTELDSWIDKFCLDADVF
                     VLVANSESTLMQTEKHFFHKVSERLSRPNIFILNNRWDASASEPEYMEEVRRQHMERCT
                     SFLVDELGVVDRSQAGDRIFFVSAKEVLNARIQKAQGMPEGGGALAEGFQVRMFEFQNF
                     ERRFEECISQSAVKTKFEQHTVRAKQIAEAVRLIMDSLHMAAREQQVYCEEMREERQDR
                     LKFIDKQLELLAQDYKLRIKQITEEVERQVSTAMAEEIRRLSVLVDDYQMDFHPSPVVL
                     KVYKNELHRHIEEGLGRNMSDRCSTAITNSLQTMQQDMIDGLKPLLPVSVRSQIDMLVP
                     RQCFSLNYDLNCDKLCADFQEDIEFHFSLGWTMLVNRFLGPKNSRRALMGYNDQVQRPI
                     PLTPANPSMPPLPQGSLTQEEFMVSMVTGLASLTSRTSMGILVVGGVVWKAVGWRLIAL
                     SFGLYGLLYVYERLTWTTKAKERAFKRQFVEHASEKLQLVISYTGSNCSHQVQQELSGT
                     FAHLCQQVDVTRENLEQEIAAMNKKIEVLDSLQSKAKLLRNKAGWLDSELNMFTHQYLQ
                     PSR
regulatory          259..842
                    note = CB7 promoter
```

regulatory_class = promoter
SEQUENCE: 77
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct gatatcacta gttattaata gtaatcaatt acggggtcat tagttcatag 240
cccatatatg gagttccgcg ttacataact tacggtaaat ggcccgcctg gctgaccgcc 300
caacgacccc cgcccattga cgtcaataat gacgtatgtt cccatagtaa cgccaatagg 360
gactttccat tgacgtcaat gggtggagta tttacggtaa actgcccact tggcagtaca 420
tcaagtgtat catatgccaa gtacgccccc tattgacgtc aatgacggta aatggcccgc 480
ctggcattat gcccagtaca tgaccttatg ggactttcct acttggcagt acatctacgt 540
attagtcatc gctattacca tggtcgaggt gagccccacg ttctgcttca ctctccccat 600
ctcccccccc tccccacccc caattttgta tttatttatt ttttaattat tttgtgcagc 660
gatgggggcg gggggggggg ggggcgcgc gccaggcggg gcggggcggg gcgaggggcg 720
gggcggggcg aggcggagag gtgcggcggc agccaatcag agcggcgcgc tccgaaagtt 780
tccttttatg gcgaggcggc ggcggcggcg gccctataaa aagcgaagcg cgcggcgggc 840
gggagtcgct gcgcgctgcc ttcgccccgt gccccgctcc gccgccgcct cgcgccgccc 900
gccccggctc tgactgaccg cgttactccc acaggtgagc gggcgggacg gcccttctcc 960
tccgggctgt aattagcgct tggtttaatg acggcttgtt tcttttctgt ggctgcgtga 1020
aagccttgag gggctccggg agggcccttt gtgcgggggg agcggctcgg ggggtgcgtg 1080
cgtgtgtgtg tgcgtgggga gcgccgcgtg cggctccgcg ctgcccggcg gctgtgagcg 1140
ctgcgggcgc ggcgcggggc tttgtgcgct ccgcagtgtg cgcgagggga gcgcggccgg 1200
gggcggtgcc ccgcggtgcg gggggggctg cgaggggaac aaaggctgcg tgcggggtgt 1260
gtgcgtgggg gggtgagcag ggggtgtggg cgcgtcggtc gggctgcaac cccccctgca 1320
ccccccctcc cgagttgctg agcacggccc ggcttcgggt gcggggctcc gtacggggcg 1380
tggcgcgggg ctcgccgtgc cgggcggggg gtggcggcag gtgggggtgc cgggcggggc 1440
ggggccgcct cgggccgggg agggctcggg ggaggggcgc ggcggccccc ggagcgccgg 1500
cggctgtcga ggcgcggcga gccgcagcca ttgcctttta tggtaatcgt gcgagagggc 1560
gcagggactt cctttgtccc aaatctgtgc ggagccgaaa tctgggaggc gccgccgcac 1620
cccctctagc gggcgcgggg cgaagcggtg cggcgccggc aggaaggaaa tgggcgggga 1680
gggccttcgt gcgtcgccgc gccgccgtcc ccttctccct ctccagcctc ggggctgtcc 1740
gcggggggac ggctgccttc ggggggggacg gggcagggcg gggttcggct tctggcgtgt 1800
gaccggcggc tctagagcct ctgctaacca tgttcatgcc ttcttctttt tcctacagct 1860
cctgggcaac gtgctggtta ttgtgctgtc tcatcatttt ggcaaagaat tcacgcgtgc 1920
taggatcccg tacgacgcgt gctagcaccg gtgccaccat gagcctgctg ttcagccggt 1980
gcaacagcat cgtgaccgtg aagaaaaaca agcggcacat ggccgaagtg aacgcctctc 2040
cactgaagca cttcgtgacc gccaagaaga agatcaacgg catcttcgag cagctgggcg 2100
cctacatcca agagagcgcc accttcctgg aagataccta cagaaacgcc gagctggacc 2160
ccgtgaccac agaggaacag gtgctggatg tgaagggcta cctgagcaaa gtgcggggca 2220
tctctgaagt gctggccaga cggcatatga aggtggcctt tttcggccgg accagcaacg 2280
gcaagagcac cgtgatcaat gccatgctgt gggacaaagt gctgccctct ggaatcggcc 2340
acaccaccaa ctgctttctg agagtggaag gcaccgacgg ccacgaggca tttctgctga 2400
cagagggctc cgaggaaaag cggagcgcca agacagtgaa ccagctggcc catgctctgc 2460
accaggataa gcagctgcat gccggaagcc tggtgtccgt gatgtggccc aatagcaagt 2520
gccctctgct gaaggacgac ctggtgctga tggatagccc cgggatcgat gtgaccaccg 2580
aactggacag ctggatcgac aagttctgcc tggacgccga cgtgttcgtg ctggtggcca 2640
atagcgagag caccctgatg cagaccgaga agcacttttt ccacaaggtg tccgagcggc 2700
tgagcagacc caatatcttt atcctgaaca acagatggga cgccagcgcc agcgagcccg 2760
agtatatgga agaagtgcgg cggcagcata tggaacggtg cacatccttt ctggtggacg 2820
agctgggcgt cgtggataga tctcaggccg gcgacagaat cttctttgtg tccgccaaag 2880
aggtgctgaa cgcccggatt cagaaagccc agggaatgcc tgaaggcgga ggtgcactgg 2940
ccgagggatt tcaagtgcgg atgttcgagt tccagaactt cgagcggaga ttcgaggagt 3000
gcatcagcca gagcgccgtc aagaccaagt tcgagcagca taccgtgcgg gccaagcaga 3060
ttgccgaagc cgtcagactg atcatggaca gcctgcatat ggccgccaga gagcagcagg 3120
tctactgcga ggaaatgcgg gaagagagac aggaccggct gaagttcatc gacaagcagc 3180
tggaactgct ggcccaggac tacaagctgc ggatcaagca gatcaccgaa gaggtggaaa 3240
gacaggtgtc caccgctatg gccgaggaaa tcagacggct gagcgtgctg gtcgacgact 3300
accagatgga ctttcacccc tctccagtgg tgctgaaagt ctacaaaaac gagctgcacc 3360
ggcacatcga ggaaggcctg ggcagaaaca tgagcgacag atgcagcacc gccatcacca 3420
atagcctgca gaccatgcag caggacatga tcgacggcct gaaacctctg ctgcctgtgt 3480
ccgtcagatc ccagatcgat atgctggtgc cccggcagtg ctttagcctg aactacgacc 3540
tgaactgcga caagctgtgc gccgatttcc aagaggacat cgagtttcac ttcagcctcg 3600
gctggacaat gctggtcaac agatttctgg gccccaagaa cagcagacgg gccctgatgg 3660
gctacaacga tcaggtgcag aggcccattc ctctgacacc cgccaatcct agcatgcctc 3720
cactgcctca gggcagcctg acacaagagg aattcatggt gtctatggtc accggcctgg 3780
ccagcctgac cagcagaaca tctatgggca tcctggtcgt cggcggcgtt gtgtggaaag 3840
ctgttggctg gcggctgatc gccctgagct ttggcctgta tggcctgctg tacgtgtacg 3900
agagactgac ctggaccacc aaggccaaag agcgggcctt caagcggcag tttgtggaac 3960
acgcctccga gaaactgcag ctggtgatca gctacaccgg cagcaattgc agccaccagg 4020
tgcagcaaga gctgtccgga acattcgccc acctgtgtca gcaggtcgac gtgaccagag 4080
agaacctgga acaagagatc gccgccatga ataagaaaat cgaggtgctc gactccctgc 4140
agagcaaggc caagctgctg agaaacaagg ccggctggct ggacagcgag ctgaatatgt 4200
tcacccacca gtacctgcag cctagccgct aataaagcgg ccgcaagctt gcacccgtac 4260
ctttgggagc gcgcgccctc gtcgtgtcgt gacgtcaccc gttctgttgg atccctggag 4320
gcttgctgaa ggctgtatgc tgttcttata aaccttgagg acagttttgg ccactgactg 4380
actgtcctca gtttataaga acaggacaca aggcctgtta ctagcactca catggaacaa 4440
atggcccaga tctagggtgg ggccacctgc cggtaggtgt gcggtaggct tttctccgtc 4500
gcaggacgca gggttcgggc ctagagctta tcgttaagct ttctagagtc gacccgggcg 4560
gcggcggccg cctaaggctc gaggatcttt ttccctctgc caaaaattat ggggacatca 4620

```
tgaagcccct tgagcatctg acttctggct aataaaggaa atttattttc attgcaatag  4680
tgtgttggaa ttttttgtgt ctctcactcg gataaggatc ttcctagagc atggctacgt  4740
agataagtag catggcgggt taatcattaa ctacaaggaa cccctagtga tggagttggc  4800
cactccctct ctgcgcgctc gctcgctcac tgaggccggg cgaccaaagg tcgcccgacg  4860
cccgggcttt gcccgggcgg cctcagtgag cgagcgagcg cgcag                  4905

SEQ ID NO: 78          moltype = AA  length = 757
FEATURE                Location/Qualifiers
REGION                 1..757
                       note = Synthetic Construct
source                 1..757
                       mol_type = protein
                       organism = synthetic construct
SEQUENCE: 78
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                           757

SEQ ID NO: 79          moltype = DNA  length = 4565
FEATURE                Location/Qualifiers
misc_feature           1..4565
                       note = Vector genome CB7.CI.hMfn2.GA.rBG
repeat_region          1..130
                       note = ITR
regulatory             259..562
                       note = enhancer - CMV IE enhancer
                       regulatory_class = enhancer
regulatory             561..842
                       note = promoter - CB promoter
                       regulatory_class = promoter
regulatory             815..818
                       note = TATA_signal - TATA signal
                       regulatory_class = TATA_box
misc_feature           935..1907
                       note = Intron - Chicken beta-actin intron
misc_feature           1940..1948
                       note = Kozak
misc_feature           2161..2181
                       note = miR538 mut
misc_feature           3316..3336
                       note = miR1518 mutated
regulatory             4244..4370
                       note = polyA_signal - rabbit beta globin (RBG) polyA
                       regulatory_class = polyA_signal_sequence
repeat_region          4436..4565
                       note = ITR
source                 1..4565
                       mol_type = other DNA
                       organism = synthetic construct
CDS                    1946..4219
                       note = huamn Mfn2 engineered
                       protein_id = 80
                       translation = MSLLFSRCNSIVTVKKNKRHMAEVNASPLKHFVTAKKKINGIFEQL
                        GAYIQESATFLEDTYRNAELDPVTTEEQVLDVKGYLSKVRGISEVLARRHMKVAFFGRT
                        SNGKSTVINAMLWDKVLPSGIGHTTNCFLRVEGTDGHEAFLLTEGSEEKRSAKTVNQLA
                        HALHQDKQLHAGSLVSVMWPNSKCPLLKDDLVLMDSPGIDVTTELDSWIDKFCLDADVF
                        VLVANSESTLMQTEKHFFHKVSERLSRPNIFILNNRWDASASEPEYMEEVRRQHMERCT
                        SFLVDELGVVDRSQAGDRIFFVSAKEVLNARIQKAQGMPEGGGALAEGFQVRMFEFQNF
                        ERRFEECISQSAVKTKFEQHTVRAKQIAEAVRLIMDSLHMAAREQQVYCEEMREERQDR
                        LKFIDKQLELLAQDYKLRIKQITEEVERQVSTAMAEEIRRLSVLVDDYQMDFHPSPVVL
                        KVYKNELHRHIEEGLGRNMSDRCSTAITNSLQTMQQDMIDGLKPLLPVSVRSQIDMLVP
                        RQCFSLNYDLNCDKLCADFQEDIEFHFSLGWTMLVNRFLGPKNSRRALMGYNDQVQRPI
                        PLTPANPSMPPLPQGSLTQEEFMVSMVTGLASLTSRTSMGILVVGGVVWKAVGWRLIAL
                        SFGLYGLLYVYERLTWTTKAKERAFKRQFVEHASEKLQLVISYTGSNCSHQVQQELSGT
                        FAHLCQQVDVTRENLEQEIAAMNKKIEVLDSLQSKAKLLRNKAGWLDSELNMFTHQYLQ
                        PSR
regulatory             259..842
                       note = CB7 promoter
                       regulatory_class = promoter
```

SEQUENCE: 79
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatct gatatcacta gttattaata gtaatcaatt acggggtcat tagttcatag 240
cccatatatg gagttccgcg ttacataact tacggtaaat ggcccgcctg gctgaccgcc 300
caacgacccc cgcccattga cgtcaataat gacgtatgtt cccatagtaa cgccaatagg 360
gactttccat tgacgtcaat gggtggagta tttacggtaa actgcccact tggcagtaca 420
tcaagtgtat catatgccaa gtacgccccc tattgacgtc aatgacggta aatggcccgc 480
ctggcattat gcccagtaca tgaccttatg ggactttcct acttggcagt acatctacgt 540
attagtcatc gctattacca tggtcgaggt gagccccacg ttctgcttca ctctccccat 600
ctcccccccc tccccacccc caattttgta tttatttatt ttttaattat tttgtgcagc 660
gatgggggcg gggggggggg gggggcgcgc gccaggcggg gcggggcggg gcgaggggcg 720
gggcggggcg aggcggagag gtgcggcggc agccaatcag agcggcgcgc tccgaaagtt 780
tccttttatg gcgaggcggc ggcggcggcg gccctataaa aagcgaagcg cgcggcgggc 840
gggagtcgct gcgcgctgcc ttcgccccgt gccccgctcc gccgccgcct cgcgccgccc 900
gccccggctc tgactgaccg cgttactccc acaggtgagc gggcgggacg gcccttctcc 960
tccgggctgt aattagcgct tggtttaatg acggcttgtt tcttttctgt ggctgcgtga 1020
aagccttgag gggctccggg agggcccttt gtgcgggggg agcggctcgg ggggtgcgtg 1080
cgtgtgtgtg tgcgtgggga gcgccgcgtg cggctccgcg ctgcccggcg gctgtgagcg 1140
ctgcgggcgc ggcgcggggc tttgtgcgct ccgcagtgtg cgcgagggga gcgcggccgg 1200
gggcggtgcc ccgcggtgcg gggggggctg cgaggggaac aaaggctgcg tgcggggtgt 1260
gtgcgtgggg gggtgagcag ggggtgtggg cgcgtcggtc gggctgcaac ccccccctgca 1320
ccccccctccc cgagttgctg agcacggccc ggcttcgggt gcggggctcc gtacggggcg 1380
tggcgcgggg ctcgccgtgc cgggcggggg gtggcggcag gtgggggtgc cgggcggggc 1440
ggggccgcct cgggccgggg agggctcggg ggaggggcgc ggcggccccc ggagcgccgg 1500
cggctgtcga ggcgcggcga gccgcagcca ttgcctttta tggtaatcgt gcgagagggc 1560
gcagggactt cctttgtccc aaatctgtgc ggagccgaaa tctgggaggc gccgccgcac 1620
cccctctagc gggcgcgggg cgaagcggtg cggcgccggc aggaaggaaa tgggcgggga 1680
gggccttcgt gcgtcgccgc gccgccgtcc ccttctccct ctccagcctc ggggctgtcc 1740
gcggggggac ggctgccttc ggggggggacg gggcagggcg gggttcggct tctggcgtgt 1800
gaccggcggc tctagagcct ctgctaacca tgttcatgcc ttcttctttt tcctacagct 1860
cctgggcaac gtgctggtta ttgtgctgtc tcatcatttt ggcaaagaat tcacgcgtgc 1920
tagcaaggat ccaccggtcg ccaccatgag cctgctgttc agccggtgca acagcatcgt 1980
gaccgtgaag aaaaacaagc ggcacatggc cgaagtgaac gcctctccac tgaagcactt 2040
cgtgaccgcc aagaagaaga tcaacggaat cttcgagcag ctgggcgcct acatccaaga 2100
gagcgccacc ttcctggaag atacctacag aaacgccgag ctggaccccg tgaccacaga 2160
ggaacaggtg ctggatgtga aggctacct gagcaaagtg cggggcatct ctgaagtgct 2220
ggccagacgg catatgaagg tggccttttt cggccggacc agcaacggca agagcaccgt 2280
gatcaatgcc atgctgtggg acaaagtgct gccctctgga atcggccaca ccaccaactg 2340
ctttctgaga gtggaaggca ccgacggcca cgaggcattt ctgctgacag agggctccga 2400
ggaaaagcgg agcgccaaga cagtgaacca gctggcccat gctctgcacc aggataagca 2460
gctgcatgcc ggaagcctgg tgtccgtgat gtggcccaat agcaagtgcc ctctgctgaa 2520
ggacgacctg gtgctgatgg atagccccgg gatcgatgtg accaccgaac tggacagctg 2580
gatcgacaag ttctgcctgg acgccgacgt gttcgtgctg gtggccaata gcgagagcac 2640
cctgatgcag accgagaagc actttttcca caaggtgtcc gagcggctga gcagacccaa 2700
tatctttatc ctgaacaaca gatgggacgc cagcgccagc gagcccgagt atatggaaga 2760
agtgcggcgg cagcatatgg aacggtgcac atcctttctg gtggacgagc tgggcgtcgt 2820
ggatagatct caggccggcg acagaatctt ctttgtgtcc gccaaagagg tgctgaacgc 2880
ccggattcag aaagcccagg gaatgcctga aggcggaggt gcactggccg agggatttca 2940
agtgcggatg ttcgagttcc agaacttcga gcggagattc gaggagtgca tcagccagag 3000
cgccgtcaag accaagttcg agcagcatac cgtgcgggcc aagcagattg ccgaagccgt 3060
cagactgatc atggacagcc tgcatatggc cgccagagag cagcaggtct actgcgagga 3120
aatgcgggaa gagagacagg accggctgaa gttcatcgac aagcagctgg aactgctggc 3180
ccaggactac aagctgcgga tcaagcagat caccgaagag gtggaaagac aggtgtccac 3240
cgctatggcc gaggaaatca gacggctgag cgtgctggtc gacgactacc agatggactt 3300
tcacccctct ccagtggtgc tgaaagtcta caaaaacgag ctgcaccggc acatcgagga 3360
aggcctgggc agaaacatga gcgacagatg cagcaccgcc atcaccaata gcctgcagac 3420
catgcagcag gacatgatcg acggcctgaa acctctgctg cctgtgtccg tcagatccca 3480
gatcgatatg ctggtgcccc ggcagtgctt tagcctgaac tacgacctga actgcgacaa 3540
gctgtgcgcc gatttccaag aggacatcga gtttcacttc agcctcggct ggacaatgct 3600
ggtcaacaga tttctgggcc ccaagaacag cagacgggcc ctgatgggct acaacgatca 3660
ggtgcagagg cccattcctc tgacacccgc caatcctagc atgcctccac tgcctcaggg 3720
cagcctgaca caagaggaat tcatggtgtc tatggtcacc ggcctggcca gcctgaccag 3780
cagaacatct atgggcatcc tggtcgtcgg cggcgttgtg tggaaagctg ttggctggcg 3840
gctgatcgcc ctgagctttg gcctgtatgg cctgctgtac gtgtacgaga gactgacctg 3900
gaccaccaag gccaaagagc gggccttcaa gcggcagttt gtggaacacg cctccgagaa 3960
actgcagctg gtgatcagct acaccggcag caattgcagc caccaggtgc agcaagagct 4020
gtccggaaca ttcgcccacc tgtgtcagca ggtcgacgtg accagagaga acctggaaca 4080
agagatcgcc gccatgaata agaaaatcga ggtgctcgac tccctgcaga gcaaggccaa 4140
gctgctgaga aacaaggccg gctggctgga cagcgagctg aatatgttca cccaccagta 4200
cctgcagcct agccgctaat aaagcggccg cctaaggctc gaggatcttt ttccctctgc 4260
caaaaattat ggggacatca tgaagcccct tgagcatctg acttctggct aataaaggaa 4320
atttattttc attgcaatag tgtgttggaa tttttttgtgt ctctcactcg gataaggatc 4380
ttcctagagc atggctacgt agataagtag catggcgggt taatcattaa ctacaaggaa 4440
cccctagtga tggagttggc cactccctct ctgcgcgctc gctcgctcac tgaggccggg 4500
cgaccaaagg tcgcccgacg cccgggcttt gcccgggcgg cctcagtgag cgagcgagcg 4560
cgcag 4565

```
SEQ ID NO: 80          moltype = AA  length = 757
FEATURE                Location/Qualifiers
REGION                 1..757
                       note = Synthetic Construct
source                 1..757
                       mol_type = protein
                       organism = synthetic construct
SEQUENCE: 80
MSLLFSRCNS IVTVKKNKRH MAEVNASPLK HFVTAKKKIN GIFEQLGAYI QESATFLEDT  60
YRNAELDPVT TEEQVLDVKG YLSKVRGISE VLARRHMKVA FFGRTSNGKS TVINAMLWDK  120
VLPSGIGHTT NCFLRVEGTD GHEAFLLTEG SEEKRSAKTV NQLAHALHQD KQLHAGSLVS  180
VMWPNSKCPL LKDDLVLMDS PGIDVTTELD SWIDKFCLDA DVFVLVANSE STLMQTEKHF  240
FHKVSERLSR PNIFILNNRW DASASEPEYM EEVRRQHMER CTSFLVDELG VVDRSQAGDR  300
IFFVSAKEVL NARIQKAQGM PEGGGALAEG FQVRMFEFQN FERRFEECIS QSAVKTKFEQ  360
HTVRAKQIAE AVRLIMDSLH MAAREQQVYC EEMREERQDR LKFIDKQLEL LAQDYKLRIK  420
QITEEVERQV STAMAEEIRR LSVLVDDYQM DFHPSPVVLK VYKNELHRHI EEGLGRNMSD  480
RCSTAITNSL QTMQQDMIDG LKPLLPVSVR SQIDMLVPRQ CFSLNYDLNC DKLCADFQED  540
IEFHFSLGWT MLVNRFLGPK NSRRALMGYN DQVQRPIPLT PANPSMPPLP QGSLTQEEFM  600
VSMVTGLASL TSRTSMGILV VGGVVWKAVG WRLIALSFGL YGLLYVYERL TWTTKAKERA  660
FKRQFVEHAS EKLQLVISYT GSNCSHQVQQ ELSGTFAHLC QQVDVTRENL EQEIAAMNKK  720
IEVLDSLQSK AKLLRNKAGW LDSELNMFTH QYLQPSR                          757

SEQ ID NO: 81          moltype = DNA  length = 2211
FEATURE                Location/Qualifiers
source                 1..2211
                       mol_type = other DNA
                       organism = adeno-associated virus hu68
CDS                    1..2211
                       note = AAVhu68
                       protein_id = 82
                       translation = MAADGYLPDWLEDNLSEGIREWWALKPGAPQPKANQQHQDNARGLV
                        LPGYKYLGPGNGLDKGEPVNEADAAALEHDKAYDQQLKAGDNPYLKYNHADAEFQERLK
                        EDTSFGGNLGRAVFQAKKRLLEPLGLVEEAAKTAPGKKRPVEQSPQEPDSSVGIGKSGA
                        QPAKKRLNFGQTGDTESVPDPQPIGEPPAAPSGVGSLTMASGGGAPVADNNEGADGVGS
                        SSGNWHCDSQWLGDRVITTSTRTWALPTYNNHLYKQISNSTSGGSSNDNAYFGYSTPWG
                        YFDFNRFHCHFSPRDWQRLINNNWGFRPKRLNFKLFNIQVKEVTDNNGVKTIANNLTST
                        VQVFTDSDYQLPYVLGSAHEGCLPPFPADVFMIPQYGYLTLNDGSQAVGRSSFYCLEYF
                        PSQMLRTGNNFQFSYEFENVPFHSSYAHSQSLDRLMNPLIDQYLYYLSKTINGSGQNQQ
                        TLKFSVAGPSNMAVQGRNYIPGPSYRQQRVSTTVTQNNNSEFAWPGASSWALNGRNSLM
                        NPGPAMASHKEGEDRFFPLSGSLIFGKQGTGRDNVDADKVMITNEEEIKTTNPVATESY
                        GQVATNHQSAQAQAQTGWVQNQGILPGMVWQDRDVYLQGPIWAKIPHTDGNFHPSPLMG
                        GFGMKHPPPQILIKNTPVPADPPTAFNKDKLNSFITQYSTGQVSVEIEWELQKENSKRW
                        NPEIQYTSNYYKSNNVEFAVNTEGVYSEPRPIGTRYLTRNL
SEQUENCE: 81
atggctgccg atggttatct tccagattgg ctcgaggaca acctcagtga aggcattcgc  60
gagtggtggg ctttgaaacc tggagcccct caacccaagg caaatcaaca acatcaagac  120
aacgctcggg gtcttgtgct tccgggttac aaataccttg gacccggcaa cggactcgac  180
aagggggagc cggtcaacga agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgt gggtattggc  480
aaatcgggtg cacagcccgc taaaaagaga ctcaatttcg gtcagactgg cgacacagag  540
tcagtccccg accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcaaaga  900
ctcatcaaca acaactgggg attccggcct aagcgactca acttcaagct cttcaacatt  960
caggtcaaag aggttacgga caacaatgga gtcaagacca tcgctaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatcta  1140
acgcttaatg atggaagcca agccgtgggt cgttcgtcct tttactgcct ggaatatttc  1200
ccgtcgcaaa tgctaagaac gggtaacaac ttccagttca gctacgagtt tgagaacgta  1260
cctttccata gcagctatgc tcacagccaa agcctggacc gactcatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactaccaac ccagtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gctttcaaca aggacaagct gaactctttc atcacccagt attctactgg ccaagtcagc  2040
gtggagattg agtgggagct gcagaaggaa aacagcaagc gctggaaccc ggagatccag  2100
```

```
tacacttcca actattacaa gtctaataat gttgaatttg ctgttaatac tgaaggtgtt  2160
tattctgaac cccgccccat tggcaccaga tacctgactc gtaatctgta a           2211

SEQ ID NO: 82          moltype = AA  length = 736
FEATURE                Location/Qualifiers
source                 1..736
                       mol_type = protein
                       note = translation of SEQ ID NO: 81
                       organism = adeno-associated virus hu68
SEQUENCE: 82
MAADGYLPDW LEDNLSEGIR EWWALKPGAP QPKANQQHQD NARGLVLPGY KYLGPGNGLD  60
KGEPVNEADA AALEHDKAYD QQLKAGDNPY LKYNHADAEF QERLKEDTSF GGNLGRAVFQ  120
AKKRLLEPLG LVEEAAKTAP GKKRPVEQSP QEPDSSVGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 83          moltype = DNA  length = 2211
FEATURE                Location/Qualifiers
source                 1..2211
                       mol_type = other DNA
                       organism = adeno-associated virus hu68
SEQUENCE: 83
atggctgccg atggttatct tccagattgg ctcgaggaca acctcagtga aggcattcgc  60
gagtggtggg ctttgaaacc tggagcccct caacccaagg caaatcaaca acatcaagac  120
aacgctcggg gtcttgtgct tccgggttac aaataccttg gacccggcaa cggactcgac  180
aagggggagc cggtcaacga agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgt gggtattggc  480
aaatcgggtg cacagcccgc taaaaagaga ctcaatttcg gtcagactgg cgacacagag  540
tcagtccccg accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcaaaga  900
ctcatcaaca acaactgggg attccggcct aagcgactca acttcaagct cttcaacatt  960
caggtcaaag aggttacgga caacaatgga gtcaagacca tcgctaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta tggatacctc  1140
accctgaacg acggcagtca ggcggtgggc cgctcatcct tctactgcct ggagtacttc  1200
ccttcgcaga tgctgaggac tggcaacaac ttccagttca gctacgagtt cgagaacgtc  1260
cctttccaca gcagctacgc ccacagccag agtttggacc gcttgatgaa ccctctgatc  1320
gaccagtacc tgtactacct gtcaaagacg atcaacggtt ctggccagaa ccagcagacg  1380
ctgaagttca gcgtggccgg gcctagcaac atggccgtcc agggcagaaa ctacatccct  1440
gggcccagct accggcagca gagagtctca accactgtga ctcagaacaa caacagtgag  1500
ttcgcctggc ctggcgccag ctcttgggcc ctcaacggcc gcaactcgct gatgaaccca  1560
ggcccagcca tggccagtca caaggagggc gaggaccgtt tcttcccttt gtctggctct  1620
ctgatcttcg gcaagcaggg gaccggcaga gacaacgtgg acgcggacaa ggtcatgatc  1680
acgaacgagg aggagatcaa gaccaccaac cctgtggcaa ccgagtccta cggccaggtg  1740
gcaaccaacc accagagcgc ccaggcacag gcgcagactg gctgggtcca gaaccagggg  1800
atcctgcctg gcatggtgtg gcaggaccgt gacgtgtacc tgcagggccc tatctgggca  1860
aagatccctc acacggacgg caacttccac ccttctcctc tgatgggcgg cttcggcatg  1920
aagcacccgc ctcctcagat cctcatcaag aacactccgg tcccggcaga ccctccgacg  1980
gccttcaaca aggacaagct gaactcattc atcactcagt actccactgg ccaggtcagc  2040
gtggagatcg agtgggagct gcagaaggag aacagcaagc gttggaaccc agagatccag  2100
tacacttcca actactacaa gtctaacaac gtggagttcg ccgtcaacac tgagggtgtg  2160
tacagtgagc ctcgccctat cggcacccgg tacctcaccc gaaacttgtg a           2211

SEQ ID NO: 84          moltype = DNA  length = 2229
FEATURE                Location/Qualifiers
source                 1..2229
                       mol_type = other DNA
                       organism = adeno-associated virus PHP.eB
CDS                    1..2229
                       note = AAV-PHP.eB
                       protein_id = 85
                       translation = MAADGYLPDWLEDNLSEGIREWWALKPGAPQPKANQQHQDNARGLV
                        LPGYKYLGPGNGLDKGEPVNAADAAALEHDKAYDQQLKAGDNPYLKYNHADAEFQERLK
                        EDTSFGGNLGRAVFQAKKRLLEPLGLVEEAAKTAPGKKRPVEQSPQEPDSSAGIGKSGA
```

```
                            QPAKKRLNFGQTGDTESVPDPQPIGEPPAAPSGVGSLTMASGGGAPVADNNEGADGVGS
                            SSGNWHCDSQWLGDRVITTSTRTWALPTYNNHLYKQISNSTSGGSSNDNAYFGYSTPWG
                            YFDFNRFHCHFSPRDWQRLINNNWGFRPKRLNFKLFNIQVKEVTDNNGVKTIANNLTST
                            VQVFTDSDYQLPYVLGSAHEGCLPPFPADVFMIPQYGYLTLNDGSQAVGRSSFYCLEYF
                            PSQMLRTGNNFQFSYEFENVPFHSSYAHSQSLDRLMNPLIDQYLYYLSRTINGSGQNQQ
                            TLKFSVAGPSNMAVQGRNYIPGPSYRQQRVSTTVTQNNNSEFAWPGASSWALNGRNSLM
                            NPGPAMASHKEGEDRFFPLSGSLIFGKQGTGRDNVDADKVMITNEEEIKTTNPVATESY
                            GQVATNHQSDGTLAVPFKAQAQTGWVQNQGILPGMVWQDRDVYLQGPIWAKIPHTDGNF
                            HPSPLMGGFGMKHPPPQILIKNTPVPADPPTAFNKDKLNSFITQYSTGQVSVEIEWELQ
                            KENSKRWNPEIQYTSNYYKSNNVEFAVNTEGVYSEPRPIGTRYLTRNL
SEQUENCE: 84
atggctgccg atggttatct tccagattgg ctcgaggaca accttagtga aggaattcgc  60
gagtggtggg ctttgaaacc tggagcccct caacccaagg caaatcaaca acatcaagac  120
aacgctagag gtcttgtgct tccgggttac aaataccttg gacccggcaa cggactcgac  180
aagggggagc cggtcaacgc agcagacgcg gcggccctcg agcacgacaa agcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct ctttaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctctagaact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggcctctca caaagaagga gaggaccgtt tctttccttt gtctggatct  1620
ttaatttttg gcaaacaagg tactggcaga gacaacgtgg atgcggacaa agtcatgata  1680
accaacgaag aagaaattaa aactactaac ccggtagcaa cggagtccta tggacaagtg  1740
gccacaaacc accagagtga tgggactttg gcggtgcctt ttaaggcaca ggcgcagacc  1800
ggttgggttc aaaaccaagg aatacttccg ggtatggttt ggcaggacag agatgtgtac  1860
ctgcaaggac ccatttgggc caaaattcct cacacggacg gcaactttca cccttctccg  1920
ctgatgggag ggtttggaat gaagcacccg cctcctcaga tcctcatcaa aaacacacct  1980
gtacctgcgg atcctccaac ggccttcaac aaggacaagc tgaactcttt catcacccag  2040
tattctactg gtcaagtcag cgtggagatc gagtgggagc tgcagaagga aaacagcaag  2100
cgctggaacc cggagatcca gtacacttcc aactattaca agtctaataa tgttgaattt  2160
gctgttaata ctgaaggtgt atatagtgaa ccccgcccca ttggcaccag atacctgact  2220
cgtaatctg                                                          2229

SEQ ID NO: 85          moltype = AA  length = 743
FEATURE                Location/Qualifiers
source                 1..743
                       mol_type = protein
                       note = translation of SEQ ID NO: 84
                       organism = adeno-associated virus PHP.eB
SEQUENCE: 85
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSDGTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                          743

SEQ ID NO: 86          moltype = DNA  length = 584
FEATURE                Location/Qualifiers
misc_feature           1..584
                       note = CB7 Promoter with CMV enhancer
source                 1..584
                       mol_type = other DNA
                       organism = synthetic construct
SEQUENCE: 86
```

```
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttaatt attttgtgca gcgatggggg cggggggggg  420
gggggggcgc gcgccaggcg gggcggggcg gggcgagggg cggggcgggg cgaggcggag  480
aggtgcggcg gcagccaatc agagcggcgc gctccgaaag tttcctttta tggcgaggcg  540
gcggcggcgg cggccctata aaaagcgaag cgcgcggcgg gcgg                584

SEQ ID NO: 87          moltype = DNA  length = 841
FEATURE                Location/Qualifiers
misc_feature           1..841
                       note = CAG promoter
source                 1..841
                       mol_type = other DNA
                       organism = synthetic construct
SEQUENCE: 87
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
cgctgccttc gccccgtgcc ccgctccgcc gccgcctcgc gccgcccgcc ccggctctga  600
ctgaccgcgt tactcccaca ggtgagcggg cgggacggcc cttctcctcc gggctgtaat  660
tagcgcttgg tttaatgacg gcttgtttct tttctgtggc tgcgtgaaag ccttgagggg  720
ctccgggagg gccctttgtg cggggggagc ggctcggggc tgtccgcggg gggacggctg  780
ccttcggggg ggacggggca gggcggggtt cggcttctgg cgtgtgaccg gcggctctag  840
a                                                                841

SEQ ID NO: 88          moltype = DNA  length = 127
FEATURE                Location/Qualifiers
misc_feature           1..127
                       note = rabbit beta-globin
source                 1..127
                       mol_type = other DNA
                       organism = synthetic construct
SEQUENCE: 88
gatctttttc cctctgccaa aaattatggg gacatcatga agccccttga gcatctgact  60
tctggctaat aaaggaaatt tattttcatt gcaatagtgt gttggaattt tttgtgtctc  120
tcactcg                                                          127

SEQ ID NO: 89          moltype = DNA  length = 59
FEATURE                Location/Qualifiers
misc_feature           1..59
                       note = miR538
source                 1..59
                       mol_type = other DNA
                       organism = synthetic construct
SEQUENCE: 89
ttgacgtcca gaacctgttc tgttttggcc actgactgac agaacaggct ggacgtcaa   59

SEQ ID NO: 90          moltype = DNA  length = 82
FEATURE                Location/Qualifiers
misc_feature           1..82
                       note = linker
source                 1..82
                       mol_type = other DNA
                       organism = synthetic construct
SEQUENCE: 90
taaagcggcc gcaagcttgc acccgtacct ttgggagcgc gcgccctcgt cgtgtcgtga  60
cgtcacccgt tctgttggat cc                                         82

SEQ ID NO: 91          moltype = DNA  length = 4233
FEATURE                Location/Qualifiers
misc_feature           1..4233
                       note = Expression cassette Syn.PI.hMfn2o.link.hMfn2
                        miR1693.WPRE.bGH
regulatory             1..460
                       note = promoter - hSyn Promoter
                       regulatory_class = promoter
misc_feature           472..604
                       note = Intron - Promega Chimeric Intron
misc_feature           635..640
```

```
                        note = Kozak
misc_feature            641..2914
                        note = human engineered Mfn2
misc_feature            3008..3030
                        note = 5' flank
misc_feature            3031..3094
                        note = hMfn2 miR1693
misc_feature            3095..3138
                        note = 3' flank
misc_feature            3241..3823
                        note = WPRE
misc_feature            4188..4233
                        note = AAV seq
source                  1..4233
                        mol_type = other DNA
                        organism = synthetic construct
SEQUENCE: 91
tcgagctgca gagggccctg cgtatgagtg caagtgggtt ttaggaccag gatgaggcgg  60
ggtgggggtg cctacctgac gaccgacccc gacccactgg acaagcaccc aacccccatt  120
ccccaaattg cgcatcccct atcagagagg gggaggggaa acaggatgcg gcgaggcgcg  180
tgcgcactgc cagcttcagc accgcggaca gtgccttcgc ccccgcctgg cggcgcgcgc  240
caccgccgcc tcagcactga aggcgcgctg acgtcactcg ccggtccccc gcaaactccc  300
cttcccggcc accttggtcg cgtccgcgcc gccgccggcc cagccggacc gcaccacgcg  360
aggcgcgaga tagggggggca cggcgcgcgac catctgcgct gcggcgccgg cgactcagcg  420
ctgcctcagt ctgcggtggg cagcggagga gtcgtgtcgt gcctgagagc ggtaagtatc  480
aaggttacaa gacaggttta aggagaccaa tagaaactgg gcttgtcgag acagagaaga  540
ctcttgcgtt tctgataggc acctattggt cttactgaca tccactttgc ctttctctcc  600
acagtacgta gaattcacgc gtgctagcac cggtgccacc atgagcctgc tgttcagccg  660
gtgcaacagc atcgtgaccg tgaagaaaaa caagcggcac atggccgaag tgaacgcctc  720
tccactgaag cacttcgtga ccgccaagaa gaagatcaac ggcatcttcg agcagctggg  780
cgcctacatc caagagagcg ccaccttcct ggaagatacc tacagaaacg ccgagctgga  840
ccccgtgacc acagaggaac aggtgctgga tgtgaagggc tacctgagca aagtgcgggg  900
catctctgaa gtgctggcca gacggcatat gaaggtggcc tttttcggcc ggaccagcaa  960
cggcaagagc accgtgatca atgccatgct gtgggacaaa gtgctgccct ctggaatcgg  1020
ccacaccacc aactgctttc tgagagtgga aggcaccgac ggccacgagg catttctgct  1080
gacagagggc tccgaggaaa agcggagcgc caagacagtg aaccagctgg cccatgctct  1140
gcaccaggat aagcagctgc atgccggaag cctggtgtcc gtgatgtggc ccaatagcaa  1200
gtgccctctg ctgaaggacg acctggtgct gatggatagc cccgggatcg atgtgaccac  1260
cgaactggac agctggatcg acaagttctg cctggacgcc gacgtgttcg tgctggtggc  1320
caatagcgag agcaccctga tgcagaccga gaagcacttt ttccacaagg tgtccgagcg  1380
gctgagcaga cccaatatct ttatcctgaa caacagatgg gacgccagcg ccagcgagcc  1440
cgagtatatg gaagaagtgc ggcggcagca tatggaacgg tgcacatcct ttctggtgga  1500
cgagctgggc gtcgtggata gatctcaggc cggcgacaga atcttctttg tgtccgccaa  1560
agaggtgctg aacgcccgga ttcagaaagc ccagggaatg cctgaaggcg gaggtgcact  1620
ggccgaggga tttcaagtgc ggatgttcga gttccagaac ttcgagcgga gattcgagga  1680
gtgcatcagc cagagcgccg tcaagaccaa gttcgagcag cataccgtgc gggccaagca  1740
gattgccgaa gccgtcagac tgatcatgga cagcctgcat atggccgcca gagagcagca  1800
ggtctactgc gaggaaatgc gggaagagag acaggaccgg ctgaagttca tcgacaagca  1860
gctggaactg ctggcccagg actacaagct gcggatcaag cagatcaccg aagaggtgga  1920
aagacaggtg tccaccgcta tggccgagga aatcagacgg ctgagcgtgc tggtcgacga  1980
ctaccagatg gactttcacc cctctccagt ggtgctgaaa gtctacaaaa acgagctgca  2040
ccggcacatc gaggaaggcc tgggcagaaa catgagcgac agatgcagca ccgccatcac  2100
caatagcctg cagaccatgc agcaggacat gatcgacggc ctgaaacctc tgctgcctgt  2160
gtccgtcaga tcccagatcg atatgctggt gccccggcag tgctttagcc tgaactacga  2220
cctgaactgc gacaagctgt gcgccgattt ccaagaggac atcgagtttc acttcagcct  2280
cggctggaca atgctggtca acagatttct gggccccaag aacagcagac gggccctgat  2340
gggctacaac gatcaggtgc agaggcccat tcctctgaca cccgccaatc ctagcatgcc  2400
tccactgcct cagggcagcc tgacacaaga ggaattcatg gtgtctatgg tcaccggcct  2460
ggccagcctg accagcagaa catctatggg catcctggtc gtcggcggcg ttgtgtggaa  2520
agctgttggc tggcggctga tcgccctgag ctttggcctg tatggcctgc tgtacgtgta  2580
cgagagactg acctggacca ccaaggccaa agagcgggcc ttcaagcggc agtttgtgga  2640
acacgcctcc gagaaactgc agctggtgat cagctacacc ggcagcaatt gcagccacca  2700
ggtgcagcaa gagctgtccg gaacattcgc ccacctgtgt cagcaggtcg acgtgaccag  2760
agagaacctg gaacaagaga tcgccgccat gaataagaaa atcgaggtgc tcgactccct  2820
gcagagcaag gccaagctgc tgagaaacaa ggccggctgg ctggacagcg agctgaatat  2880
gttcacccac cagtacctgc agcctagccg ctaataatgt acaagtaaag cgcccgcagg  2940
cttgcacccg tacctttggg agcgcgcgcc ctcgtcgtgt cgtgacgtca cccgttctgt  3000
tggatccctg gaggcttgct gaaggctgta tgctgttctt ataaaccttg aggactgttt  3060
tggccactga ctgacagtcc tcagttttata agaacaggac acaaggcctg ttactagcac  3120
tcacatggaa caaatggccc agatctaggg tggggccacc tgccggtagg tgtgcggtag  3180
gcttttctcc gtcgcaggac gcagggttcg ggcctagctt aagcttctcg agatcgataa  3240
tcaacctctg gattacaaaa tttgtgaaag attgactggt attcttaact atgttgctcc  3300
ttttacgcta tgtggatacg ctgctttaat gcctttgtat catgctattg cttcccgtat  3360
ggctttcatt ttctcctcct tgtataaatc ctggttgctg tctctttatg aggagttgtg  3420
gcccgttgtc aggcaacgtg gcgtggtgtg cactgtgttt gctgacgcaa cccccactgg  3480
ttggggcatt gccaccacct gtcagctcct ttccgggact ttcgctttcc ccctccctat  3540
tgccacggcg gaactcatcg ccgcctgcct tgcccgctgc tggacagggg ctcggctgtt  3600
gggcactgac aattccgtgg tgttgtcggg gaaatcatcg tcctttcctt ggctgctcgc  3660
ctgtgttgcc acctggattc tgcgcgggac gcccttctgc tacgtccctt cggccctcaa  3720
```

```
tccagcggac cttccttccc gcggcctgct gccggctctg cggcctcttc cgcgtcttcg  3780
ccttcgccct cagacgagtc ggatctccct ttgggccgcc tccccgcctg ctgatcgccc  3840
tgagcctggc cctggtgacc aacagccagg tgcaattgct agagtcgact ctagagcggc  3900
cgcctaaggc tcgactagag ctcgctgatc agcctcgact gtgccttcta gttgccagcc  3960
atctgttgtt tgcccctccc ccgtgccttc cttgaccctg gaaggtgcca ctcccactgt  4020
cctttcctaa taaaatgagg aaattgcatc gcattgtctg agtaggtgtc attctattct  4080
ggggggtggg gtggggcagg acagcaaggg ggaggattgg gaagacaata gcaggcatgc  4140
tggggactcg agttaagggc gaattcccga taaggatctt cctagagcat ggctacgtag  4200
ataagtagca tggcgggtta atcattaact aca                                4233
```

```
SEQ ID NO: 92          moltype = DNA  length = 4208
FEATURE                Location/Qualifiers
misc_feature           1..4208
                       note = Expression cassette Syn.PI.rMnf2o.link.rMfn2 miR1518
                        WPRE.BGH
regulatory             1..460
                       note = promoter - hSyn promoter
                       regulatory_class = promoter
misc_feature           472..604
                       note = Intron - Promega Chimeric Intron
misc_feature           641..2911
                       note = engineered human Mfn2
misc_feature           2918..3007
                       note = linker
misc_feature           3008..3030
                       note = 5' flank
misc_feature           3031..3094
                       note = miR1518
misc_feature           3095..3138
                       note = 3' flank
misc_feature           3235..3822
                       note = WPRE
misc_feature           4163..4208
                       note = AAV seq
source                 1..4208
                       mol_type = other DNA
                       organism = synthetic construct
SEQUENCE: 92
tcgagctgca gagggccctg cgtatgagtg caagtgggtt ttaggaccag gatgaggcgg  60
ggtgggggtg cctacctgac gaccgacccc gacccactgg acaagcaccc aacccccatt  120
ccccaaattg cgcatcccct atcagagagg gggaggggaa acaggatgcg gcgaggcgcg  180
tgcgcactgc cagcttcagc accgcggaca gtgccttcgc ccccgcctgg cggcgcgcgc  240
caccgccgcc tcagcactga aggcgcgctg acgtcactcg ccggtccccc gcaaactccc  300
cttcccggcc accttggtcg cgtccgcgcc gccgccggcc cagccggacc gcaccacgcg  360
aggcgcgaga tagggggggca cgggcgcgac catctgcgct gcggcgccgg cgactcagcg  420
ctgcctcagt ctgcggtggg cagcggagga gtcgtgtcgt gcctgagagc ggtaagtatc  480
aaggttacaa gacaggttta aggagaccaa tagaaactgg gcttgtcgag acagagaaga  540
ctcttgcgtt tctgataggc acctattggt cttactgaca tccactttgc ctttctctcc  600
acagtacgta gaattcacgc gtgctagcac cggtgccacc atgtctctgc tgttcagccg  660
gtgcaacagc atcgtgaccg tgaagaaaga caagaggcac atggccgaag tgaacgcctc  720
tccactgaag cacttcgtga ccgccaagaa gaagatcaac ggcatcttcg agcagctggg  780
cgcctacatc caagagtctg ccggcttcct ggaagatacc cacagaaaca ccgagctgga  840
ccccgtgacc acagaggaac aggtgctgga cgtgaagggc tacctgtcta aagtgcgggg  900
catcagcgag gtgctggcta gaaggcatat gaaggtggcc tttttcggca ggaccagcaa  960
cggcaagagc accgtgatca acgccatgct gtgggacaaa gtgctgcctt ctggcatcgg  1020
ccacaccacc aactgctttc tgagagtcgg cggcacagac ggccacgagg ctttttttgct  1080
gaccgagggc tccgaagaga agaaatccgt gaaaaccgtg aaccagctgg cccacgctct  1140
gcaccaggat gaacaactgc acgccggaag cctggtgtcc gtgatgtggc ctaacagcaa  1200
gtgccctctg ctgaaggacg acctggtgct gatggactct cctggaatcg acgtgaccac  1260
tgagctggac agctggatcg acaagttctg cctggacgcc gacgtgttcg tgctggtggc  1320
taactctgag agcaccctga tgcagaccga gaagcagttc ttccacaagg tgtccgagag  1380
gctgagcagg cccaatatct ttatcctgaa caacagatgg gacgccagcg ccagcgagcc  1440
cgagtatatg gaagaagtgc ggaggcagca tatggaaagg tgtaccagct tcctggtgga  1500
cgagctggga gtcgtggata gagcacaggc cggcgacaga atcttcttcg tgtctgccaa  1560
agaggtgctg agcgccaggg tgcagaaagc ccagggaatg cctgaaggcg gcggagcttt  1620
ggccgaggga tttcaagtgc ggatgttcga gttccagaac ttcgagcgga gattcgagga  1680
atgcatcagc cagagcgccg tcaagacaaa gttcgagcag cacacagtgc gggccaagca  1740
gatcgctgag gctgtgcggc tgatcatgga cagcctgcat atcgccgctc aagagcagag  1800
ggtgtactgc ctggaaatgc gggaagagag gcaggacagg ctgagattca tcgacaagca  1860
gctggaactg ctggcccagg actacaagct gaggatcaag cagatgaccg aagaggtgga  1920
aagacaggtg tccaccgcca tggccgagga aatccgtaga ctgtctgtgc tggtcgacga  1980
gtaccagatg gactttcacc cctctccagt ggtgctgaag gtctacaaaa acgagctgca  2040
caggcacatc gaggaaggcc tgggcagaaa catgagcgac aggtgctcta ccgctatcgc  2100
cagcagcctg cagacaatgc agcaggacat gatcgacggc ctgaagcctc tgctgcctgt  2160
gtctgtgcgg aaccagatcg atatgctggt gcccaggcag tgcttctccc tgtcctacga  2220
cctgaactgc gacaagctgt gtgccgactt ccaagaggac atcgagtttc acttcagcct  2280
cggctggaca atgctggtca acagattcct gggacctaag aactccagac gggccctgct  2340
gggatacaac gatcaggtgc aaaggcccct gcctctgaca ccagctaacc cttctatgcc  2400
tcctctgcct caaggctctc tgacccaaga ggaactgatg gtgtccatgg tcacaggcct  2460
```

-continued

```
ggcttccctg accagcagaa cctctatggg catcctggtc gtcggcggag ttgtgtggaa  2520
agctgttggc tggcgcctga tcgccctgag ctttggactg tacggactgc tgtacgtgta  2580
cgagagactg acctggacca ccagggccaa agagagggcc ttcaagaggc agttcgtgga  2640
atacgcctcc gagaaactgc agctgattat ctcctacacc ggcagcaact gcagccacca  2700
ggtgcagcaa gagctgtctg gaacattcgc ccacctgtgc cagcaggtcg acatcaccag  2760
agacaacctg gaacaagaga tcgccgctat gaataagaag gtggaagccc tggactccct  2820
gcagagcaag gctaagctgc tgagaaacaa ggccggctgg ctggactccg agctgaatat  2880
gtttatccac cagtacctgc agcctagccg ctgatgatgt acaagtaaag cggccgcaag  2940
cttgcacccg tacctttggg agcgcgcgcc ctcgtcgtgt cgtgacgtca cccgttctgt  3000
tggatccctg gaggcttgct gaaggctgta tgctgttctt ataaaccttg aggacagttt  3060
tggccactga ctgactgtcc tcagtttata agaacaggac acaaggcctg ttactagcac  3120
tcacatggaa caaatggccc agatctaggg tggggccacc tgccggtagg tgtgcggtag  3180
gcttttctcc gtcgcaggac gcagggttcg ggcctagctt ctcgagatcg ataatcaacc  3240
tctggattac aaaatttgtg aaagattgac tggtattctt aactatgttg ctccttttac  3300
gctatgtgga tacgctgctt taatgccttt gtatcatgct attgcttccc gtatggcttt  3360
cattttctcc tccttgtata aatcctggtt gctgtctctt tatgaggagt tgtggcccgt  3420
tgtcaggcaa cgtggcgtgg tgtgcactgt gtttgctgac gcaaccccca ctggttgggg  3480
cattgccacc acctgtcagc tcctttccgg gactttcgct ttccccctcc ctattgccac  3540
ggcggaactc atcgccgcct gccttgcccg ctgctggaca ggggctcggc tgttgggcac  3600
tgacaattcc gtggtgttgt cggggaaatc atcgtccttt ccttggctgc tcgcctgtgt  3660
tgccacctgg attctgcgcg ggacgtcctt ctgctacgtc ccttcggccc tcaatccagc  3720
ggaccttcct tcccgcggcc tgctgccggc tctgcggcct cttccgcgtc ttcgccttcg  3780
ccctcagacg agtcggatct ccctttgggc cgcctccccg cctgctgatc gccctgagcc  3840
tggccctggt gaccaacagc caggtgcaat tgaagctttc tagagtcgac tagagctcgc  3900
tgatcagcct cgactgtgcc ttctagttgc cagccatctg ttgtttgccc ctcccccgtg  3960
ccttccttga ccctggaagg tgccactccc actgtccttt cctaataaaa tgaggaaatt  4020
gcatcgcatt gtctgagtag gtgtcattct attctggggg gtggggtggg gcaggacagc  4080
aagggggagg attgggaaga caatagcagg catgctgggg actcgagtta agggcgaatt  4140
cccgataagg atcttcctag agcatggcta cgtagataag tagcatggcg ggttaatcat  4200
taactaca                                                           4208

SEQ ID NO: 93           moltype = DNA  length = 4283
FEATURE                 Location/Qualifiers
misc_feature            1..4283
                        note = Expression cassette
                         CAG.CI.hMfn2.GA.link.miR538.WPRE.SV40
misc_feature            1..841
                        note = CAG (CBA)
regulatory              248..529
                        note = promoter - CB promoter
                        regulatory_class = promoter
misc_feature            529..936
                        note = Intron - Hybrid intron in CAG
misc_feature            967..972
                        note = Kozak
misc_feature            973..3246
                        note = human engineered Mfn2
misc_feature            3247..3328
                        note = linker
misc_feature            3329..3356
                        note = 5' flank
misc_feature            3357..3377
                        note = miR538
misc_feature            3378..3396
                        note = 3' flank
misc_feature            3487..4075
                        note = WPRE
misc_feature            4164..4283
                        note = SV40 polyA
source                  1..4283
                        mol_type = other DNA
                        organism = synthetic construct
SEQUENCE: 93
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
cgctgccttc gccccgtgcc ccgctccgcc gccgcctcgc gccgcccgcc ccggctctga  600
ctgaccgcgt tactcccaca ggtgagcggg cgggacggcc cttctcctcc gggctgtaat  660
tagcgcttgg tttaatgacg gcttgtttct tttctgtggc tgcgtgaaag ccttgagggg  720
ctccgggagg gccctttgtg cggggggagc ggctcggggc tgtccgcggg gggacggctg  780
ccttcggggg ggacggggca gggcggggtt cggcttctgg cgtgtgaccg gcggctctag  840
agcctctgct aaccatgttc atgccttctt ctttttccta cagctcctgg gcaacgtgct  900
ggttattgtg ctgtctcatc atttggcaaa agaattggat cccgtacgac gcgtgctagc  960
```

```
accggtgcca ccatgagcct gctgttcagc cggtgcaaca gcatcgtgac cgtgaagaaa  1020
aacaagcggc acatggccga agtgaacgcc tctccactga agcacttcgt gaccgccaag  1080
aagaagatca acggcatctt cgagcagctg ggcgcctaca tccaagagag cgccaccttc  1140
ctggaagata cctacagaaa cgccgagctg gaccccgtga ccacagagga acaggtgctg  1200
gatgtgaagg gctacctgag caaagtgcgg ggcatctctg aagtgctggc cagacggcat  1260
atgaaggtgg cctttttcgg ccggaccagc aacggcaaga gcaccgtgat caatgccatg  1320
ctgtgggaca aagtgctgcc ctctggaatc ggccacacca ccaactgctt tctgagagtg  1380
gaaggcaccg acggccacga ggcatttctg ctgacagagg gctccgagga aaagcggagc  1440
gccaagacag tgaaccagct ggcccatgct ctgcaccagg ataagcagct gcatgccgga  1500
agcctggtgt ccgtgatgtg gcccaatagc aagtgccctc tgctgaagga cgacctggtg  1560
ctgatggata gccccgggat cgatgtgacc accgaactgg acagctggat cgacaagttc  1620
tgcctggacg ccgacgtgtt cgtgctggtg gccaatagcg agagcaccct gatgcagacc  1680
gagaagcact tttccacaa ggtgtccgag cggctgagca gacccaatat ctttatcctg  1740
aacaacagat gggacgccag cgccagcgag cccgagtata tggaagaagt gcggcggcag  1800
catatggaac ggtgcacatc ctttctggtg gacgagctgg gcgtcgtgga tagatctcag  1860
gccggcgaca gaatcttctt tgtgtccgcc aaagaggtgc tgaacgcccg gattcagaaa  1920
gcccagggaa tgcctgaagg cggaggtgca ctggccgagg gatttcaagt gcggatgttc  1980
gagttccaga acttcgagcg gagattcgag gagtgcatca gccagagcgc cgtcaagacc  2040
aagttcgagc agcataccgt gcgggccaag cagattgccg aagccgtcag actgatcatg  2100
gacagcctgc atatggccgc cagagagcag caggtctact gcgaggaaat gcgggaagag  2160
agacaggacc ggctgaagtt catcgacaag cagctggaac tgctggccca ggactacaag  2220
ctgcggatca agcagatcac cgaagaggtg gaaagacagg tgtccaccgc tatggccgag  2280
gaaatcagac ggctgagcgt gctggtcgac gactaccaga tggactttca cccctctcca  2340
gtggtgctga aagtctacaa aaacgagctg caccggcaca tcgaggaagg cctgggcaga  2400
aacatgagcg acagatgcag caccgccatc accaatagcc tgcagaccat gcagcaggac  2460
atgatcgacg gcctgaaacc tctgctgcct gtgtccgtca gatcccagat cgatatgctg  2520
gtgccccggc agtgctttag cctgaactac gacctgaact gcgacaagct gtgcgccgat  2580
ttccaagagg acatcgagtt tcacttcagc ctcggctgga caatgctggt caacagattt  2640
ctgggcccca agaacagcag acgggccctg atgggctaca acgatcaggt gcagaggccc  2700
attcctctga cacccgccaa tcctagcatg cctccactgc ctcagggcag cctgacacaa  2760
gaggaattca tggtgtctat ggtcaccggc ctggccagcc tgaccagcag aacatctatg  2820
ggcatcctgg tcgtcggcgg cgttgtgtgg aaagctgttg gctggcggct gatcgccctg  2880
agctttggcc tgtatggcct gctgtacgtg tacgagagac tgacctggac caccaaggcc  2940
aaagagcggg ccttcaagcg gcagtttgtg gaacacgcct ccgagaaact gcagctggtg  3000
atcagctaca ccggcagcaa ttgcagccac caggtgcagc aagagctgtc cggaacattc  3060
gcccacctgt gtcagcaggt cgacgtgacc agagagaacc tggaacaaga gatcgccgcc  3120
atgaataaga aaatcgaggt gctcgactcc ctgcagagca aggccaagct gctgagaaac  3180
aaggccggct ggctggacag cgagctgaat atgttcaccc accagtacct gcagcctagc  3240
cgctaataaa gcggccgcaa gcttgcaccc gtacctttgg gagcgcgcgc cctcgtcgtg  3300
tcgtgacgtc acccgttctg ttggatccct ggaggcttgc tgaaggctgt atgctgttga  3360
cgtccagaac ctgttctgtt ttggccactg actgacagaa caggctggac gtcaacagga  3420
cacaaggcct gttactagca ctcacatgga acaaatggcc cagatcttaa gcttctcgag  3480
atcgataatc aacctctgga ttacaaaatt tgtgaaagat tgactggtat tcttaactat  3540
gttgctcctt ttacgctatg tggatacgct gctttaatgc ctttgtatca tgctattgct  3600
tcccgtatgg ctttcatttt ctcctccttg tataaatcct ggttgctgtc tctttatgag  3660
gagttgtggc ccgttgtcag gcaacgtggc gtggtgtgca ctgtgtttgc tgacgcaacc  3720
cccactggtt ggggcattgc caccacctgt cagctccttt ccgggacttt cgctttcccc  3780
ctccctattg ccacggcgga actcatcgcc gcctgccttg cccgctgctg gacaggggct  3840
cggctgttgg gcactgacaa ttccgtggtg ttgtcgggga aatcatcgtc ctttccttgg  3900
ctgctcgcct gtgttgccac ctggattctg cgcgggacgc ccttctgcta cgtcccttcg  3960
gccctcaatc cagcggacct tccttcccgc ggcctgctgc cggctctgcg gcctcttccg  4020
cgtcttcgcc ttcgccctca gacgagtcgg atctcccttt gggccgcctc cccgcctgct  4080
gatcgccctg agcctggccc tggtgaccaa cagccaggtg caattgctag agtcgactct  4140
agagcggccg cttcgagcag acatgataag atacattgat gagtttggac aaaccacaac  4200
tagaatgcag tgaaaaaaat gctttatttg tgaaatttgt gatgctattg ctttatttgt  4260
aaccattata agctgcaata aac                                        4283
```

```
SEQ ID NO: 94          moltype = DNA  length = 4283
FEATURE                Location/Qualifiers
misc_feature           1..4283
                       note = Expression cassette
                        CAG.CI.hMfn2.GA.link.miR1518.WPRE.SV40
misc_feature           1..841
                       note = CAG (CBA)
regulatory             248..529
                       note = promoter - CB promoter
                       regulatory_class = promoter
misc_feature           529..936
                       note = Intron - Hybrid intron in CAG
misc_feature           967..972
                       note = Kozak
misc_feature           973..3246
                       note = human engineered Mfn2
misc_feature           3247..3328
                       note = linker
misc_feature           3329..3356
                       note = 5′ flank
misc_feature           3357..3377
                       note = rat miR1518
```

```
misc_feature          3378..3396
                      note = loop
misc_feature          3397..3415
                      note = rat miR1518 (sense)
misc_feature          3416..3460
                      note = 3′ flank
misc_feature          3487..4075
                      note = WPRE
misc_feature          4164..4283
                      note = SV40 polyA
source                1..4283
                      mol_type = other DNA
                      organism = synthetic construct
SEQUENCE: 94
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
cgctgccttc gccccgtgcc ccgctccgcc gccgcctcgc gccgcccgcc ccggctctga  600
ctgaccgcgt tactcccaca ggtgagcggg cgggacggcc cttctcctcc gggctgtaat  660
tagcgcttgg tttaatgacg gcttgtttct tttctgtggc tgcgtgaaag ccttgagggg  720
ctccgggagg gccctttgtg cggggggagc ggctcggggc tgtccgcggg gggacggctg  780
ccttcggggg ggacggggca gggcggggtt cggcttctgg cgtgtgaccg gcggctctag  840
agcctctgct aaccatgttc atgccttctt ctttttccta cagctcctgg gcaacgtgct  900
ggttattgtg ctgtctcatc attttggcaa agaattggat cccgtacgac gcgtgctagc  960
accggtgcca ccatgagcct gctgttcagc cggtgcaaca gcatcgtgac cgtgaagaaa  1020
aacaagcggc acatggccga agtgaacgcc tctccactga agcacttcgt gaccgccaag  1080
aagaagatca acggcatctt cgagcagctg ggcgcctaca tccaagagag cgccaccttc  1140
ctggaagata cctacagaaa cgccgagctg gaccccgtga ccacagagga acaggtgctg  1200
gatgtgaagg gctacctgag caaagtgcgg ggcatctctg aagtgctggc cagacggcat  1260
atgaaggtgg cctttttcgg ccggaccagc aacggcaaga gcaccgtgat caatgccatg  1320
ctgtgggaca aagtgctgcc ctctggaatc ggccacacca ccaactgctt tctgagagtg  1380
gaaggcaccg acggccacga ggcatttctg ctgacagagg gctccgagga aaagcggagc  1440
gccaagacag tgaaccagct ggcccatgct ctgcaccagg ataagcagct gcatgccgga  1500
agcctggtgt ccgtgatgtg gcccaatagc aagtgccctc tgctgaagga cgacctggtg  1560
ctgatggata gccccgggat cgatgtgacc accgaactgg acagctggat cgacaagttc  1620
tgcctggacg ccgacgtgtt cgtgctggtg gccaatagcg agagcaccct gatgcagacc  1680
gagaagcact tttccacaa ggtgtccgag cggctgagca gacccaatat ctttatcctg  1740
aacaacagat gggacgccag cgccagcgag cccgagtata tggaagaagt gcggcggcag  1800
catatggaac ggtgcacatc ctttctggtg gacgagctgg gcgtcgtgga tagatctcag  1860
gccggcgaca gaatcttctt tgtgtccgcc aaagaggtgc tgaacgcccg gattcagaaa  1920
gcccagggaa tgcctgaagg cggaggtgca ctggccgagg gatttcaagt gcggatgttc  1980
gagttccaga acttcgagcg gagattcgag gagtgcatca gccagagcgc cgtcaagacc  2040
aagttcgagc agcataccgt gcgggccaag cagattgccg aagccgtcag actgatcatg  2100
gacagcctgc atatggccgc cagagagcag caggtctact gcgaggaaat gcgggaagag  2160
agacaggacc ggctgaagtt catcgacaag cagctggaac tgctggccca ggactacaag  2220
ctgcggatca agcagatcac cgaagaggtg gaaagacagg tgtccaccgc tatggccgag  2280
gaaatcagac ggctgagcgt gctggtcgac gactaccaga tggactttca cccctctcca  2340
gtggtgctga aagtctacaa aaacgagctg caccggcaca tcgaggaagg cctgggcaga  2400
aacatgagcg acagatgcag caccgccatc accaatagcc tgcagaccat gcagcaggac  2460
atgatcgacg gcctgaaacc tctgctgcct gtgtccgtca gatcccagat cgatatgctg  2520
gtgccccggc agtgctttag cctgaactac gacctgaact gcgacaagct gtgcgccgat  2580
ttccaagagg acatcgagtt tcacttcagc ctcggctgga caatgctggt caacagattt  2640
ctgggcccca agaacagcag acgggccctg atgggctaca acgatcaggt gcagaggccc  2700
attcctctga cacccgccaa tcctagcatg cctccactgc ctcagggcag cctgacacaa  2760
gaggaattca tggtgtctat ggtcaccggc ctggccagcc tgaccagcag aacatctatg  2820
ggcatcctgg tcgtcggcgg cgttgtgtgg aaagctgttg gctggcggct gatcgccctg  2880
agctttggcc tgtatggcct gctgtacgtg tacgagagac tgacctggac caccaaggcc  2940
aaagagcggg ccttcaagcg gcagtttgtg gaacacgcct ccgagaaact gcagctggtg  3000
atcagctaca ccggcagcaa ttgcagccac caggtgcagc aagagctgtc cggaacattc  3060
gcccacctgt gtcagcaggt cgacgtgacc agagagaacc tggaacaaga gatcgccgcc  3120
atgaataaga aaatcgaggt gctcgactcc ctgcagagca aggccaagct gctgagaaac  3180
aaggccggct ggctggacag cgagctgaat atgttcaccc accagtacct gcagcctagc  3240
cgctaataaa gcggccgcaa gcttgcaccc gtacctttgg gagcgcgcgc cctcgtcgtg  3300
tcgtgacgtc acccgttctg ttggatccct ggaggcttgc tgaaggctgt atgctgttct  3360
tataaacctt gaggacagtt ttggccactg actgactgtc ctcagtttat aagaacagga  3420
cacaaggcct gttactagca ctcacatgga acaaatggcc cagatcttaa gcttctcgag  3480
atcgataatc aacctctgga ttacaaaatt tgtgaaagat tgactggtat tcttaactat  3540
gttgctcctt ttacgctatg tggatacgct gctttaatgc ctttgtatca tgctattgct  3600
tcccgtatgg ctttcatttt ctcctccttg tataaatcct ggttgctgtc tctttatgag  3660
gagttgtggc ccgttgtcag gcaacgtggc gtggtgtgca ctgtgtttgc tgacgcaacc  3720
cccactggtt ggggcattgc caccacctgt cagctccttt ccgggacttt cgctttcccc  3780
ctccctattg ccacggcgga actcatcgcc gcctgccttg cccgctgctg gacaggggct  3840
cggctgttgg gcactgacaa ttccgtggtg ttgtcgggga aatcatcgtc ctttccttgg  3900
```

```
ctgctcgcct gtgttgccac ctggattctg cgcgggacgc ccttctgcta cgtcccttcg  3960
gccctcaatc cagcggacct tccttcccgc ggcctgctgc cggctctgcg gcctcttccg  4020
cgtcttcgcc ttcgccctca gacgagtcgg atctcccttt gggccgcctc cccgcctgct  4080
gatcgccctg agcctggccc tggtgaccaa cagccaggtg caattgctag agtcgactct  4140
agagcggccg cttcgagcag acatgataag atacattgat gagtttggac aaaccacaac  4200
tagaatgcag tgaaaaaaat gctttatttg tgaaatttgt gatgctattg ctttatttgt  4260
aaccattata agctgcaata aac                                         4283

SEQ ID NO: 95          moltype = DNA  length = 4071
FEATURE                Location/Qualifiers
misc_feature           1..4071
                       note = Expression cassette CAG.CI.hMfn2.GA.WPRE.SV40
misc_feature           1..841
                       note = CAG (CBA)
regulatory             248..529
                       note = promoter - CB promoter
                       regulatory_class = promoter
misc_feature           529..936
                       note = Intron - Hybrid intron in CAG
misc_feature           967..972
                       note = Kozak
misc_feature           973..3246
                       note = human engineered Mfn2
misc_feature           3275..3863
                       note = WPRE
misc_feature           3952..4071
                       note = SV40 polyA
source                 1..4071
                       mol_type = other DNA
                       organism = synthetic construct
SEQUENCE: 95
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
cgctgccttc gccccgtgcc ccgctccgcc gccgcctcgc gccgcccgcc ccggctctga  600
ctgaccgcgt tactcccaca ggtgagcggg cgggacggcc cttctcctcc gggctgtaat  660
tagcgcttgg tttaatgacg gcttgtttct tttctgtggc tgcgtgaaag ccttgagggg  720
ctccgggagg gccctttgtg cggggggagc ggctcggggc tgtccgcggg gggacggctg  780
ccttcggggg ggacggggca gggcggggtt cggcttctgg cgtgtgaccg gcggctctag  840
agcctctgct aaccatgttc atgccttctt ctttttccta cagctcctgg gcaacgtgct  900
ggttattgtg ctgtctcatc attttggcaa agaattggat cccgtacgac gcgtgctagc  960
accggtgcca ccatgagcct gctgttcagc cggtgcaaca gcatcgtgac cgtgaagaaa  1020
aacaagcggc acatggccga agtgaacgcc tctccactga agcacttcgt gaccgccaag  1080
aagaagatca acggcatctt cgagcagctg ggcgcctaca tccaagagag cgccaccttc  1140
ctggaagata cctacagaaa cgccgagctg gaccccgtga ccacagagga acaggtgctg  1200
gatgtgaagg gctacctgag caaagtgcgg ggcatctctg aagtgctggc cagacggcat  1260
atgaaggtgg cctttttcgg ccggaccagc aacggcaaga gcaccgtgat caatgccatg  1320
ctgtgggaca aagtgctgcc ctctggaatc ggccacacca ccaactgctt tctgagagtg  1380
gaaggcaccg acggccacga ggcatttctg ctgacagagg gctccgagga aaagcggagc  1440
gccaagacag tgaaccagct ggcccatgct ctgcaccagg ataagcagct gcatgccgga  1500
agcctggtgt ccgtgatgtg gcccaatagc aagtgccctc tgctgaagga cgacctggtg  1560
ctgatggata gccccgggat cgatgtgacc accgaactgg acagctggat cgacaagttc  1620
tgcctggacg ccgacgtgtt cgtgctggtg gccaatagcg agagcaccct gatgcagacc  1680
gagaagcact tttccacaa ggtgtccgag cggctgagca gacccaatat ctttatcctg  1740
aacaacagat gggacgccag cgccagcgag cccgagtata tggaagaagt gcggcggcag  1800
catatggaac ggtgcacatc ctttctggtg gacgagctgg gcgtcgtgga tagatctcag  1860
gccggcgaca gaatcttctt tgtgtccgcc aaagaggtgc tgaacgcccg gattcagaaa  1920
gcccagggaa tgcctgaagg cggaggtgca ctggccgagg gatttcaagt gcggatgttc  1980
gagttccaga acttcgagcg gagattcgag gagtgcatca gccagagcgc cgtcaagacc  2040
aagttcgagc agcataccgt gcgggccaag cagattgccg aagccgtcag actgatcatg  2100
gacagcctgc atatggccgc cagagagcag caggtctact gcgaggaaat gcgggaagag  2160
agacaggacc ggctgaagtt catcgacaag cagctggaac tgctggccca ggactacaag  2220
ctgcggatca agcagatcac cgaagaggtg gaaagacagg tgtccaccgc tatggccgag  2280
gaaatcagac ggctgagcgt gctggtcgac gactaccaga tggactttca cccctctcca  2340
gtggtgctga aagtctacaa aaacgagctg caccggcaca tcgaggaagg cctgggcaga  2400
aacatgagcg acagatgcag caccgccatc accaatagcc tgcagaccat gcagcaggac  2460
atgatcgacg gcctgaaacc tctgctgcct gtgtccgtca gatcccagat cgatatgctg  2520
gtgccccggc agtgctttag cctgaactac gacctgaact gcgacaagct gtgcgccgat  2580
ttccaagagg acatcgagtt tcacttcagc ctcggctgga caatgctggt caacagattt  2640
ctgggccccca agaacagcag acgggccctg atgggctaca acgatcaggt gcagaggccc  2700
attcctctga cacccgccaa tcctagcatg cctccactgc ctcagggcag cctgacacaa  2760
gaggaattca tggtgtctat ggtcaccggc ctggccagcc tgaccagcag aacatctatg  2820
ggcatcctgg tcgtcggcgg cgttgtgtgg aaagctgttg gctggcggct gatcgccctg  2880
```

```
agctttggcc tgtatggcct gctgtacgtg tacgagagac tgacctggac caccaaggcc  2940
aaagagcggg ccttcaagcg gcagtttgtg gaacacgcct ccgagaaact gcagctggtg  3000
atcagctaca ccggcagcaa ttgcagccac caggtgcagc aagagctgtc cggaacattc  3060
gcccacctgt gtcagcaggt cgacgtgacc agagagaacc tggaacaaga gatcgccgcc  3120
atgaataaga aaatcgaggt gctcgactcc ctgcagagca aggccaagct gctgagaaac  3180
aaggccggct ggctggacag cgagctgaat atgttcaccc accagtacct gcagcctagc  3240
cgctaataat gtacttaagc ttctcgagat cgataatcaa cctctggatt acaaaatttg  3300
tgaaagattg actggtattc ttaactatgt tgctcctttt acgctatgtg gatacgctgc  3360
tttaatgcct ttgtatcatg ctattgcttc ccgtatggct ttcattttct cctccttgta  3420
taaatcctgg ttgctgtctc tttatgagga gttgtggccc gttgtcaggc aacgtggcgt  3480
ggtgtgcact gtgtttgctg acgcaacccc cactggttgg ggcattgcca ccacctgtca  3540
gctcctttcc gggactttcg ctttccccct ccctattgcc acggcggaac tcatcgccgc  3600
ctgccttgcc cgctgctgga caggggctcg gctgttgggc actgacaatt ccgtggtgtt  3660
gtcggggaaa tcatcgtcct ttccttggct gctcgcctgt gttgccacct ggattctgcg  3720
cgggacgccc ttctgctacg tcccttcggc cctcaatcca gcggaccttc cttcccgcgg  3780
cctgctgccg gctctgcggc ctcttccgcg tcttcgcctt cgccctcaga cgagtcggat  3840
ctccctttgg gccgcctccc cgcctgctga tcgccctgag cctggccctg gtgaccaaca  3900
gccaggtgca attgctagag tcgactctag agcggccgct tcgagcagac atgataagat  3960
acattgatga gtttggacaa accacaacta gaatgcagtg aaaaaaatgc tttatttgtg  4020
aaatttgtga tgctattgct ttatttgtaa ccattataag ctgcaataaa c           4071
```

```
SEQ ID NO: 96          moltype = DNA  length = 4368
FEATURE                Location/Qualifiers
misc_feature           1..4368
                       note = Expression cassette CB7.CI.hMfn2.GA.link.miR538.rBG
regulatory             1..304
                       note = enhancer - CMV IE enhancer
                       regulatory_class = enhancer
regulatory             303..584
                       note = promoter - CB promoter
                       regulatory_class = promoter
misc_feature           677..1649
                       note = Intron - chicken beta-actin intron
misc_feature           1695..1700
                       note = Kozak
misc_feature           1701..3974
                       note = human engineered Mfn2
misc_feature           3975..4056
                       note = linker
misc_feature           4057..4084
                       note = 5' flank
misc_feature           4085..4105
                       note = miR538 AS
misc_feature           4106..4124
                       note = loop
misc_feature           4125..4143
                       note = miR538 sense
misc_feature           4144..4188
                       note = 3' flank
regulatory             4242..4368
                       note = rabbit beta globin (RBG) polyA
                       regulatory_class = polyA_signal_sequence
source                 1..4368
                       mol_type = other DNA
                       organism = synthetic construct
regulatory             1..584
                       note = CB7 promoter
                       regulatory_class = promoter
SEQUENCE: 96
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta tttttaatt attttgtgca gcgatggggg cggggggggg  420
ggggggggcgc gcgccaggcg gggcggggcg gggcgagggg cggggcgggg cgaggcggag  480
aggtgcggcg gcagccaatc agagcggcgc gctccgaaag tttcctttta tggcgaggcg  540
gcggcggcgg cggccctata aaaagcgaag cgcgcggcgg gcgggagtcg ctgcgcgctg  600
ccttcgcccc gtgccccgct ccgccgccgc ctcgcgccgc ccgccccggc tctgactgac  660
cgcgttactc ccacaggtga gcgggcggga cggcccttct cctccgggct gtaattagcg  720
cttggtttaa tgacggcttg tttcttttct gtggctgcgt gaaagccttg aggggctccg  780
ggagggccct ttgtgcgggg ggagcggctc gggggggtgcg tgcgtgtgtg tgtgcgtggg  840
gagcgccgcg tgcggctccg cgctgcccgg cggctgtgag cgctgcgggc gcggcgcggg  900
gctttgtgcg ctccgcagtg tgcgcgaggg gagcgcggcc gggggcggtg ccccgcggtg  960
cggggggggc tgcgagggga acaaaggctg cgtgcggggt gtgtgcgtgg gggggtgagc  1020
agggggtgtg ggcgcgtcgg tcgggctgca acccccccctg cacccccctc cccgagttgc  1080
tgagcacggc ccggcttcgg gtgcggggct ccgtacgggg cgtggcgcgg ggctcgccgt  1140
gccgggcggg gggtggcggc aggtgggggt gccgggcggg gcggggccgc ctcgggccgg  1200
```

```
ggagggctcg ggggaggggc gcggcggccc ccggagcgcc ggcggctgtc gaggcgcggc  1260
gagccgcagc cattgccttt tatggtaatc gtgcgagagg gcgcagggac ttcctttgtc  1320
ccaaatctgt gcggagccga aatctgggag gcgccgccgc acccctcta gcgggcgcgg  1380
ggcgaagcgg tgcggcgccg gcaggaagga aatgggcggg gagggccttc gtgcgtcgcc  1440
gcgccgccgt cccttctcc ctctccagcc tcggggctgt ccgcgggggg acggctgcct  1500
tcgggggga cggggcaggg cggggttcgg cttctggcgt gtgaccggcg gctctagagc  1560
ctctgctaac catgttcatg ccttcttctt tttcctacag ctcctgggca acgtgctggt  1620
tattgtgctg tctcatcatt ttggcaaaga attcacgcgt gctaggatcc cgtacgacgc  1680
gtgctagcac cggtgccacc atgagcctgc tgttcagccg gtgcaacagc atcgtgaccg  1740
tgaagaaaaa caagcggcac atggccgaag tgaacgcctc tccactgaag cacttcgtga  1800
ccgccaagaa gaagatcaac ggcatcttcg agcagctggg cgcctacatc caagagagcg  1860
ccaccttcct ggaagatacc tacagaaacg ccgagctgga ccccgtgacc acagaggaac  1920
aggtgctgga tgtgaagggc tacctgagca aagtgcgggg catctctgaa gtgctggcca  1980
gacggcatat gaaggtggcc tttttcggcc ggaccagcaa cggcaagagc accgtgatca  2040
atgccatgct gtgggacaaa gtgctgccct ctggaatcgg ccacaccacc aactgctttc  2100
tgagagtgga aggcaccgac ggccacgagg catttctgct gacagagggc tccgaggaaa  2160
agcggagcgc caagacagtg aaccagctgg cccatgctct gcaccaggat aagcagctgc  2220
atgccggaag cctggtgtcc gtgatgtggc ccaatagcaa gtgccctctg ctgaaggacg  2280
acctggtgct gatggatagc cccgggatcg atgtgaccac cgaactggac agctggatcg  2340
acaagttctg cctggacgcc gacgtgttcg tgctggtggc caatagcgag agcaccctga  2400
tgcagaccga gaagcacttt ttccacaagg tgtccgagcg gctgagcaga cccaatatct  2460
ttatcctgaa caacagatgg gacgccagcg ccagcgagcc cgagtatatg gaagaagtgc  2520
ggcggcagca tatggaacgg tgcacatcct ttctggtgga cgagctgggc gtcgtggata  2580
gatctcaggc cggcgacaga atcttctttg tgtccgccaa agaggtgctg aacgcccgga  2640
ttcagaaagc ccagggaatg cctgaaggcg gaggtgcact ggccgaggga tttcaagtgc  2700
ggatgttcga gttccagaac ttcgagcgga gattcgagga gtgcatcagc cagagcgccg  2760
tcaagaccaa gttcgagcag cataccgtgc gggccaagca gattgccgaa gccgtcagac  2820
tgatcatgga cagcctgcat atggccgcca gagagcagca ggtctactgc gaggaaatgc  2880
gggaagagag acaggaccgg ctgaagttca tcgacaagca gctggaactg ctggcccagg  2940
actacaagct gcggatcaag cagatcaccg aagaggtgga aagacaggtg tccaccgcta  3000
tggccgagga aatcagacgg ctgagcgtgc tggtcgacga ctaccagatg gactttcacc  3060
cctctccagt ggtgctgaaa gtctacaaaa acgagctgca ccggcacatc gaggaaggcc  3120
tgggcagaaa catgagcgac agatgcagca ccgccatcac caatagcctg cagaccatgc  3180
agcaggacat gatcgacggc ctgaaacctc tgctgcctgt gtccgtcaga tcccagatcg  3240
atatgctggt gccccggcag tgctttagcc tgaactacga cctgaactgc gacaagctgt  3300
gcgccgattt ccaagaggac atcgagtttc acttcagcct cggctggaca atgctggtca  3360
acagatttct gggccccaag aacagcagac gggccctgat gggctacaac gatcaggtgc  3420
agaggcccat tcctctgaca cccgccaatc ctagcatgcc tccactgcct cagggcagcc  3480
tgacacaaga ggaattcatg gtgtctatgg tcaccggcct ggccagcctg accagcagaa  3540
catctatggg catcctggtc gtcggcggcg ttgtgtggaa agctgttggc tggcggctga  3600
tcgccctgag ctttggcctg tatggcctgc tgtacgtgta cgagagactg acctggacca  3660
ccaaggccaa agagcgggcc ttcaagcggc agtttgtgga acacgcctcc gagaaactgc  3720
agctggtgat cagctacacc ggcagcaatt gcagccacca ggtgcagcaa gagctgtccg  3780
gaacattcgc ccacctgtgt cagcaggtcg acgtgaccag agagaacctg gaacaagaga  3840
tcgccgccat gaataagaaa atcgaggtgc tcgactccct gcagagcaag gccaagctgc  3900
tgagaaacaa ggccggctgg ctggacagcg agctgaatat gttcacccac cagtacctgc  3960
agcctagccg ctaataaagc ggccgcaagc ttgcacccgt acctttggga gcgcgcgccc  4020
tcgtcgtgtc gtgacgtcac ccgttctgtt ggatccctgg aggcttgctg aaggctgtat  4080
gctgttgacg tccagaacct gttctgtttt ggccactgac tgacagaaca ggctggacgt  4140
caacaggaca caaggcctgt tactagcact cacatggaac aaatggccca gatcagcttt  4200
ctagagtcga cccgggcggc ggcggccgcc taaggctcga ggatcttttt ccctctgcca  4260
aaaattatgg ggacatcatg aagcccttg agcatctgac ttctggctaa taaaggaaat  4320
ttattttcat tgcaatagtg tgttggaatt ttttgtgtct ctcactcg              4368
```

```
SEQ ID NO: 97          moltype = DNA  length = 4452
FEATURE                Location/Qualifiers
misc_feature           1..4452
                       note = Expression cassette CB7.CI.hMfn2.GA.link.miR1518.rBG
regulatory             1..304
                       note = enhancer - CMV IE enhancer
                       regulatory_class = enhancer
regulatory             303..584
                       note = promoter - CB promoter
                       regulatory_class = promoter
misc_feature           677..1649
                       note = Intron - chicken beta actone intron
misc_feature           1695..1700
                       note = Kozak
misc_feature           1701..3974
                       note = human engineered Mfn2
misc_feature           3975..4056
                       note = linker
misc_feature           4057..4084
                       note = 5' flank
misc_feature           4085..4105
                       note = rat miR1518 AS
misc_feature           4106..4124
                       note = loop
misc_feature           4125..4143
```

```
                         note = rat miR1518 sense
misc_feature             4144..4188
                         note = 3' flank
regulatory               4326..4452
                         note = rabbit beta globin (RBG) polyA
                         regulatory_class = polyA_signal_sequence
source                   1..4452
                         mol_type = other DNA
                         organism = synthetic construct
regulatory               1..584
                         note = CB7 promoter
                         regulatory_class = promoter
SEQUENCE: 97
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta ttttttaatt attttgtgca gcgatggggg cggggggggg  420
ggggggggcgc gcgccaggcg gggcggggcg gggcgagggg cggggcgggg cgaggcggag  480
aggtgcggcg gcagccaatc agagcggcgc gctccgaaag tttcctttta tggcgaggcg  540
gcggcggcgg cggccctata aaaagcgaag cgcgcggcgg gcgggagtcg ctgcgcgctg  600
ccttcgcccc gtgccccgct ccgccgccgc ctcgcgccgc ccgccccggc tctgactgac  660
cgcgttactc ccacaggtga gcgggcggga cggcccttct cctccgggct gtaattagcg  720
cttggtttaa tgacggcttg tttcttttct gtggctgcgt gaaagccttg aggggctccg  780
ggagggccct ttgtgcgggg ggagcggctc ggggggtgcg tgcgtgtgtg tgtgcgtggg  840
gagcgccgcg tgcggctccg cgctgcccgg cggctgtgag cgctgcgggc gcggcgcggg  900
gctttgtgcg ctccgcagtg tgcgcgaggg gagcgcggcc gggggcggtg ccccgcggtg  960
cgggggggggc tgcgaggggga acaaaggctg cgtgcggggt gtgtgcgtgg gggggtgagc  1020
agggggtgtg ggcgcgtcgg tcgggctgca acccccccctg caccccccctc cccgagttgc  1080
tgagcacggc ccggcttcgg gtgcggggct ccgtacgggg cgtggcgcgg ggctcgccgt  1140
gccgggcggg gggtggcggc aggtgggggt gccgggcggg gcggggccgc ctcgggccgg  1200
ggagggctcg ggggagggggc gcggcggccc ccggagcgcc ggcggctgtc gaggcgcggc  1260
gagccgcagc cattgccttt tatggtaatc gtgcgagagg gcgcagggac ttcctttgtc  1320
ccaaatctgt gcggagccga aatctgggag gcgccgccgc accccctcta gcgggcgcgg  1380
ggcgaagcgg tgcggcgccg gcaggaagga aatgggcggg gagggccttc gtgcgtcgcc  1440
gcgccgccgt ccccttctcc ctctccagcc tcggggctgt ccgcgggggg acggctgcct  1500
tcgggggggga cggggcaggg cggggttcgg cttctggcgt gtgaccggcg gctctagagc  1560
ctctgctaac catgttcatg ccttcttctt tttcctacag ctcctgggca acgtgctggt  1620
tattgtgctg tctcatcatt ttggcaaaga attcacgcgt gctaggatcc cgtacgacgc  1680
gtgctagcac cggtgccacc atgagcctgc tgttcagccg gtgcaacagc atcgtgaccg  1740
tgaagaaaaa caagcggcac atggccgaag tgaacgcctc tccactgaag cacttcgtga  1800
ccgccaagaa gaagatcaac ggcatcttcg agcagctggg cgcctacatc caagagagcg  1860
ccaccttcct ggaagatacc tacagaaacg ccgagctgga ccccgtgacc acagaggaac  1920
aggtgctgga tgtgaagggc tacctgagca aagtgcgggg catctctgaa gtgctggcca  1980
gacggcatat gaaggtggcc tttttcggcc ggaccagcaa cggcaagagc accgtgatca  2040
atgccatgct gtgggacaaa gtgctgccct ctggaatcgg ccacaccacc aactgctttc  2100
tgagagtgga aggcaccgac ggccacgagg catttctgct gacagagggc tccgaggaaa  2160
agcggagcgc caagacagtg aaccagctgg cccatgctct gcaccaggat aagcagctgc  2220
atgccggaag cctggtgtcc gtgatgtggc ccaatagcaa gtgccctctg ctgaaggacg  2280
acctggtgct gatggatagc cccgggatcg atgtgaccac cgaactggac agctggatcg  2340
acaagttctg cctggacgcc gacgtgttcg tgctggtggc caatagcgag agcaccctga  2400
tgcagaccga gaagcacttt ttccacaagg tgtccgagcg gctgagcaga cccaatatct  2460
ttatcctgaa caacagatgg gacgccagcg ccagcgagcc cgagtatatg gaagaagtgc  2520
ggcggcagca tatggaacgg tgcacatcct ttctggtgga cgagctgggc gtcgtggata  2580
gatctcaggc cggcgacaga atcttctttg tgtccgccaa agaggtgctg aacgcccgga  2640
ttcagaaagc ccagggaatg cctgaaggcg gaggtgcact ggccgaggga tttcaagtgc  2700
ggatgttcga gttccagaac ttcgagcgga gattcgagga gtgcatcagc cagagcgccg  2760
tcaagaccaa gttcgagcag cataccgtgc gggccaagca gattgccgaa gccgtcagac  2820
tgatcatgga cagcctgcat atggccgcca gagagcagca ggtctactgc gaggaaatgc  2880
gggaagagag acaggaccgg ctgaagttca tcgacaagca gctggaactg ctggcccagg  2940
actacaagct gcggatcaag cagatcaccg aagaggtgga aagacaggtg tccaccgcta  3000
tggccgagga aatcagacgg ctgagcgtgc tggtcgacga ctaccagatg gactttcacc  3060
cctctccagt ggtgctgaaa gtctacaaaa acgagctgca ccggcacatc gaggaaggcc  3120
tgggcagaaa catgagcgac agatgcagca ccgccatcac caatagcctg cagaccatgc  3180
agcaggacat gatcgacggc ctgaaacctc tgctgcctgt gtccgtcaga tcccagatcg  3240
atatgctggt gccccggcag tgctttagcc tgaactacga cctgaactgc gacaagctgt  3300
gcgccgattt ccaagaggac atcgagtttc acttcagcct cggctggaca atgctggtca  3360
acagatttct gggccccaag aacagcagac gggccctgat gggctacaac gatcaggtgc  3420
agaggcccat tcctctgaca cccgccaatc ctagcatgcc tccactgcct cagggcagcc  3480
tgacacaaga ggaattcatg gtgtctatgg tcaccggcct ggccagcctg accagcagaa  3540
catctatggg catcctggtc gtcggcggcg ttgtgtggaa agctgttggc tggcggctga  3600
tcgccctgag ctttggcctg tatggcctgc tgtacgtgta cgagagactg acctggacca  3660
ccaaggccaa agagcgggcc ttcaagcggc agtttgtgga acacgcctcc gagaaactgc  3720
agctggtgat cagctacacc ggcagcaatt gcagccacca ggtgcagcaa gagctgtccg  3780
gaacattcgc ccacctgtgt cagcaggtcg acgtgaccag agagaacctg gaacaagaga  3840
tcgccgccat gaataagaaa atcgaggtgc tcgactccct gcagagcaag gccaagctgc  3900
tgagaaacaa ggccggctgg ctggacagcg agctgaatat gttcacccac cagtacctgc  3960
```

```
agcctagccg ctaataaagc ggccgcaagc ttgcacccgt acctttggga gcgcgcgccc  4020
tcgtcgtgtc gtgacgtcac ccgttctgtt ggatccctgg aggcttgctg aaggctgtat  4080
gctgttctta taaaccttga ggacagtttt ggccactgac tgactgtcct cagtttataa  4140
gaacaggaca caaggcctgt tactagcact cacatggaac aaatggccca gatctagggt  4200
ggggccacct gccggtaggt gtgcggtagg cttttctccg tcgcaggacg cagggttcgg  4260
gcctagagct tatcgttaag ctttctagag tcgacccggg cggcggcggc cgcctaaggc  4320
tcgaggatct tttccctct gccaaaaatt atggggacat catgaagccc cttgagcatc  4380
tgacttctgg ctaataaagg aaatttattt tcattgcaat agtgtgttgg aatttttgt  4440
gtctctcact cg                                                       4452

SEQ ID NO: 98          moltype = DNA  length = 4112
FEATURE                Location/Qualifiers
misc_feature           1..4112
                       note = Expression cassette CB7.CI.hMfn2.GA.rBG
regulatory             1..304
                       note = enhancer - CMV IE enhancer
                       regulatory_class = enhancer
regulatory             303..584
                       note = promoter - CB promoter
                       regulatory_class = promoter
misc_feature           677..1649
                       note = Intron - chicken beta actin intron
misc_feature           1682..1687
                       note = Kozak
misc_feature           1688..3961
                       note = human engineered Mfn2
regulatory             3986..4112
                       note = rabbit beta globin (RBG) polyA
                       regulatory_class = polyA_signal_sequence
source                 1..4112
                       mol_type = other DNA
                       organism = synthetic construct
regulatory             1..584
                       note = CB7 promoter
                       regulatory_class = promoter
SEQUENCE: 98
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catggtcgag gtgagcccca cgttctgctt cactctcccc atctcccccc cctccccacc  360
cccaattttg tatttattta ttttttaatt attttgtgca gcgatggggg cggggggggg  420
ggggggggcgc gcgccaggcg gggcggggcg gggcgagggg cggggcgggg cgaggcggag  480
aggtgcggcg gcagccaatc agagcggcgc gctccgaaag tttcctttta tggcgaggcg  540
gcggcggcgg cggccctata aaaagcgaag cgcgcggcgg gcgggagtcg ctgcgcgctg  600
ccttcgcccc gtgccccgct ccgccgccgc ctcgcgccgc ccgccccggc tctgactgac  660
cgcgttactc ccacaggtga gcgggcggga cggcccttct cctccgggct gtaattagcg  720
cttggtttaa tgacggcttg tttcttttct gtggctgcgt gaaagccttg aggggctccg  780
ggagggccct ttgtgcgggg ggagcggctc ggggggtgcg tgcgtgtgtg tgtgcgtggg  840
gagcgccgcg tgcggctccg cgctgcccgg cggctgtgag cgctgcgggc gcggcgcggg  900
gctttgtgcg ctccgcagtg tgcgcgaggg gagcgcggcc gggggcggtg ccccgcggtg  960
cgggggggggc tgcgagggga acaaaggctg cgtgcggggt gtgtgcgtgg gggggtgagc  1020
agggggtgtg ggcgcgtcgg tcgggctgca accccccctg caccccctc cccgagttgc  1080
tgagcacggc ccggcttcgg gtgcggggct ccgtacgggg cgtggcgcgg ggctcgccgt  1140
gccgggcggg gggtggcggc aggtgggggt gccgggcggg gcggggccgc ctcgggccgg  1200
ggagggctcg gggggagggc gcggcggccc ccggagcgcc ggcggctgtc gaggcgcggc  1260
gagccgcagc cattgccttt tatggtaatc gtgcgagagg gcgcagggac ttcctttgtc  1320
ccaaatctgt gcggagccga aatctgggag gcgccgccgc acccccctcta gcgggcgcgg  1380
ggcgaagcgg tgcggcgccg gcaggaagga aatgggcggg gagggccttc gtgcgtcgcc  1440
gcgccgccgt ccccttctcc ctctccagcc tcggggctgt ccgcgggggg acggctgcct  1500
tcggggggga cggggcaggg cggggttcgg cttctggcgt gtgaccggcg gctctagagc  1560
ctctgctaac catgttcatg ccttcttctt tttcctacag ctcctgggca acgtgctggt  1620
tattgtgctg tctcatcatt ttggcaaaga attcacgcgt gctagcaagg atccaccggt  1680
cgccaccatg agcctgctgt tcagccggtg caacagcatc gtgaccgtga agaaaaacaa  1740
gcggcacatg gccgaagtga acgcctctcc actgaagcac ttcgtgaccg ccaagaagaa  1800
gatcaacgga atcttcgagc agctgggcgc ctacatccaa gagagcgcca ccttcctgga  1860
agatacctac agaaacgccg agctggaccc cgtgaccaca gaggaacagg tgctggatgt  1920
gaagggctac ctgagcaaag tgcggggcat ctctgaagtg ctggccagac ggcatatgaa  1980
ggtggccttt ttcggccgga ccagcaacgg caagagcacc gtgatcaatg ccatgctgtg  2040
ggacaaagtg ctgccctctg gaatcggcca caccaccaac tgctttctga gagtggaagg  2100
caccgacggc cacgaggcat ttctgctgac agagggctcc gaggaaaagc ggagcgccaa  2160
gacagtgaac cagctggccc atgctctgca ccaggataag cagctgcatg ccggaagcct  2220
ggtgtccgtg atgtggccca atagcaagtg ccctctgctg aaggacgacc tggtgctgat  2280
ggatagcccc gggatcgatg tgaccaccga actggacagc tggatcgaca agttctgcct  2340
ggacgccgac gtgttcgtgc tggtggccaa tagcgagagc accctgatgc agaccgagaa  2400
gcactttttc cacaaggtgt ccgagcggct gagcagaccc aatatcttta tcctgaacaa  2460
cagatgggac gccagcgcca gcgagcccga gtatatggaa gaagtgcggc ggcagcatat  2520
ggaacggtgc acatcctttc tggtggacga gctgggcgtc gtggatagat ctcaggccgg  2580
```

```
cgacagaatc ttctttgtgt ccgccaaaga ggtgctgaac gcccggattc agaaagccca  2640
gggaatgcct gaaggcggag gtgcactggc cgagggattt caagtgcgga tgttcgagtt  2700
ccagaacttc gagcggagat tcgaggagtg catcagccag agcgccgtca agaccaagtt  2760
cgagcagcat accgtgcggg ccaagcagat tgccgaagcc gtcagactga tcatggacag  2820
cctgcatatg gccgccagag agcagcaggt ctactgcgag gaaatgcggg aagagagaca  2880
ggaccggctg aagttcatcg acaagcagct ggaactgctg gcccaggact acaagctgcg  2940
gatcaagcag atcaccgaag aggtggaaag acaggtgtcc accgctatgg ccgaggaaat  3000
cagacggctg agcgtgctgg tcgacgacta ccagatggac tttcacccct ctccagtggt  3060
gctgaaagtc tacaaaaacg agctgcaccg gcacatcgag gaaggcctgg gcagaaacat  3120
gagcgacaga tgcagcaccg ccatcaccaa tagcctgcag accatgcagc aggacatgat  3180
cgacggcctg aaacctctgc tgcctgtgtc cgtcagatcc cagatcgata tgctggtgcc  3240
ccggcagtgc tttagcctga actacgacct gaactgcgac aagctgtgcg ccgatttcca  3300
agaggacatc gagtttcact tcagcctcgg ctggacaatg ctggtcaaca gatttctggg  3360
ccccaagaac agcagacggg ccctgatggg ctacaacgat caggtgcaga ggcccattcc  3420
tctgacaccc gccaatccta gcatgcctcc actgcctcag ggcagcctga cacaagagga  3480
attcatggtg tctatggtca ccggcctggc cagcctgacc agcagaacat ctatgggcat  3540
cctggtcgtc ggcggcgttg tgtggaaagc tgttggctgg cggctgatcg ccctgagctt  3600
tggcctgtat ggcctgctgt acgtgtacga gagactgacc tggaccacca aggccaaaga  3660
gcgggccttc aagcggcagt ttgtggaaca cgcctccgag aaactgcagc tggtgatcag  3720
ctacaccggc agcaattgca gccaccaggt gcagcaagag ctgtccggaa cattcgccca  3780
cctgtgtcag caggtcgacg tgaccagaga gaacctggaa caagagatcg ccgccatgaa  3840
taagaaaatc gaggtgctcg actccctgca gagcaaggcc aagctgctga gaaacaaggc  3900
cggctggctg gacagcgagc tgaatatgtt cacccaccag tacctgcagc ctagccgcta  3960
ataaagcggc cgcctaaggc tcgaggatct tttccctct gccaaaaatt atggggacat  4020
catgaagccc cttgagcatc tgacttctgg ctaataaagg aaatttattt tcattgcaat  4080
agtgtgttgg aatttttgt gtctctcact cg                                4112
```

```
SEQ ID NO: 99          moltype = DNA  length = 973
FEATURE                Location/Qualifiers
misc_feature           1..973
                       note = chicken beta actin intron
source                 1..973
                       mol_type = other DNA
                       organism = synthetic construct
SEQUENCE: 99
gtgagcgggc gggacggccc ttctcctccg ggctgtaatt agcgcttggt ttaatgacgg  60
cttgtttctt ttctgtggct gcgtgaaagc cttgaggggc tccgggaggg ccctttgtgc  120
ggggggagcg gctcgggggg tgcgtgcgtg tgtgtgtgcg tggggagcgc cgcgtgcggc  180
tccgcgctgc ccggcggctg tgagcgctgc gggcgcggcg cggggctttg tgcgctccgc  240
agtgtgcgcg aggggagcgc ggccgggggc ggtgccccgc ggtgcggggg gggctgcgag  300
gggaacaaag gctgcgtgcg gggtgtgtgc gtgggggggt gagcaggggg tgtgggcgcg  360
tcggtcgggc tgcaacccc cctgcacccc cctccccgag ttgctgagca cggcccggct  420
tcgggtgcgg ggctccgtac ggggcgtggc gcggggctcg ccgtgccggg cggggggtgg  480
cggcaggtgg gggtgccggg cggggcgggg ccgcctcggg ccggggaggg ctcgggggag  540
gggcgcggcg gcccccggag cgccggcggc tgtcgaggcg cggcgagccg cagccattgc  600
cttttatggt aatcgtgcga gagggcgcag ggacttcctt tgtcccaaat ctgtgcggag  660
ccgaaatctg ggaggcgccg ccgcaccccc tctagcgggc gcggggcgaa gcggtgcggc  720
gccggcagga aggaaatggg cggggagggc cttcgtgcgt cgccgcgccg ccgtcccctt  780
ctccctctcc agcctcgggg ctgtccgcgg ggggacggct gccttcgggg gggacggggc  840
agggcggggt tcggcttctg gcgtgtgacc ggcggctcta gagcctctgc taaccatgtt  900
catgccttct tctttttcct acagctcctg ggcaacgtgc tggttattgt gctgtctcat  960
cattttggca aag                                                    973
```

```
SEQ ID NO: 100         moltype = DNA  length = 132
FEATURE                Location/Qualifiers
misc_feature           1..132
                       note = miR538 (with flank sequences)
source                 1..132
                       mol_type = other DNA
                       organism = synthetic construct
SEQUENCE: 100
ctggaggctt gctgaaggct gtatgctgtt gacgtccaga acctgttctg ttttggccac  60
tgactgacag aacaggctgg acgtcaacag gacacaaggc ctgttactag cactcacatg  120
gaacaaatgg cc                                                     132
```

```
SEQ ID NO: 101         moltype = DNA  length = 542
FEATURE                Location/Qualifiers
misc_feature           1..542
                       note = WPRE element (mut)
source                 1..542
                       mol_type = other DNA
                       organism = synthetic construct
SEQUENCE: 101
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
```

-continued

```
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cg                                                                  542

SEQ ID NO: 102         moltype = DNA  length = 304
FEATURE                Location/Qualifiers
source                 1..304
                       mol_type = other DNA
                       organism = synthetic construct
misc_feature           1..304
                       note = CB promoter
SEQUENCE: 102
cgttacataa cttacggtaa atggcccgcc tggctgaccg cccaacgacc cccgcccatt  60
gacgtcaata atgacgtatg ttcccatagt aacgccaata gggactttcc attgacgtca  120
atgggtggag tatttacggt aaactgccca cttggcagta catcaagtgt atcatatgcc  180
aagtacgccc cctattgacg tcaatgacgg taaatggccc gcctggcatt atgcccagta  240
catgacctta tgggactttc ctacttggca gtacatctac gtattagtca tcgctattac  300
catg                                                                304

SEQ ID NO: 103         moltype = DNA  length = 282
FEATURE                Location/Qualifiers
source                 1..282
                       mol_type = other DNA
                       organism = synthetic construct
misc_feature           1..282
                       note = CMV IE enhancer
SEQUENCE: 103
tggtcgaggt gagccccacg ttctgcttca ctctccccat ctcccccccc tccccacccc  60
caattttgta tttatttatt ttttaattat tttgtgcagc gatgggggcg gggggggggg  120
gggggcgcgc gccaggcggg gcggggcggg gcgaggggcg gggcggggcg aggcggagag  180
gtgcggcggc agccaatcag agcggcgcgc tccgaaagtt tccttttatg gcgaggcggc  240
ggcggcggcg gccctataaa aagcgaagcg cgcggcgggc gg                      282

SEQ ID NO: 104         moltype = DNA  length = 21
FEATURE                Location/Qualifiers
source                 1..21
                       mol_type = other DNA
                       organism = synthetic construct
SEQUENCE: 104
ggaacaggtg ctggatgtga a                                             21

SEQ ID NO: 105         moltype = DNA  length = 21
FEATURE                Location/Qualifiers
source                 1..21
                       mol_type = other DNA
                       organism = synthetic construct
SEQUENCE: 105
ggtgctgaaa gtctacaaaa a                                             21

SEQ ID NO: 106         moltype = DNA  length = 21
FEATURE                Location/Qualifiers
source                 1..21
                       mol_type = other DNA
                       organism = synthetic construct
SEQUENCE: 106
ttcttataaa ccttgaggac a                                             21

SEQ ID NO: 107         moltype = DNA  length = 19
FEATURE                Location/Qualifiers
source                 1..19
                       mol_type = other DNA
                       organism = synthetic construct
SEQUENCE: 107
gttttggcca ctgactgac                                                19
```

COMPOSITIONS USEFUL FOR TREATMENT OF CHARCOT-MARIE-TOOTH DISEASE

CROSS-REFERENCE TO RELATED APPLICATIONS

This is a National Stage Entry under 35 U.S.C. 371 of International Patent Application No. PCT/US2022/076939, filed Sep. 23, 2022, which claims priority to U.S. Provisional Application No. 63/248,132, filed Sep. 24, 2021, U.S. Provisional Application No. 63/297,962, filed Jan. 10, 2022, and U.S. Provisional Application No. 63/341,583, filed May 13, 2022. These applications are incorporated by reference herein in their entirety.

BACKGROUND OF THE INVENTION

Charcot-Marie-Tooth (CMT) neuropathy is a heterogeneous group of inherited diseases found in peripheral nerves. CMT is a common disorder affecting both children and adults. Charcot-Marie Tooth disease (CMT) or hereditary motor and sensory neuropathy (HMSN) are the most commonly used names for inherited neuropathies that are not part of a syndrome (Klein, C. J., Duan, X., Shy, M. E., 2013. Inherited neuropathies: Clinical overview and update. Muscle Nerve; Bassam, B., 2014. Charcot-Marie-Tooth Disease Variants-Classification, Clinical, and Genetic Features and Rational Diagnostic Evaluation. J. Clin. Neuromusc. Dis. 15, 117-128; Scherer, S. S., Shy, M. E., 2015. CMT Subtypes and Disease Burden in Patients Enrolled in the INC Natural History Study (6601) from 2009-2013. J. Neurol. Neurosurg. Psychiat. 86, 873-878).

The dominantly inherited axonal forms of CMT neuropathy (type 2 CMT disorders) have normal or slightly reduced velocities with reduced motor and sensory compound action potential amplitudes, and axonal loss is the chief finding in biopsied nerves. Dominant mutations in the Mitofusin2 (MFN2) gene, a protein required for mitochondrial fusion and transport along axons, cause CMT2A (Zuchner, S., et al., 2004. Mutations in the mitochondrial GTPase mitofusin 2 cause Charcot-Marie-Tooth neuropathy type 2A. Nat Genet 36, 449-451). CMT2A is estimated to cause up to 7% of all CMT, and is the most common form of type 2 CMT (Freidman. V., et al., 2015. CMT Subtypes and Disease Burden in Patients Enrolled in the INC Natural History Study (6601) from 2009-2013. J. Neurol. Neurosurg. Psychiat. 86, 873-878). Different MFN2 mutations cause different degrees of neuropathy.

Most MFN2 mutations cause a severe, early onset, axonal neuropathy, and are de novo mutations. Other MFN2 dominant mutations cause a milder axonal neuropathy with a later onset (Lawson, V. H., et al, 2005. Clinical and electrophysiologic features of CMT2A with mutations in the mitofusin 2 gene. Neurology 65, 197-204; Chung, K. W., et al., 2006. Early onset severe and late-onset mild Charcot-Marie-Tooth disease with mitofusin 2 (MFN2) mutations. Brain 129, 2103-2118; Verhoeven, K., et al., 2006. MFN2 mutation distribution and genotype/phenotype correlation in Charcot-Marie-Tooth type 2. Brain 129, 2093-2102; Feely, S. M. E., et al., 2011, MFN2 mutations cause severe phenotypes in most patients with CMT2A. Neurology 76, 1690-1696). More rarely, recessive MFN2 mutations may cause severe, early onset, axonal neuropathy. Mfn2 mutations selectively toxic to lower motor neurons and primary sensory neurons in dorsal root ganglia (DRG).

Some dominant mutations in MFN2 produce myelopathy or optic atrophy; these complicated forms of CMT2 are sometimes referred to HMSN-V and HMSN-VI, respectively, but are not only caused by MFN2 mutations (Scherer, S. S., et al., 2015. Peripheral neuropathies in Rosenberg's Molecular and Genetic Basis of Neurological and Psychiatric Disease, 5th ed. Elsevier, Philadelphia, pp. 1051-1074).

Mammals have two mitofusin genes, Mfn1 and Mfn2, which have distinct but overlapping distributions, and both of which can promote mitochondrial fusion through trans-interactions (Chen, H., Chan, D. C., 2005. Emerging functions of mammalian mitochondrial fusion and fission. Hum. Mol. Genet. 14, R283-R289). Nearly all of the mutations in the MFN2 gene cause amino acid substitutions as single point mutations, including but not restricted to the GTPase domain (Cartoni, R., Martinou, J. C., 2009. Role of mitofusin 2 mutations in the physiopathology of Charcot-Marie-Tooth disease type 2A. Exp. Neurol. 218, 268-273). Because loss-of-function mutations of MFN2 also cause a severe axonal neuropathy (Nicholson, G. A., et al, 2008. Severe early-onset axonal neuropathy with homozygous and compound heterozygous MFN2 mutations. Neurology 70, 1678-1681), and result in reduced mitochondrial fusion (Chen, H., Chan, D. C., 2005. Emerging functions of mammalian mitochondrial fusion and fission. Hum. Mol. Genet. 14, R283-R289), it is possible that dominant MFN2 mutations have a dominant-negative effect on mitochondrial fusion (Detmer, S. A., Chan, D. C., 2007. Complementation between mouse Mfn1 and Mfn2 protects mitochondrial fusion defects caused by CMT2A disease mutations. J. Cell Biol. 176, 405-414: Baloh, R. H., et al., 2007. Altered axonal mitochondrial transport in the pathogenesis of Charcot-Marie-Tooth disease from mitofusin 2 mutations. J Neurosci 27, 422-430; Misko, A., et al., 2010. Mitofusin 2 is necessary for transport of axonal mitochondria and interacts with the Miro/Milton complex. J Neurosci 30, 4232-4240: Misko, A. L., et al., 2012. Mitofusin2 mutations disrupt axonal mitochondrial positioning and promote axon degeneration. J Neurosci 32, 4145-4155).

What are needed are treatments useful for reducing the symptoms, severity and/or progression of CMT2A and related disorders.

SUMMARY OF THE INVENTION

In one aspect provided herein is a recombinant adeno-associated virus (rAAV) comprising an AAV capsid and packaged therein a vector genome, wherein the vector genome comprises: (a) an AAV 5' inverted terminal repeat (ITR); (b) an CB7.CI.hMfn2.GA.link.miR538.rBG expression cassette comprising at least one open reading frame (ORF) comprising (i) an engineered nucleic acid sequence of SEQ ID NO: 11 or a sequence at least 90% identical thereto encoding a human mitofusin 2 (hMfn2) and at least one miRNA coding sequence which is specific for a target site in an endogenous human mitofusin 2 nucleic acid sequence in a patient having a disorder associated with deficient hMfn2, (ii) a spacer sequence located between (i) and (iii), and (iii) at least one miRNA coding sequence which is specific for a target site in an endogenous human mitofusin 2 nucleic acid sequence in the patient, wherein the at least one miRNA comprises miR538, wherein the engineered nucleic acid sequence of (i) lacks the target site for the at least one miRNA of (iii), thereby preventing the at least one miRNA from targeting the engineered hMfn2 coding sequence, wherein the regulatory control sequences comprise a CB7 promoter comprising a cytomegalovirus immediate early (CMV IE) enhancer and a chicken beta actin (CB) promoter, and further comprising a chicken beta-actin intron (CI), and a rabbit beta globin (rBG) polyadenylation (polyA) signal; and (c) an AAV 3' ITR. In certain embodiments, the engineered hMfn2 coding sequence has the sequence at least 90% identical to SEQ ID NO: 11, and wherein nt 216 to 236 of SEQ ID NO: 11 (SEQ ID NO: 104) and/or nt 1371 to 1391 of SEQ ID NO: 11 (SEQ ID NO: 105) of the engineered hMfn2 coding sequence are conserved. In certain embodiments, the at least one miRNA comprises a sequence of one or more of an miRNA targeting sequence comprising SEQ ID NO: 89 (miR538, 59 nt) or a sequence at least 99% identical to SEQ ID NO: 89, wherein the at least one miRNA does not bind to the engineered hMfn2 coding sequence of (a) or its encoded messenger RNA (mRNA). In certain embodiments, the at least one miRNA comprises a sequence of one or more of an miRNA targeting sequence and further comprises a 5' flank sequence and a 3' flank sequence, wherein the miR538 comprises nucleic acid sequence of SEQ ID NO: 100. In certain embodiments, the spacer of (ii) is 75 nucleotides to about 250 nucleotides in length, optionally wherein the spacer comprises nucleic acid sequence of SEQ ID NO: 90. In certain embodiments, the CB7 promoter comprises nucleic acid sequence of SEQ ID NO: 86, the chicken beta-actin intron (CI) comprises nucleic acid sequence of SEQ ID NO: 99, and the rabbit beta-globin polyA signal comprises nucleic acid sequence of SEQ ID NO: 88. In certain embodiments, the rAAV comprises a vector genome comprising the expression cassette which comprises nucleic acid sequence of SEQ ID NO: 96 or a sequence at least 99% identical to SEQ ID NO: 96. In certain embodiments, the rAAV comprises a vector genome which comprises nucleic acid sequence of SEQ ID NO: 75 or sequence at least 99% identical to SEQ ID NO: 75. In certain embodiments. the rAAV comprises AAV capsid which is an AAVhu68, AAVrh91, AAV9, or AAV1 capsid. In certain embodiments, the rAAV is for use in treating Charcot-Marie-Tooth 2A (CMT2A) disease or neuropathy.

In another aspect provided herein is a composition comprising a stock of rAAV as described herein and one or more of an aqueous suspension media, excipient, and/or diluent. In certain embodiments, the composition is formulated for system delivery or intrathecal delivery, optionally wherein the intrathecal delivery is an intracerebroventricular (ICV) injection or an intracisterna magna (ICM) injection.

In a further aspect, provided herein is a method for treating a patient having Charcot-Marie-Tooth 2A (CMT2A) disease or neuropathy comprising delivering an effective amount of the recombinant AAV or the composition as described herein to a patient in need thereof.

In a further aspect, provided herein is a method for treating a patient having Charcot-Marie-Tooth 2A (CMT2A) disease or neuropathy comprising delivering an effective amount of the recombinant AAV or the composition as described herein to a patient in need thereof.

Further provided herein are the rAAV as described herein for treatment of patients having Charcot-Marie-Tooth 2A (CMT2A) disease or neuropathy, and the rAAV as described herein for use in preparing a medicament for treatment of a patient having Charcot-Marie-Tooth 2A (CMT2A) disease or neuropathy.

In another aspect, provided herein is a recombinant nucleic acid molecule comprising: (a) an AAV 5' inverted terminal repeat (ITR); (b) an CB7.CI.hMfn2.GA.link.miR538.rBG expression cassette comprising at least one open reading frame (ORF) comprising (i) an engineered nucleic acid sequence of SEQ ID NO: 11 or a sequence at least 90% identical thereto encoding human mitofusin 2 (hMfn2) and at least one miRNA coding sequence which is specific for a target site in an endogenous human mitofusin 2 nucleic acid sequence in a patient having a disorder associated with deficient hMfn2, (ii) a spacer sequence located between (i) and (iii), and (iii) at least one miRNA coding sequence which is specific for a target site in an endogenous human mitofusin 2 nucleic acid sequence in the patient, wherein at the at least one miRNA comprises miR538, wherein the engineered nucleic acid sequence of (i) lacks the target site for the at least one miRNA of (iii), thereby preventing the at least one miRNA from targeting the engineered hMfn2 coding sequence, wherein the regulatory control sequences comprise a CB7 promoter comprising a cytomegalovirus immediate early (CMV IE) enhancer and a chicken beta actin (CB) promoter, and further comprising a chicken beta-actin intron (CI), and a rabbit beta globin (rBG) polyadenylation (polyA) signal; and (c) an AAV 3'ITR, optionally wherein the expression cassette comprises nucleic acid sequence of SEQ ID NO: 96. In certain embodiments, the recombinant nucleic acid molecule is a plasmid. In another aspect, provided herein is a production host cell comprising a recombinant nucleic acid molecule as described herein, a nucleic acid sequence encoding an AAV capsid protein. and sufficient AAV rep functions and helper functions to permit packaging of the vector genome into the AAV capsid, optionally wherein the AAV capsid is an AAVhu68, AAVrh91, AAV9, or AAV1 capsid.

These and other advantages will be apparent from the Detailed Description of the Invention which follows.

BRIEF DESCRIPTION OF THE DRAWINGS

FIG. 1A illustrates knockdown of endogenous Mfn2 RNA, as measured by qPCR, in mouse brain in B6 mice following intravenous delivery of AAV-mediated delivery of miRNA. FIG. 1B illustrates knock down of endogenous mfn2 RNA, as measured by qPCR, in mouse spinal cord in B6 mice following intravenous delivery of AAV-mediated delivery of miRNA.

FIG. 2A illustrates mouse Mfn (mMfn2) RNA fold expression in spinal cord. FIG. 2B illustrates rat Mfn engineered (rMfn2co) RNA fold expression in spinal cord. FIG. 2C illustrates miR1518 RNA fold expression in spinal cord.

FIG. 6A illustrates fold expression of miR1518 and miR1693, as measured by qPCR with miR1518 primers. FIG. 6B illustrates fold expression of miR1518 and miR1693, as measured by qPCR with miR1693 primers.

FIG. 9A show endogenous Mfn2 knockdown in HEK293 cells as measured by qPCR and plotted as fold expression, following transfection with various vectors comprising CB7 promoter, (CB7.CI.hMfn2.GA.WPRE.RBG; CB7.CI.hMfn2.GA.LINK.miR1518.RBG; CB7.CI.hMfn2.GA.LINK.miR538.RBG. FIG. 9B show endogenous Mfn2 knockdown in HEK293 cells as measured by qPCR and plotted as fold expression, following transfection with various vectors comprising a CAG promoter CAG.CI.hMfn2.GA.WPRE.SV40; CAG.CI.hMfn2.GA.LINK.miR1518.WPRE.SV40: CAG.CI.hMfn2.GA.LINK.miR538.WPRE.SV40.

FIG. 12A shows a comparison of expression levels, as measured by qPCR and plotted as fold expression, of mature miR1518 in Mfn2-null MEF cell line, following transfection with vectors comprising either CB7 or CAG promoter. FIG. 12B shows a comparison of expression levels, as measured by qPCR and plotted as fold expression, of mature miR538 in Mfn2-null MEF cell line, following transfection with vectors comprising either CB7 or CAG promoter. FIG. 12C shows a comparison of expression levels, as measured by qPCR and plotted as fold expression, of mature miR1518 and miR538 in Mfn2-null MEF cell line, following transfection with vectors comprising either CB7 or CAG promoter.

FIG. 13A show schematic representation of the mice genotype. FIG. 13B shows mice phenotype characterization, characterized by relative expression levels endogenous and FLAG-tagged MFN2 in brain as measured by western blotting. FIG. 13C shows mice phenotype characterization, characterized by relative expression levels endogenous and FLAG-tagged MFN2 in spinal cord as measured by western blotting. FIG. 13D shows measured weight in (g) of the mice in the CMT2A mouse model (nTg, MFN2$^{WT}$, and MFN2$^{R49Q}$). FIG. 13E shows mice phenotype characterization, as measured by the latency to fall (sec). FIG. 13F shows mice phenotype characterization, as measured by grip strength (g).

FIG. 14A shows body weight results (plotted as (g)) as measured in mice groups G1 to G7. FIG. 14B shows survival results (plotted as probability of survival over day 0 to 50) as measured in mice groups G1 to G7.

DETAILED DESCRIPTION OF THE INVENTION

Figure 1A:
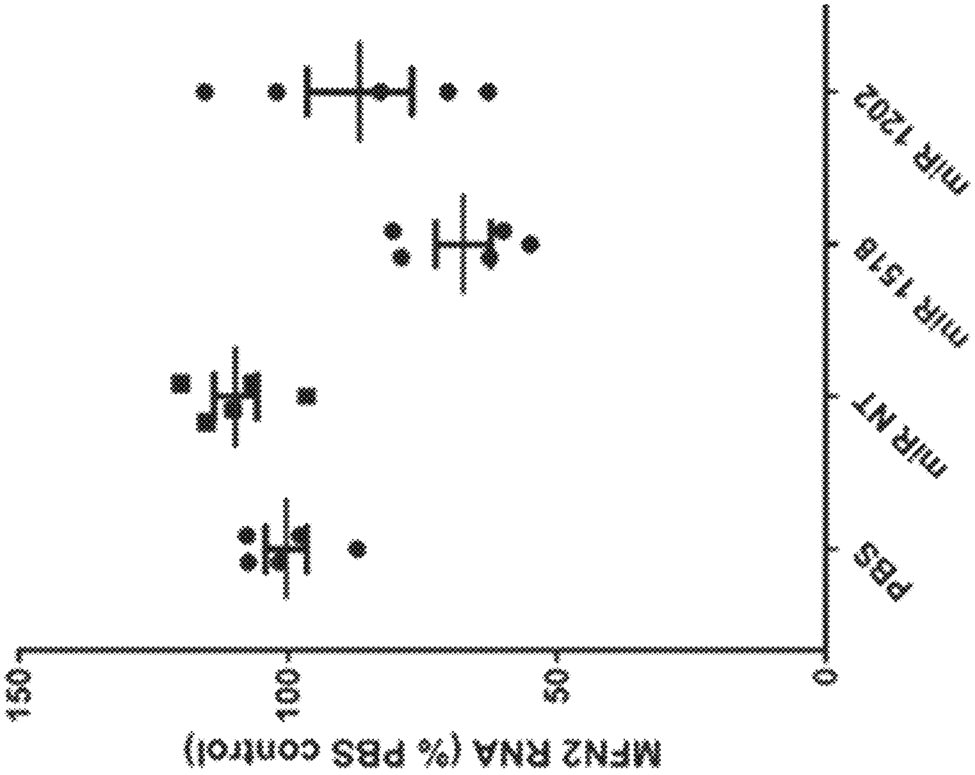
FIG. 1A and FIG. 1B illustrate mitofusin 2 (Mfn2) miRNA selection (knockdown of endogenous Mfn2 with various miRNA).

Sequences, vectors and compositions are provided here for co-administering to a patient a nucleic acid sequence which expresses human mitofusin 2 (or hMfn2) protein and a nucleic acid sequence encoding at least one miRNA which specifically targets a site in the endogenous human mitofusin 2 gene of the patient which target site is not present on human mitofusin 2 engineered coding sequence. Suitably, the human mitofusin 2 coding sequence is engineered to remove the specific target site for the encoded miRNA. Novel engineered human mitofusin 2 coding sequences and novel miRNA sequences are provided herein. These may be used alone or in combination with each other and/or other therapeutics for the treatment of CMT2A.

Viral and non-viral vectors and compositions useful for treating patients having symptoms associated with defects in human mitofusin 2 expression and/or patients having CMT2A are provided herein.

In certain embodiments, a recombinant adeno-associated virus (rAAV) comprising an AAV capsid and a vector genome is provided. In certain embodiments, the rAAV comprises an AAV capsid and packaged therein a vector genome, wherein the vector genome comprises CB7.CI.hMfn2.GA.link.miR538.rBG comprising: (a) an AAV 5' inverted terminal repeat (ITR), (b) an expression cassette comprising at least one open reading frame (ORF) comprising an engineered nucleic acid sequence encoding human mitofusin 2 (hMfn2) and at least one miRNA coding sequence which is specific for a target site in an endogenous human mitofusin 2 nucleic acid sequence in a CMT2 patient; and (c) an AAV 3'ITR, wherein the expression cassette comprises at least one ORF operably linked to regulatory control sequences which direct expression thereof in a cell, wherein the at least one ORF comprises: (i) an engineered nucleic acid sequence encoding human mitofusin 2 (hMfn2); (ii) a spacer sequence located between (i) and (iii); and (iii) at least one miRNA coding sequence which is specific for a target site in an endogenous human mitofusin 2 nucleic acid sequence in a CMT2 patient, wherein the miRNA is miR538; wherein the engineered nucleic acid sequence of (i) lacks the target site for the at least one miRNA of (iii), thereby preventing the at least one miRNA from targeting the engineered hMfn2 coding sequence; and wherein the regulatory control sequences comprise a CB7 hybrid promoter comprising a cytomegalovirus immediate early (CMV IE) enhancer and a chicken beta actin promoter (CB) promoter, a chicken beta-actin intron (CI), and a rabbit beta globin (RBG) polyadenylation (polyA) signal. In certain embodiments, the AAV capsid is selected from AAV9, AAVhu68, AAV1 or AAVrh91. In certain embodiments, the spacer is 75 nucleotides to about 250 nucleotides in length. In certain embodiments, the miR538 comprises targeting sequence of nucleic acid sequence of SEQ ID NO: 59. In certain embodiments, the miR538 comprises nucleic acid sequence of SEQ ID NO: 100. In certain embodiments, the regulatory control sequences comprise a CB7 hybrid promoter having nucleic acid sequence of SEQ ID NO: 86, a chicken beta actin promoter having nucleic acid sequence of SEQ ID NO:99, and/or a rabbit beta globin polyA having nucleic acid sequence of SEQ ID NO: 88. In certain embodiments, the vector genome comprises an expression cassette comprising nucleic acid sequence of SEQ ID NO: 96 or a sequence at least 99% identical to SEQ ID NO: 96. n certain embodiments, the vector genome comprises an expression cassette comprising nucleic acid sequence of SEQ ID NO: 93, 94, or 95 or a sequence at least 99% identical to SEQ ID NO: 93, 94, or 95, respectively. In certain embodiments, the vector genome comprises an AAV2 5' inverted terminal repeat (ITR) sequence, a CB7 promoter, an intron, the engineered hMfn2 coding sequence, a spacer, a miR538 targeting sequence, a rabbit beta globin polyadenylation (poly A), and an AAV2 3' ITR. In certain embodiments, the vector genome comprises nucleic acid sequence of SEQ ID NO: 75 or a sequence at least 99% identical to SEQ ID NO: 75. In certain embodiments, the rAAV is for use in treating Charcot-Marie-Tooth 2A (CMT2A) disease or neuropathy. In certain embodiments, the rAAV is formulated for intrathecal delivery, optionally wherein the intrathecal delivery is an intracerebroventricular (ICV) injection or an intracisternal magna (ICM) injection.

In one aspect, a vector is provided which comprises an engineered human mitofusin 2 coding sequence operably linked to regulatory sequences which direct expression thereof in a human target cell. In certain embodiments, a vector is provided which comprises a nucleic acid sequence encoding at least one hairpin miRNA, wherein the encoded miRNA is specific for endogenous human mitofusin 2 in a human subject operably linked to regulatory sequences which direct expression thereof in the subject. In certain embodiments, a vector or other composition comprises both the engineered human mitofusin 2 coding sequence and the at least one miRNA coding sequence. In such an embodiment, the engineered mitofusin 2 coding sequence lacks the target site for the at least one miRNA, thereby preventing the miRNA from targeting the engineered human mitofusin 2 coding sequence.

In certain embodiments, the vector is a replication-defective viral vector which comprises a vector genome comprising the human mitofusin 2 coding sequences, the coding sequence for the at least one miRNA and the regulatory sequences. In certain embodiments, the viral vector is a recombinant adeno-associated virus (rAAV) particle having an AAV capsid which has the packaged therein the vector genome. In certain embodiments, the AAV capsid is AAVhu68, AAV1 or AAVrh91.

In certain embodiments, a vector is provided which comprises an engineered mitofusin 2 coding sequence has the nucleic acid sequence of SEQ ID NO: 11 or a sequence at least 90% identical thereto, provided that the nucleic acid sequences targeted by the encoded miRNA are different from the endogenous human mitofusin 2 sequence.

In certain embodiments, a vector is provided which comprises a nucleic acid sequence comprising at least one miRNA coding sequence which comprises one or more of: (a) an miRNA coding sequence comprising SEQ ID NO 15 (miR1693, 64 nt); (b) an miRNA coding sequence comprising at least 60 consecutive nucleotides of SEQ ID NO: 15; (c) an miRNA coding sequence comprising at least 99% identity to SEQ ID NO: 15 which comprises a sequence with 100% identity to about nucleotide 6 to about nucleotide 26 of SEQ ID NO: 15 (or SEQ ID NO: 68); (d) an miRNA coding sequence comprising one or more of:

(i) SEQ ID NO: 27
TTGACGTCCAGAACCTGTTCT;

(ii) SEQ ID NO: 28
AGAAGTGGGCACTTAGAGTTG;

(iii) SEQ ID NO: 29
TTCAGAAGTGGGCACTTAGAG;

(iv) SEQ ID NO: 30
TTGTCAATCCAGCTGTCCAGC;

(v) SEQ ID NO: 31
CAAACTTGGTCTTCACTGCAG;

(vi) SEQ ID NO: 32
AAACCTTGAGGACTACTGGAG;

(vii) SEQ ID NO: 33
TAACCATGGAAACCATGAACT;

(viii) SEQ ID NO: 34
ACAACAAGAATGCCCATGGAG;

(ix) SEQ ID NO: 35
AAAGGTCCCAGACAGTTCCTG;

(x) SEQ ID NO: 36
TGTTCATGGCGGCAATTTCCT;

(xi) SEQ ID NO: 37
TGAGGTTGGCTATTGATTGAC;

(xii) SEQ ID NO: 38
TTCTCACACAGTCAACACCTT;

(xiii) SEQ ID NO: 39
TTTCCTCGCAGTAAACCTGCT;

(xiv) SEQ ID NO: 40
AGAAATGGAACTCAATGTCTT;

(xv) SEQ ID NO: 41
TGAACAGGACATCACCTGTGA;

(xvi) SEQ ID NO: 42
AATACAAGCAGGTATGTGAAC;

(xvii) SEQ ID NO: 43
TAAACCTGCTGCTCCCGAGCC;

(xviii) SEQ ID NO: 44
TAGAGGAGGCCATAGAGCCCA;

(xix) SEQ ID NO: 45
TCTACCCGCAGGAAGCAATTG;
or (xx) SEQ ID NO: 46
CTCCTTAGCAGACACAAAGAA, or combinations of any of (i) through (xx). In certain embodiments, a single nucleic acid molecule comprises both the human mitofusin 2 coding sequence and the miRNA coding sequence and the nucleic acid molecule further comprises a spacer of at least 75 nucleotides between the hMfn2 coding sequence and the coding sequence at least one miRNA. In certain embodiments, the vector is a non-viral vector.

In certain embodiments, the composition comprises a recombinant nucleic acid sequence encoding an engineered human mitofusin 2 coding sequence operably linked to regulatory sequences which direct expression thereof in a human target cell and a nucleic acid sequence encoding at least one miRNA specific for endogenous human mitofusin 2 in a CMT2A patient operably linked to regulatory sequences which direct expression thereof in the subject, wherein the engineered mitofusin 2 coding sequence lacks a target site for the encoded at least one miRNA, thereby preventing the miRNA from targeting the engineered human mitofusin 2 coding sequence.

In certain embodiments, a pharmaceutical composition comprising the vector, rAAV, or a composition, and a pharmaceutically acceptable aqueous suspending liquid, excipient, and/or diluent.

In certain embodiments, a method for treating a patient having Charcot-Marie-Tooth (CMT) neuropathy is provided comprising delivering an effective amount of the vector, a recombinant AAV, or a composition to a patient in need thereof. In certain embodiments, a method for reducing neuropathy in a patient having Charcot-Marie-Tooth (CMT) neuropathy is provided which comprises delivering an effective amount of the vector, a recombinant AAV, or a composition to a patient in need thereof. In certain embodiments, a method for treating a patient is provided, wherein the method additionally comprising a combination with one or more co-therapies selected from: acetaminophen, nonsteroidal anti-inflammatory drugs (NSAIDs), tricyclic antidepressants or antiepileptic drugs, such as carbamazepine or gabapentin.

In certain embodiments, a combination regimen for treating a patient having CMT2A is provided which comprises co-administering (a) a recombinant nucleic acid sequence encoding an engineered human mitofusin 2 coding sequence operably linked to regulatory sequences which direct expression thereof in a human target cell, wherein the human mitofusin 2 coding sequence has the sequence of SEQ ID NO: 11 or a sequence at least 95% identical thereto and which differs from endogenous human mitofusin 2 in the CMT2A patient by having a mismatch in the miRNA target sequence of (b), (b) at least one miRNA specific for an endogenous human mitofusin 2 sequence in a human CMT2A subject, wherein the mRNA is operably linked to regulatory sequences which direct expression thereof in the subject.

In certain embodiments, a combination regimen for treating a patient having CMT2A is provided which comprises co-administering: (a) a recombinant nucleic acid sequence encoding an engineered human mitofusin 2 coding sequence operably linked to regulatory sequences which direct expression thereof in a human target cell, wherein the human mitofusin 2 coding sequence is engineered to differs from endogenous human mitofusin 2 in the CMT2A patient by having a mismatch in the miRNA target sequence of (b), (b) at least one miRNA specific for an endogenous human mitofusin 2 sequence in a human CMT2A subject, wherein the miRNA is operably linked to regulatory sequences which direct expression thereof in the subject. In certain embodiments, a first vector comprises the nucleic acid (a) and a second, different vector, comprises at least one miRNA (b). In certain embodiments, the first vector and/or the second vector are each a viral vector which may be same or different. In certain embodiments, the first and/or second vector are a non-viral vector.

In certain embodiments, provided herein is a recombinant nucleic acid molecule comprising a nucleic acid sequence of the vector genome described herein, optionally wherein the recombinant nucleic acid molecule is a plasmid. In certain embodiments, the production host cell comprising recombinant nucleic acid molecule is provided herein. In certain embodiments, provided herein is a rAAV production system useful for producing the rAAV, as described herein, wherein the production system comprises a cell culture comprising: (a) a nucleic acid sequence encoding a AAV capsid protein; (b) a vector genome; and (c) sufficient AAV rep functions and helper functions to permit packaging of the vector genome into the AAV capsid.

As used herein the term "endogenous mitofusin 2" refers to the mitofusin 2 gene which encodes the mitofusin 2 protein in patients or humans having a disorder associated with deficient mitofusin 2, such as Charcot-Marie-Tooth (CMT) disease type 2, more specifically CMT2A, or hereditary motor and sensory neuropathy type VI (HMSN VI). See also, Oh, J., et al., Hereditary Motor and Sensory Neuropathy Type VI with Bilateral Middle Cerebellar Peduncle Involvement, Exp Neurobiol. 2014 September; 23(3):266-269. Patients with CMT2A may have a number of missense mutations or allelic variants. See, also, omim.org/allelic Variants/608507, describing various allelic variants. Autosomal dominant Charcot-Marie-Tooth (CMT) disease type 2A2A (CMT2A2A) is caused by heterozygous mutation in the MFN2 gene (608507) on chromosome 1p36.2. Homozygous or compound heterozygous mutation in the MFN2 gene causes autosomal recessive CMT2A2B (617087), a more severe disorder with earlier onset. Another form of CMT2A mapping to chromosome 1p36.2, CMT2A1 (118210), is caused by mutation in the KIF1B gene (605995). See also hereditary motor and sensory neuropathy VI (HMSN6; 601152), an allelic disorder with overlapping features.

The native, functional, human Mfn2a gene, such as is found endogenously in patients without CMT2A, is reproduced in SEQ ID NO: 18 and the native, functional, human Mf2A protein is reproduced in SEQ ID NO: 19. Mitofusin 2 is made in many types of cells and tissues, including muscles, the spinal cord, and the nerves that connect the brain and spinal cord to muscles and to sensory cells that detect sensations such as touch, pain, heat, and sound (peripheral nerves). This gene may alternatively be called: CMT2A2, CRPP1, KIAA0214, MARF, MFN2_Human or mitochondrial assembly regulatory factor. See, OMIM.org/entry/609260, accessed Jul. 12, 2020. In certain embodiments, functional Mfn2 proteins having less than 100% identity to the amino acid sequence of SEQ ID NO: 19 may be delivered by the compositions provided herein (e.g., Mfn2 having 97% to 100% identity to SEQ ID NO: 19). In such embodiments, the enzymatic and binding function of native functional human Mfn2 are preferably retained. See, also, UniProtKB-09140 (e.g., binding sites at position 305 and 307 are conserved and/or nucleotide binding sites at nucleotides 106-111 and/or 258-261 are conserved).

In one embodiment, an engineered mitofusin 2 coding sequence is provided which has the nucleic acid sequence of SEQ ID NO: 11 or a sequence of about 90%, at least 95% identical, at least 97% identical, at least 98% identical, or 99% to 100% identical to SEQ ID NO: 11 and which expresses the human mitofusin 2 protein found in non-CMT2A patients. See, e.g., SEQ ID NO: 19. See, also SEQ ID NO: 2 and SEQ ID NO: 4.

In certain embodiments, an engineered mitofusin 2 coding sequence is provided which has the nucleic acid sequence of SEQ ID NO: 11 or a sequence at least 80% identical, at least 90% identical, at least 95% identical, or at least 99% identical, provided that nt 216 to 236 of SEQ ID NO: 11 (also referred to as SEQ ID NO: 104) are conserved (e.g., 100% identical, or at least 99% identical), e.g., when the engineered coding sequence is co-administered with the miR538 coding sequence.

In certain embodiments, an engineered mitofusin 2 coding sequence is provided which has the nucleic acid sequence of SEQ ID NO: 11 or a sequence at least 80% identical, at least 90% identical, at least 95% identical, or at least 99% identical, provided that nt 1371 to 1391 of SEQ ID NO: 11 (also referred to as SEQ ID NO: 105) are conserved (e.g., 100% identical, or at least 99% identical), e.g., when the engineered coding sequence is co-administered with the miR1518 coding sequence. Suitably, the sequence having identity to SEQ ID NO: 11 expresses the same protein. See, e.g., SEQ ID NO: 19; SEQ ID NO: 2 and SEQ ID NO: 4.

In one embodiment, an engineered mitofusin 2 coding sequence is provided which has the nucleic acid sequence of SEQ ID NO: 28 or a sequence at least 90%, at least 95% identical, at least 97% identical, at least 98% identical, at least 99% identical, and/or at least 99% to 100% identical to SEQ ID NO: 24.

A "5' UTR" is upstream of the initiation codon for a gene product coding sequence. The 5' UTR is generally shorter than the 3' UTR. Generally, the 5' UTR is about 3 nucleotides to about 200 nucleotides in length, but may optionally be longer.

A "3' UTR" is downstream of the coding sequence for a gene product and is generally longer than the 5' UTR. In certain embodiments, the 3' UTR is about 200 nucleotides to about 800 nucleotides in length, but may optionally be longer or shorter.

As used herein, an "miRNA" refers to a microRNA which is a small non-coding RNA molecule which regulates mRNA and stops it from being translated to protein. Generally, hairpin-forming RNAs have a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue. As used herein, the miRNA contains a "seed sequence" which is a region of nucleotides which specifically binds to mRNA (e.g., in the endogenous hMfn2) by complementary base pairing, leading to destruction or silencing of the mRNA. Such silencing may result in downregulation rather than complete extinguishing of the endogenous hMfn2. Unless otherwise specified, the term “miRNA” encompasses artificial microRNA (amiRNA), which are artificially designed.

A “self-complementary nucleic acid” refers to a nucleic acid capable of hybridizing with itself (i.e, folding back upon itself) to form a single-stranded duplex structure, due to the complementarity (e.g., base-pairing) of the nucleotides within the nucleic acid strand. Self-complementary nucleic acids can form a variety of secondary structures, such as hairpin loops, loops, bulges, junctions and internal bulges. Certain self-complementary nucleic acids (e.g., miRNA or AmiRNA) perform regulatory functions, such as gene silencing.

The encoded miRNA provided herein have been designed to specifically target the endogenous human mitofusin 2 gene in patients having a disorder associated with deficient hMfn2. In certain embodiments, the disorder is CMT2A disease or neuropathy. In certain embodiments the miRNA coding sequence comprises an anti-sense sequence in the following Table 1, SEQ ID NOs: 27-46, 68, and 89.

TABLE 1

| miR # | Target hMfn2 Sequence | SEQ ID NO: | miRNA Antisense sequence | SEQ ID NO: |
|---|---|---|---|---|
| 538 | AGAACAGGTTCTGGACG TCAA | 47 | TTGACGTCCAG AACCTGTTCT | 27 |
| 874 | CAACTCTAAGTGCCCAC TTCT | 48 | AGAAGTGGGCA CTTAGAGTTG | 28 |
| 877 | CTCTAAGTGCCCACTTCT GAA | 49 | TTCAGAAGTGG GCACTTAGAG | 29 |
| 946 | GCTGGACAGCTGGATTG ACAA | 50 | TTGTCAATCCA GCTGTCCAGC | 30 |
| 1377 | CTGCAGTGAAGACCAAG TTTG | 51 | CAAACTTGGTC TTCACTGCAG | 31 |
| 1686 | CTCCAGTAGTCCTCAAG GTTT | 52 | AAACCTTGAGG ACTACTGGAG | 32 |
| 2115 | AGTTCATGGTTTCCATG GTTA | 53 | TAACCATGGAA ACCATGAACT | 33 |
| 2164 | CTCCATGGGCATTCTTGT TGT | 54 | ACAACAAGAAT GCCCATGGAG | 34 |
| 2390 | CAGGAACTGTCTGGGAC CTTT | 55 | AAAGGTCCCAG ACAGTTCCTG | 35 |
| 2457 | AGGAAATTGCCGCCATG AACA | 56 | TGTTCATGGCG GCAATTTCCT | 36 |
| 1693 | AGTCCTCAAGGTTTATA AGAA | 57 | TTCTTATAAACC TTGAGGACT | 68 |
| | GTCAATCAATAGCCAAC CTCA | 58 | TGAGGTTGGCT ATTGATTGAC | 37 |
| | AAGGTGTTGACTGTGTG AGAA | 59 | TTCTCACACAGT CAACACCTT | 38 |
| | AGCAGGTTTACTGCGAG GAAA | 60 | TTTCCTCGCAGT AAACCTGCT | 39 |
| | AAGACATTGAGTTCCAT TTCT | 61 | AGAAATGGAAC TCAATGTCTT | 40 |
| | TCACAGGTGATGTCCTG TTCA | 62 | TGAACAGGACA TCACCTGTGA | 41 |

TABLE 1-continued

| miR # | Target hMfn2 Sequence | SEQ ID NO: | miRNA Antisense sequence | SEQ ID NO: |
|---|---|---|---|---|
| | GTTCACATACCTGCTTGT ATT | 63 | AATACAAGCAG GTATGTGAAC | 42 |
| | GGCTCGGGAGCAGCAGG TTTA | 64 | TAAACCTGCTG CTCCCGAGCC | 43 |
| | TGGGCTCTATGGCCTCC TCTA | 65 | TAGAGGAGGCC ATAGAGCCCA | 44 |
| | CAATTGCTTCCTGCGGG TAGA | 66 | TCTACCCGCAG GAAGCAATTG | 45 |
| | TTCTTTGTGTCTGCTAAG GAG | 67 | CTCCTTAGCAG ACACAAAGAA | 46 |

In certain embodiments, the seed sequence is 100% identical to the antisense sequence describe in the table. In certain embodiments, the seed sequence is located on the mature miRNA (5' to 3') and is generally starts at position 2 to 7, 2 to 8, or about 6 nucleotides from the 5' end of the miRNA sense strand (from the 5' end of the sense (+) strand) of the miRNA, although it may be longer than in length. In certain embodiments, the length of the seed sequence is no less than about 30% of the length of the miRNA sequence, which may be at least 7 nucleotides to about 28 nucleotides in length, at least 8 nucleotides to about 28 nucleotides in length, 7 nucleotides to 28 nucleotides, 8 nucleotides to 18 nucleotides, 12 nucleotides to 28 nucleotides in length, about 20 to about 26 nucleotides, about 21 nucleotides, about 24 nucleotides, or about 26 nucleotides. In the examples provided herein, the miRNA is delivered in the form of a stem-loop miRNA precursor sequences, e.g., about 50 to about 80 nucleotides in length, or about 55 nucleotides to about 70 nucleotides, or 60 to 65 nucleotides in length. In certain embodiments, this miRNA precursor comprises about 5 nucleotides, about a 21-nucleotide seed sequence, about a 19-nucleotide stem loop and about a 19-nucleotide sense sequence, wherein the sense sequence corresponds to the anti-sense sequence with one or two nucleotides being mismatched. An example of a suitable miRNA coding sequence is the miR1693 sequence of SEQ ID NO: 15. In certain embodiments, the miRNA coding sequence comprises SEQ ID NO: 15 (miR1693, 64 nt); an miRNA coding sequence comprising at least 60 consecutive nucleotides of SEQ ID NO: 15; or an miRNA coding sequence comprising at least 99% identity to SEQ ID NO: 15 which comprises a sequence with 100% identity to about nucleotide 6 to about nucleotide 26 of SEQ ID NO: 15 (or SEQ ID NO: 68). In certain embodiments, another sequences of the table above may be substituted in positions 6 to 26 of SEQ ID NO: 15 (or SEQ ID NO: 68). In still another embodiment, positions 6 to 26 of SEQ ID NO: 15 are retained, and an alternative sequence is selected for the stem-loop sequence. In certain embodiments, the miRNA coding sequence comprises SEQ ID NO: 16 (miR1518, 59 nt), a sequence comprising at least 99% identity to SEQ ID NO: 16. In certain embodiments, the miRNA coding sequence comprises SEQ ID NO: 89 (miR538, 59 nt), or a sequence comprising at least 99% identity to SEQ ID NO: 89. In certain embodiments, alternative stem-loop sequences are selected, wherein an anti-sense strand of stem is nt 6 to 26 of SEQ ID NO: 16 (or SEQ ID NO: 106), or nt 1 to 21 of SEQ ID NO: 89 (or SEQ ID NO: 27), and wherein loop sequence is nt 22 to 40 of SEQ ID NO: 89 (or SEQ ID NO: 107).

In certain embodiments, the nucleic acid molecules (e.g., an expression cassette or vector genome) may contain more than one miRNA coding sequence. Such may comprise an miRNA coding sequence having the sequence of one, two or more of: (a) an miRNA coding sequence comprising SEQ ID NO: 15 (miR1693, 64 nt); (b) an miRNA coding sequence comprising at least 60 consecutive nucleotides of SEQ ID NO: 15; (c) an miRNA coding sequence comprising at least 99% identity to SEQ ID NO:15 which comprises a sequence with 100% identity to about nucleotide 6 to about nucleotide 26 of SEQ ID NO: 15 (or SEQ ID NO: 68); and/or (d) an miRNA coding sequence comprising one or more of:

(i) SEQ ID NO: 27
TTGACGTCCAGAACCTGTTCT;

(ii) SEQ ID NO: 28
AGAAGTGGGCACTTAGAGTTG;

(iii) SEQ ID NO: 29
TTCAGAAGTGGGCACTTAGAG;

(iv) SEQ ID NO: 30
TTGTCAATCCAGCTGTCCAGC;

(v) SEQ ID NO: 31
CAAACTTGGTCTTCACTGCAG;

(vi) SEQ ID NO: 32
AAACCTTGAGGACTACTGGAG;

(vii) SEQ ID NO: 33
TAACCATGGAAACCATGAACT;

(viii) SEQ ID NO: 34
ACAACAAGAATGCCCATGGAG;

(ix) SEQ ID NO: 35
AAAGGTCCCAGACAGTTCCTG;

(x) SEQ ID NO: 36
TGTTCATGGCGGCAATTTCCT;

(xi) SEQ ID NO: 37
TGAGGTTGGCTATTGATTGAC;

(xii) SEQ ID NO: 38
TTCTCACACAGTCAACACCTT;

(xiii) SEQ ID NO: 39
TTTCCTCGCAGTAAACCTGCT;

(xiv) SEQ ID NO: 40
AGAAATGGAACTCAATGTCTT;

(xv) SEQ ID NO: 41
TGAACAGGACATCACCTGTGA;

-continued (xvi) SEQ ID NO: 42
AATACAAGCAGGTATGTGAAC;

(xvii) SEQ ID NO: 43
TAAACCTGCTGCTCCCGAGCC;

(xviii) SEQ ID NO: 44
TAGAGGAGGCCATAGAGCCCA;

(xix) SEQ ID NO: 45
TCTACCCGCAGGAAGCAATTG;
or (xx) SEQ ID NO: 46
CTCCTTAGCAGACACAAAGAA, or combinations of any of (i) through (xx). In certain embodiments, the nucleic acid molecules (e.g., an expression cassette or vector genome) may contain one, two or more miRNA coding sequence of SEQ ID NO: 16 (miR1518). In certain embodiments, the nucleic acid molecules (e.g., an expression cassette or vector genome) may contain one, two or more miRNA coding sequence of SEQ ID NO: 89 (miR538).

As used herein, an "miRNA target sequence" is a sequence located on the DNA positive strand (5' to 3') (e.g., of hMfn2) and is at least partially complementary to a miRNA sequence, including the miRNA seed sequence. The miRNA target sequence is exogenous to the untranslated region of the encoded transgene product and is designed to be specifically targeted by miRNA in cells in which repression of transgene expression is desired. Without wishing to be bound by theory, because hMfn2 is a ubiquitous protein and excess expression may be associated with toxicity and/or other negative side effects, the miRNA preferentially target the endogenous hMfn2 gene while avoiding targeting the engineered hMfn2 gene which is delivered to the CMT2A patient. More particularly, the sequences encoding the hMfn2 which are delivered via a vector are designed to contain altered codon sequences at the target site.

Typically, the miRNA target sequence is at least 7 nucleotides to about 28 nucleotides in length, at least 8 nucleotides to about 28 nucleotides in length, 7 nucleotides to 28 nucleotides, 8 nucleotides to 18 nucleotides, 12 nucleotides to 28 nucleotides in length, about 20 to about 26 nucleotides, about 22 nucleotides, about 24 nucleotides, or about 26 nucleotides, and which contains at least one consecutive region (e.g., 7 or 8 nucleotides) which is complementary to the miRNA seed sequence. In certain embodiments, the target sequence comprises a sequence with exact complementarity (100%) or partial complementarity to the miRNA seed sequence with some mismatches. In certain embodiments, the target sequence comprises at least 7 to 8 nucleotides which are 100% complementary to the miRNA seed sequence. In certain embodiments, the target sequence consists of a sequence which is 100% complementary to the miRNA seed sequence. In certain embodiments, the target sequence contains multiple copies (e.g., two or three copies) of the sequence which is 100% complementary to the seed sequence. In certain embodiments, the region of 100% complementarity comprises at least 30% of the length of the target sequence. In certain embodiments, the remainder of the target sequence has at least about 80% to about 99% complementarity to the miRNA. In certain embodiments, in an expression cassette containing a DNA positive strand, the miRNA target sequence is the reverse complement of the miRNA.

Thus, the sequences provided herein which are 95% to 99.9% identical to the Mfn2 coding sequences of SEQ ID NO: 11 and 24, are designed to avoid reverting to a native human sequence to which a selected miRNA in the construct is targeted.

In certain embodiments, the miRNA preferentially targets the endogenous hMfn2 gene while avoiding targeting the engineered hMfn2 gene, wherein the endogenous hMfn2 nucleic acid sequence is of SEQ ID NO: 18. In certain embodiments, the miRNA coding sequence comprises one or more of: (i) TTGACGTCCAGAACCTGTTCT, SEQ ID NO: 27, targeting nt 216-236 of SEQ ID NO: 18; (ii) AGAAGTGGGCACTTAGAGTTG, SEQ ID NO: 28, targeting nt 552-572 of SEQ ID No: 18; (iii) TTCAGAAGTGGGCACTTAGAG, SEQ ID NO: 29, targeting nt 555-575 of SEQ ID NO: 18; (iv) TTGTCAATCCAGCTGTCCAGC, SEQ ID NO: 30, targeting nt 624-644 of SEQ ID NO: 18; (v) CAAACTTGGTCTTCACTGCAG, SEQ ID NO: 31, targeting nt 1055-1075 of SEQ ID NO: 18; (vi) AAACCTTGAGGACTACTGGAG, SEQ ID NO: 32, targeting nt 1364-1384 of SEQ ID NO: 18; (vii) TAACCATGGAAACCATGAACT, SEQ ID NO: 33, targeting nt 1793-1813 of SEQ ID NO: 18; (viii) ACAACAAGAATGCCCATGGAG, SEQ ID NO: 34, targeting nt 1842-1862 of SEQ ID NO: 18; (ix) AAAGGTCCCAGACAGTTCCTG, SEQ ID NO: 35, targeting nt 2068-2088 of SEQ ID NO: 181; (x) TGTTCATGGCGGCAATTTCCT, SEQ ID NO: 36, targeting nt 2135-2155 of SEQ ID NO: 18; (xi) TGAGGTTGGCTATTGATTGAC, SEQ ID NO: 37, targeting 5'UTR; (xii) TTCTCACACAGTCAACACCTT, SEQ ID NO: 38, targeting 3'UTR; (xiii) TTTCCTCGCAGTAAACCTGCT, SEQ ID NO: 39, targeting nt 1157-1177 of SEQ ID NO: 18; (xiv) AGAAATGGAACTCAATGTCTT, SEQ ID NO: 40, targeting nt 1616-1636 of SEQ ID NO: 18; (xv) TGAACAGGACATCACCTGTGA, SEQ ID NO: 41, targeting 3'UTR; (xvi) AATACAAGCAGGTATGTGAAC. SEQ ID NO: 42, targeting 3'UTR; (xvii) TAAACCTGCTGCTCCCGAGCC, SEQ ID NO: 43, targeting nt 1146-1166 of SEQ ID NO: 18; (xviii) TAGAGGAGGCCATAGAGCCCA, SEQ ID NO: 44, targeting nt 1914-1934 of SEQ ID NO: 18; (xix) TCTACCCGCAGGAAGCAATTG, SEQ ID NO: 45, targeting nt 390-410 of SEQ ID NO: 18; or (xx) CTCCTTAGCAGACACAAAGAA, SEQ ID NO: 46, targeting nt 904-924 of SEQ ID NO: 18.

In certain embodiments, the engineered hMfn2 nucleic acid sequence is of SEQ ID NO: 11 or 24. In certain embodiments the engineered hMfn2 nucleic acid sequence is of SEQ ID NO: 18 wherein 1, 2, 3, or 4 nucleotide mismatches are present in the regions of nucleotides: (i) nt 216-236 of SEQ ID NO: 18; (ii) nt 552-572 of SEQ ID NO: 18; (iii) nt 555-575 of SEQ ID NO: 18; (iv) nt 624-644 of SEQ ID NO: 18; (v) nt 1055-1075 of SEQ ID NO: 18; (vi) nt 1364-1384 of SEQ ID NO: 18; (vii) nt 1793-1813 of SEQ ID NO: 18; (viii) nt 1842-1862 of SEQ ID NO: 18; (ix) nt 2068-2088 of SEQ ID NO: 18; (x) nt 2135-2155 of SEQ ID NO: 18; (xi) nt 1157-1177 of SEQ ID NO: 18; (xii) nt 1616-1636 of SEQ ID NO: 18; (xiii) nt 1146-1166 of SEQ ID NO: 18; (xiv) nt 1914-1934 of SEQ ID NO: 18; (xv) nt 390-410 of SEQ ID NO: 18; or (xvi) nt 904-924 of SEQ ID NO: 18.

In certain embodiments, the least one miRNA coding sequence further comprises a 5' flank sequence and 3' flank sequence. In certain embodiments, the at least one miRNA comprises 5' flank—antisense strand—loop—sense strand—3' flank. In certain embodiments, the at least one miRNA comprises 5' flank—antisense strand comprising SEQ ID NO: 17—loop—sense strand comprising SEQ ID NO: 47—3' flank. In certain embodiments, the least one miRNA coding sequence further comprises a 5' flank sequence—SEQ ID NO: 89—3' flank sequence. In certain embodiments, the at least one miRNA is miR538 having nucleic acid sequence of SEQ ID NO: 100.

In certain embodiments, a single nucleic acid (e.g., an expression cassette or vector genome containing same) contains both the engineered hMfn2 coding sequence and at least one miRNA coding sequence, wherein the miRNA is specifically targeted to a region of the endogenous human Mfn2 sequence which is not present in the engineered hMfn2 sequence. In certain embodiments, the human mitofusin 2 coding sequence is upstream (5') of the at least one miRNA and these two elements are separated by a spacer or linker sequence. In certain embodiments, there is at least 75 nucleotides between the stop codon of the hMfn2 coding sequence and the start of the most 5' miRNA coding sequence. In certain embodiments, the spacer is about 75 nucleotides to about 300 nucleotides, or about 75 nucleotides to about 250 nucleotides, or about 75 nucleotides to about 200 nucleotides, or about 75 nucleotides to about 150 nucleotides, or about 75 nucleotides to about 100 nucleotides, or about 80 nucleotides to about 300 nucleotides, or about 80 nucleotides to about 250 nucleotides, or about 80 nucleotides to about 200 nucleotides, or about 80 nucleotides to about 150 nucleotides, or about 80 nucleotides to about 100 nucleotides. Optionally, the engineered hMfn2 coding sequence and the at least one miRNA coding sequence are separated by about 75 nucleotides. Suitably, the spacer sequence is a non-coding sequence which lacks any restriction enzyme sites. Optionally, the spacer may include one or more intron sequences. In certain embodiments, one or more of the miRNA sequences may be located within the intron. In certain embodiments, the linker sequence is SEQ ID NO: 17. In certain embodiments, the linker sequence is SEQ ID NO: 90.

In certain embodiments, the engineered hMfn2 coding sequence and the miRNA coding sequence(s) are delivered via different nucleic acid sequences, e.g., two or more different vectors, a combination comprising a vector and an LNP, etc. In certain embodiments, the two different vectors are AAV vectors. In certain embodiments, these vectors have different expression cassettes. In other embodiments, these vectors have the same capsid. In other embodiments, the vectors have different embodiments. In certain embodiments, the miRNA coding sequence(s) are delivered via an LNP or another non-viral delivery system. In certain embodiments, the engineered hMfn2 sequence is delivered via an LNP or another non-viral delivery system. In certain embodiments, combinations of two or more different delivery systems (e.g., viral and non-viral, two different non-viral) are used. In these and other embodiments, the two or more different vectors or other delivery systems may be administered substantially simultaneously, or one or more of these systems may be delivered before the other. In certain embodiments, the engineered hMfn2 sequence is SEQ ID NO: 11, or a sequence 90% to 100% identical thereto which encodes an mRNA which is not bound by the miR with which it is co-administered and which encodes hMfn2. In certain embodiments, the engineered hMfn2 sequence is SEQ ID NO: 24, or a sequence 90% to 100% identical thereto which encodes an mRNA which is not bound by the miR with which it is co-administered and which encodes hMfn2. In certain embodiments, the miR is miR538 having the sequence of SEQ ID NO: 89 which targets endogenous hMfn2 in the subject, but which does not target the engineered hMfn2 cDNA sequence or engineered encoded mRNA sequence.

As used herein, the terms "AAV.hMfn2" or "rAAV.hMfn2" are used to refer to a recombinant adeno-associated virus which has an AAV capsid having therewithin a vector genome comprising a human mitofusin 2 coding sequence (e.g., a cDNA) under the control of regulatory sequences. As used herein, the terms "AAV.hMfn2 miRXXX" or "rAAV.hMfn2.miRXXX" are used to refer to a recombinant adeno-associated virus which has an AAV capsid having therewithin a vector genome comprising an miR targeting an endogenous human mitofusin 2 coding sequence.

Specific capsid types may be specified, such as, e.g., AAV1.hMfn2 or rAAV1.hMfn2, which refers to a recombinant AAV having an AAV1 capsid; AAVhu68.hMfn2 or AAVhu68.Mfn2, which refers to recombinant AAV having an AAVhu68 capsid. AAVrh91.hMfn2 or AAVrh91.Mfn2, which refers to recombinant AAV having an AAVrh91 capsid.

A "recombinant AAV" or "TAAV" is a DNAse-resistant viral particle containing two elements, an AAV capsid and a vector genome containing at least non-AAV coding sequences packaged within the AAV capsid. Unless otherwise specified, this term may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends (i.e., AAV5' ITR and AAV3' ITR) of the vector genome in order to allow the gene and regulatory sequences located between the ITRs to be packaged within the AAV capsid. Generally, an AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. Various AAVs may be selected as sources for capsids of AAV viral vectors as identified above. In one embodiment, the AAV capsid is an AAV9 capsid or an engineered variant thereof. In certain embodiments, the variant AAV9 capsid is an AAV9.PhP.eB capsid (nucleic acid sequence of SEQ ID NO: 84; amino acid sequence of SEQ ID NO: 85). In certain embodiments, the PhP.eB capsid is selected for use in mouse studies and is a suitable model for a clade F vector (e.g., AAVhu68) in humans. In certain embodiments, the capsid protein is designated by a number or a combination of numbers and letters following the term "AAV" in the name of the rAAV vector. Unless otherwise specified, the AAV capsid, ITRs, and other selected AAV components described herein, may be readily selected from among any AAV, including, without limitation, the AAVs identified as AAV1, AAV2, AAV3, AAV4, AAV5, AAV6, AAV7, AAV8, AAV9, AAVrh10, AAVhu37, AAVrh32.33, AAV8bp, AAV7M8 and AAVAnc80, AAV1, AAV2, AAV3, AAV4, AAV5, AAV6, AAV7, AAV8, AAV9.47, AAV9 (hu14), AAV10, AAV11, AAV12, AAVrh8, AAVrh74, AAV-DJ8, AAV-DJ, AAVhu68, and AAV9 variants (e.g., U.S. Provisional Application No. 63/119,863, filed Dec. 1, 2020), without limitation. See. e.g., WO 2019/168961 and WO 2019/169004, both for Novel AAV Vectors Having Reduced Capsid Deamidation and Uses Therefor; US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10), WO 2005/033321, WO 2018/160582 (AAVhu68), which are incorporated herein by reference. See, also WO 2019/168961 and WO 2019/169004, describing deamidation profiles for these and other AAV capsids. Other suitable AAVs may include, without limitation, AAVrh90 [PCT/US20/30273, filed Apr. 28, 2020], AAVrh91 [PCT/US20/30266, filed Apr. 28, 2020 and U.S. Provisional Patent Applications No. 63/109,734, filed Nov. 4, 2020 and U.S. Provisional Patent Application No. 63/065,616, filed Aug. 14, 2020] AAVrh92, AAVrh93, AAVrh91.93 [PCT/US20/30281, filed Apr. 28, 2020], which are incorporated by reference herein. Other suitable AAV include AAV3B variants which are described in PCT/US20/56511, filed Oct. 20, 2020, which claims the benefit of US Provisional Patent Application No. 62/924,112, filed Oct. 21, 2019, and U.S. Provisional Patent Application No. 63/025,753, filed May 15, 2020, describing AAV3B.AR2.01, AAV3B.AR2.02, AAV3B.AR2.03, AAV3B.AR2.04, AAV3B.AR2.05, AAV3B.AR2.06, AAV3B.AR2.07, AAV3B.AR2.08, AAV3B.AR2.10, AAV3B.AR2.11, AAV3B.AR2.12, AAV3B.AR2.13, AAV3B.AR2.14, AAV3B.AR2.15, AAV3B.AR2.16, or AAV3B.AR2.17, which are incorporated herein by reference. These documents also describe other AAV capsids which may be selected for generating rAAV and are incorporated by reference. Among the AAVs isolated or engineered from human or non-human primates (NHP) and well characterized, human AAV2 is the first AAV that was developed as a gene transfer vector; it has been widely used for efficient gene transfer experiments in different target tissues and animal models.

As used herein, a "vector genome" refers to the nucleic acid sequence packaged inside a parvovirus (e.g., rAAV) capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s) (i.e., transgene(s)), and an AAV 3' ITR. ITRs from AAV2, a different source AAV than the capsid, or other than full-length ITRs may be selected. In certain embodiments, the ITRs are from the same AAV source as the AAV which provides the rep function during production or a trans-complementing AAV. Further, other ITRs, e.g., self-complementary (scAAV) ITRs, may be used. Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue. Suitable components of a vector genome are discussed in more detail herein.

In one example, a "vector genome" contains, at a minimum, from 5' to 3', a vector-specific sequence, a nucleic acid sequence comprising an engineered human Mfn2 coding sequence and optionally an miRNA sequences targeting the endogenous Mfn2 operably linked to regulatory control sequences (which direct their expression in a target cell), where the vector-specific sequence may be a terminal repeat sequence which specifically packages the vector genome into a viral vector capsid or envelope protein. For example, AAV inverted terminal repeats are utilized for packaging into AAV and certain other parvovirus capsids.

In certain embodiments, a composition is provided which comprises an aqueous liquid suitable for intrathecal injection and a stock of vector (e.g., rAAV having a AAV capsid which preferentially targets cells in the central nervous system and/or the dorsal root ganglia (e.g., CNS, including, e.g., nerve cells (such as, pyramidal, purkinje, granule, spindle, and interneuron cells) and glia cells (such as astrocytes, oligodendrocytes, microglia, and ependymal cells), wherein the vector having an engineered hMfn2 coding sequence and/or an at least one miRNA specific endogenous hMfn2 for delivery to the central nervous system (CNS). In certain embodiments, the composition comprising one or more vectors as described herein is formulated for sub-occipital injection into the cisterna magna (intra-cisterna magna). In certain embodiments, the composition is administered via a computed tomography-(CT-) rAAV injection. In certain embodiments, the composition is administered using Ommaya reservoir. In certain embodiments, the patient is administered a single dose of the composition.

As used herein, an "expression cassette" refers to a nucleic acid molecule which comprises a biologically useful nucleic acid sequence (e.g., a gene cDNA encoding a protein, enzyme or other useful gene product, mRNA, etc.) and regulatory sequences operably linked thereto which direct or modulate transcription, translation, and/or expression of the nucleic acid sequence and its gene product. As used herein, "operably linked" sequences include both regulatory sequences that are contiguous or non-contiguous with the nucleic acid sequence and regulatory sequences that act in trans or cis nucleic acid sequence. Such regulatory sequences typically include, e.g., one or more of a promoter, an enhancer, an intron, a Kozak sequence, a polyadenylation sequence, and a TATA signal. The expression cassette may contain regulatory sequences upstream (5' to) of the gene sequence, e.g., one or more of a promoter, an enhancer, an intron, etc., and one or more of an enhancer, or regulatory sequences downstream (3' to) a gene sequence, e.g., 3' untranslated region (3' UTR) comprising a polyadenylation site, among other elements. In certain embodiments, the regulatory sequences are operably linked to the nucleic acid sequence of a gene product, wherein the regulatory sequences are separated from nucleic acid sequence of a gene product by an intervening nucleic acid sequences, i.e., 5'-untranslated regions (5'UTR). In certain embodiments, the expression cassette comprises nucleic acid sequence of one or more of gene products. In some embodiments, the expression cassette can be a monocistronic or a bicistronic expression cassette. In other embodiments, the term "transgene" refers to one or more DNA sequences from an exogenous source which are inserted into a target cell.

Typically, such an expression cassette can be used for generating a viral vector or vector genome and contains the coding sequence for the gene product described herein flanked by packaging signals of the viral genome and other expression control sequences such as those described herein. In certain embodiments, a vector genome may contain two or more expression cassettes.

In certain embodiments, vector genome comprises an expression cassette comprising the nucleic acid sequence: i) Syn.PI.hMfn2eng.link.hMfn2.miR1693.WPRE.bGH (nt 223 to 4455 of SEQ ID NO: 1 or SEQ ID NO: 91); ii) CB7.CI.hMfn2.GA.RBG (nt 259 to 4370 of SEQ ID NO: 79 or SEQ ID NO: 98); iii) CB7.CI.hMfn2.GA.LINK.miR1518.RBG (nt 259 to 4710 of SEQ ID NO: 77 or SEQ ID NO: 97); iv) CB7.CI.hMfn2.GA.LINK.miR538.RBG (nt 259 to 4626 of SEQ ID NO: 75 or SEQ ID NO: 96); v) CAG.CI.hMfn2.GA.WPRE.SV40 (nt 192 to 4262 of SEQ ID NO: 73 or SEQ ID NO: 95); vi) CAG.CI.hMfn2.GA.LINK.miR1518.WPRE.SV40 (nt 192 to 4474 of SEQ ID NO: 71 or SEQ ID NO: 94); vii) CAG.CI.hMfn2.GA.LINK.miR538.WPRE.SV40 (nt 192 to 4474 of SEQ ID NO: 69 or SEQ ID NO: 93); or viii) Syn.PI.rMnf2eng.link.rMfn2 miR1518 WPRE.BGH (nt 223 to 4430 of SEQ ID NO: 3 or SEQ ID NO: 92). In certain embodiments, vector genome comprises an expression cassette comprising the nucleic acid sequence: CB7.CI.hMfn2.GA.LINK.miR538.RBG (nt 259 to 4626 of SEQ ID NO: 75 or SEQ ID NO: 96)

In certain embodiment expression cassette comprises the hMfn2 coding sequences (and/or miRNA sequences targeting the endogenous Mfn2), promoter, and may include other regulatory sequences therefor, which cassette may be packaged into a vector (e.g., rAAV, lentivirus, retrovirus, etc.).

AAV

Recombinant parvoviruses are particularly well suited as vectors for treatment of disorder associated with deficient hMfn2, or CMT2A. As described herein, recombinant parvoviruses may contain an AAV capsid (or bocavirus capsid). In certain embodiments, the capsid targets cells within the dorsal root ganglion and/or cells within the lower motor neurons and/or primary sensory neurons. In certain embodiments, compositions provided herein may have a single rAAV stock which comprises an rAAV comprising an engineered hMfn2 and an miRNA specifically targeting endogenous hMfn2 in order to downregulate the endogenous hMfn2 levels and to reduce any toxicity associated with overexpression of hMfn2. In other embodiments, an rAAV may be comprise the hMfn2 and may be co-administered with a different vector comprising an miRNA which downregulates endogenous hMfn2. In other embodiments, an rAAV may be comprise the at least one miRNA which downregulates endogenous hMfn2 and a second vector (or other composition) delivers the hMfn2.

For example, vectors generated using AAV capsids from Clade F (e.g., AAVhu68 or AAV9) can be used to produce vectors which target and express hMfn2 in the CNS. Alternatively, vectors generated using AAV capsids from Clade A (e.g., AAV1, AAVrh91) may be selected. In still other embodiments, other parvovirus or other AAV viruses may be suitable sources of AAV capsids.

An AAV1 capsid refers to a capsid having AAV vp1 proteins, AAV vp2 proteins and AAV vp3 proteins. In particular embodiments, the AAV1 capsid comprises a predetermined ratio of AAV vp1 proteins, AAV vp2 proteins and AAV vp3 proteins of about 1:1:10 assembled into a T1 icosahedron capsid of 60 total vp proteins. An AAV1 capsid is capable of packaging genomic sequences to form an AAV particle (e.g., a recombinant AAV where the genome is a vector genome). Typically, the capsid nucleic acid sequences encoding the longest of the vp proteins. i.e., VP1, is expressed in trans during production of an rAAV having an AAV1 capsid are described in, e.g., U.S. Pat. Nos. 6,759,237, 7,105,345, 7,186,552, 8,637,255, and 9,567,607, which are incorporated herein by reference. See, also, WO 2018/168961, which is incorporated by reference. In certain embodiments, AAV1 is characterized by a capsid composition of a heterogenous population of VP isoforms which are deamidated as defined in WO 2018/160582, incorporated herein by reference in its entirety, based on the total amount of VP proteins in the capsid, as determined using mass spectrometry. In certain embodiments, the AAV capsid is modified at one or more of the following positions, in the ranges provided below, as determined using mass spectrometry. Suitable modifications include those described in the paragraph above labelled modulation of deamidation, which is incorporated herein. In certain embodiments, one or more of the following positions, or the glycine following the N is modified as described herein. In certain embodiments, an AAV1 mutant is constructed in which the glycine following the N at position 57, 383, 512 and/or 718 are preserved (i.e., remain unmodified). In certain embodiments, the NG at the four positions identified in the preceding sentence are preserved with the native sequence. In certain embodiments, an artificial NG is introduced into a different position than one of the positions as defined and identified in WO 2018/160582, incorporated herein by reference.

As used herein, an AAVhu68 capsid refers to a capsid as defined in WO 2018/160582, incorporated herein by reference. As described herein, a rAAVhu68 has a rAAVhu68 capsid produced in a production system expressing capsids from an AAVhu68 nucleic acid. In certain embodiments, the AAVhu68 nucleic acid sequence is SEQ ID NO: 81, encoding and for an amino acid sequence of SEQ ID NO 82. In certain embodiments, the AAVhu68 nucleic acid sequence is SEQ ID NO: 83, encoding for an amino acid sequence of SEQ ID NO: 82. The rAAVhu68 resulting from production using a single nucleic acid sequence vp1 produces the heterogenous populations of vp1 proteins, vp2 proteins and vp3 proteins. These subpopulations include, at a minimum, deamidated asparagine (N or Asn) residues. For example, asparagines in asparagine—glycine pairs are highly deamidated. In certain embodiments, the vp2 and/or vp3 proteins may be expressed additionally or alternatively from different nucleic acid sequences than the vp1, e.g., to alter the ratio of the vp proteins in a selected expression system. In certain embodiments, the AAVhu68 capsid coding sequence is a coding sequence which is useful in manufacturing of recombinant AAV (rAAV) for generating higher yields of recombinant AAV having AAVhu68 capsids. See also, U.S. Provisional Patent Application No. 63/093,275, filed Oct. 18, 2020, and International Patent Application No. PCTPCT/US2021/055436, filed Oct. 18, 2021, which are incorporated herein by reference in their entireties.

Genomic sequences which are packaged into an AAV capsid and delivered to a host cell are typically composed of, at a minimum, a transgene and its regulatory sequences (e.g., expression cassette), and AAV inverted terminal repeats (ITRs). Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences.

The ITRs are the genetic elements responsible for the replication and packaging of the genome during vector production and are the only viral cis elements required to generate rAAV. In one embodiment, the ITRs are from an AAV different than that supplying a capsid. In a preferred embodiment, the ITR sequences from AAV2, or the deleted version thereof (ΔITR), which may be used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, AAV vector genome comprises an AAV 5' ITR, the nucleic acid sequences encoding the gene product (s) and any regulatory sequences, and an AAV 3' ITR. However, other configurations of these elements may be suitable. In one embodiment, a self-complementary AAV is provided. A shortened version of the 5' ITR, termed AITR, has been described in which the D-sequence and terminal resolution site (trs) are deleted. In certain embodiments, the vector genome includes a shortened AAV2 ITR of 130 base pairs, wherein the external "a" element is deleted. The shortened ITR is reverted back to the wild-type length of 145 base pairs during vector DNA amplification using the internal A element as a template. In other embodiments, the full-length AAV 5' and 3' ITRs are used.

In addition to the major elements identified above for the vector (e.g., an rAAV), the vector also includes conventional control elements necessary which are operably linked to the transgene in a manner which permits its transcription, translation and/or expression in a cell. As used herein, the term "expression" or "gene expression" refers to the process by which information from a gene is used in the synthesis of a functional gene product. The gene product may be a protein, a peptide, or a nucleic acid polymer (such as an RNA, a DNA or a PNA).

As used herein, the term "regulatory sequence", "regulatory control sequences" or "expression control sequence" refers to nucleic acid sequences, such as initiator sequences, enhancer sequences, and promoter sequences, which induce, repress, or otherwise control the transcription of protein encoding nucleic acid sequences to which they are operably linked. The regulatory control elements typically contain a promoter sequence as part of the expression control sequences, e.g., located between the selected 5' ITR sequence and the coding sequence. In particularly desirable embodiments, a tissues specific promoter for the central nervous system is selected. For example, the promoter may be a neural cell promoter, e.g., gfaABC(1)D promoter (Addgene #50473)), or the human Syn promoter (the sequence is available from Addgene, Ref. #50465).

Other suitable promoters may include. e.g., constitutive promoters, regulatable promoters [see, e.g., WO 2011/126808 and WO 2013/04943], tissue specific promoters, or a promoter responsive to physiologic cues may be used may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter (CB promoter). In certain embodiments, the promoter is a CB promoter comprising nucleic acid sequence of SEQ ID NO: 102. In addition to a promoter a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer (CMV IE enhancer). In certain embodiments, the enhancer is a CMV IE enhancer comprising nucleic acid sequence of SEQ ID NO: 103. This enhancer may be present in two copies which are located adjacent to one another. Alternatively, the dual copies of the enhancer may be separated by one or more sequences. In still another embodiment, the expression cassette further contains an intron, e.g., the chicken beta-actin intron. In certain embodiments, the chicken beta-actin intron comprises nucleic acid sequence of SEQ ID NO: 99. Other suitable introns include those known in the art, e.g., such as are described in WO 2011/126808. Examples of suitable polyA sequences include, e.g., rabbit beta globin (RBG), SV40, SV50, bovine growth hormone (bGH), human growth hormone, and synthetic polyAs. In certain embodiments, the polyA is SV40 polyA. In certain embodiments, the polyA is rabbit beta globin poly A (RBG or rBG). In certain embodiments, the rabbit beta-globin polyA signal comprises nucleic acid sequence of SEQ ID NO: 88. Optionally, one or more sequences may be selected to stabilize mRNA. An example of such a sequence is a post-transcriptional regulatory element from hepatitis viruses of woodchuck (WPRE) sequence. In certain embodiments, the WPRE is a variant that has been mutated to eliminate expression of the woodchuck hepatitis B virus X (WHX) protein, including, for example, mutations in the start codon of the WHX gene. In certain embodiments, modified WPRE element is engineered to eliminate expression of the WHX protein, wherein the modified WPRE is a mutated version that contains five-point mutations in the putative promoter region of the WHX gene, along with an additional mutation in the start codon of the WHX gene (ATG mutated to TTG). This mutant WPRE is considered sufficient to eliminate expression of truncated WHX protein based on sensitive flow cytometry analyses of various human cell lines transduced with lentivirus containing a WPRE-GFP fusion construct (Zanta-Boussif et al., 2009). See also, Kingsman S. M., Mitrophanous K., & Olsen J. C. (2005), Potential Oncogene Activity of the Woodchuck Hepatitis Post-Transcriptional Regulatory Element (WPRE)." Gene Ther. 12(1):3-4; and Zanta-Boussif M. A., Charrier S., Brice-Ouzet A., Martin S., Opolon P., Thrasher A. J., Hope T. J., & Galy A. (2009). Validation of a Mutated Pre-Sequence Allowing High and Sustained Transgene Expression While Abrogating Why-X Protein Synthesis: Application to the Gene Therapy of Was, Gene Ther. 16(5):605-19, both of which are incorporated herein by reference in its entirety. In certain embodiments, the WPRE element comprises nucleotides 1093 to 1683 of the GenBank: J02442.1 (591 nucleotides; SEQ ID NO: 40). In certain embodiments, the WPRE element comprises nucleic acid sequence of SEQ ID NO: 39. In other embodiments, enhancers are selected from a non-viral source. In certain embodiments, no WPRE sequence is present. In certain embodiments, the WPRE sequence may be engineered upstream of the poly A sequence and downstream of the coding. In certain embodiments, the WPRE element comprises nucleic acid sequence of SEQ ID NO: 101.

In certain embodiments, the vector genome comprises a tissue specific promoter. In some embodiments, the tissue specific promoter is a human synapsin promoter. In certain embodiments, the human synapsin promoter comprises nucleic acid sequence of SEQ ID NO: 6. In certain embodiments, the vector genome comprises a constitutive promoter, wherein the promoter is a CB7 promoter or a CAG promoter. In certain embodiments, the CB7 promoter (i.e., CB7 hybrid promoter) comprises CMV IE enhancer, a chicken beta actin promoter and optionally a linker. In certain embodiments, the CB7 hybrid promoter comprises nucleic acid sequence of SEQ ID NO: 86. In certain embodiments, the CAG promoter comprises nucleic acid sequence of SEQ ID NO: 87.

In one embodiment, the vector genome comprises: an AAV 5' ITR, a promoter, an optional enhancer, an optional intron, a coding sequence for human Mfn2 (hMfn2 or huMfn2) comprising same, a poly A, and an AAV 3' ITR. In certain embodiments, the vector genome comprises: a AAV 5' ITR, a promoter, an optional enhancer, an optional intron, a coding sequence for human Mfn2 comprising same, a poly A, and an AAV 3' ITR. In certain embodiments, the vector genome comprises: a AAV 5' ITR, a promoter, an optional enhancer, an optional intron, a huMfn2 coding sequence, a poly A, and an AAV 3' ITR. In certain embodiments, the vector genome comprises: an AAV2 5' ITR, an EF1a promoter, an optional enhancer, an optional promoter, huMfn2, an SV40 poly A, and an AAV2 3' ITR. In certain embodiments, the vector genome is AAV2 5' ITR, UbC promoter, optional enhancer, optional intron, huMfn2, an SV40 poly A, and an AAV2 3' ITR. In certain embodiments, the vector genome is AAV2 5' ITR, CB7 promoter, an intron, huMfn2, an SV40 poly A, and an AAV2 3' ITR. In certain embodiment, the vector genome is an AAV2 5' ITR, CB7 promoter, intron, huMfn2, a rabbit beta globin poly A, and an AAV2 3' ITR. In certain embodiment, the vector genome is an AAV2 5' ITR, CB7 promoter, intron, an engineered huMfn2, a linker, a miR targeted to endogenous huMfn2 sequence, a rabbit beta globin poly A, and an AAV2 3' ITR. In certain embodiment, the vector genome is an AAV2 5' ITR, CB7 promoter, intron, an engineered huMfn2, a linker, a miR1518 sequence, a rabbit beta globin poly A, and an AAV2 3' ITR. In certain embodiment, the vector genome is an AAV2 5' ITR, CB7 promoter, intron, an engineered huMfn2, a linker, a miR538, a rabbit beta globin poly A, and an AAV2 3' ITR. In certain embodiment, the vector genome is an AAV2 5' ITR, CB7 promoter (comprising CMV IE enhancer and CB promoter), a chicken beta actin intron, an engineered huMfn2, a linker, a miR538, a rabbit beta globin poly A, and an AAV2 3' ITR. See, e.g., SEQ ID NOs: 1, 3, 69, 71, 73, 75, 77, and 79. In certain embodiment, the vector genome comprises nucleic acid sequence pf SEQ ID NO: 75. The huMfn2 coding sequences are selected from those defined in the present specification. See, e.g., SEQ ID NO: 11 or a sequence 95% to 99.9% identical thereto, or SEQ ID NO: 11 or a sequence 95% to 99.9% identical thereto, or a fragment thereof as defined herein. Other elements of the vector genome or variations on these sequences may be selected for the vector genomes for certain embodiments of this invention.

In certain embodiments, the rAAV comprises an AAV capsid and packaged therein a vector genome, wherein the vector genome comprises CB7.CI.hMfn2.GA.link.miR538.rBG comprising: (a) an AAV 5' inverted terminal repeat (ITR), (b) an expression cassette comprising at least one open reading frame (ORF) comprising an engineered nucleic acid sequence encoding human mitofusin 2 (hMfn2) and at least one miRNA coding sequence which is specific for a target site in an endogenous human mitofusin 2 nucleic acid sequence in a CMT2 patient; and (c) an AAV 3'ITR, wherein the expression cassette comprises at least one ORF operably linked to regulatory control sequences which direct expression thereof in a cell, wherein the at least one ORF comprises: (i) an engineered nucleic acid sequence encoding human mitofusin 2 (hMfn2); (ii) a spacer sequence located between (i) and (iii); and (iii) at least one miRNA coding sequence which is specific for a target site in an endogenous human mitofusin 2 nucleic acid sequence in a CMT2 patient, wherein the miRNA is miR538; wherein the engineered nucleic acid sequence of (i) lacks the target site for the at least one miRNA of (iii), thereby preventing the at least one miRNA from targeting the engineered hMfn2 coding sequence; and wherein the regulatory control sequences comprise a CB7 hybrid promoter comprising a cytomegalovirus immediate early (CMV IE) enhancer and a chicken beta actin promoter (CB) promoter, a chicken beta-actin intron (CI), and a rabbit beta globin (rBG or RBG) polyadenylation (polyA) signal.

In certain embodiments, the rAAV comprises a vector genome comprising an expression cassette comprising nucleic acid sequence: i) Syn.PI.hMfn2eng.link.hMfn2.miR1693.WPRE.bGH (nt 223 to 4455 of SEQ ID NO: 1 or SEQ ID NO: 91); ii) CB7.CI.hMfn2.GA.RBG (nt 259 to 4370 of SEQ ID NO: 79 or SEQ ID NO: 98); iii) CB7.CI.hMfn2.GA.LINK.miR1518.RBG (nt 259 to 4710 of SEQ ID NO: 77 or SEQ ID NO: 97); iv) CB7.CI.hMfn2.GA.LINK.miR538.RBG (nt 259 to 4626 of SEQ ID NO: 75 or SEQ ID NO: 96); v) CAG.CI.hMfn2.GA.WPRE.SV40 (nt 192 to 4262 of SEQ ID NO: 73 or SEQ ID NO: 95); vi) CAG.CI.hMfn2.GA.LINK.miR1518.WPRE.SV40 (nt 192 to 4474 of SEQ ID NO: 71 or SEQ ID NO: 94); vii) CAG.CI.hMfn2.GA.LINK.miR538.WPRE.SV40 (nt 192 to 4474 of SEQ ID NO: 69 or SEQ ID NO: 93); or viii) Syn.PI.rMnf2eng.link.rMfn2 miR1518 WPRE.BGH (nt 223 to 4430 of SEQ ID NO: 3 or SEQ ID NO: 92).

In certain embodiments, the rAAV comprises an expression cassette comprising nucleic acid sequence of SEQ ID NO: 96, or a sequence at least 99% identical to SEQ ID NO: 96. In certain embodiments, the rAAV comprises a vector genome comprising nucleic acid sequence of SEQ ID NO: 75 or a sequence at least 99% identical to SEQ ID NO: 75.

Vector Production

Provided herein also is an rAAV production system useful producing the rAAV, as described herein, wherein the production system comprises a cell culture comprising: (a) a nucleic acid sequence encoding a AAV capsid protein; (b) a vector genome; and (c) sufficient AAV rep functions and helper functions to permit packaging of the vector genome into the AAV capsid.

In certain embodiments, provided herein is a recombinant nucleic acid molecule comprising: (a) an AAV 5' inverted terminal repeat (ITR), (b) an expression cassette comprising at least one open reading frame (ORF) comprising an engineered nucleic acid sequence encoding human mitofusin 2 (hMfn2) and at least one miRNA coding sequence which is specific for a target site in an endogenous human mitofusin 2 nucleic acid sequence in a patient having disorder associated with deficient hMfn2 (e.g., CMT2A); and (c) an AAV 3'ITR, wherein the expression cassette comprises at least one ORF operably linked to regulatory control sequences which direct expression thereof in a cell, wherein the at least one ORF comprises: (i) an engineered nucleic acid sequence encoding human mitofusin 2 (hMfn2) having nucleic acid sequence of SEQ ID NO: 11; (ii) a spacer sequence located between (i) and (iii); and (iii) at least one miRNA coding sequence which is specific for a target site in an endogenous human mitofusin 2 nucleic acid sequence in the patient, wherein the miRNA is miR538 which comprises a targeting sequence having nucleic acid sequence of SEQ ID NO: 89: wherein the engineered nucleic acid sequence of (i) lacks the target site for the at least one miRNA of (iii), thereby preventing the at least one miRNA from targeting the engineered hMfn2 coding sequence; and wherein the regulatory control sequences comprise a CB7 hybrid promoter comprising a cytomegalovirus immediate early (CMV IE) enhancer and a chicken beta actin promoter (CB) promoter, a chicken beta-actin intron (CI), and a rabbit beta globin (rBG or RBG) polyadenylation (polyA) signal. In certain embodiments, the recombinant nucleic acid molecule comprises expression cassette comprising nucleic acid sequence of SEQ ID NO: 96. In certain embodiments, the recombinant nucleic acid molecule comprises a vector genome comprising nucleic acid sequence of SEQ ID NO: 75. In certain embodiments, the nucleic acid molecule is a plasmid.

For use in producing an AAV viral vector (e.g., a recombinant (r) AAV), the expression cassettes can be carried on any suitable vector, e.g., a plasmid, which is delivered to a production (packaging) host cell. The plasmids useful in this invention may be engineered such that they are suitable for replication and packaging in vitro in prokaryotic cells, insect cells, mammalian cells, among others. Suitable transfection techniques and production host cells are known and/or can be readily designed by one of skill in the art.

TABLE 2

| AAV Vector | SEQ ID NOS (vector genome) |
|---|---|
| Syn.PI.hMfn2eng.link.hMfn2.miR1693.WPRE.bGH | 1 |
| Syn.PI.rMnf2eng.link.rMfn2 miR1518 WPRE.BGH | 3 |
| CB7.CI.hMfn2.GA.RBG | 79 |
| CB7.CI.hMfn2.GA.LINK.miR1518.RBG | 77 |
| CB7.CI.hMfn2.GA.LINK.miR538.RBG | 75 |
| CAG.CI.hMfn2.GA.WPRE.SV40 | 73 |
| CAG.CI.hMfn2.GA.LINK.miR1518.WPRE.SV40 | 71 |
| CAG.CI.hMfn2.GA.LINK.miR538.WPRE.SV40 | 69 |

In certain embodiments, the production plasmid comprises a vector genome for packaging into a capsid which comprises: (a) an engineered nucleic acid sequence encoding human mitofusin 2; (b) a spacer sequence located between (a) and (c); (c) at least one miRNA sequence specific for endogenous human mitofusin 2 in a patient having disorder associated with deficient hMfn2 (e.g., CMT2A) located 3' to the sequence of (a) and (b); wherein the engineered nucleic acid sequence of (a) lacks the target site for the at least one miRNA, thereby preventing the miRNA from targeting the engineered human mitofusin 2 coding sequence; (c) regulatory sequences operably linked to (a) and (c). In certain embodiments, the production plasmid comprises a vector genome comprising nucleic acid sequence of SEQ ID NO: 1, 3, 69, 71, 73, 75, 77, or 79. In certain embodiments, the production plasmid comprises a vector genome comprising nucleic acid sequence of SEQ ID NO: 75.

Methods for generating and isolating AAVs suitable for use as vectors are known in the art. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to an AAV production (packaging) cell by any suitable method, including transfection, electroporation, liposome delivery, membrane fusion techniques, high velocity DNA-coated pellets, viral infection and protoplast fusion. Stable AAV production (packaging) cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette as described herein flanked by AAV inverted terminal repeats (ITRs) and a transgene; and sufficient helper functions to permit packaging of the expression cassette into the AAV capsid protein. Also provided herein is the host cell which contains a nucleic acid sequence encoding an AAV capsid; a functional rep gene; a vector genome as described; and sufficient helper functions to permit packaging of the vector genome into the AAV capsid protein. In one embodiment, the host cell is a HEK 293 cell. These methods are described in more detail in WO2017160360 A2, which is incorporated by reference herein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture (i.e., packaging host cell or production host cell) useful for producing a recombinant AAV is provided. Such a cell culture contains a nucleic acid which expresses the AAV capsid protein in the host cell; a nucleic acid molecule suitable for packaging into the AAV capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAV capsid. In one embodiment, the cell culture is composed of mammalian cells (e.g., human embryonic kidney 293 cells, among others) or insect cells (e.g., baculovirus).

Typically, the rep functions are from the same AAV source as the AAV providing the ITRs flanking the vector genome. In the examples herein, the AAV2 ITRs are selected and the AAV2 rep is used. Optionally, other rep sequences or another rep source (and optionally another ITR source) may be selected. For example, the rep may be, but is not limited to, AAV1 rep protein, AAV2 rep protein; or rep 78, rep 68, rep 52, rep 40, rep68/78 and rep40/52; or a fragment thereof; or another source. Optionally, the rep and cap sequences are on the same genetic element in the cell culture. There may be a spacer between the rep sequence and cap gene. Any of these AAV or mutant AAV capsid sequences may be under the control of exogenous regulatory control sequences which direct expression thereof in a host cell.

In one embodiment, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media.

In certain embodiments, the manufacturing process for rAAV.hMfn2 involves method as described in U.S. Provisional Patent Application No. 63/371,597, filed Aug. 16, 2022, and U.S. Provisional Patent Application No. 63/371,592, filed Aug. 16, 2022, which are incorporated herein by reference in its entirety.

In certain embodiments, the manufacturing process for rAAV.hMfn2 involves transient transfection of HEK293 cells with plasmid DNA. A single batch or multiple batches are produced by PEI-mediated triple transfection of HEK293 cells in PALL iCELL is bioreactors. Harvested AAV material are purified sequentially by clarification, TFF, affinity chromatography, and anion exchange chromatography in disposable, closed bioprocessing systems where possible.

The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065, which are incorporated herein by reference.

The crude cell harvest may thereafter be subject to additional method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in International Patent Application No. PCT/US2016/065970, filed Dec. 9, 2016, which is incorporated by reference herein. Purification methods for AAV8, International Patent Application No. PCT/US2016/065976, filed Dec. 9, 2016, and rh 10, International Patent Application No. PCT/US16/66013, filed Dec. 9, 2016, entitled "Scalable Purification Method for AAVrh10", also filed Dec. 11, 2015, and for AAV1, International Patent Application No. PCT/US2016/065974, filed Dec. 9, 2016, for "Scalable Purification Method for AAV1", filed Dec. 11, 2015, are all incorporated by reference herein.

To calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e., SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad-spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2-fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000-fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAV particles having packaged genomic sequences from genome-deficient AAV intermediates involves subjecting a suspension comprising recombinant AAV viral particles and AAV capsid intermediates to fast performance liquid chromatography, wherein the AAV viral particles and AAV intermediates are bound to a strong anion exchange resin equilibrated at a high pH, and subjected to a salt gradient while monitoring eluate for ultraviolet absorbance at about 260 and about 280. The pH may be adjusted depending upon the AAV selected. See, e.g., WO2017/160360 (AAV9), WO2017/100704 (AA Vrh10), WO 2017/100676 (e.g., AAV8), and WO 2017/100674 (AAV1), which are incorporated by reference herein. In this method, the AAV full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2 serotype. Under these ionic conditions, a significant percentage of residual cellular DNA and proteins flow through the column, while AAV particles are efficiently captured.

Non-AAV and Non-Viral Vectors

A "vector" as used herein is a biological or chemical moiety comprising a nucleic acid sequence which can be introduced into an appropriate target cell for replication or expression of said nucleic acid sequence. Examples of a vector includes but not limited to a recombinant virus, a plasmid, Lipoplexes, a Polymersome, Polyplexes, a dendrimer, a cell penetrating peptide (CPP) conjugate, a magnetic particle, or a nanoparticle. In one embodiment, a vector is a nucleic acid molecule into which an exogenous or heterologous or engineered hMfn2 coding sequence (and/or at least one miRNA) may be inserted, which can then be introduced into an appropriate target cell. Such vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and "artificial chromosomes". Conventional methods of generation, production, characterization or quantification of the vectors are available to one of skill in the art.

In one embodiment, the vector is a non-viral plasmid that comprises an expression cassette described thereof, e.g., "naked DNA", "naked plasmid DNA", RNA, mRNA, shRNA, RNAi, etc. Optionally the plasmid or other nucleic acid sequence is delivered via a suitable device, e.g., via electrospray, electroporation. In other embodiments, the nucleic acid molecule is coupled with various compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., WO2014/089486, US 2018/0353616A1, US2013/0037977A1, WO2015/074085A1, U.S. Pat. Nos. 9,670,152B2, and 8,853,377B2, X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference.

In certain embodiment, a non-viral vector is used for delivery of an miRNA transcript targeting endogenous hMfn2 at a site not present in the co-administered engineered hMfn2 sequence. In some embodiments, the miRNA is delivered at an amount greater than about 0.5 mg/kg (e.g., greater than about 1.0 mg/kg, 1.5 mg/kg, 2.0 mg/kg, 2.5 mg/kg, 3.0 mg/kg, 4.0 mg/kg, 5.0 mg/kg, 6.0 mg/kg, 7.0 mg/kg, 8.0 mg/kg, 9.0 mg/kg, or 10.0 mg/kg) body weight of miRNA per dose. In some embodiments, the miRNA is delivered at an amount ranging from about 0.1-100 mg/kg (e.g., about 0.1-90 mg/kg, 0.1-80 mg/kg, 0.1-70 mg/kg, 0.1-60 mg/kg, 0.1-50 mg/kg, 0.1-40 mg/kg, 0.1-30 mg/kg, 0.1-20 mg/kg, 0.1-10 mg/kg) body weight of miRNA per dose. In some embodiments, the miRNA is delivered at an amount of or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg per dose.

In certain embodiments, miRNA transcripts are encapsulated in a lipid nanoparticle (LNP). As used herein, the phrase "lipid nanoparticle" refers to a transfer vehicle comprising one or more lipids (e.g., cationic lipids, non-cationic lipids, and PEG-modified lipids). Preferably, the lipid nanoparticles are formulated to deliver one or more miRNA to one or more target cells (e.g., dorsal root ganglion, lower motor neurons and/or upper motor neurons, or the cell types identified above in the CNS). Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a miRNA to a target cell. Useful lipid nanoparticles for miRNA comprise a cationic lipid to encapsulate and/or enhance the delivery of miRNA into the target cell that will act as a depot for protein production. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available. See, e.g., WO2014/089486, US 2018/0353616A1, and U.S. Pat. No. 8,853,377B2, which are incorporated by reference. In certain embodiments, LNP formulation is performed using routine procedures comprising cholesterol, ionizable lipid, helper lipid, PEG-lipid and polymer forming a lipid bilayer around encapsulated mRNA (Kowalski et al., 2019, Mol. Ther. 27(4):710-728). In some embodiments. LNP comprises a cationic lipids (i.e. N-[1-(2,3-dioleoyloxy)propyl]-N,N,N-trimethylammonium chloride (DOTMA), or 1,2-dioleoyl-3-trimethylammonium-propane (DOTAP)) with helper lipid DOPE. In some embodiments, LNP comprises an ionizable lipid Dlin-MC3-DMA ionizable lipids, or diketopiperazine-based ionizable lipids (cKK-E12). In some embodiments, polymer comprises a polyethyleneimine (PEI), or a poly(β-amino)esters (PBAEs). See, e.g., WO2014/089486, US 2018/0353616A1, US2013/0037977A1, WO2015/074085A1, U.S. Pat. Nos. 9,670,152B2, and 8,853,377B2, which are incorporated by reference.

In certain embodiments, the vector described herein is a "replication-defective virus" or a "viral vector" which refers to a synthetic or artificial viral particle in which an expression cassette containing a nucleic acid sequence encoding an engineered hMfn2 and/or at least one miRNA targeting endogenous hMfn2 at a site not present on the sequence of the engineered hMfn2. Replication-defective viruses cannot generate progeny virions but retain the ability to infect target cells. In one embodiment, the genome of the viral vector does not include genes encoding the enzymes required to replicate (the genome can be engineered to be "gutless"-containing only the nucleic acid sequence encoding E2 flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, a recombinant viral vector may be any suitable replication-defective viral vector, including, e.g., a recombinant adeno-associated virus (AAV), an adenovirus, a bocavirus, a hybrid AAV/bocavirus, a herpes simplex virus or a lentivirus.

As used herein, the term "host cell" may refer to the production (packaging) cell line in which a vector (e.g., a recombinant AAV) is produced. A host cell may be a prokaryotic or eukaryotic cell (e.g., human, insect, or yeast) that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. Examples of host cells may include, but are not limited to an isolated cell, a cell culture, an Escherichia coli cell, a yeast cell, a human cell, a non-human cell, a mammalian cell, a non-mammalian cell, an insect cell, an HEK-293 cell, a liver cell, a kidney cell, a cell of the central nervous system, a neuron, a glial cell, or a stem cell.

As used herein, the term "target cell" refers to any target cell in which expression of the hMfn2 and/or miRNA is desired. In certain embodiments, the term "target cell" is intended to reference the cells of the subject being treated for disorder or neuropathy associated with deficient hMfn2, or CMT2A disease or neuropathy. Examples of target cells may include, but are not limited to, cells within the central nervous system.

Compositions

Provided herein are compositions containing at least one vector comprising hMfn2.miR (e.g., an rAAV.hMfn2.miR stock) and/or at least one vector comprising miR and/or at least one vector comprising stock, and an optional carrier, excipient and/or preservative. In certain embodiments, the composition comprising a stock of rAAV as described herein, and an aqueous media. In certain embodiments, provided herein are pharmaceutical composition comprising the rAAV as described herein, or the vector as described herein, and a pharmaceutically acceptable aqueous suspending liquid, excipient, and/or diluent. In certain embodiments, the pharmaceutical composition or the composition is formulated for an intrathecal delivery, optionally wherein the intrathecal delivery is an intracerebroventricular (ICV) injection or an intracisterna magna (ICM) injection. In certain embodiments, the at least one vector comprising hMfn2.miR is an rAAV.hMfn2.miR538. In certain embodiments, the at least one vector is an AAVhu68.hMfn2.miR538.

As used herein, a "stock" of rAAV refers to a population of rAAV. Despite heterogeneity in their capsid proteins due to deamidation, rAAV in a stock are expected to 5 share an identical vector genome. A stock can include rAAV having capsids with, for example, heterogeneous deamidation patterns characteristic of the selected AAV capsid proteins and a selected production system. The stock may be produced from a single production system or pooled from multiple runs of the production system. A variety of production systems, including but not limited to those described herein, may be selected.

In certain embodiments, a composition comprises at least virus stock which is a recombinant AAV (rAAV) suitable for use in treating disorder or neuropathy associated with deficient hMfn2 alone or in combination with other vector stock or composition. In certain embodiments, a composition comprises at least virus stock which is a recombinant AAV (rAAV) suitable for use in treating CMT2A disease or neuropathy alone or in combination with other vector stock or composition. In certain embodiments, the composition is suitable for use in preparing a medicament for treating disorder or neuropathy associated with deficient hMfn2. In certain embodiments, the composition is suitable for use in preparing a medicament for treating CMT2A disease or neuropathy. In certain embodiments, a composition comprises a virus stock which is a recombinant AAV (rAAV) suitable for use in treating disorder or neuropathy associated with deficient hMfn2. In certain embodiments, a composition comprises a virus stock which is a recombinant AAV (rAAV) suitable for use in treating CMT2A disease or neuropathy, said rAAV comprising: (a) an adeno-associated virus capsid, and (b) a vector genome packaged in the AAV capsid, said vector genome comprising AAV inverted terminal repeats, a coding sequence for an engineered human mitofusin 2, a spacer sequence, a coding sequence for at least one miRNA specifically targeted to endogenous human mitofusin at a site not present in the engineered human mitofusin coding sequence, and regulatory sequences which direct expression of the encoded gene products. In certain embodiments, a composition comprises separate vector stock comprising rAAV comprising: (a) an adeno-associated virus capsid, and (b) a vector genome packaged in the AAV capsid, said vector genome comprising AAV inverted terminal repeats, a coding sequence for an engineered human mitofusin 2, and regulatory sequences which direct expression of the encoded gene product and/or a separate vector stock comprising (a) an adeno-associated virus capsid, and (b) a vector genome packaged in the AAV capsid, said vector genome comprising AAV inverted terminal repeats, a coding sequence for at least one miRNA specifically targeted to endogenous human mitofusin 2 at a site not present in the engineered human mitofusin 2 coding sequence, and regulatory sequences which direct expression of the encoded gene product. In certain embodiments, the vector genome comprises a promoter, an enhancer, an intron, a human Mfn2 coding sequence, and a polyadenylation signal. In certain embodiments, the intron consists of a chicken beta actin splice donor and a rabbit β splice acceptor element. In certain embodiments, the vector genome further comprises an AAV2 5' ITR and an AAV2 3' ITR which flank all elements of the vector genome.

The rAAV.hMfn2.miR (rAAV.hMfn2 or another vector) may be suspended in a physiologically compatible carrier to be administered to a human patient having disorder or neuropathy associated with deficient hMfn2. The rAAV.hMfn2.miR (rAAV.hMfn2 or another vector) may be suspended in a physiologically compatible carrier to be administered to a human CMT2A patient. In certain embodiments, for administration to a human patient, the vector is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5. pH 7 to 7.7, or pH 7.2 to 7.8. As the pH of the cerebrospinal fluid is about 7.28 to about 7.32, or a pH of 7.2 to 7.4, for intrathecal delivery, a pH within this range may be desired; whereas for intravenous delivery, a pH of about 6.8 to about 7.2 may be desired. However, other pHs within the broadest ranges and these subranges may be selected for other route of delivery.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2 or a pH of 7.4.

In another embodiment, the formulation may contain a buffered saline aqueous solution comprising 1 mM Sodium Phosphate (Na3PO4), 150 mM sodium chloride (NaCl), 3 mM potassium chloride (KCl), 1.4 mM calcium chloride (CaCl2), 0.8 mM magnesium chloride (MgCl2), and 0.001% Kolliphor® 188. See, e.g., harvardapparatus.com/harvard-apparatus-perfusion-fluid.html. In certain embodiments, Harvard's buffer is preferred.

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions may contain, in addition to the vector (e.g., rAAV) and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Optionally, routes other than intrathecal administration may be used, such as, e.g., direct delivery to a desired organ (e.g., the liver (optionally via the hepatic artery), lung, heart, eye, kidney), oral, inhalation, intranasal, intratracheal, intraarterial, intraocular, intravenous, intramuscular, subcutaneous, intradermal, and other parental routes of administration. Routes of administration may be combined, if desired.

Dosages of the vector will depend primarily on factors such as the condition being treated, the age, weight and health of the patient, and may thus vary among patients. For example, a therapeutically effective human dosage of viral vector is generally in the range of from about 25 to about 1000 microliters to about 100 mL of solution containing concentrations of from about $1\times10^{9}$ to $1\times10^{16}$ genomes virus vector (to treat an average subject of 70 kg in body weight) including all integers or fractional amounts within the range, and preferably $1.0\times10^{12}$ GC to $1.0\times10^{14}$ GC for a human patient. In one embodiment, the compositions are formulated to contain at least $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, for human application the dose can range from $1\times10^{10}$ to about $1\times10^{12}$ GC per dose including all integers or fractional amounts within the range.

In certain embodiments, the dose is in the range of about $1\times10^{9}$ GC/g brain mass to about $1\times10^{12}$ GC/g brain mass. In certain embodiments, the dose is in the range of about $1\times10^{10}$ GC/g brain mass to about $3.33\times10^{11}$ GC/g brain mass. In certain embodiments, the dose is in the range of about $3.33\times10^{11}$ GC/g brain mass to about $1.1\times10^{12}$ GC/g brain mass. In certain embodiments, the dose is in the range of about $1.1\times10^{12}$ GC/g brain mass to about $3.33\times10^{13}$ GC/g brain mass. In certain embodiments, the dose is lower than $3.33\times10^{11}$ GC/g brain mass. In certain embodiments, the dose is lower than $1.1\times10^{12}$ GC/g brain mass. In certain embodiments, the dose is lower than $3.33\times10^{13}$ GC/g brain mass. In certain embodiments, the dose is about $1\times10^{10}$ GC/g brain mass. In certain embodiments, the dose is about $2\times10^{10}$ GC/g brain mass. In certain embodiments, the dose is about $2\times10^{10}$ GC/g brain mass. In certain embodiments, the dose is about $3\times10^{10}$ GC/g brain mass. In certain embodiments, the dose is about $4\times10^{10}$ GC/g brain mass. In certain embodiments, the dose is about $5\times10^{10}$ GC/g brain mass. In certain embodiments, the dose about $6\times10^{10}$ GC/g brain mass. In certain embodiments, the dose is about $7\times10^{10}$ GC/g brain mass. In certain embodiments, the dose about $8\times10^{10}$ GC/g brain mass. In certain embodiments, the dose is about $9\times10^{10}$ GC/g brain mass. In certain embodiments, the dose is about $1\times10^{11}$ GC/g brain mass. In certain embodiments, the dose is about $2\times10^{11}$ GC/g brain mass. In certain embodiments, the dose is about $3\times10^{11}$ GC/g brain mass. In certain embodiments, the dose is about $4\times10^{11}$ GC/g brain mass. In certain embodiments, the dose is administered to humans as a flat dose in the range of about $1.44\times10^{13}$ to $4.33\times10^{14}$ GC of the rAAV. In certain embodiments, the dose is administered to humans as a flat dose in the range of about $1.44\times10^{13}$ to $2\times10^{14}$ GC of the rAAV. In certain embodiments, the dose is administered to humans as a flat dose in the range of about $3\times10^{13}$ to $1\times10^{14}$ GC of the rAAV. In certain embodiments, the dose is administered to humans as a flat dose in the range of about $5\times10^{13}$ to $1\times10^{14}$ GC of the rAAV. In some embodiments, the compositions can be formulated in dosage units to contain an amount of AAV that is in the range of about $1\times10^{13}$ to $8\times10^{14}$ GC of the rAAV. In some embodiments, the compositions can be formulated in dosage units to contain an amount of rAAV that is in the range of about $1.44\times10^{13}$ to $4.33\times10^{14}$ GC of the rAAV. In some embodiments, the compositions can be formulated in dosage units to contain an amount of rAAV that is in the range of about $3\times10^{13}$ to $1\times10^{14}$ GC of the rAAV. In some embodiments, the compositions can be formulated in dosage units to contain an amount of rAAV that is in the range of about $5\times10^{13}$ to $1\times10^{14}$ GC of the rAAV.

In certain embodiments, the vector is administered to a subject in a single dose. In certain embodiments, vector may be delivered via multiple injections (for example 2 doses) is desired.

The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions provided herein.

As used herein, the terms "intrathecal delivery" or "intrathecal administration" refer to a route of administration via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna (i.e., intra cisterna magna, or ICM). In certain embodiments, the intrathecal administration is performed as described in US Patent Publication No. 2018-0339065 A1, published Nov. 29, 2019, which is incorporated herein by reference in its entirety. In certain embodiments, the CNS administration is performed using Ommaya Reservoir (also referred to as Ommaya device or Ommaya system).

As used herein, the terms "intracisternal delivery" or "intracisternal administration" refer to a route of administration directly into the cerebrospinal fluid of the cisterna magna cerebellomedularis, more specifically via a suboccipital puncture or by direct injection into the cisterna magna or via permanently positioned tube.

Compositions comprising the miR target sequences described herein for repressing endogenous hMfn2 (e.g., in patients having a disorder or neuropathy associated with deficient hMfn2, or in CMT2A patients) are generally targeted to one or more different cell types within the central nervous system, including, but not limited to, neurons (including. e.g., lower motor neurons and/or primary sensory neurons. These may include, e.g., pyramidal, purkinje, granule, spindle, and interneuron cells).

Uses

The vectors and compositions provided herein are useful for treating a patient disorder or neuropathy associated with deficient hMfn2, patients having Charcot-Marie-Tooth (CMT) disorder, neuropathy, or various symptoms associated therewith. Charcot-Marie-Tooth Type 2 (CMT2) is a subtype of CMT, and CMT2A is the most common sub-type of CMT2. CMT2A is an inherited motor and sensory neuropathy. Patients develop progressive muscle weakness and atrophy beginning in the feet, ankles, and legs. CMT2A is caused by mutation of the Mitofusin 2 (Mfn2) gene. See also, [ncbi.nlm.nih.gov/books/NBK1511/], and [mda.org/disease/charcot-marie-tooth/types/cmt2]. A combination regimen or co-therapy for treating a patient having disorder or neuropathy associated with deficient hMfn2 is provided. A combination regimen or co-therapy for treating a patient having CMT2A is also provided. In certain embodiments, this regimen or co-therapy comprises co-administering (a) a recombinant nucleic acid sequence encoding an engineered human mitofusin 2 coding sequence operably linked to regulatory sequences which direct expression thereof in a human target cell, wherein the human mitofusin 2 coding sequence has the sequence of SEQ ID NO: 15 or a sequence at least 95% identical thereto and which differs from endogenous human mitofusin 2 in the patient having disorder or neuropathy associated with deficient hMfn2, or CMT2A by having a mismatch in the miRNA target sequence of (b), and (b) a coding sequence for at least one miRNA specific for an endogenous human mitofusin 2 sequence in a human subject having disorder or neuropathy associated with deficient hMfn2, or CMT2A, wherein the mRNA is operably linked to regulatory sequences which direct expression thereof in the subject.

In certain embodiments, this regimen or co-therapy comprises co-administering (a) a recombinant nucleic acid sequence encoding an engineered human mitofusin 2 coding sequence operably linked to regulatory sequences which direct expression thereof in a human target cell, wherein the engineered human mitofusin 2 coding sequence has the sequence of SEQ ID NO: 11 or a sequence at least 95% identical thereto and which differs from endogenous human mitofusin 2 in the patient having disorder or neuropathy associated with deficient hMfn2, or CMT2A by having a mismatch in the miRNA target sequence of (b), and (b) a coding sequence for at least one miRNA specific for an endogenous human mitofusin 2 sequence in a human subject having disorder or neuropathy associated with deficient hMfn2, or CMT2A, wherein the at least one miRNA coding sequence is operably linked to regulatory sequences which direct expression thereof in the subject, and wherein the at least one miRNA coding sequence comprises a sequence of one or more of an miRNA targeting sequence comprising SEQ ID NO: 89 (miR538, 59 nt) or an miRNA comprising one or more of antisense sequence of SEQ ID NO: 27.

In certain embodiments, this regimen or co-therapy for treating a patient having disorder or neuropathy associated with deficient hMfn2, or CMT2A comprises co-administering (a) a recombinant nucleic acid sequence encoding an engineered human mitofusin 2 coding sequence operably linked to regulatory sequences which direct expression thereof in a human target cell, wherein the human mitofusin 2 coding sequence is engineered to differs from endogenous human mitofusin 2 in the patient by having a mismatch in the miRNA target sequence of (b), and (b) a coding sequence for at least one miRNA specific for an endogenous human mitofusin 2 sequence in the patient, wherein the miRNA coding sequence is operably linked to regulatory sequences which direct expression thereof in the subject, and wherein the at least one miRNA coding sequence has a sequence of one or more of: an miRNA coding sequence comprising SEQ ID NO: 15 (miR1693, 64 nt); an miRNA coding sequence comprising at least 60 consecutive nucleotides of SEQ ID NO: 15; an miRNA coding sequence comprising at least 99% identity to SEQ ID NO: 15 which comprises a sequence with 100% identity to about nucleotide 6 to about nucleotide 26 of SEQ ID NO: 15 (or SEQ ID NO: 68); or an miRNA coding sequence comprising one or more of:

(i) TTGACGTCCAGAACCTGTTCT, ; SEQ ID NO: 27

(ii) AGAAGTGGGCACTTAGAGTTG, ; SEQ ID NO: 28

(iii) TTCAGAAGTGGGCACTTAGAG, ; SEQ ID NO: 29

(iv) TTGTCAATCCAGCTGTCCAGC, ; SEQ ID NO: 30

(v) CAAACTTGGTCTTCACTGCAG, ; SEQ ID NO: 31

(vi) AAACCTTGAGGACTACTGGAG, ; SEQ ID NO: 32

(vii) TAACCATGGAAACCATGAACT, ; SEQ ID NO: 33

(viii) ACAACAAGAATGCCCATGGAG, ; SEQ ID NO: 34

(ix) AAAGGTCCCAGACAGTTCCTG, ; SEQ ID NO: 35

(x) TGTTCATGGCGGCAATTTCCT, ; SEQ ID NO: 36

(xi) TGAGGTTGGCTATTGATTGAC, ; SEQ ID NO: 37

(xii) TTCTCACACAGICAACACCTT, ; SEQ ID NO: 38

(xiii) TTTCCTCGCAGTAAACCTGCT, ; SEQ ID NO: 39

(xiv) AGAAATGGAACTCAATGTCTT, ; SEQ ID NO: 40

(xv) TGAACAGGACATCACCTGTGA, ; SEQ ID NO: 41

(xvi) AATACAAGCAGGTATGTGAAC, ; SEQ ID NO: 42

(xvii) TAAACCTGCTGCTCCCGAGCC, ; SEQ ID NO: 43

(xviii) TAGAGGAGGCCATAGAGCCCA, ; SEQ ID NO: 44

-continued

```
(xix)
                                    SEQ ID NO: 45
TCTACCCGCAGGAAGCAATTG,; or

(xx)
                                    SEQ ID NO: 46
CTCCTTAGCAGACACAAAGAA,,
```

or combinations of any of (i) through (xx). In certain embodiments, this regimen or co-therapy for treating a patient having disorder or neuropathy associated with deficient hMfn2, or CMT2A comprises co-administering (a) a recombinant nucleic acid sequence encoding an engineered human mitofusin 2 coding sequence comprising SEQ ID NO: 11 operably linked to regulatory sequences which direct expression thereof in a human target cell, wherein the human mitofusin 2 coding sequence is engineered to differs from endogenous human mitofusin 2 in the patient by having a mismatch in the miRNA target sequence of (b), and (b) a coding sequence for at least one miRNA specific for an endogenous human mitofusin 2 sequence in the patient, wherein the miRNA coding sequence is operably linked to regulatory sequences which direct expression thereof in the subject, and wherein the at least one miRNA coding sequence has a sequence of one or more of: an miRNA coding sequence comprising TTGACGTCCAG-AACCTGTTCT, SEQ ID NO: 27. In certain embodiments, a first vector comprises the nucleic acid (a) and a second, different vector, comprises at least one miRNA (b). In certain embodiments, the first vector is a viral vector and/or the second vector is a viral vector and the first and the second viral vector may be from the same virus source or may be different. In certain embodiments, the first vector is a non-viral vector, the second vector is a non-viral vector and the first and the second vectors may be same composition or may be different.

In certain embodiments, the vectors and compositions provided herein are useful for treating patients having Mfn2-induced lipomatosis. In certain embodiments, the vectors and compositions provided herein are useful for treating patients having multiple symmetric lipomatosis. Multiple symmetric lipomatosis is associated with rare genetic mutation in Mfn2 gene, and characterizable by large deposits and accumulate of fat tissue in upper bodies and gradually lose fat tissue in arms and legs (Rocha, N., et al., Human biallelic MFN2 mutations induce mitochondrial dysfunction, upper body adipose hyperplasia, and suppression of leptin expression, eLife, 2017, 6:1-27, Apr. 19, 2017). In certain embodiments, the vectors and compositions provided herein are useful for treating patients having severe early-onset neuropathy due to Mfn2 deficiency. In certain embodiments, the vectors and compositions provided herein are useful for treating patients having Alzheimer's Disease (AD), Parkinson's Disease (PD), cardiomyopathies, and Mfn2-associated pathogenesis in various cancers. It has been evidenced that there is a suggested link between Mfn2 deregulation and AD and PD, e.g., link between single nucleotide polymorphism in the Mfn2 gene and AD risk (Filadi, R., et al., Cell Death and Disease, 2018, 9:330).

Optionally, the vectors and compositions provided herein may be used in combination with one or more co-therapies selected from: acetaminophen, nonsteroidal anti-inflammatory drugs (NSAIDs), tricyclic antidepressants or antiepileptic drugs, such as carbamazepine or gabapentin. In still other embodiments, the vectors may be delivered in a combination with an immunomodulatory regimen involving one or more steroids, e.g., prednisone.

As used herein, the term Computed Tomography (CT) refers to radiography in which a three-dimensional image of a body structure is constructed by computer from a series of plane cross-sectional images made along an axis.

Kit

In certain embodiments, a kit is provided which includes a concentrated vector suspended in a formulation (optionally frozen), optional dilution buffer, and devices and components required for intrathecal, intracerebroventricular or intracisternal administration. In one embodiment, the kit provides sufficient buffer to allow for injection. Such buffer may allow for about a 1:1 to a 1:5 dilution of the concentrated vector, or more. In other embodiments, higher or lower amounts of buffer or sterile water are included to allow for dose titration and other adjustments by the treating clinician. In still other embodiments, one or more components of the device are included in the kit. Suitable dilution buffer is available, such as, a saline, a phosphate buffered saline (PBS) or a glycerol/PBS.

It should be understood that the compositions in kit described herein are intended to be applied to other compositions, regiments, aspects, embodiments and methods described across the Specification.

Apparatus and Method for Delivery of a Pharmaceutical Composition

In one aspect, the vectors, rAAV or compositions thereof provided herein may be administered intrathecally via the method and/or the device provided in this section and described in WO 2017/136500 and WO 2018/160582, which are incorporated by reference herein. Alternatively, other devices and methods may be selected. In certain embodiments, the method comprises the steps of CT-guided suboccipital injection via spinal needle into the cisterna magna of a patient. As used herein, the term Computed Tomography (CT) refers to radiography in which a three-dimensional image of a body structure is constructed by computer from a series of plane cross-sectional images made along an axis. In certain embodiments, the apparatus is described in US Patent Publication No. 2018-0339065 A1, published Nov. 29, 2019, which is incorporated herein by reference in its entirety. In certain embodiments, the vectors, rAAV or compositions thereof provided herein may be administered using Ommaya Reservoir.

It should be understood that the compositions in the device described herein are intended to be applied to other compositions, regiments, aspects, embodiments and methods described across the Specification.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Unless otherwise specified by an upper range, it will be understood that a percentage of identity is a minimum level of identity and encompasses all higher levels of identity up to 100% identity to the reference sequence. Unless otherwise specified, it will be understood that a percentage of identity is a minimum level of identity and encompasses all higher levels of identity up to 100% identity to the reference sequence. For example, "95% identity" and "at least 95% identity" may be used interchangeably and include 95, 96, 97, 98, 99 up to 100% identity to the referenced sequence, and all fractions therebetween.

Unless otherwise specified, numerical values will be understood to be subject to conventional mathematic rounding rules.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13): 2682-2690 (1999).

It is to be noted that the term "a" or "an" refers to one or more. As such, the terms "a (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%, e.g., ±1, ±2, ±3, ±4, ±5, ±6, ±7, ±8, ±9, ±10, or values therebetween) from the reference given, unless otherwise specified.

As used herein, "disease", "disorder" and "condition" are used interchangeably, to indicate an abnormal state in a subject.

As used herein, the term "CMT2A-related symptom(s)" or "symptom(s)" refers to symptom(s) found in CMT2A patients as well as in CMT2A animal models. Early symptoms of CMT2A may include one or more of clumsiness, slight difficulty in walking because of trouble picking up the feet, weak leg muscles, fatigue, absence of reflexes. Common symptoms of CMT2A include, foot deformity (very high arched foot/feet), difficulty lifting foot at the ankle (foot drop), curled toes (known as hammer toes), loss of lower leg muscle, which leads to skinny calves, numbness or burning sensation in the feet or hands, "Slapping" when walking (feet hit the floor hard when walking), weakness of the hips, legs, or feet, leg and hand cramps, Loss of balance, tripping, and falling, difficulty grasping and holding objects and opening jars and bottles, pain (both nerve pain and arthritic pain). Later symptoms of CMT2A may include, e.g., a similar symptoms in the arms and hands, curvature of the spine (scoliosis). Other reported/known symptoms of CMT2A may include, e.g., speech and swallowing difficulties, breathing difficulties, especially when lying flat, hearing loss, vision loss, vocal cord paralysis.

"Patient" or "subject" as used herein means a male or female human, and animal models (including, e.g., dogs, non-human primates, rodents, or other suitable models) used for clinical research. In one embodiment, the subject of these methods and compositions is a human diagnosed with CMT2A. In certain embodiments, the human subject of these methods and compositions is a prenatal, a newborn, an infant, a toddler, a preschool, a grade-schooler, a teen, a young adult or an adult. In a further embodiment, the subject of these methods and compositions is a pediatric CTM2A patient.

As used herein, the term "a therapeutic level" means an Mfn2 activity at least about 5%, about 8%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, more than 100%, about 2-fold, about 3-fold, or about 5-fold of a healthy control. Suitable assays for measuring the activity of an hMfn2 are known in the art. In some embodiments, such therapeutic levels of the one or more subunit protein may result in alleviation of the CMT2A related symptom(s); reversal of certain CMT2A-related symptoms and/or prevention of progression of CMT2A-related certain symptoms; or any combination thereof. In certain embodiments, the human Mfn2 delivered by the compositions and regimens provided herein has the amino acid sequence of a functional endogenous wild-type protein. In certain embodiments, the sequence is the amino acid sequence of SEQ ID NO: 19 or a functional protein which is at about 95 to 100% identity to functional, human Mfn2 protein.

The term "expression" is used herein in its broadest meaning and comprises the production of RNA or of RNA and protein. With respect to RNA, the term "expression" or "translation" relates in particular to the production of peptides or proteins. Expression may be transient or may be stable.

Additionally optionally, an expression cassette (and a vector genome) may comprise one or more dorsal root ganglion (drg)-miRNA targeting sequences in the UTR, e.g., to reduce drg toxicity and/or axonopathy. See, e.g., PCT/US2019/67872, filed Dec. 20, 2019 and now published as WO 2020/132455, U.S. Provisional Patent Application No. 63/023,593, filed May 12, 2020, and U.S. Provisional Patent Application No. 63/038,488, filed Jun. 12, 2020, all entitled "Compositions for Drg-Specific Reduction of Transgene Expression", which are incorporated herein in their entireties. In some embodiments, an expression cassette may be delivered via a genetic element (e.g., a plasmid) to a packaging host cell and packaged into the capsid of a viral vector (e.g., a viral particle).

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

As described herein, regulatory elements comprise but not limited to: promoter; enhancer; transcription factor; transcription terminator; efficient RNA processing signals such as splicing and polyadenylation signals (polyA); sequences that stabilize cytoplasmic mRNA, for example Woodchuck Hepatitis Virus (WHP) Posttranscriptional Regulatory Element (WPRE); sequences that enhance translation efficiency (i.e., Kozak consensus sequence).

The term "translation" in the context of the present invention relates to a process at the ribosome, wherein an mRNA strand controls the assembly of an amino acid sequence to generate a protein or a peptide.

Expression cassettes containing engineered hMfn2 coding sequences are provided herein, e.g., Syn.PI.hMfn2eng.link.hMfn2.miR1693.WPRE.bGH (nt 223 to 4455 of SEQ ID NO: 1 or SEQ ID NO: 91); CB7.CI.hMfn2.GA.RBG (nt 259 to 4370 of SEQ ID NO: 79 or SEQ ID NO: 98); CB7.CI.hMfn2.GA.LINK.miR1518.RBG (nt 259 to 4710 of SEQ ID NO: 77 or SEQ ID NO: 97); CB7.CI.hMfn2.GA.LINK.miR538.RBG (nt 259 to 4626 of SEQ ID NO: 75 or SEQ ID NO: 96); CAG.CI.hMfn2.GA.WPRE.SV40 (nt 192 to 4262 of SEQ ID NO: 73 or SEQ ID NO: 95); CAG.CI.hMfn2.GA.LINK.miR1518.WPRE.SV40 (nt 192 to 4474 of SEQ ID NO: 71 or SEQ ID NO: 94); and CAG.CI.hMfn2.GA.LINK.miR538.WPRE.SV40 (nt 192 to 4474 of SEQ ID NO: 69 or SEQ ID NO: 93).

Expression cassettes containing engineered rMfn2 coding sequences are provided herein, e.g., Syn.PI.rMnf2eng. link-.rMfn2 miR1518 WPRE.BGH (nt 223 to 4430 of SEQ ID NO: 3 or SEQ ID NO: 92).

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

The following examples are illustrative and are not intended to limit the present invention.

Charcot-Marie-Tooth Type 2A (CMT2A) is an inherited motor and sensory neuropathy. Patients develop progressive muscle weakness and atrophy beginning in the feet, ankles, and legs. CMT2A is caused by mutation of the Mitofusin 2 (Mfn2) gene. Mfn2 is a GTPase protein that forms homomers and heteromers with Mitofusin 1 (Mfn1) and functions in mitochondrial fusion, metabolism, and transport along axons. Mutation of Mfn2 disrupts fusion of mitochondria which leads to toxic aggregation. A Mfn2 mutations are selectively toxic to lower motor neurons and primary sensory neurons in dorsal root ganglia (DRG). Complete loss of Mfn2 is known to be lethal. In most cases of CMT2A is caused by autosomal dominant missense mutations that act in a dominant-negative manner. In rare cases, CMT2A is caused by recessive loss-of-function mutations.

A gene therapy was developed to restore mitofusin-2 expression by overexpression of Mfn2 to overcome dominant negative activity of mutant Mfn2. An AAV gene therapy technology is used to transfer an Mfn2 expression cassette into neurons. In some embodiments an Mfn2 expression cassette contains a miRNA connected via a linker, wherein miRNA is targeted to knock down mutant (defective) Mfn2, to eliminate mutant Mfn2 and supply with normal mitofurin-2 protein. The injection of the therapeutic article is delivered via intra-cisterna magna (ICM), or intravenously. ICM delivery of AAV efficiently targets lower motor neurons and primary sensor neurons. A Mfn2 expression cassette, with engineered Mfn2 gene, highly optimized for expression in humans was used in combination with an AAV capsid with highly improved central nervous system (CNS) transduction.

Briefly, in studies below, various miRNA sequences targeting endogenous Mfn2 were screened and selected in vitro in HEK293 cells. The selected candidate miRNA resulted in approximately 60% knockdown of human Mfn2 protein in HEK293 cells. The selected candidate miRNA was then cloned into a vector expressing a codon optimized and miRNA resistant Mfn2 transgene. Vectors containing different arrangements of sequences and promoters were tested for expression and activity of both miRNA and transgene in HEK293 cells and Mfn2-knockout cell lines. We found that Mfn2 transgene expression is highly regulated in cell types already expressing endogenous Mfn2, therefore, we used Mfn2-null mouse embryonic fibroblasts (MEFs) to screen for expression of our transgene-containing constructs. The selected candidate miRNA in combination with the Mfn2 transgene expressed 40% of wildtype levels of the Mfn2 as measured in Mfn2-null MEFs and the miRNA achieved knockdown of 34% of endogenous Mfn2 in HEK293 cells. The selected vectors (i.e., comprising an engineered coding sequence of Mfn2 transgene with or without miRNA, under hSyn, CB7 or CAG promoter) were then packaged in AAV for in vivo testing in both wildtype C57BL/6J mice and the Mfn2(R94Q) mouse model.

Wildtype mice were injected intravenously with PHP.eB vectors via tail vein. We confirmed expression of the Mfn2 transgene and miRNA in vivo in the spinal cords of these mice via qPCR and Western blot. After confirmation, vectors were packaged into AAVhu68 for testing in the Mfn2(R94Q) mouse model. The Mfn2(R94Q) mouse model displays hindlimb weakness that can be measured using several different behavioral methods including grip strength. In addition, these mice show increased degeneration of motor neurons in the spinal cord and tibial nerve. Mfn2(R94Q) mice received intracerebroventricular (ICV) dosing with vehicle or one of three different vectors. Grip strength data indicated that both combination vectors had statistically significant restoration of muscle strength at 6 weeks and 4 months and performed better than the vector containing only the Mfn2 transgene. In addition, one combination vector showed significant improvement in body weight at the same time points.

From these studies, we have identified a potential candidate vector for the treatment of CMT2A. This vector restores wildtype Mfn2 while simultaneously knocking down endogenous mutant and wildtype Mfn2. Mfn2(R94Q) mice dosed with a combination vector had increased muscle strength and body weight compared to other vectors and untreated littermates. In addition, the vector is tested in nonhuman primates to determine vector toxicity to the CNS and peripheral nerves. Expression and knockdown of Mfn2 is also determined via laser capture microdissection of motor neurons from the spinal cord of the nonhuman primates. Together, these data confirm that a combination vector strategy may be an important route to gene therapy for CMT2A.

Example 1: CMT2A Vector Strategy

In an AAV transgene cassette strategy 1, we generated a Mfn expression cassette comprising a promoter, an intron, an engineered Mfn2 cDNA and polyA. In AAV transgene cassette strategy 2, we generated a Mfn2 expression cassette comprising a promoter, an intron, an engineered Mfn2 cDNA, which was engineered to optimize for expression and resistant to the miRNA, an miRNA targeting endogenous mutant Mfn2 and a polyA. Additionally, in an AAV transgene strategy 2, a construct was identified for efficient expression of a miRNA and cDNA in vivo, wherein the construct comprised a synapsin promoter, a cDNA (engineered Mfn2), a linker, a miRNA, wherein a miRNA located at the 3' end of cDNA, a WRPE enhancer, and polyA (data not shown).

Figure 15A:
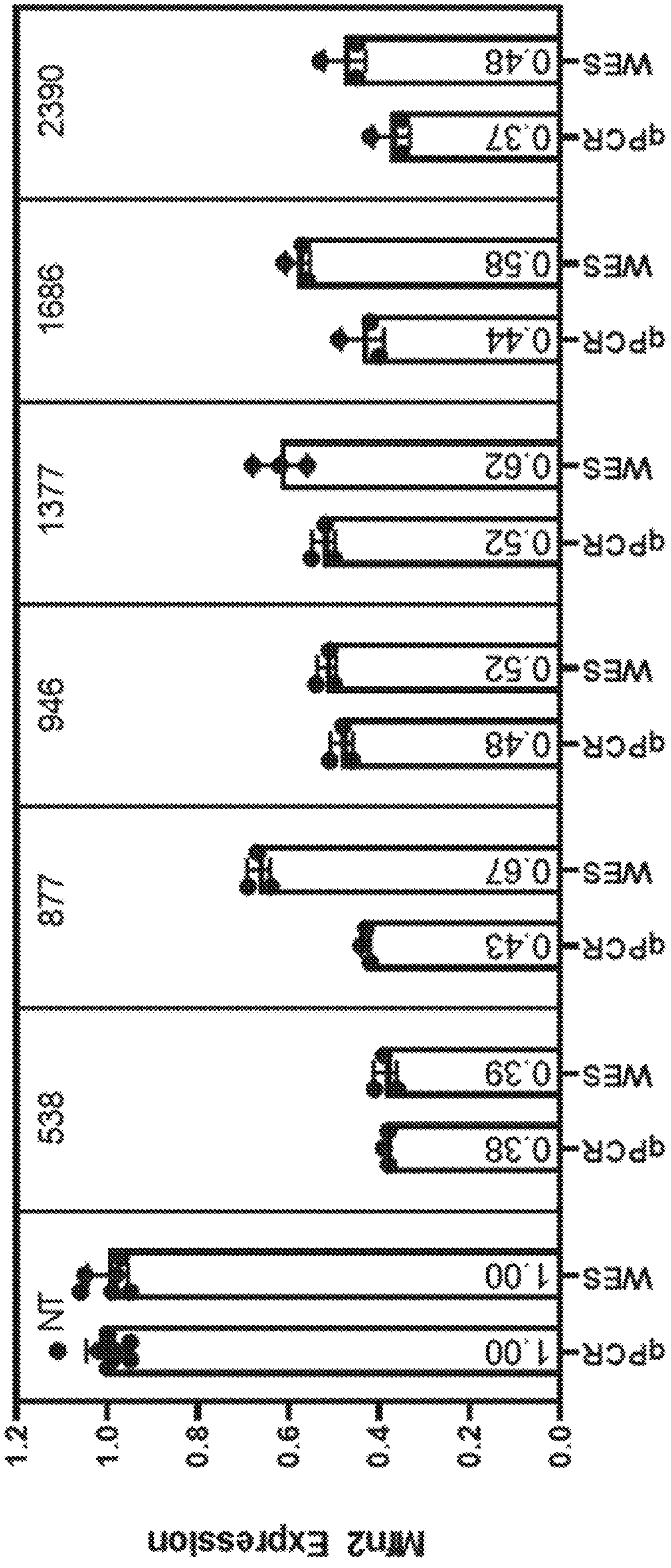
FIG. 15A shows knockdown of endogenous MFN2 in vitro in human cell line following transfection with a non-targeted miRNA (NT) or six candidate miRNAs. Mfn2 expression was graphed as level MFN2 RNA measured by qPCR, and level MFN2 protein measured by WES, and normalized to NT miRNA treated levels.
Figure 15B:
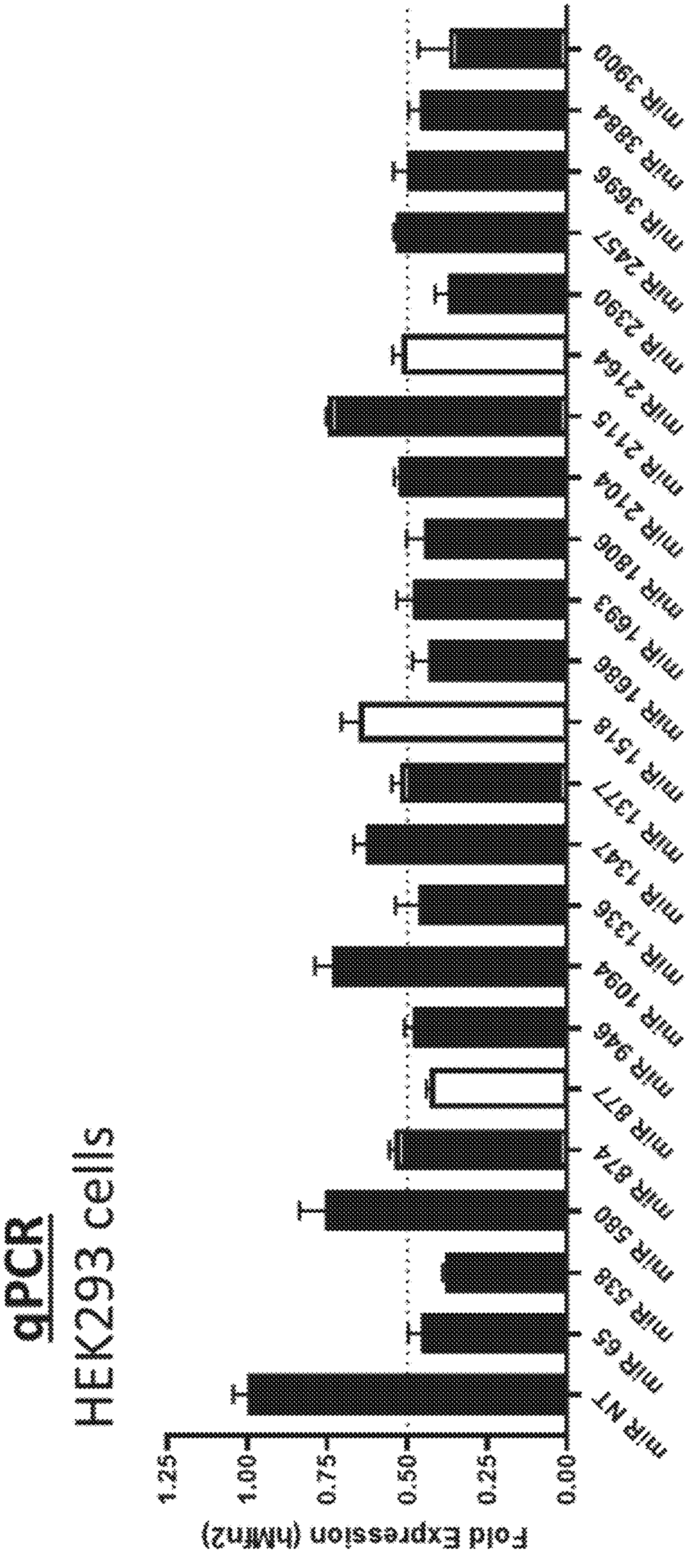
FIG. 15B shows results of knockdown of endogenous MFN2 in vitro in human cell line following transfection with a non-targeted miRNA (NT) or twenty-two (22) candidate miRNAs. Mfn2 expression was graphed as fold expression of hMfn2 measured by qPCR, and normalized to NT miRNA treated levels.
Figure 15C:
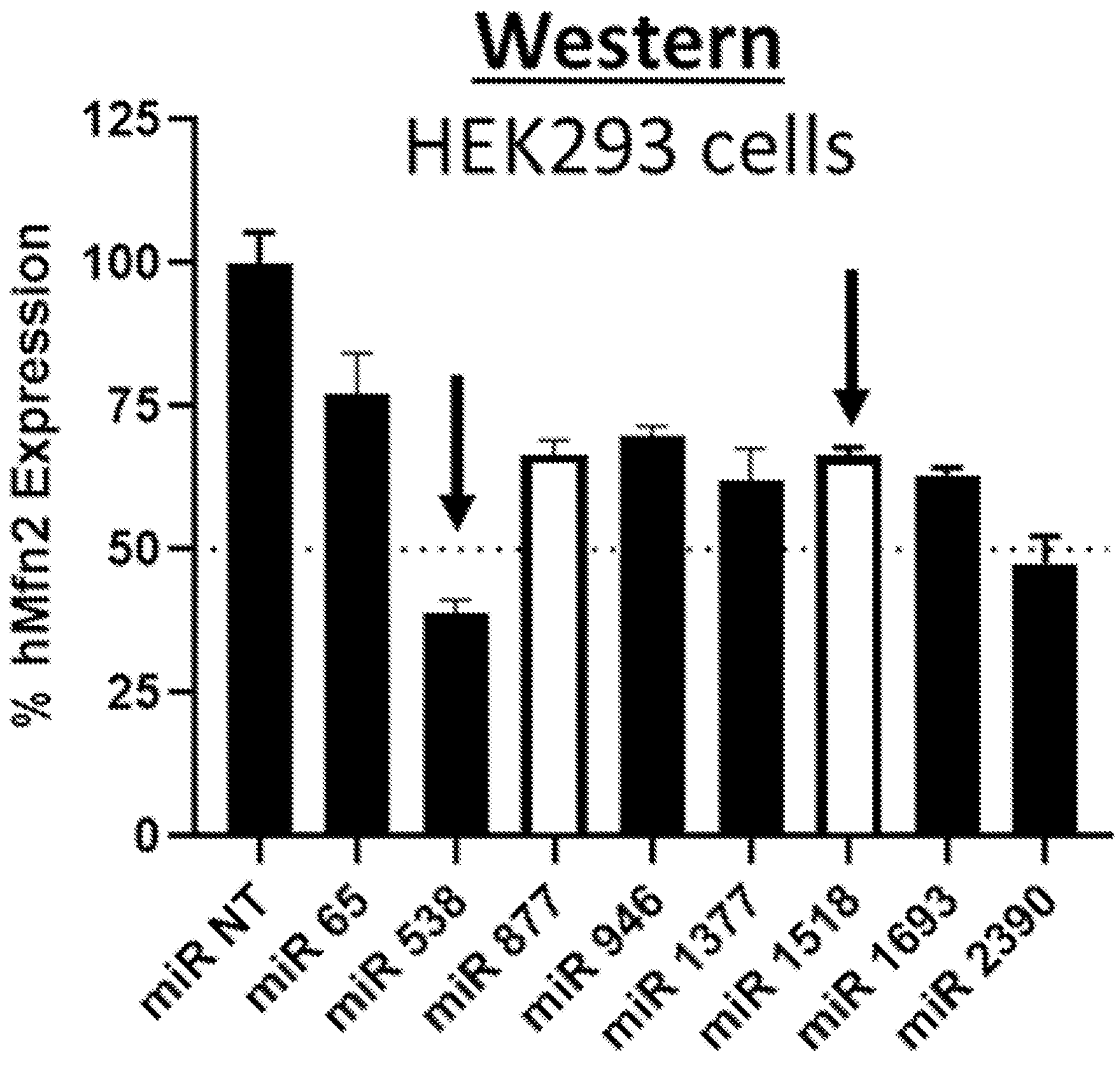
FIG. 15C shows results of knockdown of endogenous MFN2 in vitro in human cell line following transfection with a non-targeted miRNA (NT) or eight (8) candidate miRNAs. Mfn2 expression was graphed as % hMfn2 Expression measured and quantified by western blot (WES), and normalized to NT miRNA treated levels.

To knock down endogenous Mfn2 gene, various miRNA sequences various miRNA sequences were examined: miR238, miR1202, miR1518, and miR2282, among others, data for which is not shown, were examined. For western blot analysis, rat B104 cells were transfected with in vitro Block-iT plasmids (ThermoFisher) containing a CMV promoter, emGFP transgene, a cloning site for miRNA and TK polyA. miRNAs were designed using Block-iT online software. Cells were transfected and selected for expression with blasticidin. Surviving cells were mostly positive for GFP and overall transfection efficiency could be determined. B104 cells were harvested after 72 hours and prepared for western blot analysis. Western blot was probed with antibodies against Mfn2 and b-actin as loading control. Additionally, knockdown of endogenous Mfn2 was confirmed in vitro in human cell line. FIG. 15A shows knockdown of endogenous MFN2 in vitro in human cell line following transfection with a non-targeted miRNA (NT) or six candidate miRNAs. Mfn2 expression was graphed as level MFN2 RNA measured by qPCR, and level MFN2 protein measured by WES, and normalized to NT miRNA treated levels. See also, FIGS. 15B and 15C. FIG. 15B shows results of knockdown of endogenous MFN2 in vitro in human cell line following transfection with a non-targeted miRNA (NT) or twenty-two (22) candidate miRNAs. Mfn2 expression was graphed as fold expression of hMfn2 measured by qPCR, and normalized to NT miRNA treated levels. FIG. 15C shows results of knockdown of endogenous MFN2 in vitro in human cell line following transfection with a non-targeted miRNA (NT) or eight (8) candidate miRNAs. Mfn2 expression was graphed as % hMfn2 Expression measured and quantified by western blot (WES), and normalized to NT miRNA treated levels.

Figure 1B:
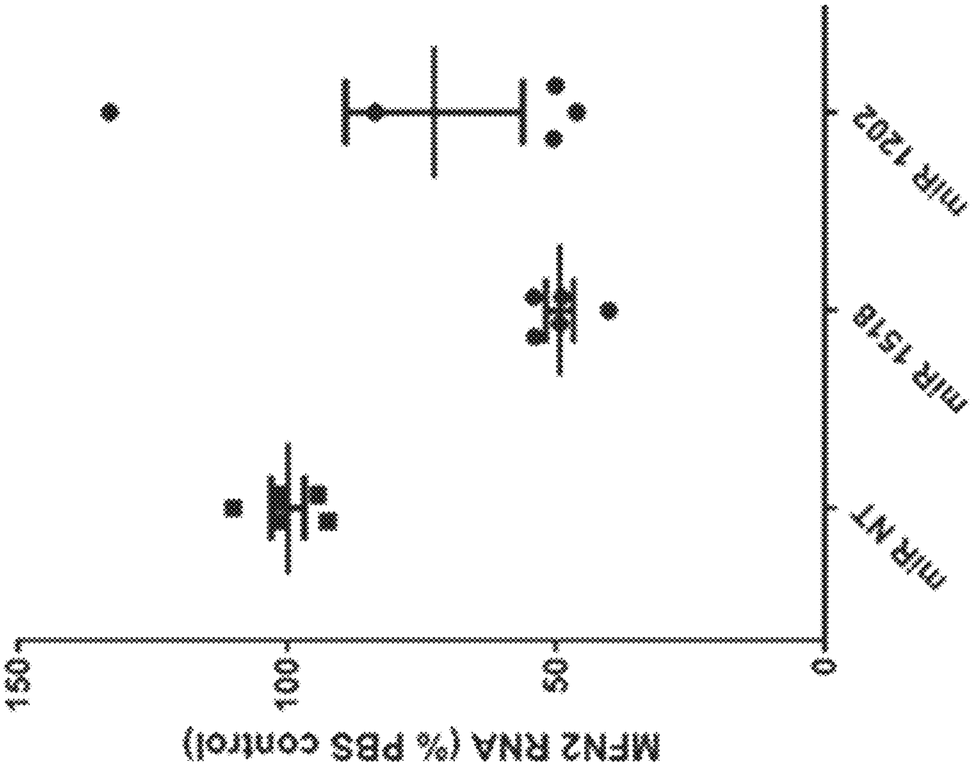

FIG. 1A and FIG. 1B illustrate knockdown of endogenous Mfn2 RNA, as measured by qPCR, in mouse brain (FIG. 1A) and spinal cord (FIG. 1B) in B6 mice following intravenous administration of AAV-mediated delivery of miRNA. Mice were necropsied at day 14 post administration, following which brain and spinal cord tissues were harvested and homogenized. RNA was extracted from the samples and used for qPCR with TaqMan primers against Mfn2. Four treatment groups were examined (N=5 per group): PBS, AAV9.PHP.eB.CB7.miR_NT (non-targeted at a dose of $3\times10^{11}$ GC), AAV9.PHP.eB.CB7.miR_1518 (at a dose of $3\times10^{11}$ GC), and AAV9.PHP.eB.CB7.miR_1202 (at a dose of $3\times10^{11}$ GC). Among the sequences examined, miR1518 illustrated best knockdown of endogenous Mfn2.

Figure 2A:
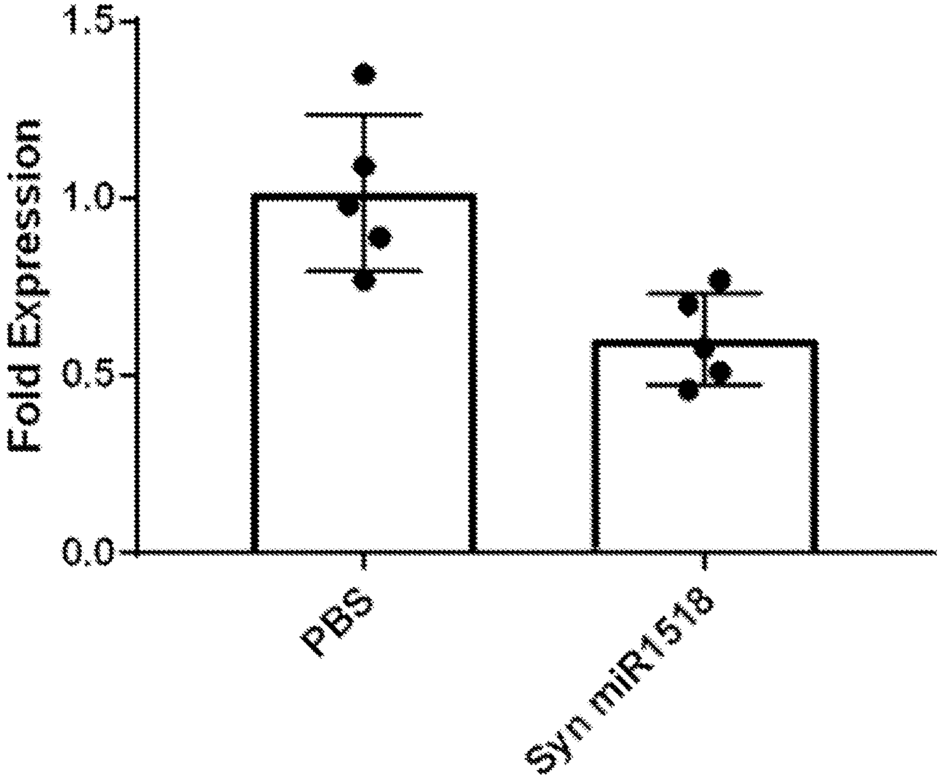
FIG. 2A to FIG. 2C illustrate Mfn2 RNA fold expression following delivery AAV vector comprising Mfn2 cDNA transgene (i.e., engineered nucleic acid sequence encoding Mfn2) and miR1518, wherein AAV vector was administered in mice intravenously at a dose of $3\times10^{11}$ GC.
Figure 2B:
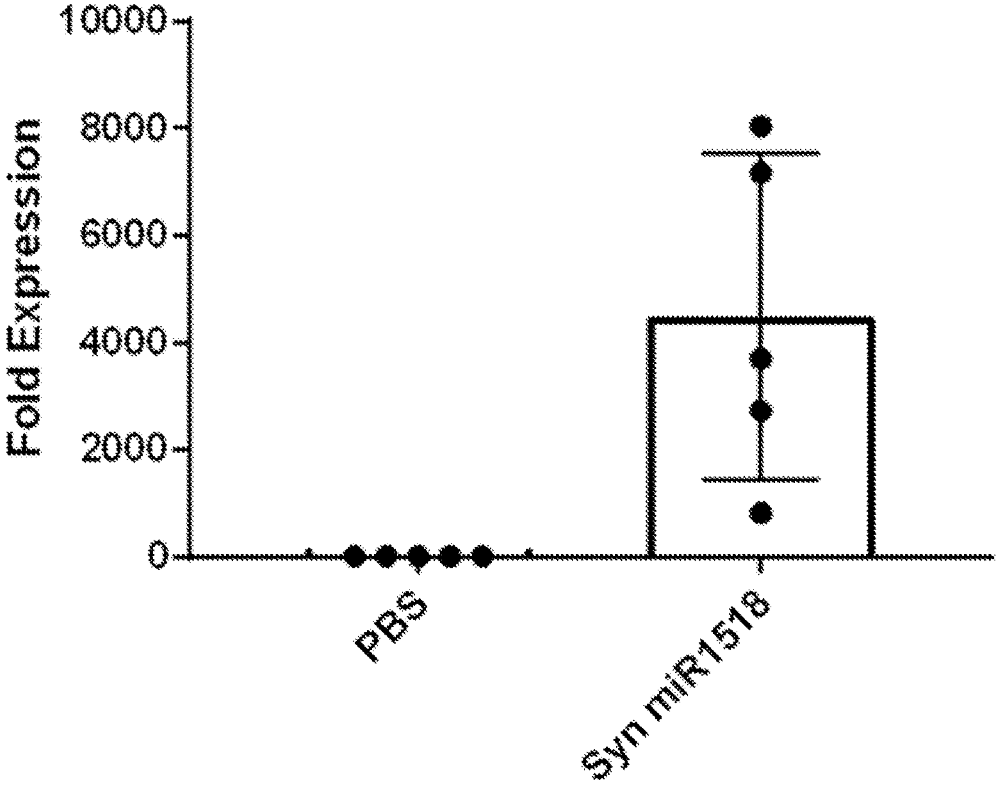
Figure 2C:
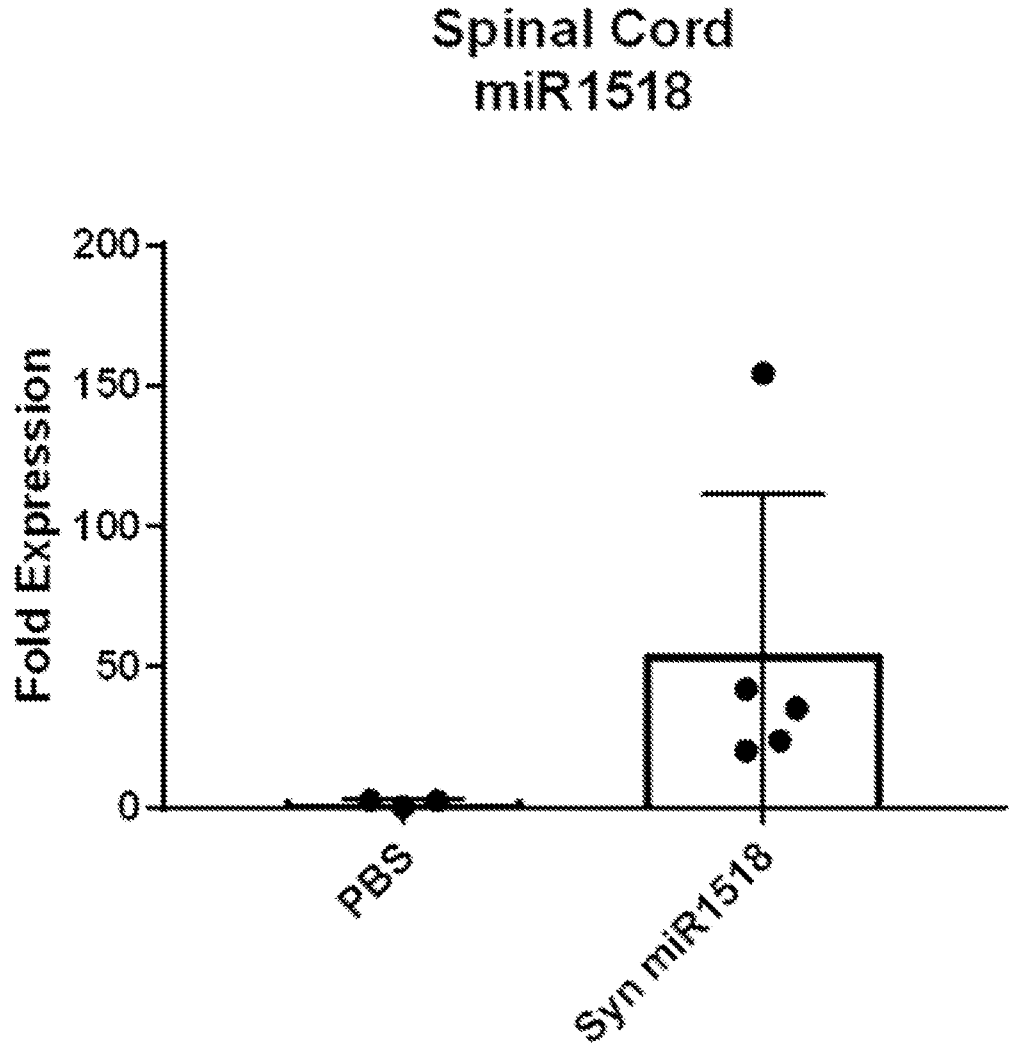
Figure 3:
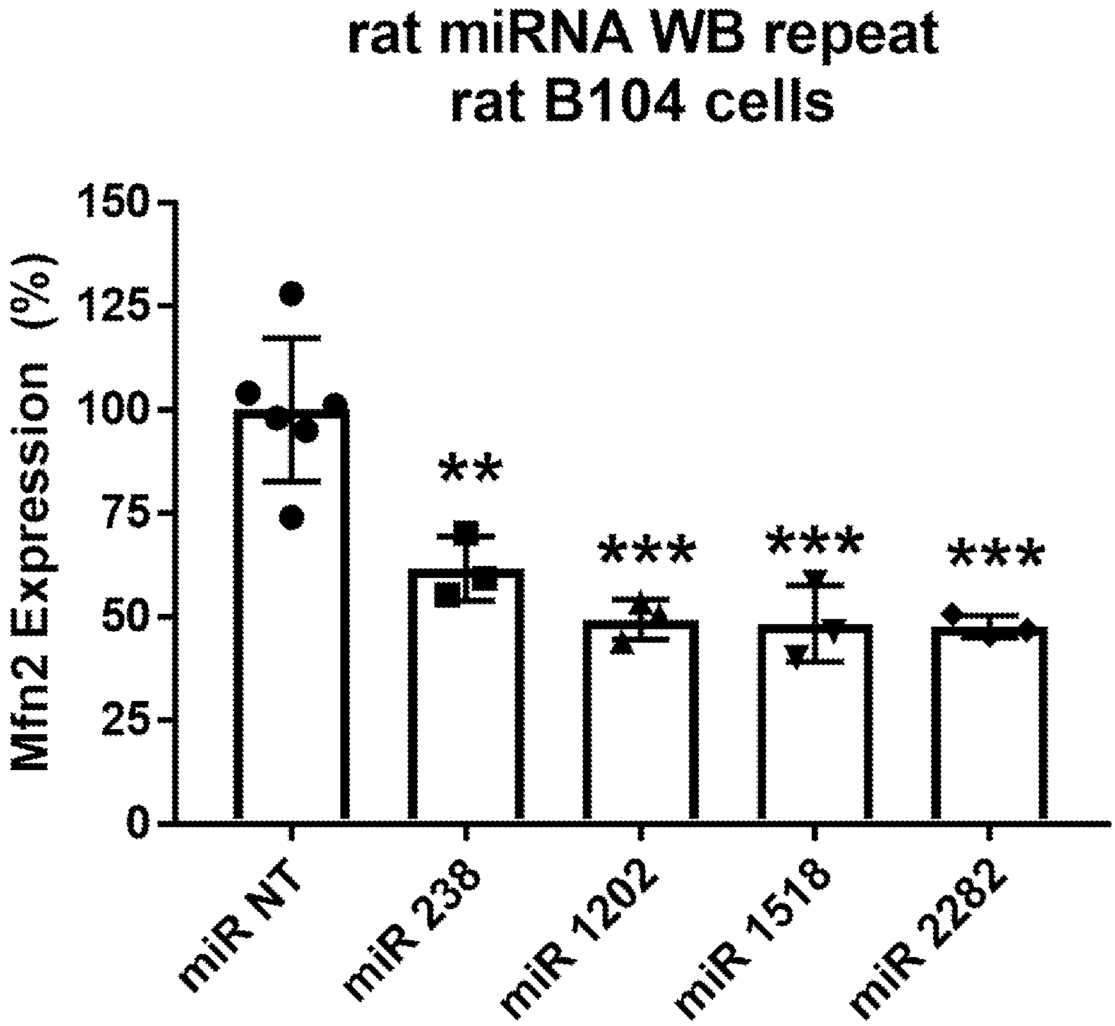
FIG. 3 illustrates plotted quantitation of western blot signal measuring percent expression of mitofurin-2 protein following miRNA treatment of B104 rat cells. Mitofurin-2 expression is plotted from calculated value of percent total over loading control of beta-actin.

FIG. 2A to FIG. 2C illustrate Mfn2 RNA fold expression following delivery AAV vector comprising rat Mfn2 (rMfn2) cDNA transgene and mR1518, wherein AAV vector was administered in mice intravenously at a dose of $3\times10^{11}$ GC. Mice were necropsied at day 14 post administration, following which brain and spinal cord tissues were harvested and homogenized. RNA was extracted from the samples and used for qPCR with TaqMan primers against Mfn2. Two treatment groups were examined (N=5 per group): PBS and AAV9.PHP.eB.CB7.miR_1518+rMfn2.

Figure 4:
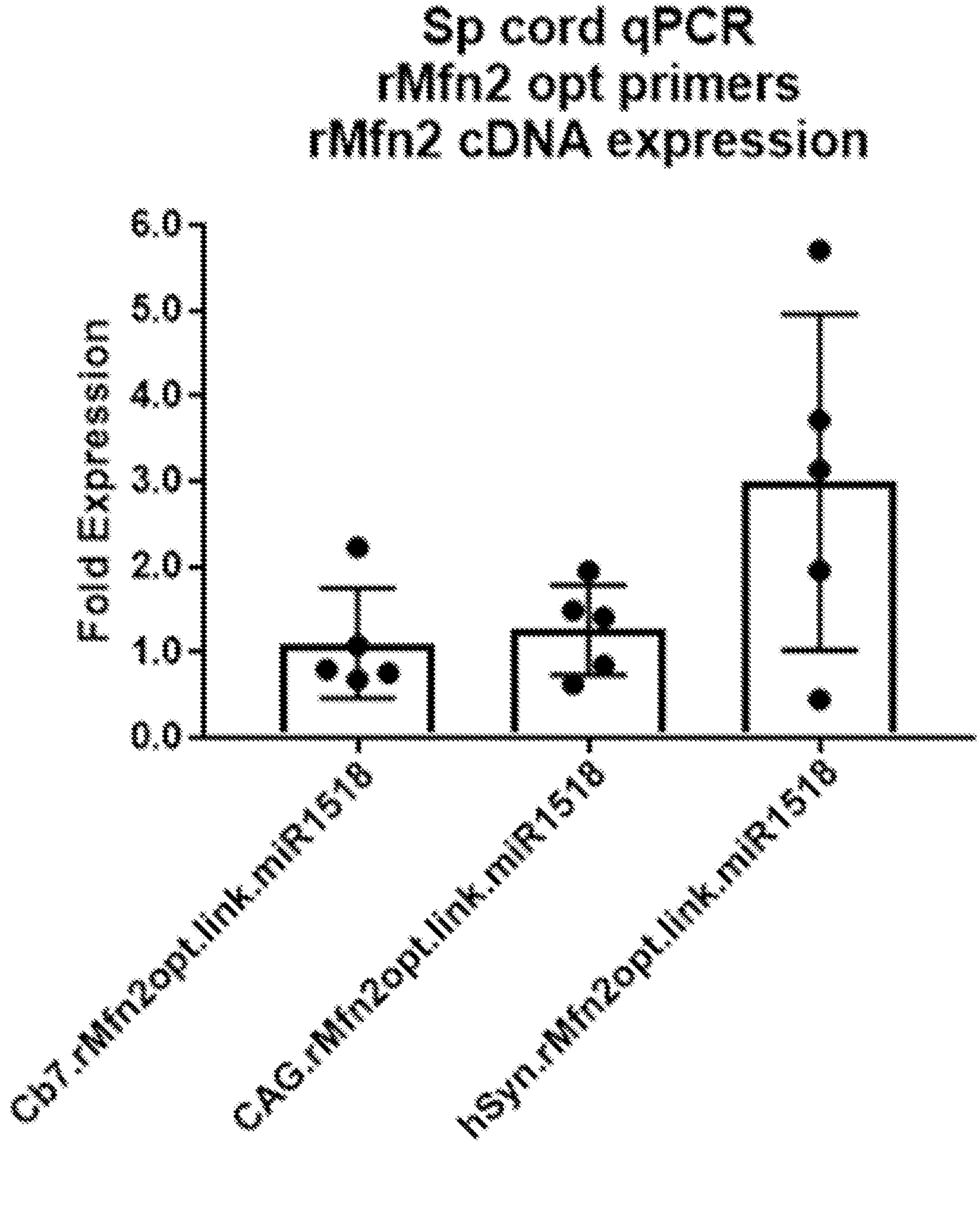
FIG. 4 illustrates plotted quantitation of fold-expression of rat Mfn2 (rMfn2) cDNA expression in spinal cord of treated mice following AAV vector delivery of engineered rMfn2 cDNA transgene with miR1518.

Example 2: Mouse Study of AAV Vector Comprising Expression Cassette of an Engineered Mfn2 Transgene with miRNA In initial study, wildtype mice were injected intravenously with $3\times10^{11}$ GC of AAV vectors comprising an engineered rat Mfn2 (rMfn2) cDNA nucleic acid sequence (SEQ ID NO: 12) and miRNA1518 (SEQ ID NO: 16). Four treatment groups were examined (N=5 in each group): PBS, AAV9-PHP.eB.CAG.rMfn2 opt.link.rMfn2miR1518.WPRE.SV40, AAV9-PHP.eB.CB7.CI.rMfn2 opt.link.rMfn2miR1518.rBG, and AAV9-PHP.eB.hSyn.PI.rMfn2opt.link.rMfn2miR1518.WPRE.bGH (wherein the vector genome is of SEQ ID NO: 3). Mice were sacrificed 14 days post injection. Brain and spinal cord were harvested and homogenized. RNA was extracted from the samples and used for qPCR with TaqMan primers against rat Mfn2 engineered cDNA. FIG. 4 illustrates plotted quantitation of fold-expression of rat Mfn2 (rMfn2) cDNA expression in spinal cord of treated mice following AAV vector delivery of engineered rMfn2 cDNA transgene with miR1518.

Figure 5:
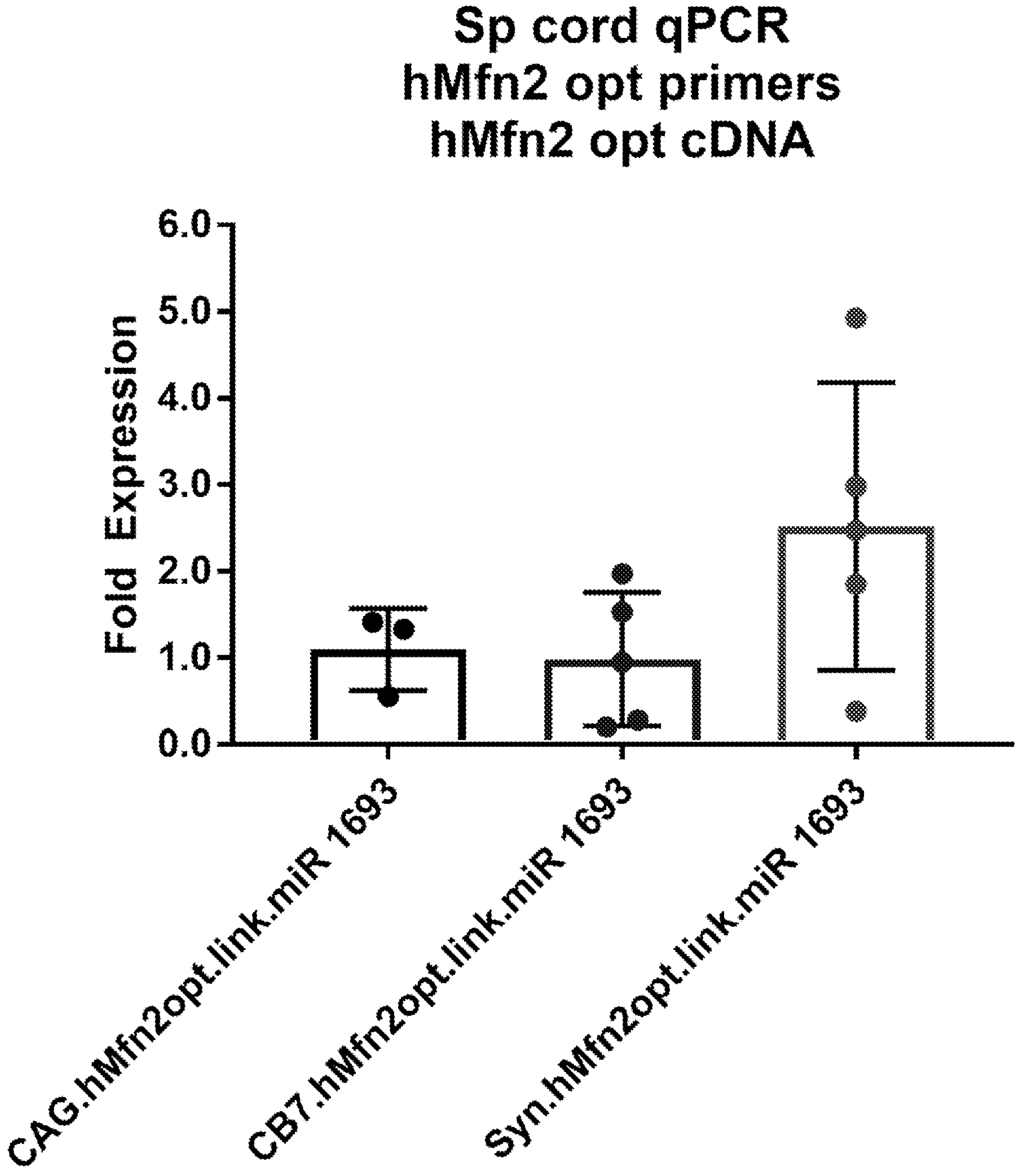
FIG. 5 illustrates plotted quantitation of fold-expression of human Mfn2 (hMfn2) cDNA expression in spinal cord of treated mice following AAV vector delivery of engineered hMfn2 cDNA transgene with miR1693.

In a further examination, wildtype mice were injected intravenously with $3\times10^{11}$ GC of AAV vectors, comprising an engineered human Mfn2 (hMfn2) cDNA nucleic acid sequence (SEQ ID NO: 11) and miRNA1693 (SEQ ID NO: 15). Four treatment groups were examined (N=5 in each group): PBS, AAV9-PHP.eB.CAG.hMfn2opt.link.hMfn2miR1693.WPRE.SV40. AAV9-PHP.eB.CB7.CI.hMfn2opt.link.hMfn2miR1693.rBG, AAV9-PHP.eB.hSyn.PI.hMfn2opt.link.hMfn2miR1693.WPRE.SV40 (wherein vector genome is of SEQ ID NO: 1). Mice were sacrificed 14 days post injection. Brain and spinal cord were harvested and homogenized. RNA was extracted from the samples and used for qPCR with TaqMan primers against human Mfn2 engineered cDNA. FIG. 5 illustrates plotted quantitation of fold-expression of human Mfn2 (hMfn2) cDNA expression in spinal cord of treated mice following AAV vector delivery of engineered hMfn2 cDNA transgene with miR1693.

In both studied examining human and rat Mfn2 expression, among AAV vectors delivered, various promoters were examined, such as CB7, CAG and neuron specific human synapsin (hSyn). AAV vectors comprising hSyn promoters exhibited highest fold-expression of Mfn2 cDNA in spinal cord tissue.

Figure 6A:
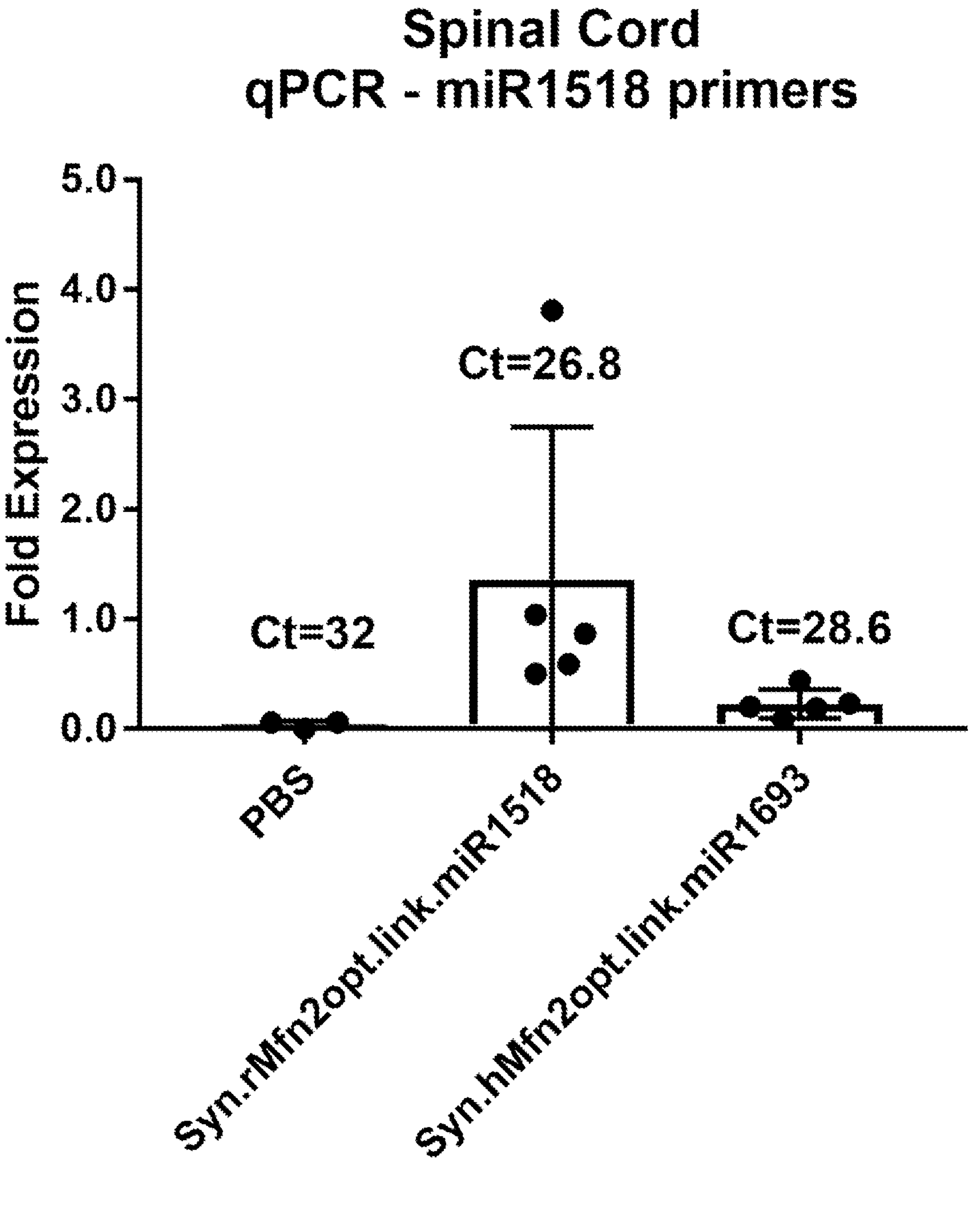
FIG. 6A and FIG. 6B illustrate total amount of mature miRNA processed from the AAV vectors following intravenous delivery in mice.
Figure 6B:
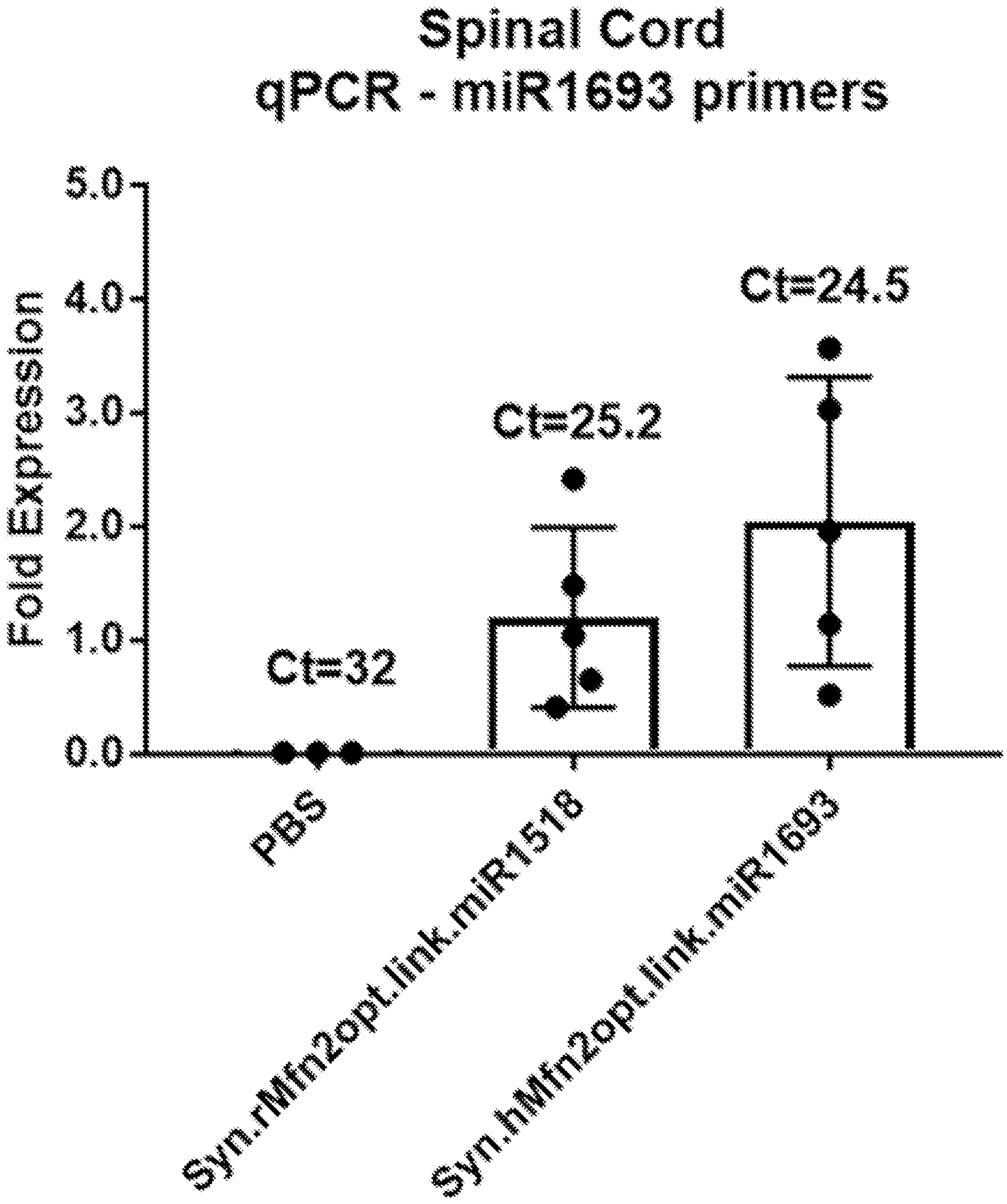

Furthermore, total amount of mature miRNA processed from AAV vectors were examined using an established procedure disclosed in Chen et al., Real-time quantification of micr-RNAs by stem-loop RT-PCR, Nucleic Acid Research, 2005, 33 (20). Wildtype mice were injected intravenously with $3\times10^{11}$ GC of AAV vectors or control group PBS. AAV genome vector of treatment group 1 comprised expression cassette for hMfn2 with miR1693 (SEQ ID NO: 1) which further comprising an engineered human Mfn2 (hMfn2) cDNA nucleic acid sequence (SEQ ID NO: 11) connected via linker (SEQ ID NO: 17) to miRNA1693 (SEQ ID NO: 15). AAV vector of treatment group 2 comprising an expression cassette for rMfn2 with miR1518 (SEQ ID NO: 3), further comprising an engineered rat Mfn2 (rMfn2) cDNA nucleic acid sequence (SEQ ID NO: 12) connected via linker (SEQ ID NO: 17) to miRNA1518 (SEQ ID NO: 16). Following treatment, mice were sacrificed at 14 days post injection. Brain and spinal cord were harvested and homogenized. RNA was extracted from the samples and used for custom miRNA Assay. The custom miRNA assay consists of a custom stem-loop RT primer to create the cDNA and then custom small RNA:stem loop TaqMan primers to amplify the miRNA. This assay measures the total amount of mature miRNA processed from the vector. FIG. 6A and FIG. 6B illustrate total amount of mature miRNA processed from the AAV vectors following intravenous delivery in mice.

In summary, hSyn promoter (SEQ ID NO: 6) appears to be best promoter for maximum spinal cord expression. AAV vectors comprising "link" (for "linker") is an important spacer between the cDNA and miRNA necessary for proper miRNA excision and processing for RNAi. A smaller linker was tried due to cloning ease but was not functional. qPCR analysis suggests adequate expression of rat Mfn2 and human Mfn2 when co-delivered with miRNA targeting endogenous mutant Mfn2.

Example 3. Transfection Efficiency of AAV Vectors in HEK293 and Mfn2-Null Cells In this study we generated and examined various AAV vectors comprising a transgene of human Mfn2 engineered sequence, as listed in Table 3 below.

TABLE 3

| AAV Vector | SEQ ID NOS (AAV vector) |
|---|---|
| CB7.CI.hMfn2.GA.RBG | 79 |
| CB7.CI.hMfn2.GA.LINK.miR1518.RBG | 77 |
| CB7.CI.hMfn2.GA.LINK.miR538.RBG | 75 |
| CAG.CI.hMfn2.GA.WPRE.SV40 | 73 |
| CAG.CI.hMfn2.GA.LINK.miR1518.WPRE.SV40 | 71 |
| CAG.CI.hMfn2.GA.LINK.miR538.WPRE.SV40 | 69 |

Mfn2 Null MEF is a mouse cell line lacking Mfn2 which was used to detect expression of Mfn2 cDNA in vectors. Additionally, HEK293 cells, which is a human cell line which express Mfn 2, was used in transfection with above-identified vectors. Following transfection cell lysates were analyzed for overall Mfn protein expression via western blot, endogenous Mfn2 knockdown via qPCR, and presence of miRNA via qPCR. Western blot quantification was performed with Wes platform. The analysis of Mfn expression in Mfn2-null MEF cells quantified only Mfn2 protein produced by vector because cell line lacks Mfn2 expression. For qPCR miRNA detection assay, a stem-loop primer was used for reverse transcription (RT) of mature miRNA, a TaqMan probe set was used for amplification of mature miRNA to show expression and/or processing of miRNA. For qPCR for measuring endogenous human Mfn2 knockdown, a TaqMan primer/probe set was used, which distinguishes between HEK293 endogenous Mfn2 and vector Mfn2. For Wes-based Mfn2 protein quantitation and antibody to Mfn2 was used which cross-reacts with endogenous and vector produced Mfn2, therefore probing for overall Mfn2 overexpression.

Figure 7:
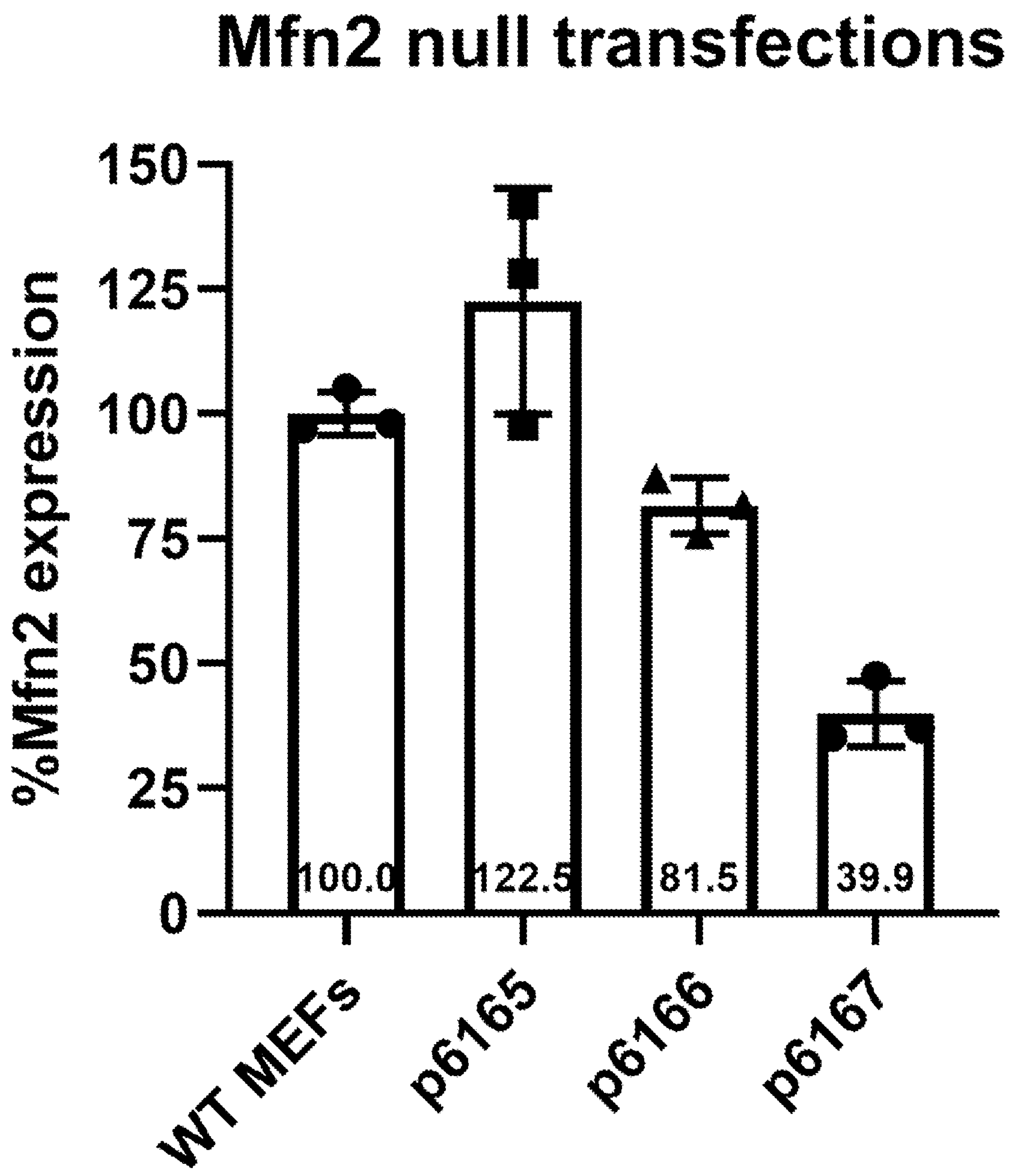
FIG. 7 shows expression levels of Mfn2 (Mfn2 expressed from vector) in Mfn2-null MEF cell line following transfection with various vectors comprising CB7 promoter; expression levels shown as plotted quantitation of western blot signal measuring expression of mitofurin-2 (Mfn2) following transfections with CB7.CI.hMfn2.GA.WPRE.RBG; CB7.CI.hMfn2.GA.LINK.miR1518.RBG; CB7.CI.hMfn2.GA.LINK.miR538.RBG.

FIG. 7 shows expression levels of Mfn2 in Mfn2-null MEF cell line following transfection with various vectors comprising CB7 promoter. Furthermore, FIG. 7 shows plotted quantitation of western blot signal measuring expression of mitofurin-2 (Mfn2) following transfections with CB7.CI.hMfn2.GA.WPRE.RBG (p6165); CB7.CI.hMfn2.GA.LINK.miR1518.RBG (p6166); CB7.CI.hMfn2.GA.LINK.miR538.RBG (p6167). Quantitation is plotted as percent expression; transfection efficiency was determined to be about 40% as measured by flow cytometry and approximated by visual observation. For a western blot probed for expression levels of Mfn2 (data not shown), b-actin was used as a loading control (Mfn2: 2 μg loaded; b-actin: 0.27 μg loaded; exposure used for quantification 4 seconds).

Figure 8:
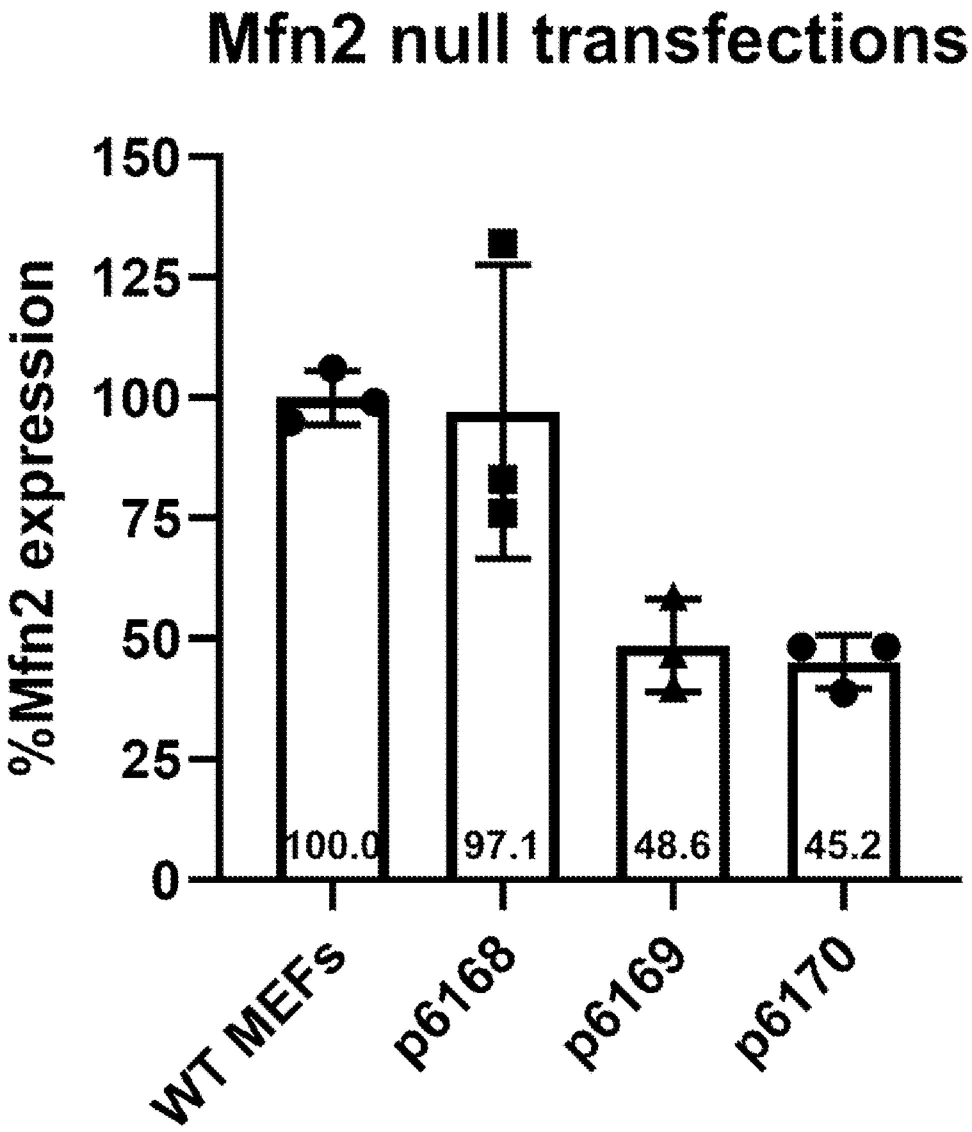
FIG. 8 shows expression levels of Mfn2 (Mfn2 expressed from vector) in Mfn2-null MEF cell line following transfection with various vectors comprising CAG promoter; expression levels shown as plotted quantitation of western blot signal measuring expression of mitofurin-2 (Mfn2) following transfections with CAG.CI.hMfn2.GA.WPRE.SV40; CAG.CI.hMfn2.GA.LINK.miR1518.WPRE.SV40; CAG.CI.hMfn2.GA.LINK.miR538.WPRE.SV40.

FIG. 8 shows expression levels of Mfn2 in Mfn2-null MEF cell line following transfection with various vectors comprising CAG promoter. Furthermore, FIG. 8 shows plotted quantitation of western blot signal measuring expression of mitofurin-2 (Mfn2) following transfections with CAG.CI.hMfn2.GA.WPRE.SV40; CAG.CI.hMfn2.GA.LINK.miR1518.WPRE.SV40; CAG.CI.hMfn2.GA.LINK.miR538.WPRE.SV40. Quantitation is plotted as percent expression; transfection efficiency was determined to be about 40% as measured by flow cytometry and approximated by visual observation. For a western blot probed for expression levels of Mfn2, b-actin was used as a loading control (Mfn2: 2 μg loaded; b-actin: 0.27 μg loaded; exposure used for quantification 4 seconds).

Figure 9A:
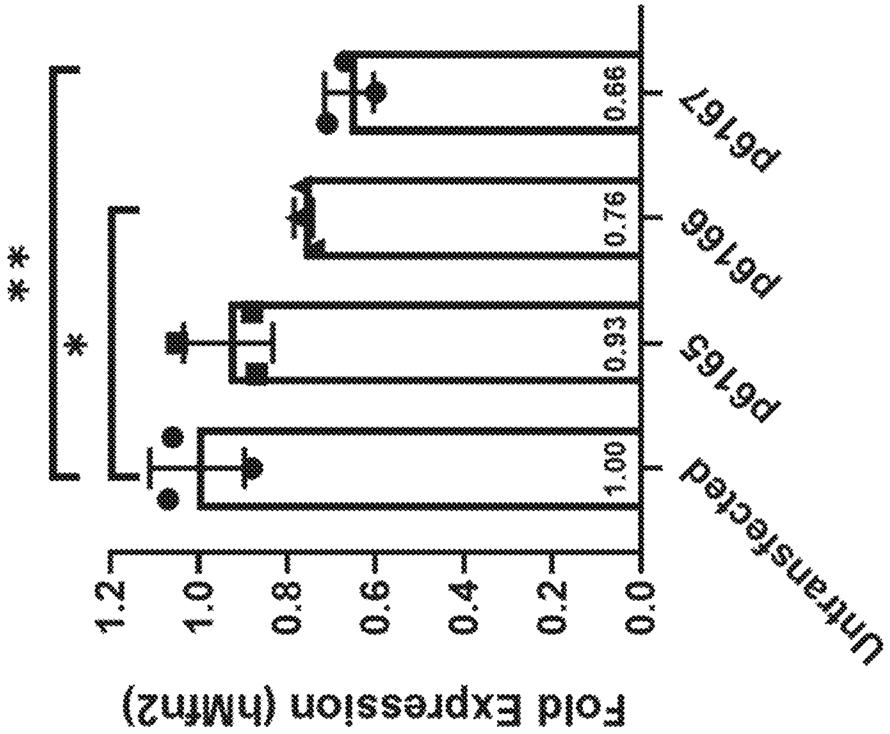
FIG. 9A and FIG. 9B show expression levels of Mfn2 in HEK293 cell line following transfection with various vectors comprising either CB7 or CAG promoter.
Figure 9B:
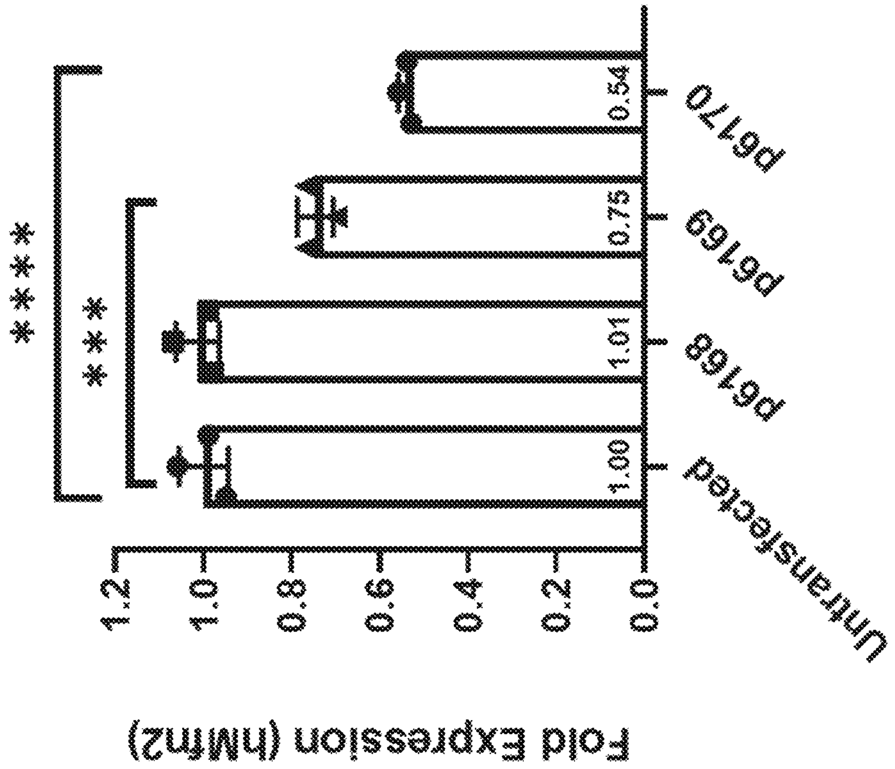

FIG. 9A and FIG. 9B show expression levels of Mfn2 in HEK293 cell line following transfection with various vectors comprising either CB7 or CAG promoter. High transfection efficiency was observed. FIG. 9A show endogenous Mfn2 knockdown in HEK293 cells as measured by qPCR and plotted as fold expression, following transfection with various vectors comprising CB7 promoter, (CB7.CI.hMfn2.GA.WPRE.RBG; CB7.CI.hMfn2.GA.LINK.miR1518. RBG; CB7.CI.hMfn2.GA.LINK.miR538.RBG). FIG. 9B show endogenous Mfn2 knockdown in HEK293 cells as measured by qPCR and plotted as fold expression, following transfection with various vectors comprising CAG promoter (CAG.CI.hMfn2.GA.WPRE.SV40; CAG.CI.hMfn2.GA.LINK.miR1518.WPRE.SV40; CAG.CI.hMfn2.GA.LINK.miR538.WPRE.SV40).

Figure 10:
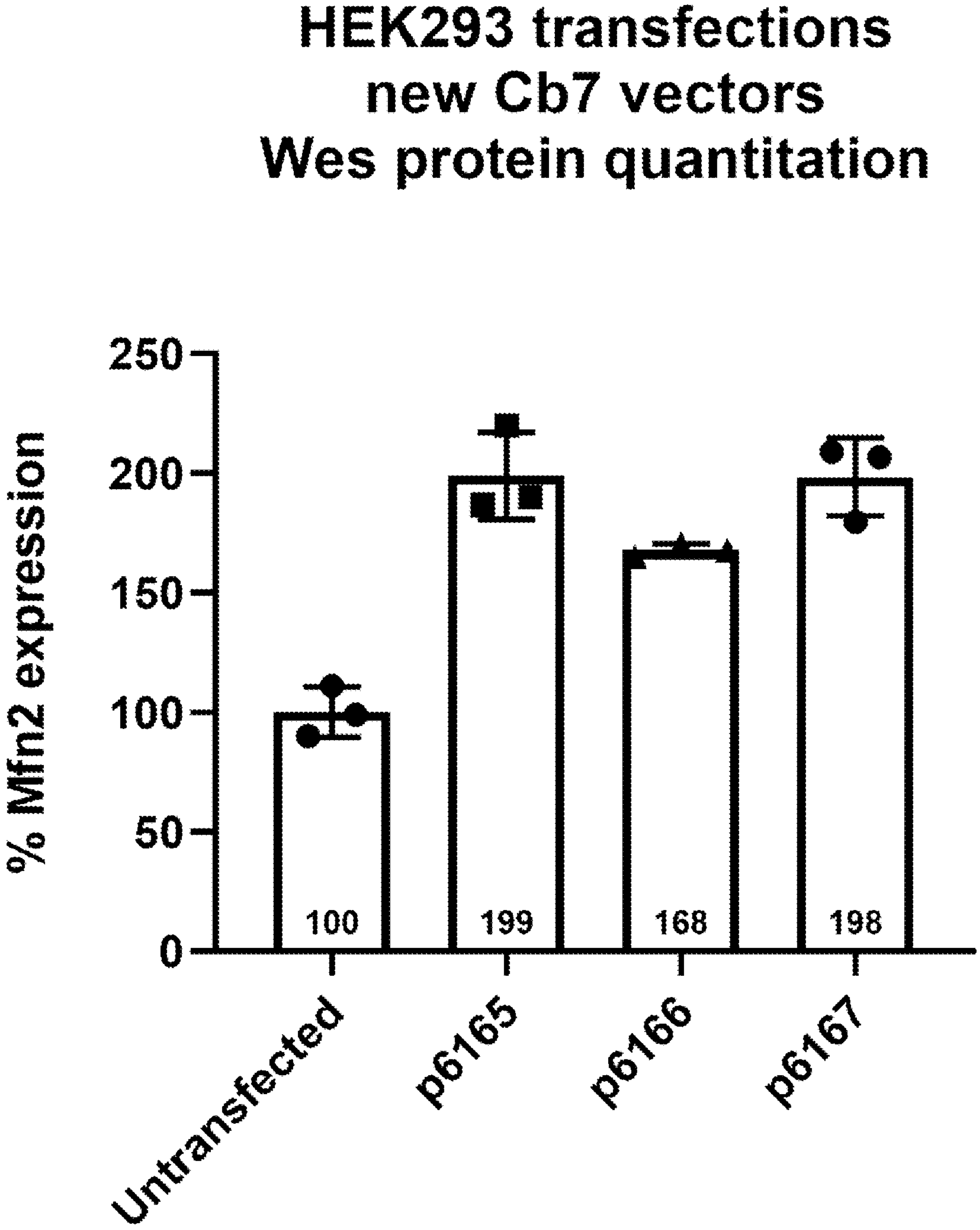
FIG. 10 shows expression levels of Mfn2 (endogenous Mfn2 and Mfn2 expressed from vector) in HEK293 cell line following transfection with various vectors comprising CB7 promoter; expression levels shown as plotted quantitation of western blot signal measuring expression of mitofurin-2 (Mfn2) following transfections with CB7.CI.hMfn2.GA.WPRE.RBG; CB7.CI.hMfn2.GA.LINK.miR1518.RBG; CB7.CI.hMfn2.GA.LINK.miR538.RBG. Quantitation is plotted as percent expression; transfection efficiency was determined to be about 95%.

FIG. 10 shows expression levels of Mfn2 (endogenous Mfn2 and Mfn2 expressed from vector) in HEK293 cell line following transfection with various vectors comprising CB7 promoter. Furthermore, FIG. 10 shows plotted quantitation of western blot signal measuring expression of mitofurin-2 (Mfn2) following transfections with CB7.CI.hMfn2. GA.WPRE.RBG: CB7.CI.hMfn2.GA.LINK. miR1518. RBG; CB7.CI.hMfn2.GA.LINK.miR538.RBG. Quantitation is plotted as percent expression; transfection efficiency was determined to be about 95%. For a western blot probed for expression levels of Mfn2, b-actin was used as a loading control (Mfn2: 0.78 μg loaded; b-actin: 0.78 μg loaded; exposure used for quantification 4 seconds).

Figure 11:
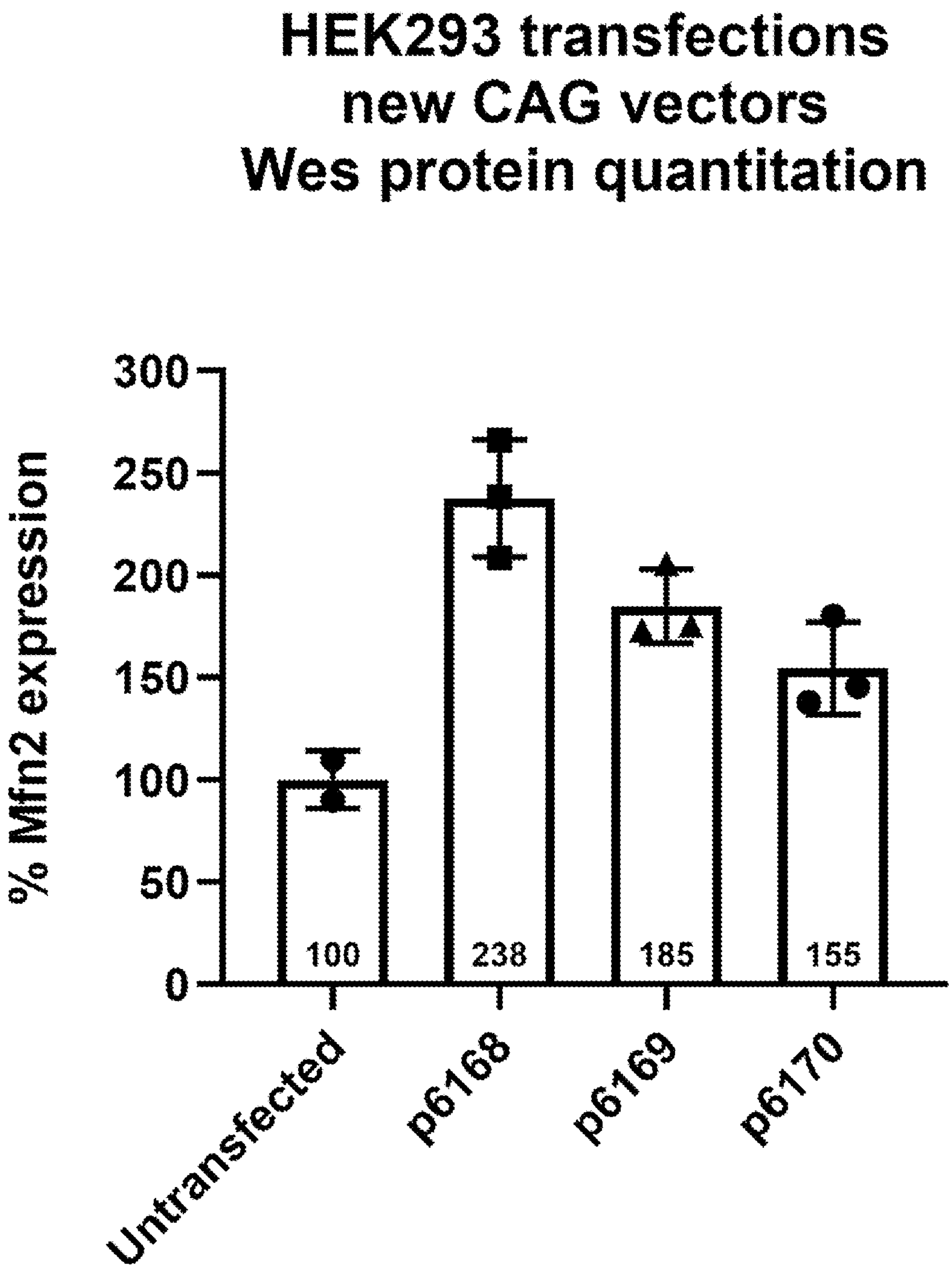
FIG. 11 shows expression levels of Mfn2 (endogenous Mfn2 and Mfn2 expressed from vector) in HEK293 cell line following transfection with various vectors comprising CAG promoter; expression levels shown as plotted quantitation of western blot signal measuring expression of mitofurin-2 (Mfn2) following transfections with CAG.CI.hMfn2. GA.WPRE.SV40; CAG.CI.hMfn2.GA.LINK.miR1518. WPRE.SV40; CAG.CI.hMfn2.GA.LINK.miR538. WPRE.SV40. Quantitation is plotted as percent expression; transfection efficiency was determined to be about 95%.

FIG. 11 shows expression levels of Mfn2 (endogenous Mfn2 and Mfn2 expressed from vector) in HEK293 cell line following transfection with various vectors comprising CAG promoter. Furthermore, FIG. 11 shows plotted quantitation of western blot signal measuring expression of mitofurin-2 (Mfn2) following transfections with CAG.CI.h Mfn2.GA.WPRE.SV40; CAG.CI.hMfn2.GA.LINK. miR1518.WPRE.SV40; CAG.CI.hMfn2.GA.LINK. miR538.WPRE.SV40. Quantitation is plotted as percent expression; transfection efficiency was determined to be about 95%. For a western blot probed for expression levels of Mfn2, b-actin was used as a loading control (Mfn2: 0.78 μg loaded; b-actin: 0.78 μg loaded; exposure used for quantification 4 seconds).

Figure 12A:
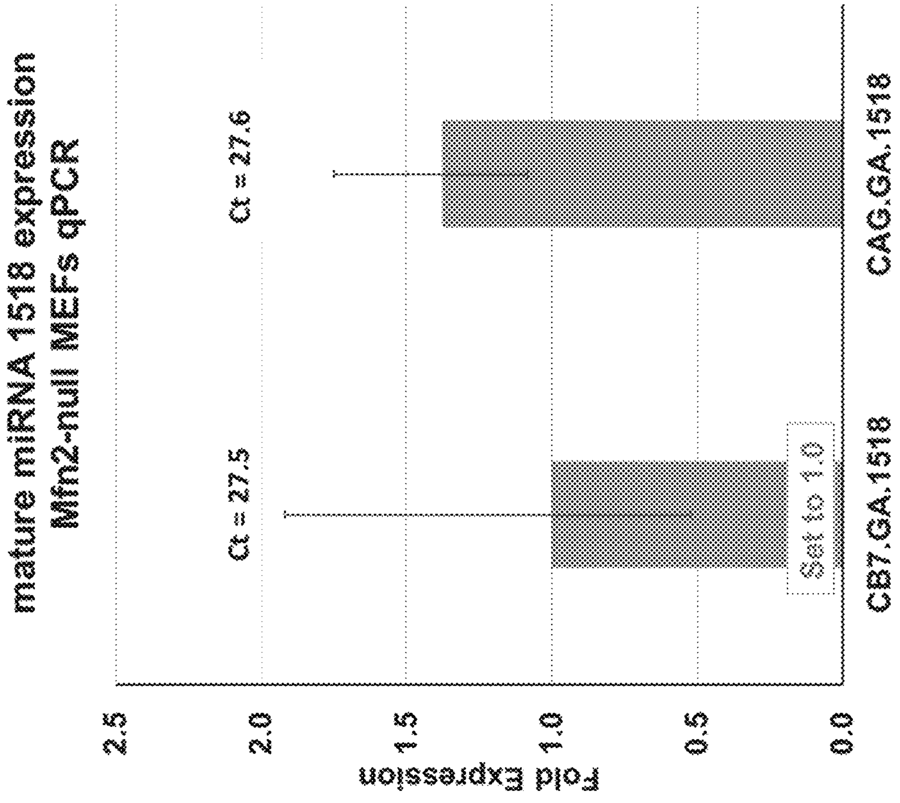
FIG. 12A to FIG. 12C show expression levels, as measured by qPCR, of mature miRNA (miR1518 or miR538) in Mfn2-null MEF cell line (ATCC; CRL-2933), following transfection with various vectors comprising either CB7 or CAG promoter.
Figure 12B:
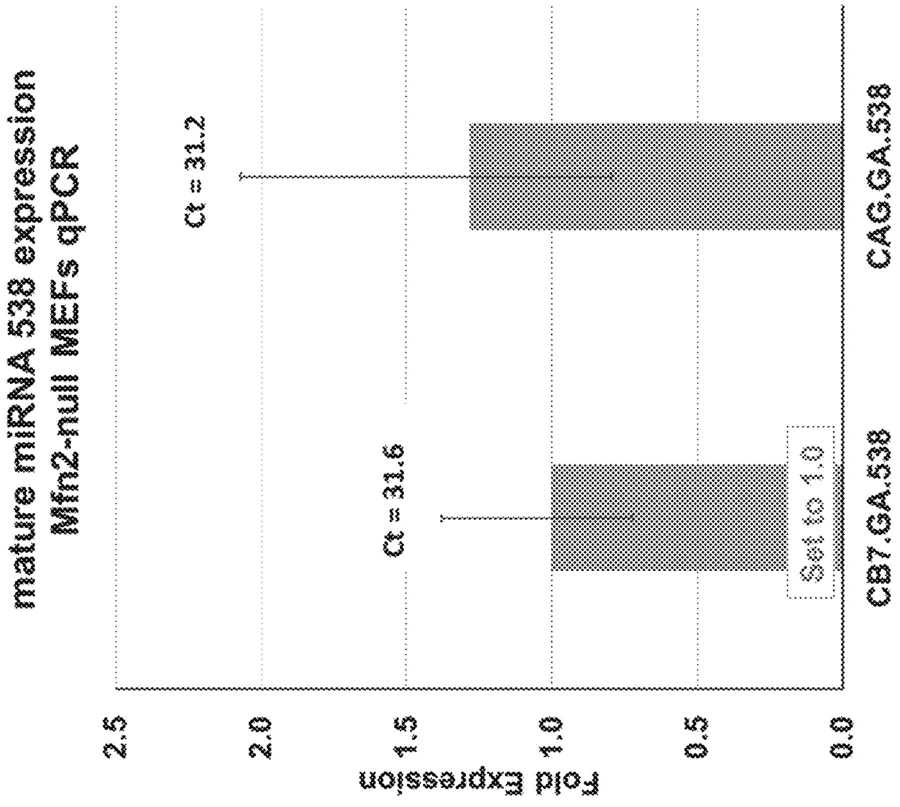
Figure 12C:
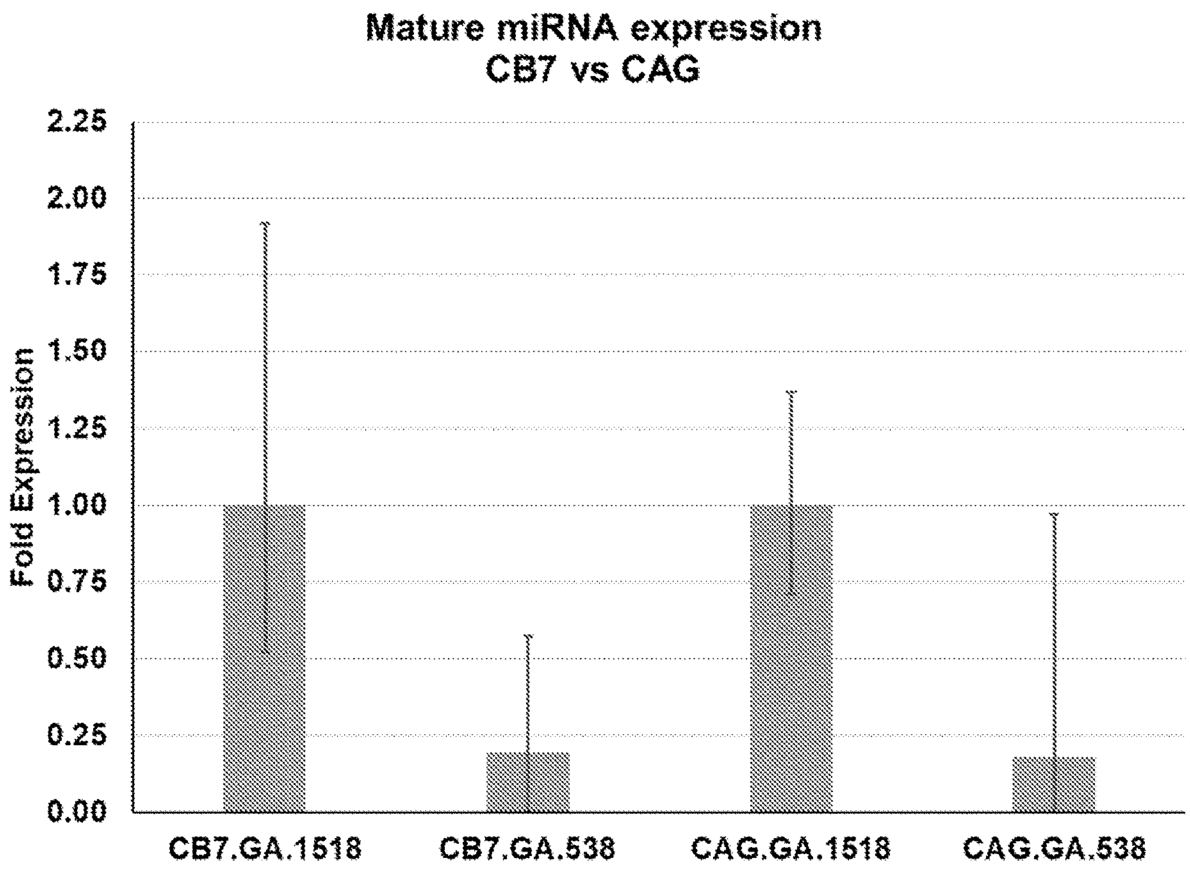

FIG. 12A to FIG. 12C show expression levels, as measured by qPCR, of mature miRNA (miR1518 or MiR538) in Mfn2-null MEF cell line, following transfection with various vectors comprising either CB7 or CAG promoter. FIG. 12A shows a comparison of expression levels, as measured by qPCR and plotted as fold expression, of mature miR1518 in Mfn2-null MEF cell line, following transfection with vectors comprising either CB7 or CAG promoter. FIG. 12B shows a comparison of expression levels, as measured by qPCR and plotted as fold expression, of mature miR538 in Mfn2-null MEF cell line, following transfection with vectors comprising either CB7 or CAG promoter. FIG. 12C shows a comparison of expression levels, as measured by qPCR and plotted as fold expression, of mature miR1518 and miR538 in Mfn2-null MEF cell line, following transfection with vectors comprising either CB7 or CAG promoter.

Example 4. Gene Therapy Vectors for Efficacy in MFN2$^{R94Q}$ Mice (C57BL/6J-Tg(Thy1-MFN2*), a Model of Charcot-Marie-Tooth Disease Type 2A Seven (7) hemizygous male MFN2$^{R94Q}$ mice (C57BL/6J-Tg (Thy1-MFN2*)44Balo/J, JAX stock #029745), two (2) male C57BL/6J mice (JAX stock #000664), and eighteen (18) female C57BL/6J mice (JAX stock #000664) were transferred to our in vivo research laboratory in Bar Harbor, ME. The mice were ear notched for identification, genotype (s) confirmed and housed in individually and positively ventilated polysulfonate cages with HEPA filtered air at a density of 3 mice per cage (two females with one male). The animal room wad lighted entirely with artificial fluorescent lighting, with a controlled 12 h light/dark cycle (6 am to 6 pm light). The normal temperature and relative humidity ranges in the animal rooms were 22±4° C. and 50±15%, respectively. The animal rooms were set to have 15 air exchanges per hour. Filtered tap water, acidified to a pH of 2.5 to 3.0, and normal rodent chow were provided ad libitum. The mice were used as breeders to raise the study cohort of 10 male C57BL/6J mice and 60 male hemizygous MFN2$^{R94Q}$ mice in two rounds of breeding. At P0-P1, a total of seventy (70) mice were enrolled in the study.

TABLE 4

| Group | #Mice | Genotype | Compound | Age at Dosing | Dosing Route | Dosing Frequency | Tissue Collection |
|---|---|---|---|---|---|---|---|
| 1 | 10 | WT | Vehicle | P0-P1 | ICV injection | Single Dose | Spinal cord; Tibial nerve |
| 2 | 10 | HEMI | Vehicle | | | | |
| 3 | 10 | HEMI | Vector 1 | | | | |
| 4 | 10 | HEMI | Vector 2 | | | | |
| 5 | 10 | HEMI | Vector 3 | | | | |
| 6 | 10 | HEMI | Vector 4 | | | | |
| 7 | 10 | HEMI | Vector 5 | | | | |
| Total | 70 | | | | | | |

Figure 13A:
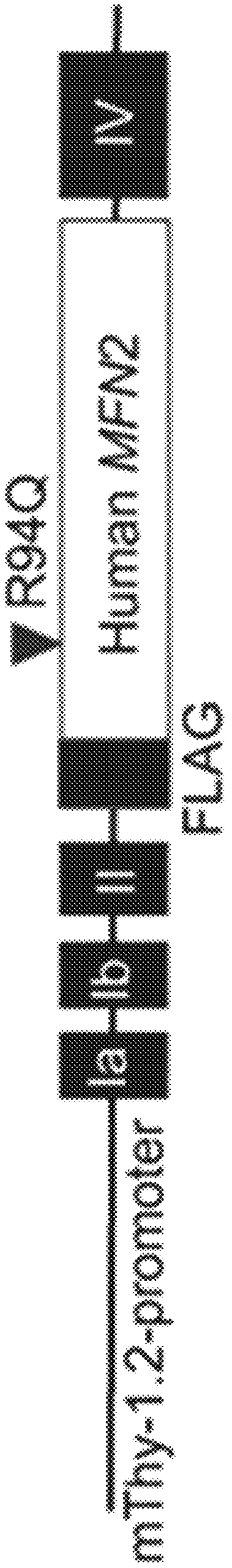
FIG. 13A to FIG. 13F show characterization of a mouse model.
Figure 13B:
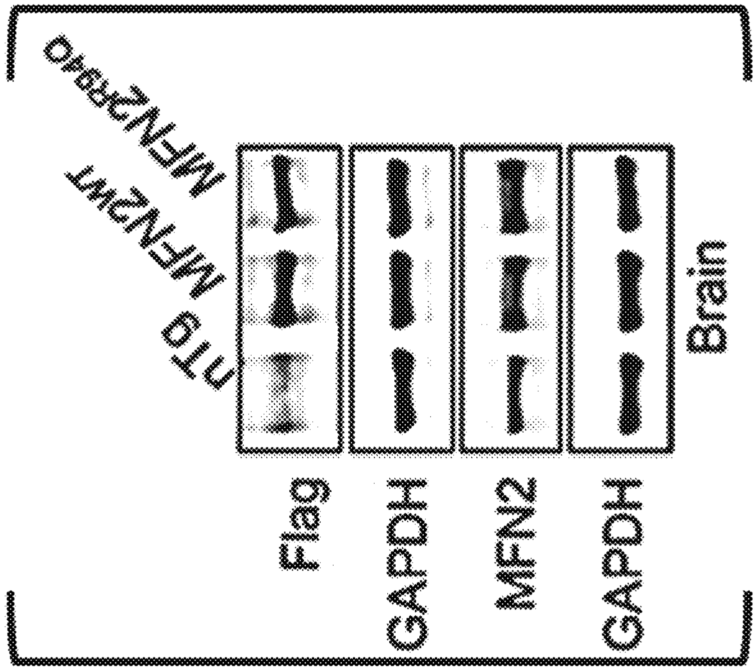
Figure 13C:
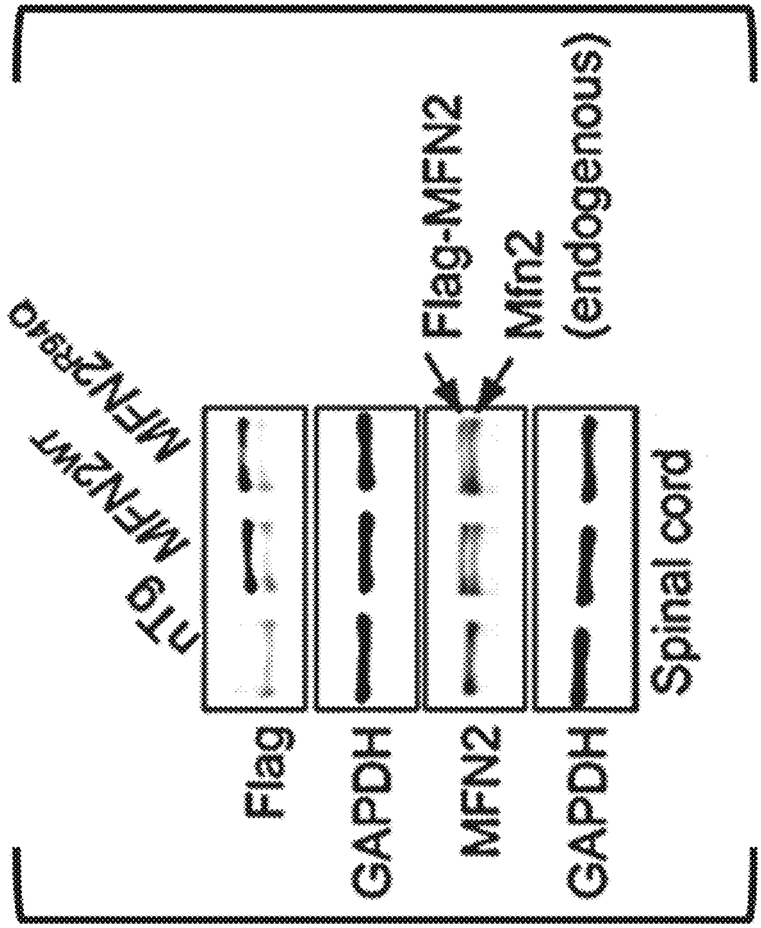
Figure 13D:
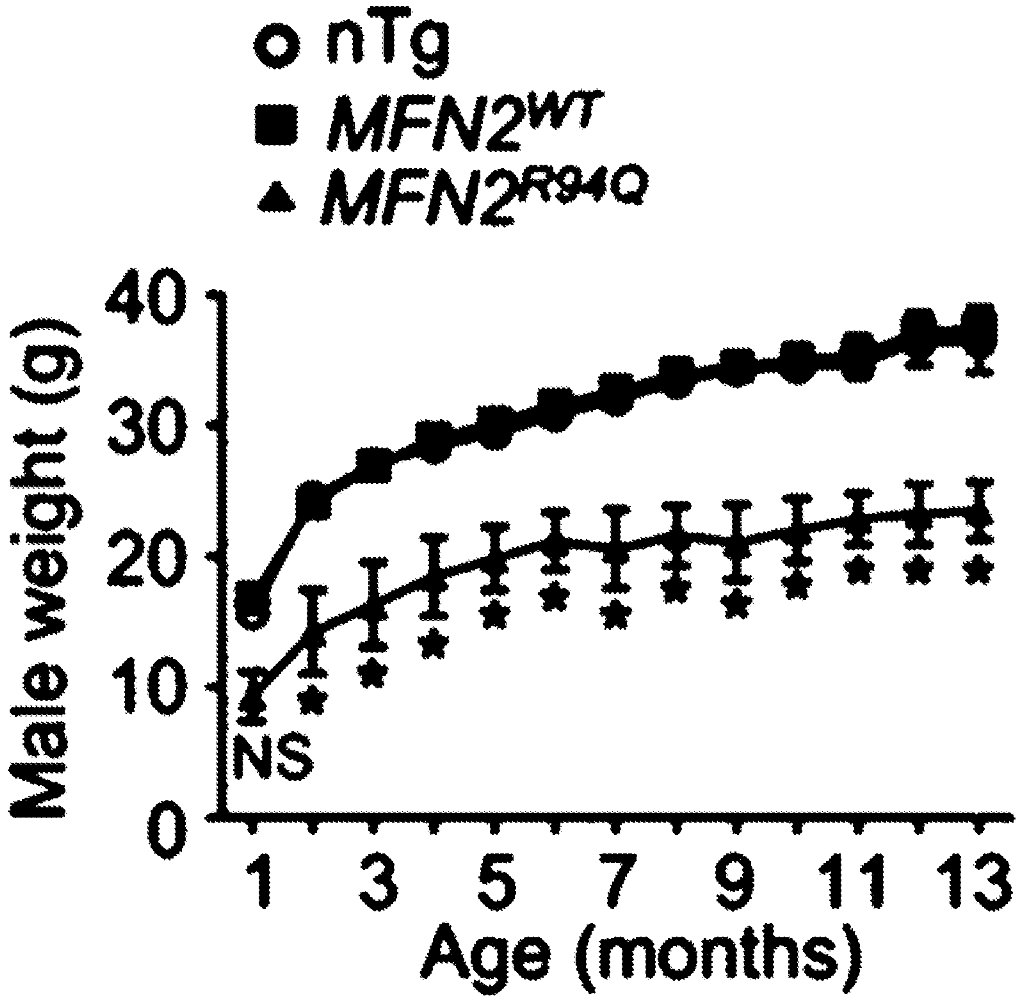
Figure 13E:
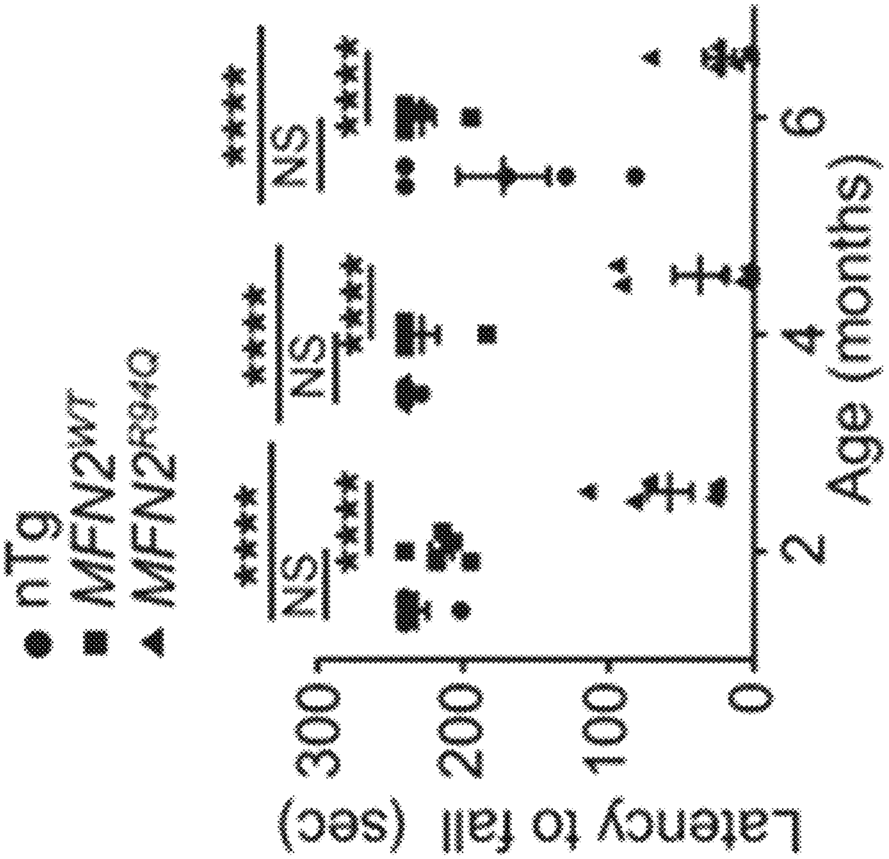
Figure 13F:
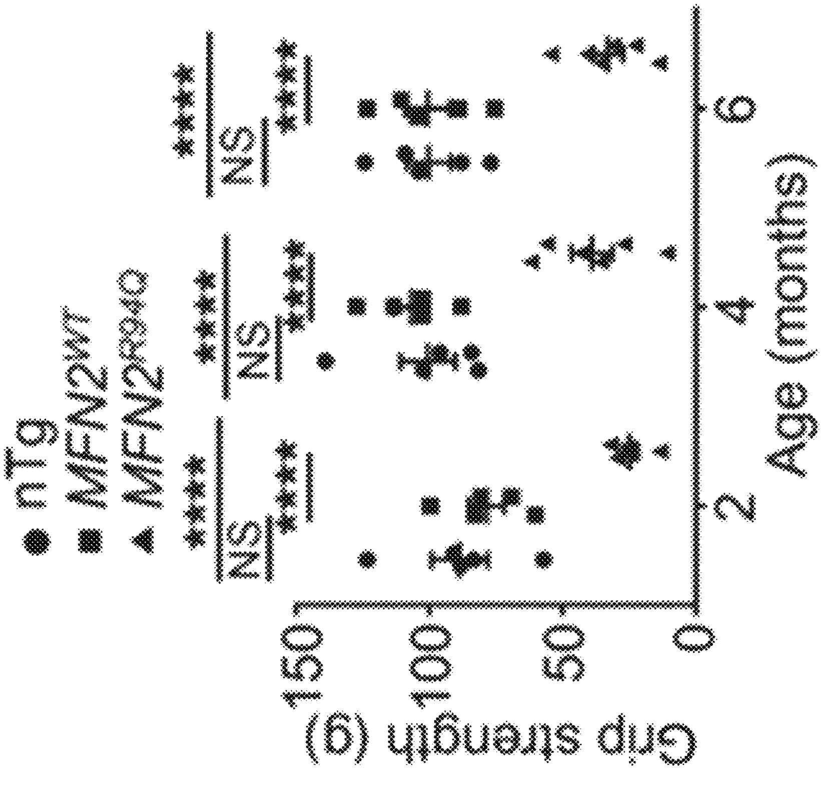

FIG. 13A to FIG. 13F show characterization of mouse model. FIG. 13A show schematic representation of the mice genotype. FIG. 13B shows mice phenotype characterization, characterized by relative expression levels endogenous and FLAG-tagged MFN2 in brain as measured by western blotting. FIG. 13C shows mice phenotype characterization, characterized by relative expression levels endogenous and FLAG-tagged MFN2 in spial cord as measured by western blotting. FIG. 13D shows measured weight in (g) of the mice in CMT2A mouse model (nTg, MFN2$^{WT}$, and MFN2$^{R49Q}$). FIG. 13E shows mice phenotype characterization, as measured by the latency to fall (sec). FIG. 13F shows mice phenotype characterization, as measured by grip strength (g).

In this study, mice are dosed at P0-P1 by neonatal ICV injection according to the table 4 above. Body weights of mice are measured weekly. At 15-17 weeks of age, the following tests are performed on each mouse: rotarod test, grip strength test, visual acuity test (optokinetic response), optional procedure. Additionally, Compound Muscle Action Potential (CMAP) testing is performed. At 17-19 weeks of age, mice are necropsied and the following tissues are collected: spinal cord, tibial nerve. The collected tissues are fixed in EM fixative and embedded in epoxy resin. One section is cut from each tissue. Sections are the stained with Toluidine Blue. Stained slides are scanned. For each of the scanned sections, the following parameters are determined: axon size distributions, axon counts, axon areas. The axon area distributions are then plotted for each group.

Figure 14A:
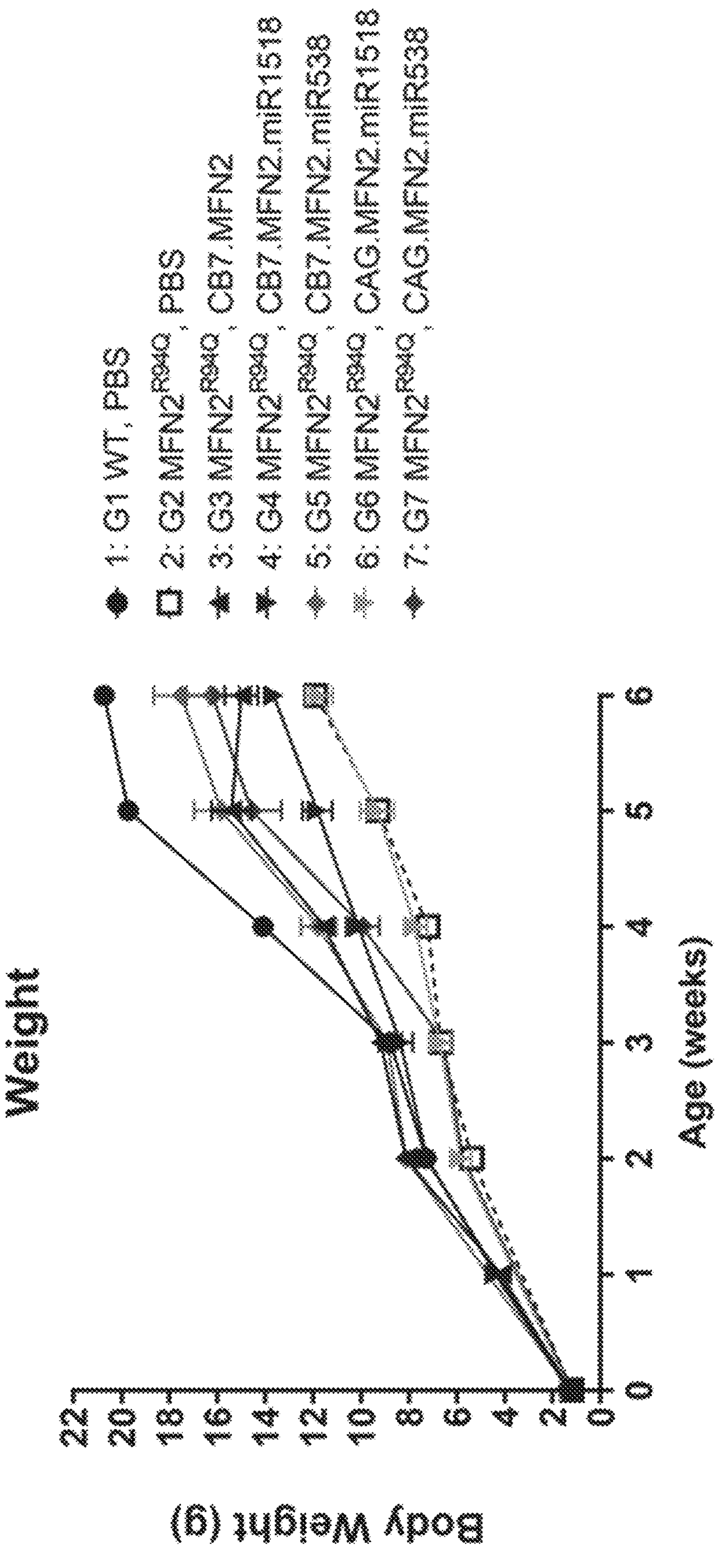
FIG. 14A and FIG. 14B show results of the pharmacological study in MFN2$^{R94Q}$ mice (Study groups: G1—wild type (WT) mice, PBS; G2—MFN2$^{R94Q}$ mice, PBS; G3—MFN2$^{R94Q}$ mice, CB7.MFN2; G4—MFN2$^{R94Q}$ mice, CB7.MFN2.miR1518; G5—MFN2$^{R94Q}$ mice, CB7.MFN2.miR538; G6—MFN2$^{R94Q}$ mice, CAG.MFN2.miR1518; G7—MFN2$^{R94Q}$ mice, CAG.MFN2.miR538).
Figure 14B:
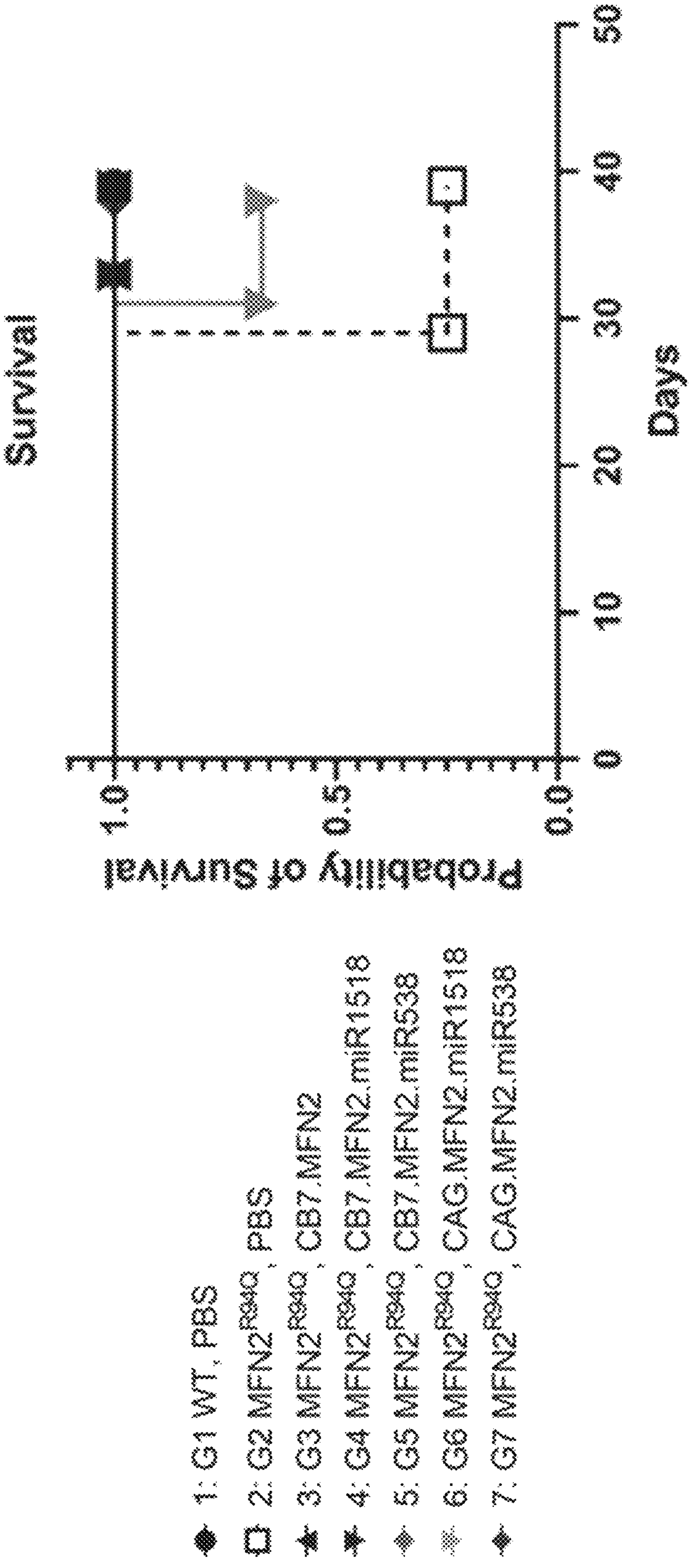

In a pharmacological study, for the first cohort, 4-7 mice per group were used. The study was a blinded study. Briefly, male MFN2$^{R94W}$ mice were used in the treatment groups to which candidate AAVhu68 vectors were administered. Newborn ICV injection was used as a route of administration, with bilaterally administered dose of 3 μL of $7.5\times10^{10}$ GC AAV vectors. Weight was measured weekly. Grip strength was measured at 6 weeks. FIG. 14A and FIG. 14B show results of the pilot pharmacological study in MFN2$^{R94Q}$ mice (Study groups: G1—wild type (WT) mice, PBS; G2—MFN2$^{R94Q}$ mice, PBS; G3—MFN2$^{R94Q}$ mice, CB7.MFN2; G4—MFN2$^{R94Q}$ mice, CB7.MFN2.miR1518; G5—MFN2$^{R94Q}$ mice, CB7.MFN2.miR538; G6—MFN2$^{R94Q}$ mice, CAG.MFN2.miR1518; G7—MFN2$^{R94Q}$ mice, CAG.MFN2.miR538). FIG. 14A shows body weight results (plotted as (g)) as measured in mice groups G1 to G7. FIG. 14B shows survival results (plotted as probability of survival over day 0 to 50) as measured in mice groups G1 to G7 (also referenced to as Groups 1-7).

Figure 16A:
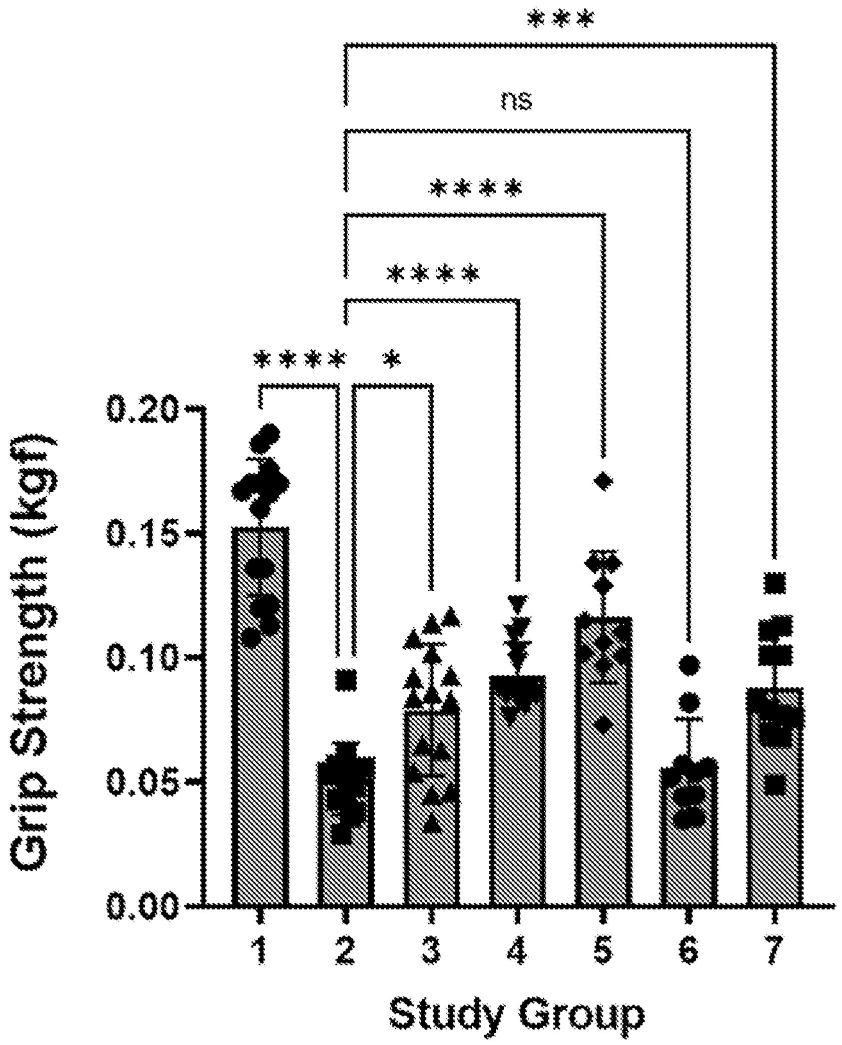
FIG. 16A shows measured grip strength results (plotted as kilogram-force (kgf)) of the pharmacological study in MFN2$^{R94Q}$ or WT (control) mice at 6-weeks post AAV or PBS (control) administration.
Figure 16B:
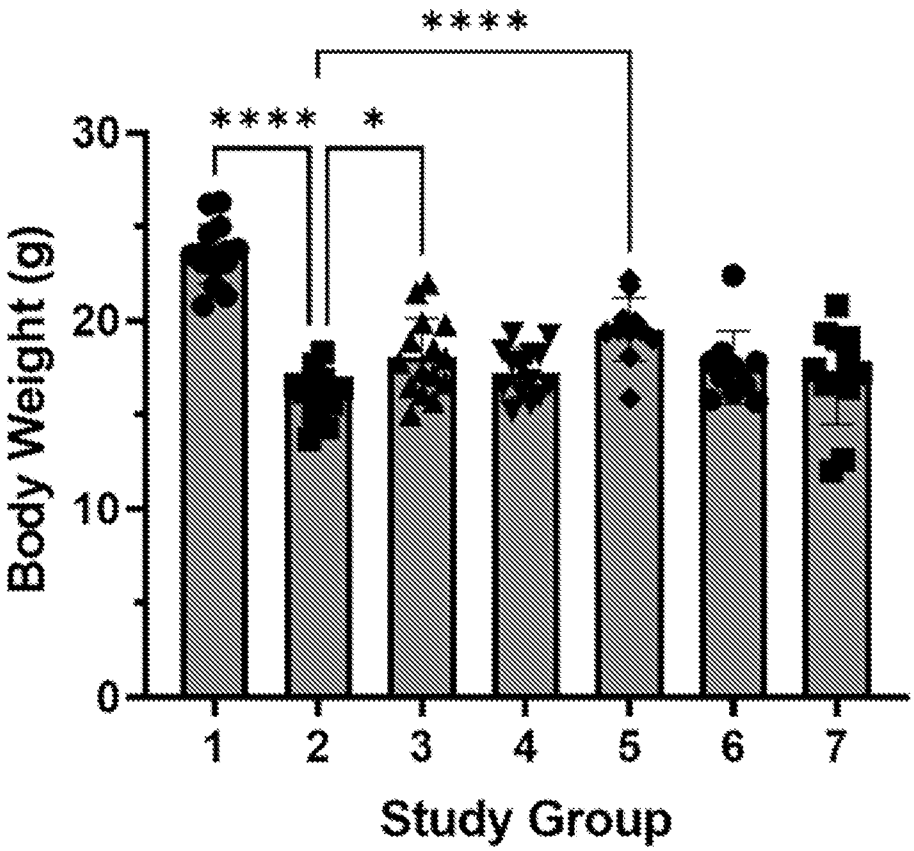
FIG. 16B shows measured body weight results (plotted as (g) of the pharmacological study in MFN2$^{R94Q}$ or WT (control) mice at 6-weeks post AAV or PBS (control) administration.
Figure 17A:
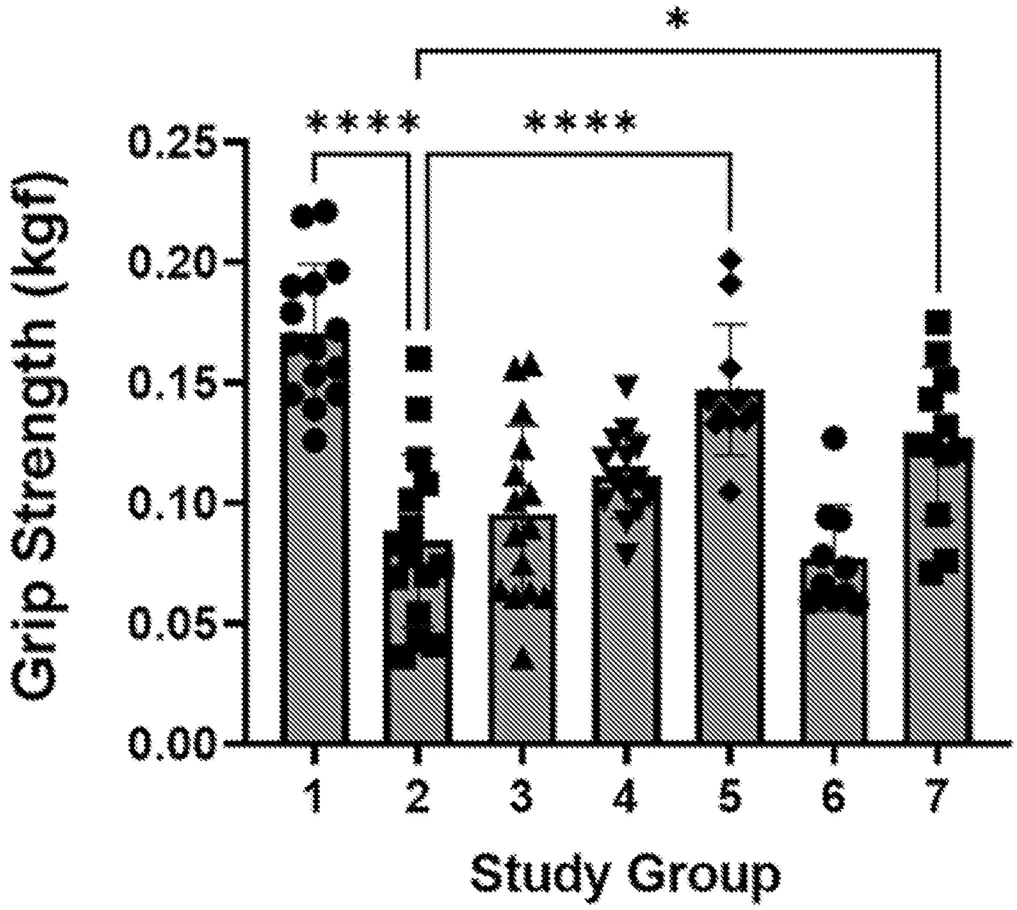
FIG. 17A shows measured grip strength results (plotted as (kgf)) of the pharmacological study in MFN2$^{R94Q}$ or WT (control) mice at 4-month post AAV or PBS (control) administration.
Figure 17B:
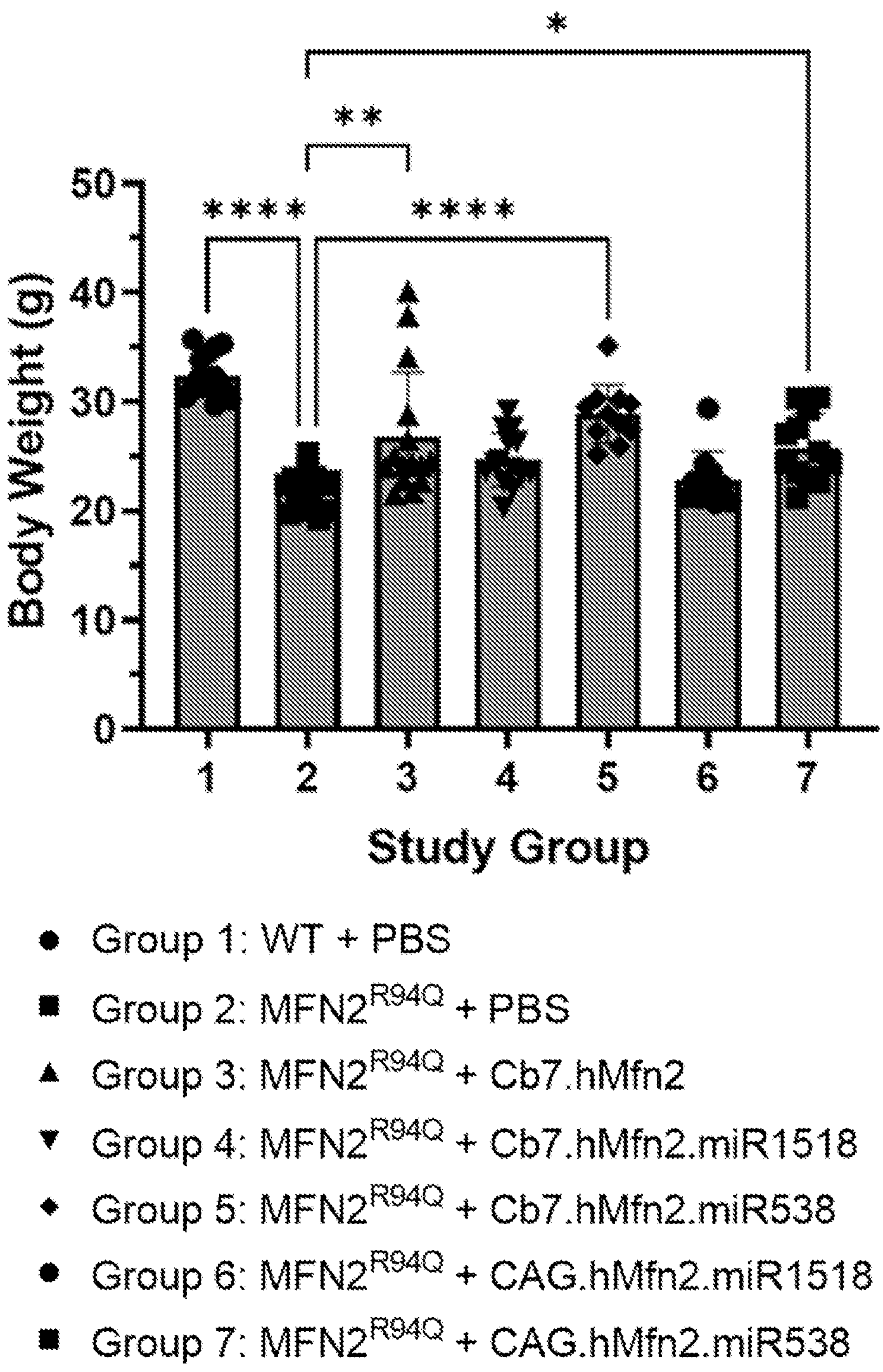
FIG. 17B shows measured body weight results (plotted as (g) of the pharmacological study in MFN2$^{R94Q}$ or WT (control) mice at 4-month post AAV or PBS (control) administration.

Data was collected at 6-weeks and at 4-months post AAV vector (or PBS) administration. FIG. 16A shows grip strength results (plotted as (kgf)) of the pharmacological study in MFN2$^{R94Q}$ or WT (control) mice at 6-weeks post AAV or PBS (control) administration (Groups 1-7, as indicated). FIG. 16B shows measured body weight results (plotted as (g) of the pharmacological study in MFN2$^{R94Q}$ or WT (control) mice at 6-weeks post AAV or PBS (control) administration (Groups 1-7, as indicated). FIG. 17A shows grip strength results (plotted as (kgf)) of the pharmacological study in MFN2$^{R94Q}$ or WT (control) mice at 4-month post AAV or PBS (control) administration (Groups 1-7, as indicated). FIG. 17B shows measured body weight results (plotted as (g) of the pharmacological study in MFN2$^{R94Q}$ or WT (control) mice at 4-month post AAV or PBS (control) administration (Groups 1-7, as indicated). These results confirm that the AAV-miRNA vector ameliorates distal limb weakness (grip strength) following ICV delivery in MFN2 mutant mice.

Overall, the above-mentioned data from studies in cell culture and mice show that knockdown of Mfn2 was achieved in vitro and in vivo using artificial miRNAs. Furthermore, the combination vector strategy improved the phenotype of a mouse model of CMT2A, and the combination strategy performed better than cDNA expression alone.

Example 5. AAV Vector Co-Administering hMfn2 and miR Targeting Endogenous hMfn2

In this study, AAVhu68.CB7.CI.hMfn2.miR538.RBG (also referenced as AAVhu68.CB7.CI.hMfn2.GA.LINK.miR538.RBG) vector is administered in Rhesus Macaque (*Macaca mulatta*) or *Cynomolgus Macaque* (non-human primates (NHP) via Intra-Cisterna Magna (ICM) injection, utilizing cerebrospinal fluid (CSF) to achieve widespread distribution from a single injection.

Test Article. The AAVhu68.CB7.CI.hMfn2.GA.LINK.miR538.RBG is used in this study. A certificate of analysis verifying quality and purity of the test article is included in the final study report.

Preparation. Calculations for test article dilutions are performed and verified by trained GTP personnel prior to making dilutions. Test article dilutions are performed by designated personnel on the day of injection. Test article dilutions are verified by additional designated personnel. Diluted test article are kept on wet ice or at 2-8° C. for up to 8 hours until injection.

Archival Samples. Archival samples of test and control articles are retained by designated personnel and stored at ≤−60° C.

Test Article Analysis. The designated personnel is responsible for assuring that the test article meets the release requirements. A certificate of analysis is provided by Vector Core for inclusion with study records. All results are recorded. Copies of the data are provided to for inclusion in the study notebook.

Unused Test Article. Unused test article provided to NPRP personnel are stored on wet ice prior to being returned for archiving. Archival samples are stored at ≤−60° C.

Test System. Rhesus Macaque (*Macaca mulatta*) or *Cynomolgus Macaque* is used in this study.

Justification for Test System Selection. This study involves intra-cisterna magna (ICM) delivery of a miRNA test article (vector) for CNS diseases. The dimensions of the CNS in the NHP act as a representative model of our clinical target population. This study provides critical data on the dose and route of administration-related pharmacokinetics and safety of the test article after ICM injection in rhesus macaques. In this study, 2 animals are used. The NHPs are selected from male or female, 4-5 years of age, and about 3-10 kg.

Acclimation Period and Care. Quarantine and acclimation, animal husbandry and care are conducted in accordance with Standard Operating Procedures (SOP) procedures. Macaques are housed in stainless steel caging in CTRB. Husbandry and care are provided by DVR personnel.

Certified Primate Diet 5048 or a similar diet appropriate for nonhuman primates is supplied to study animals. Water is available from an automatic watering system and is accessible to all macaques ad libitum. Macaques are monitored by the veterinary staff for any conditions requiring possible intervention. The Study Director is consulted whenever possible to determine the appropriate course of action. However, in emergency situations, including possible euthanasia, decisions are made by the veterinary staff as needed and the Study Director is advised as soon as possible. Enrichment in the form of food rewards, conspecific interaction, and manipulanda are provided. Animals are maintained on a 12-hour light/dark cycle controlled by Building Automation. The desired temperature range is 64-84° F. (18-29° C.). Temperature is maintained in this range to the maximum extent possible. The desired humidity range is 30-70%. Humidity is maintained in this range to the maximum extent possible. Each macaque has been previously identified with a unique identification number that has been tattooed on its chest by the supplier. Both animals are included in a single treatment group.

Study design procedures. Two rhesus macaques are used in the study. Both macaques are included in a single treatment group. Baseline blood samples, including CSF, CBC, serum chemistry, and baseline biomarker assessment are collected from all macaques on day 0 prior to dosing. Vitals are also obtained from each macaque. On day 0, macaques are sedated; weighed and vital signs are recorded prior to test article administration.

For test Article Administration (AAVhu68.CB7.CI.hMfn2. GA.LINK.miR538.RBG), macaques are anesthetized and appropriate analgesics are administered in accordance with SOP. Macaques are dosed with test article via sub-occipital puncture into the cisterna magna. For the Intra-Cisterna Magna (ICM) Puncture Procedure, anesthetized macaques are transferred from animal holding to the Procedure Room and placed on an x-ray table in the lateral decubitus position with the head flexed forward for CSF collection and dosing into the cisterna magna. The site of injection is aseptically prepared. Using aseptic technique, a 21-27 gauge, 1-1.5 inch Quincke spinal needle (Becton Dickinson) is advanced into the sub-occipital space until the flow of CSF is observed. 1 mL of CSF is collected for baseline analysis, prior to dosing. The anatomical structures that is traversed include the skin, subcutaneous fat, epidural space, dura and atlanto-occipital fascia. The needle is directed at the wider superior gap of the cisterna magna to avoid blood contamination and potential brainstem injury. Correct placement of needle puncture is verified via myelography, using a fluoroscope (OEC9800 C-Arm, GE). After CSF collection, a small bore T extension catheter is connected to the spinal needle to facilitate dosing of Iohexol (Trade Name: Omnipaque 180 mg/mL, General Electric Healthcare) contrast media and test article. Up to 2 mL of Iohexol is administered via the catheter and spinal needle. After verifying needle placement via CSF return and visualization of the needle by fluoroscopy, a syringe containing the test article is connected to a flexible linker containing the test article and injected at a rate of approximately 2 ml/minute. After administration, the needle is removed, and direct pressure is applied to the puncture site. The macaques receive ICM administration of test article (AAVhu68.CB7.CI.hMfn2.GA.LINK.miR538.RBG) at a dose of $3\times10^{13}$ GC ($3.33\times10^{11}$ GC/g brain). The total volume of injected per macaque is 1.0 mL. Doses and volumes are documented in the study records.

For observations, on selected time points as listed on the Study Schedule (Table 5), the macaque(s) are monitored for additional parameters beyond the daily observations, including but not limited to vital signs, clinical pathology, collection of serum and CSF.

For blood draws, animals are bled from a peripheral vein for a general safety panel which includes: neutralizing antibodies to AAV, hematology, clinical chemistry. Procedures for blood collection are performed in accordance with SOP. Additional blood samples are collected to measure changes in biomarkers (pharmacodynamic markers). The frequency of blood draws for complete blood counts, serum chemistry, biomarkers, neutralizing antibodies to AAV are as defined in the Study Schedule (Table 5) of the study protocol.

For antibody assays (neutralizing antibodies to AAV, serum), the blood sample (up to 2 mL) is collected via red top tubes (w/or w/o serum separator), allowed to clot, and centrifuged. Study personnel isolates the serum. Serum is divided into two individually marked microcentrifuge tubes (labeled with Study number, Animal ID, Group number, time point, neutralizing Abs, and date) for every Antibody time point and stored at ≤−60° C.

For cell counts and differentials, blood samples for complete blood counts with differentials and platelet count are collected in labeled lavender top tubes (Study number, Animal ID, Group number, time point, CBC and date of collection), up to 2 mL and stored at 4° C. Blood is sent to Antech Diagnostics, Inc. overnight (with ice packs for lavender top tubes) for blood cell counts including platelet counts and differentials. The following parameters are analyzed for red cell count, hemoglobin, hematocrit, platelet count, leukocyte count, leukocyte differential, mean corpuscular volume (MCV), mean corpuscular hemoglobin (MCH), red blood cell morphology.

For clinical chemistries, blood samples of (up to 2 mL) are collected in labeled red top tubes, allowed to clot, and centrifuged. The serum is separated, put into labeled microcentrifuge tubes (Study number, Animal ID, Group number, time point, Chemistry and date of collection, and sent to Antech Diagnostics, Inc. overnight on ice packs for analysis. The following parameters are analyzed: alkaline phosphatase, bilirubin (total), creatinine, gamma-Glutamyl Transpeptidase, glucose, serum Alanine Aminotransferase, serum aspartate aminotransferase, albumin, albumin/globulin ratio (calculated), aldolase, blood urea nitrogen, calcium, chloride, creatinine kinase and isoforms, globulin (calculated as total protein minus albumin=globulin), lactate dehydrogenase, phosphorus, inorganic, potassium, sodium, total protein.

For biomarker analysis, blood sample (up to 2 mL) is collected via red top tubes (w/or w/o serum separator), allowed to clot, and centrifuged. Study personnel isolates the serum. Serum is then divided into 2¬individually marked microcentrifuge tubes (Study number, Animal ID, Group number, time point, serum biomarker, and date of collection). Samples are be stored at ≤−60° C.

For PBMC/tissue lymphocyte isolation and ELISPOT, blood samples (6-10 mL) are collected into sodium heparin (green top tubes) and PBMCs are isolated according to SOP. Blood collection tubes are labeled with Study number, Animal ID. Group number, Species, Time point, PBMC, and Date of Collection. Lymphocytes are harvested from spleen, liver and bone marrow according to SOPs. ELISPOT for capsid and transgene T cell responses are performed according to SOP.

For CSF collection, up to 1 mL of CSF is collected for analysis and biomarker assessment. For all CSF collection time points including Study Day 0, macaques are anesthetized in accordance with SOP and transferred from animal holding to the Procedure Room where they are placed in the lateral decubitus position with the head flexed forward for CSF collection. The hair over the back of the head and cervical spine is clipped. The occipital protuberance at the back of the skull and the wings of the atlas (C1) is palpated. The site of injection is aseptically prepared. Using aseptic technique, a 21-27 gauge, 1-1.5 inch Quincke spinal needle (BD) or 21-27 gauge needle is advanced into the cisterna magna until the flow of CSF is observed. The anatomical structures that are traversed include the skin, subcutaneous fat, epidural space, dura and atlanto-occipital fascia. The needle is directed at the wider superior gap of the cisterna magna to avoid blood contamination and potential brainstem injury. Post CSF collection, the needle is removed and direct pressure applied to the puncture site. Samples are collected in sterile 1.5 mL Eppendorf tubes labeled with the Study number, Animal ID, group number, time point, CSF, and date of collection. Samples are placed on wet ice, and immediately aliquoted for CSF clin pathology (blood cell counts and differentials and total protein quantification) and CSF biomarkers. CSF is collected at frequencies outlined in the Study Schedule (Table 5) of the study protocol.

For CSF clin pathology, CSF (0.5 mL) is aliquoted into lavender top tubes (labeled with the Study number, Animal ID, group number, time point, CSF clin path, and date of with ice packs) for blood cell counts and differentials and total protein quantification.

For CSF biomarkers, all remaining CSF (unused for CSF clin path—up to 1 mL) collected in 2 sterile 1.5 mL Eppendorf tubes is centrifuged at 800 g for 5 minutes. Study personnel isolates the supernatant and aliquot into cryovials (labeled with the Study number, Animal ID, group number, time point, CSF biomarker, and date of collection). Samples are shipped on wet ice.

Additionally, on all days selected for monitoring, each macaque is sedated, weighed and have its respiratory and heart rates monitored, and body temperature taken via rectal thermometers prior to any blood samples being taken. The blood samples for PBMC isolation are transported at room temperature. Other samples are transported on wet ice.

The study is performed according to the schedule as described in Table 5 below.

TABLE 5

| Study Timepoint | Sample/Procedure | N |
|---|---|---|
| Study Day 0 | Body Weight, Temperature, Respiratory Rate, Heart Rate | 2 |
| | Biomarker (baseline) (RC) | 2 |
| | CSF (baseline) (CV + LT) | 2 |
| | Neurological Monitoring | 2 |
| | Clin path (baseline) (LT, RC) | 2 |
| | Nerve conduction velocity testing | 2 |
| | Antibodies (baseline) (RC) | 2 |
| | Immunology (baseline) (PBMC) (GT) | 2 |
| | ICM vector $3\times10^{13}$ GC | 2 |

TABLE 5-continued

| Study Timepoint | Sample/Procedure | N |
|---|---|---|
| Study Day 7 | Body Weight, Temperature, Respiratory Rate, Heart Rate | 2 |
| (±2 days) | Biomarker (RC) | 2 |
| | Clin path (LT, RC) | 2 |
| Study Day 14 | Body Weight, Temperature, Respiratory Rate, Heart Rate | 2 |
| (±2 days) | Biomarker (RC) | 2 |
| | CSF (CV + LT) | 2 |
| | Clin path (LT, RC) | 2 |
| Study Day 21 | Body Weight, Temperature, Respiratory Rate, Heart Rate | 2 |
| (±2 days) | Biomarker (RC) | 2 |
| | Clin path (LT, RC) | 2 |
| Study Day 28 | Body Weight, Temperature, Respiratory Rate, Heart Rate | 2 |
| (±2 days) | Biomarker (RC) | 2 |
| | Clin path (LT, RC) | 2 |
| | Neurological Monitoring | 2 |
| | Nerve conduction velocity testing | 2 |
| Terminal Day 35 | Body Weight, Temperature, Respiratory Rate, Heart Rate | 2 |
| (±2 days) | Neurological monitoring | 2 |
| | Biomarker (RC) | 2 |
| | CSF (CV + LT) | 2 |
| | Clin path (LT, RC) | 2 |
| | Antibodies (RC) | 2 |
| | Immunology (PBMC) (GT) | 2 |
| | Nerve conduction velocity testing | 2 |
| | Necropsy | 2 |
| | Tissues to be harvested | 2 |

When macaques are necropsied, tissues described in Table 6 below are collected.

TABLE 6

Tissues to be Collected at Time of Necropsy for Histopathology and Biodistribution

| | Histopathology | | Biodistribution | | Lymphocyte |
|---|---|---|---|---|---|
| Organ | Req. | Coll. | Req. | Coll. | isolation |
| Chest tattoo | ✓ | | | | |
| Ascending aorta (proximal) | ✓ | | ✓ | | |
| Bone marrow, rib | ✓ | | | | |
| Bone marrow, femur | | | ✓ | | ✓ |
| Brain right hemisphere[A] | ✓ | | | | |
| Frontal Cortex[A] | | | ✓ | | |
| Parietal Cortex[A] | | | ✓ | | |
| Temporal Cortex[A] | | | ✓ | | |
| Occipital Cortex[A] | | | ✓ | | |
| Hippocampus[A] | | | ✓ | | |
| Cerebellum[A] | | | ✓ | | |
| Medulla[A] | | | ✓ | | |
| Cranial nerves IX, X, XI | ✓ R&L | | | | |
| Dorsal root ganglia, cervical[B] | ✓ | | ✓ | | |
| Dorsal root ganglia, thoracic[B] | ✓ | | ✓ | | |
| Dorsal root ganglia, lumbar[B] | ✓ | | ✓ | | |
| Epididymis | ✓ right | | ✓ left | | |
| Eye | ✓ right | | ✓ left | | |
| Gall bladder | ✓ | | ✓ | | |
| Heart[C] | ✓ | | ✓ left ventricle | | |
| Kidney, right | ✓ | | ✓ | | |
| Kidney, left | ✓ | | ✓ | | |
| Liver, left lobe | ✓ | | ✓ | | ✓ |
| Liver, right lobe | ✓ | | ✓ | | |
| Lung, left | ✓ | | ✓ | | |

TABLE 6-continued

Tissues to be Collected at Time of Necropsy for Histopathology and Biodistribution

| | Histopathology | | Biodistribution | | Lymphocyte |
|---|---|---|---|---|---|
| Organ | Req. | Coll. | Req. | Coll. | isolation |
| Lung, right | ✓ | | ✓ | | |
| Lymph node, deep cervical | | | ✓ | | |
| Lymph node, mandibular | ✓ | | ✓ | | |
| Lymph node, mesenteric | ✓ | | ✓ | | |
| Muscle, quadriceps femoris | ✓ right | | ✓ left | | |
| Nerve, sciatic | ✓ R&L | | ✓ left | | |
| Nerve, tibial | ✓ R&L | | ✓ left | | |
| Nerve, peroneal | ✓ R&L | | ✓ left | | |
| Nerve, median Proximal | ✓ R&L | | ✓ left | | |
| Nerve, median Distal | ✓ R&L | | | | |
| Nerve, radial | ✓ R&L | | ✓ left | | |
| Nerve, sural | ✓ R&L | | ✓ left | | |
| Nerve, ulnar | ✓ R&L | | ✓ left | | |
| Optic nerve (CN II) | ✓ right | | ✓ left | | |
| Ovary | ✓ right | | ✓ left | | |
| Pancreas | ✓ | | ✓ | | |
| Pituitary | ✓ | | ✓ | | |
| Skin with mammary | ✓ | | | | |
| Injection site | ✓ | | | | |
| Spinal Cord, cervical[D] | ✓ | | ✓ | | |
| Spinal cord, thoracic[D] | ✓ | | ✓ | | |
| Spinal cord, lumbar[D] | ✓ | | ✓ | | |
| Spleen | ✓ | | ✓ | | ✓ |
| Testis | ✓ right | | ✓ left | | |
| Thymus | ✓ | | ✓ | | |
| Thyroid gland (with parathyroid) | ✓ right | | ✓ left | | |
| Trigeminal nerve ganglia | ✓ right | | ✓ left[E] | | |
| Gross lesions (if any)[F] | ✓ | | ✓ | | |

✓ = Tissue are collected and processed for indicated assay,
Req. = Required by Protocol,
Coll. = Collected,
N/A = Not Applicable
Abbreviations:
L, left;
R, right

[A] The brain is collected whole and then divided in half along the midsagittal plane. The entire right half of the brain is placed in 10% neutral buffered formalin for histopathology and further trimmed and processed according to "Pardo et al., 2012, Technical Guide for Nervous System Sampling of the Cynomolgus Monkey for General Toxicity Studies, Toxicologic Pathology 40: 624-636". Samples for biodistribution are collected from the left hemisphere and stored at ≤−60° C.

[B] A minimum of 3 cervical, 3 thoracic and 3 lumbar dorsal root ganglia are sampled and fixed in three tissue cassettes for histopathology (cervical, thoracic, lumbar). In addition, the 3 contralateral cervical dorsal root ganglia, 3 contralateral thoracic dorsal root ganglia, and 3 contralateral 3 lumbar dorsal root ganglia are sampled and frozen ≤−60° C. for biodistribution.

[C] Sections of heart should include the right and left ventricles (with AV valves) and interventricular septum (with valves).

[D] Each spinal cord is divided into cervical, thoracic, and lumbar segments labeled C, T, or L, respectively. Each spinal cord segment is divided into three sections. The 3 C, T, or L sections are each numbered 1-3. From each animal, there is a total of 9 spinal cord sections generated, numbered C1-3, T1-3, and L1-3. From each spinal cord segment, section 1 (C1, T1, L1) is used for histopathological analysis. From each spinal cord segment, section 2 (C2, T2, L2) are used for biodistribution analysis (RNA and protein analysis, 2 tubes). From each spinal cord segment, section 3 (C3, T3, L3) are formalin fixed and paraffin embedded for LCM.

[E] Portion of trigeminal nerve is collected for possible occupational health exposure and stored in ≤−60° C.

[F] Gross observations made at necropsy for which histopathology is not appropriate (e.g., fluid, matted hair, missing anatomic parts) are collected.

Experimental Evaluation: Observations

For viability checks (In-Cage), the macaques are monitored by daily visual observation for general appearance, signs of toxicity which may include but are not limited to neurologic signs or lethargy, distress and changes in behavior. This is performed by personnel in accordance with SOPs. The Veterinarian and Study Director are notified for any unusual conditions. Treatment are conducted only after approval by the Veterinarian and Study Director, except in case of emergency imperiling the macaque or for humanely sacrificing the macaque if the Secondary Veterinarian and Study Director cannot be contacted in a timely manner.

Macaques found dead or euthanized due to their moribund state are evaluated in the same manner as terminal sacrificed macaques. A complete set of tissues are collected and any gross lesions recorded.

Additionally, all macaques are visually examined each time they are anesthetized. At the time of necropsy, the macaques are examined for gross abnormalities. All changes are noted. Macaques are weighed at the beginning of the study, at necropsy, and at every time point in which they are sedated.

Food consumption is not monitored. Water is administered ad lib and standard diet with enrichment foods are given to the macaques.

On the days selected for monitoring, Sensory Nerve Conduction Studies are performed.

For neurological exam, on the days selected for monitoring, a Nonhuman Primate Neurological Assessment is performed. The neurological assessment is divided in to 5 sections: Mentation, Posture and Gait, Proprioception, Cranial Nerves, and Spinal Reflexes.

For postmortem analysis, gross postmortem examinations are performed on all macaques, including macaques euthanized in a moribund condition or found dead. All abnormal observations are recorded.

Since this study requires an ongoing evaluation of animals, therefore time of necropsy is determined at a later time point. Any animals that die unexpectedly are necropsied as soon as practical. For all unscheduled deaths, clinical pathology, extensive gross pathology, and histopathology are performed on a complete list of tissues, which are collected under the discretion of the study pathologist. Other analyses (immune response, etc.) are included as appropriate in an attempt to determine possible cause of death. Tissues are collected on all animals as outlined in table 6. Gross observations made at necropsy for which histopathology is not appropriate (e.g., fluid, matted hair, missing anatomic parts) are not collected.

The macaques surviving to the end of their study period are euthanized. The macaques are first be sedated and are then euthanized. Death is confirmed by absence of heartbeat and respiration. The macaque may be exsanguinated to help ensure death.

All tissues are preserved which are listed in Table 6. Tissues are fixed by placement in 10% neutral buffered formalin for paraffin embedding. Eyes used for histopathologic examination are fixed in modified Davidson's solution prior to paraffin embedding.

For biodistribution analysis, a section of each tissue in table 6 is frozen down to −80° C. as quickly as possible. At the discretion of the Study Director, DNA is extracted from tissues, and vector biodistribution is evaluated by quantitative PCR.

For histopathological analysis, a subset or all tissues in Table 6 are stained with hematoxylin and eosin (H&E). Additional procedures and/or other stains may be employed at the discretion of the Study Pathologist to identify/clarify histologic features and are documented in the final report. All data documenting experimental details and study procedures and observations are recorded and maintained in the study binder. At the completion of the study, all reports and raw data are maintained in the archives. Preserved specimens and tissues are archived and stored. Study Director determines the need for final disposition of these materials. All data documenting experimental details and study procedures and observations are recorded and maintained by the GTP personnel in dedicated notebooks and study binders.

Assays Which are Performed on Tissues Collected at Necropsy

Following conclusion of the study, macaques are necropsied with tissues harvested for full pathology (for list of tissues collected at necropsy see Table 6).

For histopathology, hematoxylin and eosin (H&E) stains are performed on all or a subset of tissues listed for collection for histopathology, at the discretion of the Study Director. Additional appropriate stains may be employed based on histopathological findings. For Mfn2 cDNA and miRNA expression, tissue sections preserved in formalin and paraffin embedded (FFPE) are processed and motor neurons are laser-capture microdissected. Motor neurons isolated from the spinal cord are RNA extracted and qPCR is performed to determine level of Mfn2 knockdown, levels of Mfn2 cDNA expression and levels of miRNA expression using specific primer sets. Knockdown of Mfn2 and expression of Mfn2 cDNA may also be evaluated in tissue sample lysates by qPCR and Western blot. Immunohistochemistry for Mfn2 may be performed on brain and spinal cord tissues. Briefly, paraffin sections are incubated with an antibody raised against the Mfn2 protein. For biodistribution, a section of a section of each tissue in Table 6 is frozen down to ≤−60° C. as quickly as possible. DNA may be extracted from tissues, and vector biodistribution is evaluated by quantitative PCR. For tissue lymphocyte isolation and ELISPOT, lymphocytes may be harvested from spleen and bone marrow and ELISPOT for capsid and transgene T cell responses are performed.

Figure 18A:
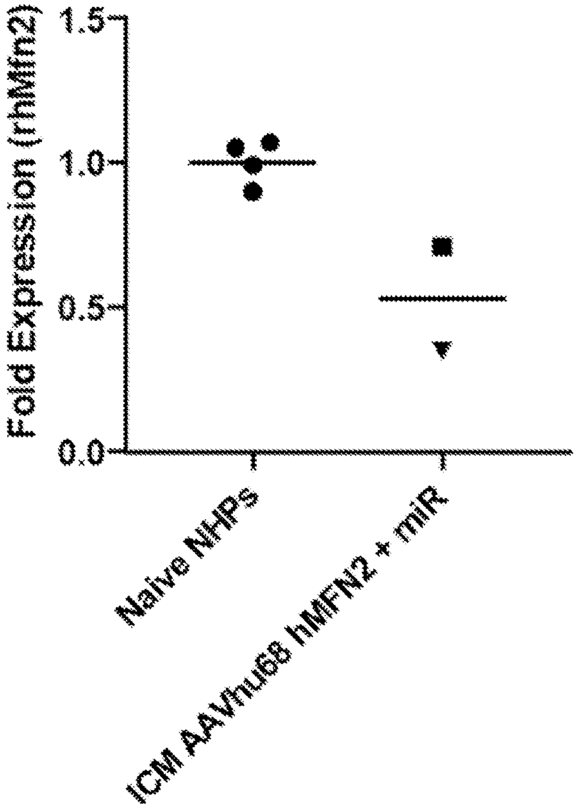
FIG. 18A shows hMfn2 fold-expression of endogenous Mfn2 RNA in non-human primates following AAVhu68.CB7.CI.hMfn2.miR538.RBG administration.
Figure 18B:
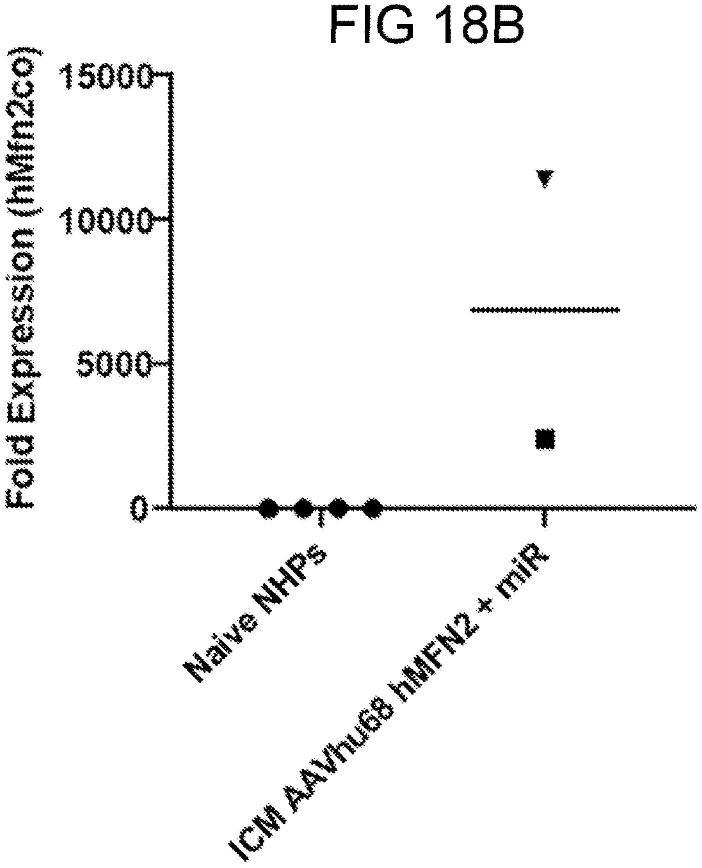
FIG. 18B shows hMfn2 fold-expression of transgene Mfn2 RNA in non-human primates following AAVhu68.CB7.CI.hMfn2.miR538.RBG administration.

Initially we performed a pilot study in which we examined MFN2 knockdown/replacement in nonhuman primates (NHPs). Briefly, AAVhu68.CB7.CI.hMfn2.miR538.RBG was administered via intracisterna magna (ICM) injection (N=2, plus 3-4 naïve controls). Motor neuron laser capture was utilized for sample collection, which samples were analyzed (i.e., quantification) of endogenous MFN2 RNA and transgene RNA. In-life safety endpoints including cage side observations, serum chemistry, complete blood counts, nerve conduction studies, and CSF chemistry and cytology demonstrated no evidence of vector-related toxicity after 35 days. Furthermore, no significant pathological findings were observed in any tissues including dorsal root ganglia (DRGs, data not shown). Vector expression was detected via qPCR of LCM spinal cord. Knockdown of endogenous Mfn2 was measured in both NHPs. Human Mfn2 cDNA was also detected in NHPs. FIG. 18A shows hMfn2 fold-expression of endogenous Mfn2 RNA in non-human primates following AAVhu68.CB7.CI.hMfn2.miR538.RBG administration. FIG. 18B shows hMfn2 fold-expression of transgene Mfn2 RNA in non-human primates following AAVhu68.CB7.CI.hMfn2.miR538.RBG administration. These results show that expression of cDNA and knockdown of miRNA was confirmed in motor neurons.

Overall, the results of the above-described mouse and cell culture studies show that knockdown of Mfn2 was achieved in vitro and in vivo using artificial miRNAs, that the combination vector strategy improved the phenotype of a mouse model of CMT2A, and that the combination strategy performed better than cDNA expression alone. Furthermore, the results of the above-described studies in nonhuman primates show that no toxicity was observed in the CNS or DRGs of non-human primates, and that expression of cDNA and knockdown of miRNA was confirmed in motor neurons.

REFERENCES

1. Feely et al., Neurology 76:1690-6, 2011.
2. Pipis et al., Brain: 143:3589-3602, 2020.
3. Fridman et al., J Neurol Neurosurg Psychiatry 86: 873-8, 2015.

All patents, patent publications, and other publications listed in this specification are incorporated herein by reference. The electronic sequence listing filed herewith named "UPN-22-9851PCT_20220923.xml" with size of 339,245 bytes, created on date of Sep. 23, 2022, and the contents of the electronic sequence listing (e.g., the sequences and text therein) are incorporated herein by reference in entirety. U.S. Provisional Patent Application No. 63/051,336, filed Jul. 13, 2020, and U.S. Provisional Patent Application No. 63/173,045 filed Apr. 9, 2021 are incorporated herein by reference. International Patent Application No. PCT/US2021/041406, filed Jul. 13, 2021, is incorporated herein by reference in its entirety. U.S. Provisional Patent Application No. 63/248,132, filed Sep. 24, 2021, and U.S. Provisional Patent Application No. 63/297,962, filed Jan. 10, 2022, and U.S. Provisional Patent Application No. 63/341,583, filed May 13, 2022 are incorporated herein by reference in its entirety. While the invention has been described with reference to a particularly preferred embodiment, it will be appreciated that modifications can be made without departing from the spirit of the invention. Such modifications are intended to fall within the scope of the appended claims.

The invention claimed is:

1. A recombinant adeno-associated virus (rAAV) comprising an AAV capsid and packaged therein a vector genome, wherein the vector genome comprises:

(a) an AAV 5' inverted terminal repeat (ITR);

(b) an CB7.CI.hMfn2.GA.link.miR538.rBG expression cassette comprising at least one open reading frame (ORF) comprising (i) an engineered nucleic acid sequence of SEQ ID NO: 11 or a sequence at least 90% identical thereto encoding a human mitofusin 2 (hMfn2), (ii) a spacer sequence located between (i) and (iii), and (iii) at least one miRNA coding sequence which is specific for a target site in an endogenous human mitofusin 2 nucleic acid sequence in a patient having a disorder associated with deficient hMfn2, wherein at the at least one miRNA comprises miR538, wherein the engineered nucleic acid sequence of (i) lacks the target site for the at least one miRNA of (iii), thereby preventing the at least one miRNA from targeting the engineered hMfn2 coding sequence;

wherein the regulatory control sequences comprise a cytomegalovirus immediate early (CMV IE)

enhancer and a chicken beta actin (CB) promoter, and further comprising a chicken beta-actin intron (CI), and a rabbit beta globin (rBG) polyadenylation (polyA) signal; and (c) an AAV 3' ITR.

2. The rAAV according to claim 1, wherein the engineered hMfn2 coding sequence has the sequence at least 90% identical to SEQ ID NO: 11, and wherein nucleotides (nt) 216 to 236 of SEQ ID NO: 11 (SEQ ID NO: 104) and/or nt 1371 to 1391 of SEQ ID NO: 11 (SEQ ID NO: 105) of the engineered hMfn2 coding sequence are conserved.

3. The rAAV according to claim 1, wherein the at least one miRNA comprises a sequence of one or more of an miRNA targeting sequence comprising SEQ ID NO: 89 (miR538, 59 nt) or a sequence at least 99% identical to SEQ ID NO: 89, wherein the at least one miRNA does not bind to the engineered hMfn2 coding sequence of (i) or its encoded messenger RNA (mRNA).

4. The rAAV according to claim 1, wherein the at least one miRNA comprises a sequence of one or more of an miRNA targeting sequence and further comprises a 5' flank sequence and a 3' flank sequence, wherein the miR538 comprises nucleic acid sequence of SEQ ID NO: 100.

5. The rAAV according to claim 1, wherein the spacer (ii) is 75 nucleotides to about 250 nucleotides in length.

6. The rAAV according to claim 1, wherein the spacer (ii) comprises nucleic acid sequence of SEQ ID NO: 90.

7. The rAAV according to claim 1, wherein the at least one miRNA coding sequence further comprising more than one miRNA coding sequence.

8. The rAAV according to claim 1, wherein the promoter comprises nucleic acid sequence of SEQ ID NO: 86.

9. The rAAV according to claim 1, wherein the chicken beta-actin intron (CI) comprises nucleic acid sequence of SEQ ID NO: 99.

10. The rAAV according to claim 1, wherein the rabbit beta-globin polyA signal comprises nucleic acid sequence of SEQ ID NO: 88.

11. The rAAV according to claim 1, wherein the expression cassette comprises nucleic acid sequence of SEQ ID NO: 96 or a sequence at least 99% identical to SEQ ID NO: 96.

12. The rAAV according to claim 1, wherein the vector genome comprises nucleic acid sequence of SEQ ID NO: 75 or sequence at least 99% identical to SEQ ID NO: 75.

13. The rAAV according to claim 1, wherein the AAV capsid is an AAVhu68, AAVrh91, AAV9, or AAV1 capsid.

14. A composition comprising a stock of rAAV according to claim 1 and one or more of an aqueous suspension media, excipient, and/or diluent.

15. The composition according to claim 14, which comprises the stock of rAAV in suspension, is formulated for system delivery or intrathecal delivery, optionally wherein the intrathecal delivery is an intracerebroventricular (ICV) injection or an intracisterna magna (ICM) injection.

16. A method for treating a patient having Charcot-Marie-Tooth 2A (CMT2A) disease comprising delivering an effective amount of the AAV according to claim 1 to a patient in need thereof.

17. A method for reducing neuropathy in a patient having Charcot-Marie-Tooth 2A (CMT2A) disease or neuropathy comprising delivering an effective amount of the AAV according to claim 1 to a patient in need thereof.

18. A recombinant nucleic acid molecule comprising:

(a) an AAV 5' inverted terminal repeat (ITR);

(b) an CB7.CI.hMfn2.GA.link.miR538.rBG expression cassette comprising at least one open reading frame (ORF) comprising (i) an engineered nucleic acid sequence of SEQ ID NO: 11 or a sequence at least 90% identical thereto encoding human mitofusin 2 (hMfn2), (ii) a spacer sequence located between (i) and (iii), and (iii) at least one miRNA coding sequence which is specific for a target site in an endogenous human mitofusin 2 nucleic acid sequence in a patient having a disorder associated with deficient hMfn2, wherein at the at least one miRNA comprises miR538, wherein the engineered nucleic acid sequence of (i) lacks the target site for the at least one miRNA of (iii), thereby preventing the at least one miRNA from targeting the engineered hMfn2 coding sequence, wherein the regulatory control sequences comprise a cytomegalovirus immediate early (CMV IE) enhancer and a chicken beta actin (CB) promoter, and further comprising a chicken beta-actin intron (CI), and a rabbit beta globin (rBG) polyadenylation (polyA) signal; and (c) an AAV 3'ITR.

19. The recombinant nucleic acid molecule according to claim 18, wherein the expression cassette comprises nucleic acid sequence of SEQ ID NO: 96.

20. The recombinant nucleic acid molecule according to claim 18, wherein the molecule is a plasmid.

21. A production host cell comprising a recombinant nucleic acid molecule according to claim 18, a nucleic acid sequence encoding an AAV capsid protein, and sufficient AAV rep functions and helper functions to permit packaging of the vector genome into the AAV capsid.

22. The production host cell according to claim 21, wherein the AAV capsid is an AAVhu68, AAVrh91, AAV9, or AAV1 capsid.

* * * * *